(12) United States Patent
Liu et al.

(10) Patent No.: US 12,115,152 B2
(45) Date of Patent: Oct. 15, 2024

(54) PAN-RAF KINASE INHIBITOR AND USE THEREOF

(71) Applicant: HEFEI INSTITUTES OF PHYSICAL SCIENCE, CHINESE ACADEMY OF SCIENCES, Anhui (CN)

(72) Inventors: Qing Song Liu, Anhui (CN); Jing Liu, Anhui (CN); Xi Xiang Li, Anhui (CN); Ao Li Wang, Anhui (CN); Zi Ping Qi, Anhui (CN); Qing Wang Liu, Anhui (CN); Zong Ru Jiang, Anhui (CN); Feng Ming Zou, Anhui (CN); Wen Chao Wang, Anhui (CN); Chen Hu, Anhui (CN); Cheng Chen, Anhui (CN); Li Wang, Anhui (CN)

(73) Assignee: TARAPEUTICS SCIENCE INC., Anhui (CN)

(*) Notice: Subject to any disclaimer, the term of this patent is extended or adjusted under 35 U.S.C. 154(b) by 536 days.

(21) Appl. No.: 17/433,395

(22) PCT Filed: Mar. 7, 2019

(86) PCT No.: PCT/CN2019/077272
§ 371 (c)(1),
(2) Date: Aug. 24, 2021

(87) PCT Pub. No.: WO2020/172906
PCT Pub. Date: Sep. 3, 2020

(65) Prior Publication Data
US 2022/0143001 A1    May 12, 2022

(30) Foreign Application Priority Data
Feb. 26, 2019    (CN) .................. 201910139510.X

(51) Int. Cl.
| A61K 31/4439 | (2006.01) |
| A61K 31/4365 | (2006.01) |
| A61K 31/497 | (2006.01) |
| A61K 31/536 | (2006.01) |
| A61P 35/00 | (2006.01) |

(52) U.S. Cl.
CPC ...... *A61K 31/4439* (2013.01); *A61K 31/4365* (2013.01); *A61K 31/497* (2013.01); *A61K 31/536* (2013.01); *A61P 35/00* (2018.01)

(58) Field of Classification Search
CPC ............ A61K 31/4439; A61K 31/4365; A61K 31/497; A61K 31/536; A61P 35/00
USPC .................................................. 514/255.05
See application file for complete search history.

(56) References Cited

U.S. PATENT DOCUMENTS

2006/0100204 A1    5/2006    Cogan et al.

FOREIGN PATENT DOCUMENTS

| CN | 101501023 A | 8/2009 |
| JP | 2009542771 A | 12/2009 |
| WO | 2011117381 A1 | 9/2011 |

OTHER PUBLICATIONS

Belikov, V.G., "Pharmaceutical Chemistry", textbook, 2007, Moscow, "MEDpress-inform", pp. 27-29, (in Russian); the relevance of which is described on pp. 6-7 of the English translation of the Russian Office Action dated Jul. 29, 2022.
Chou, T.-C., "Drug Combination Studies and Their Synergy Quantification Using the Chou-Talalay Method", Cancer Res; 70(2), 2010, pp. 440-446.
Dyson, G., et al., "Chemistry of synthetic drugs", translated from English; Moscow, Mir publ. house, 1964, pp. 12-19, (in Russian); the relevance of which is described on pp. 6-7 of the English translation of the Russian Office Action dated Jul. 29, 2022.
Hu, L., et al., Design, synthesis, and biological activity of phenyl-pyrazole derivatives as BCR-ABL kinase inhibitors. Bioorg Med Chem. 2015;23(13): pp. 3147-3152.
Kukes, "Clinical pharmacokinetics: a textbook for universities", Ed. by V.G. Kukes, Moscow, GEOTAR-Media, 2006, pp. 40-41, (in Russian); the relevance of which is described on pp. 6-7 of the English translation of the Russian Office Action dated Jul. 29, 2022.
Kummerer, K., "Pharmaceuticals in the environment", Annual Review of Environment and Resources, 2010, V.35, pp. 57-75.
Mashkovsky, M.D., "Medicinal products", Moscow, "Medicine", 1993, part 1, p. 8, (in Russian); the relevance of which is described on pp. 6-7 of the English translation of the Russian Office Action dated Jul. 29, 2022.
Official Action of the substantive examination dated Jul. 29, 2022 received in Russian Application No. 2021124474/04(051440), 27 pages.
Sarkisyan, K.H., et al., "Clinical Pharmacology of Biotransformation of Medicinal Products in the Educational Process of Students", International Journal of Experimental Education 8, 2013, pp. 101-103 (English abstract only).

(Continued)

*Primary Examiner* — Kristin A Vajda
(74) *Attorney, Agent, or Firm* — Scully, Scott, Murphy & Presser, P.C.

(57) ABSTRACT

The present invention provides a novel pan-RAF kinase inhibitor, comprising a compound of formula (I) or a pharmaceutically acceptable salt, solvate, ester, acid, metabolite or prodrug thereof. The present invention also provides a use or method of the compound of formula (I) in the treatment or prevention of a disorder related to the activity of RAF and/or RAS kinase.

(I)

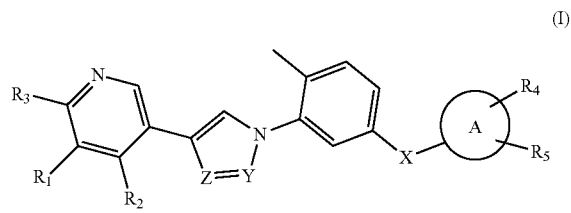

17 Claims, 6 Drawing Sheets

(56) References Cited

OTHER PUBLICATIONS

Stout, T.J., et al., "High throughput structural biology in drug discovery: protein kinases", Curr Pharm Des., 2004, pp. 1069-1082, 10.
Vereychik, "Toxicological chemistry: textbook", T.H. Vergeychik; ed. Prof. E.N. Vergeychik.-M.: MEDpress inform, 2009, pp. 37-38, (in Russian); the relevance of which is described on pp. 6-7 of the English translation of the Russian Office Action dated Jul. 29, 2022.
Extended European Search Report dated Aug. 5, 2022 received in EP Application No. 19916848.5, 7 pages.
Notice of Reasons for Refusal dated Sep. 27, 2022 received in Japanese Application No. 2021-549734, 6 pages.
International Search Report dated Sep. 2, 2019 issued in PCT/CN2019/077272.
Hu, Liming et al., "Design, synthesis, and biological activity of phenyl-pyrazole derivatives as BCR-ABL kinase inhibitors", Bioorganic & Medicinal Chemistry (May 12, 2015), vol. 23, No. 13, pp. 3147-3152.

PAN-RAF KINASE INHIBITOR AND USE THEREOF

TECHNICAL FIELD

The present application provides a compound as kinase inhibitor, a pharmaceutical composition comprising the compound, and the use of the compound in therapy. In particular, the present application discloses a derivative of pyrazoles or imidazoles suitable for inhibiting RAF and/or RAS kinase and for treating a disease mediated by RAF and/or RAS kinase.

BACKGROUND OF THE INVENTION

The RAF gene family includes BRAF, ARAF and CRAF. BRAF is an oncogene located on the long arm of chromosome 7, and encodes a protein having 766 amino acid residues. This protein is a serine/threonine-specific kinase, acting as an important transduction factor in the RAS/RAF/MEK/ERK signaling pathway. Only after the BRAF protein is phosphorylated by RAS kinase, the BRAF protein has a kinase activity to activate the MEK protein downstream, and then the MEK protein activates the ERK protein. The ERK protein enters into the cell nucleus, and then activates various proteins downstream to start transcription of various genes downstream, resulting in proliferation and division of cells. When a V600E mutation occurs in BRAF, the amino acid residue at position 600 of BRAF is changed from valine to glutamate, and the BRAF protein is always in an activated state. In the tumors having a RAS mutation, the continuous activation of the RAS protein leads to the formation of a BRAF-BRAF homodimer or a BRAF-CRAF heterodimer downstream, which transmits the activation signal downstream and promotes a malignant proliferation of tumor cells. Therefore, the development of small-molecule targeted drugs targeting pan-RAF can simultaneously inhibit the cancers caused by a BRAF V600E mutation and a RAS mutation.

At present, Vemurafenib, Dabrafenib and LGX818 as BRAF inhibitors have been approved for the treatment of melanoma carrying a BRAF mutation. However, the above drugs do not work in the tumour carrying a RAS mutation. The reason is mainly that the RAS mutation can lead to the formation of a dimer of BRAF and CRAF, and inhibition of BRAF can activate CRAF in turn. Secondly, the BRAF inhibitors on the market have a weak inhibitory effect on CRAF, and thus the BRAF inhibitors lose their anti-cancer effect. Therefore, the development of Pan-RAF inhibitors that can simultaneously act on the BRAF and CRAF proteins and can effectively inhibit the activities of MEK and ERK downstream has been a focus in the research and development of RAF inhibitors.

SUMMARY OF THE INVENTION

The present invention provides a selective kinase inhibitor, comprising a compound of formula (I) or a pharmaceutically acceptable salt, solvate, ester, acid, metabolite or prodrug thereof:

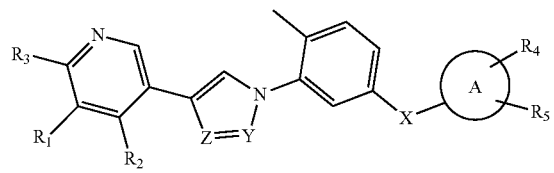

Formula (I)

wherein,

X is selected from the group consisting of

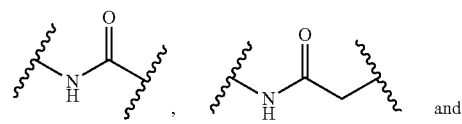

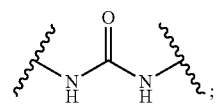

one of Y and Z is carbon and the other is nitrogen, preferably, Y is nitrogen and Z is carbon;

A ring is selected from the group consisting of

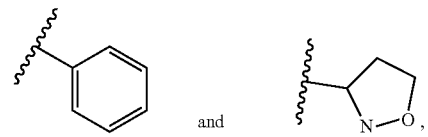 [SMILES: *c1ccccc1 ; *C1CCON1]

preferably, A is

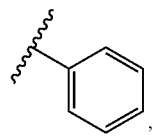 [SMILES: *c1ccccc1]

and the substituents $R_4$ and $R_5$ are located at the meta- and para-positions of the benzene ring, respectively;

$R_1$, $R_2$ and $R_3$ are each independently selected from the group consisting of H, cyano, $C_{1-6}$ alkyl, $C_{1-6}$ alkoxy, $C_{1-6}$ hydroxyalkyl, $C_{1-6}$ hydroxyalkoxy, $C_{3-6}$ cycloalkyl $C_{1-6}$ alkoxy, $C_{1-6}$ alkoxy $C_{1-6}$ alkoxy, phenyl, pyridyl, phenyl $C_{1-6}$ alkoxy, furyl $C_{1-6}$ alkoxy, heterocycloalkyl optionally substituted with $R_6$, heterocycloalkylphenyl optionally substituted with $R_6$, heterocycloalkylcarbonyl optionally substituted with $R_6$, heterocycloalkyloxy optionally substituted with $R_6$, heterocycloalkyl $C_{1-6}$ alkoxy optionally substituted with $R_6$, heterocycloalkyl $C_{1-6}$ alkanoylamino optionally substituted with $R_6$, $C_{3-6}$ cycloalkyl $C_{1-6}$ alkanoylamino, and $C_{1-6}$ alkylaminocarbonyl $C_{1-6}$ alkoxy, or $R_1$ together with $R_3$ forms

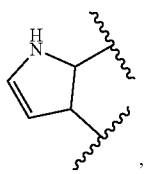
, wherein $R_1$, $R_2$ and $R_3$ are not H at the same time;

$R_4$ and $R_5$ are each independently selected from the group consisting of H, $C_{1-6}$ alkyl, $C_{1-6}$ haloalkyl, $C_{1-6}$ cyanoalkyl, heterocycloalkyl $C_{1-6}$ alkyl optionally substituted with $R_6$, phenyl optionally substituted with $R_6$, heteroaryl optionally substituted with $R_6$, and aminosulfonyl, or $R_4$ together with $R_5$ forms

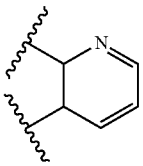
, and $R_4$ and $R_5$ are not H at the same time;

$R_6$ is independently selected from the group consisting of oxo, $C_{1-6}$ alkyl, $C_{2-6}$ alkanoyl, $C_{1-6}$ alkylsulfonyl, $C_{1-6}$ alkylamino $C_{2-6}$ alkanoyl, and $C_{1-6}$ haloalkyl.

The "heterocycloalkyl" as described above is preferably a 4- to 6-membered heterocycloalkyl containing oxygen and/or nitrogen atom(s), such as, pyrrolidinyl, morpholinyl, piperazinyl, tetrahydropyranyl, tetrahydrofuranyl, oxetanyl, azetidinyl or the like. Further, the nitrogen atom or carbon atom of those heterocycloalkyls may optionally substituted with a $R_6$ group selected from the group consisting of oxo (=O), $C_{1-6}$ alkyl, $C_{2-6}$ alkanoyl, $C_{1-6}$ alkylsulfonyl, $C_{1-6}$ alkylamino $C_{2-6}$ alkanoyl, and $C_{1-6}$ haloalkyl.

In a preferred embodiment of the present invention, $R_1$, $R_2$ and $R_3$ are each independently selected from the group consisting of H, cyano, $C_{1-6}$ alkyl (such as, methyl, ethyl, n-propyl, iso-propyl, n-butyl, tert-butyl or the like), $C_{1-6}$ hydroxyalkoxy (such as, hydroxymethoxy, 2-hydroxyethoxy, 3-hydorxypropoxy, 4-hydroxybutoxy or the like), $C_{3-6}$ cycloalkyl $C_{1-6}$ alkoxy (such as cyclopentylmethoxy or the like), $C_{1-6}$ alkoxy $C_{1-6}$ alkoxy (such as, 2-methoxyethoxy or the like), phenyl, pyridyl (such as, 2-pyridyl, 3-pyridyl, 4-pyridyl), phenyl $C_{1-6}$ alkoxy (such as, phenyl methoxy or the like), furyl $C_{1-6}$ alkoxy (such as, furan-3-ylmethoxy or the like), heterocycloalkyl optionally substituted with $R_6$ (such as, N-morpholinyl, piperazin-1-yl, 4-methyl-piperazin-1-yl or the like), heterocycloalkylphenyl optionally substituted with $R_6$ (such as, 4-methyl-piperazin-ylphenyl or the like), heterocycloalkylcarbonyl optionally substituted with $R_6$ (such as, 4-methyl-piperizan-1-ylcarbonyl or the like), heterocycloalkyloxy optionally substituted with $R_6$ (such as, tetrahydropyran-4-yloxy, tetrahydrofuran-3-yloxy, oxetan-3-yloxy, azetidin-3-yloxy or the like), heterocycloalkyl $C_{1-6}$ alkoxy optionally substituted with $R_6$ (such as, 2-morpholinoethoxy, 3-morpholinopropoxy, tetrahydrofuran-2-ylmethoxy, tetrahydrofuran-3-ylmethoxy, tetrahydropyran-4-ylmethoxy, oxetan-3-ylmethoxy, pyrrolidin-3-ylmethoxy or the like), heterocycloalkyl $C_{1-6}$ alkanoylamino optionally substituted with $R_6$ (such as, tetrahydropyran-4-ylformylamino, tetrahydrofuran-3-ylformylamino, tetrahydropyran-4-ylacetylamino, tetrahydrofuran-3-ylacetylamino, 3-methyl-oxetan-3-ylformylamino, 3-oxadicyclo[3.1.0]hexan-6-ylformylamino or the like), $C_{3-6}$ cycloalkyl $C_{1-6}$ alkanoylamino (such as, cyclopropylformylamino or the like), and $C_{1-6}$ alkylaminocarbonyl $C_{1-6}$ alkoxy (such a dimethylaminocarbonylmethoxy or the like), or $R_1$ together with $R_3$ forms

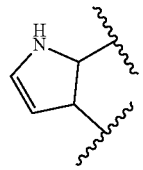
, wherein $R_1$, $R_2$ and $R_3$ are not H at the same time;

In another preferred embodiment of the present invention, provided is a selective pan-RAF kinase inhibitor, comprising a compound of formula (Ia) or a pharmaceutically acceptable salt, solvate, ester, acid, metabolite or prodrug thereof:

Formula (Ia)

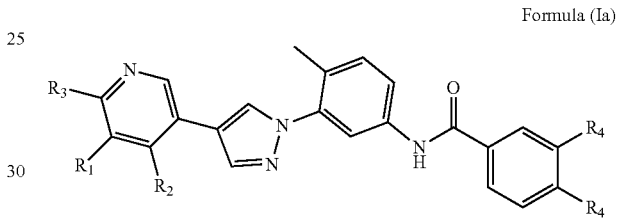

wherein, $R_1$, $R_2$, $R_3$, $R_4$ and $R_5$ are as defined above.

In a more preferred embodiment, $R_1$ is selected from the group consisting of H, pyridyl, heterocycloalkyl, heterocycloalkylphenyl optionally substituted with $C_{1-6}$ alkyl, heterocycloalkyloxy, heterocycloalkyl $C_{1-6}$ alkoxy, and $C_{1-6}$ alkylaminocarbonyl $C_{1-6}$ alkoxy;

$R_2$ is selected from the group consisting of H, $C_{1-6}$ alkyl, $C_{1-6}$ hydroxyalkoxy, $C_{1-6}$ alkoxy $C_{1-6}$ alkoxy, heterocycloalkyloxy, and heterocycloalkyl $C_{1-6}$ alkoxy;

$R_3$ is selected from the group consisting of H, and $C_{3-6}$ cycloalkyl $C_{1-6}$ alkanoylamino;

wherein $R_1$, $R_2$ and $R_3$ are not H at the same time;

$R_4$ is selected from the group consisting of $C_{1-6}$ haloalkyl, and $C_{1-6}$ cyanoalkyl;

$R_5$ is selected from the group consisting of H, $C_{1-6}$ alkyl, and heterocycloalkyl $C_{1-6}$ alkyl optionally substituted with $C_{1-6}$ alkyl.

In a particularly preferred embodiment, $R_1$ is selected from the group consisting of 3-pyridyl, 4-pyridyl, N-morpholinyl, heterocycloalkyloxy, heterocycloalkyl $C_{1-6}$ alkoxy, and $C_{1-6}$ alkylaminocarbonyl $C_{1-6}$ alkoxy; $R_4$ is selected from the group consisting of $C_{1-6}$ haloalkyl, and $C_{1-6}$ cyanoalkyl; each of $R_2$, $R_3$ and $R_5$ is H.

In another particularly preferred embodiment, $R_2$ is selected from the group consisting of $C_{1-6}$ hydroxyalkoxy, $C_{1-6}$ alkoxy $C_{1-6}$ alkoxy, heterocycloalkyloxy, and heterocycloalkyl $C_{1-6}$ alkoxy; $R_4$ is selected from the group consisting of $C_{1-6}$ haloalkyl and $C_{1-6}$ cyanoalkyl; each of $R_1$, $R_3$ and $R_5$ is H.

In another embodiment of the present invention, provided is a selective pan-RAF kinase inhibitor, comprising a compound of formula (Ib) or a pharmaceutically acceptable salt, solvate, ester, acid, metabolite or prodrug thereof:

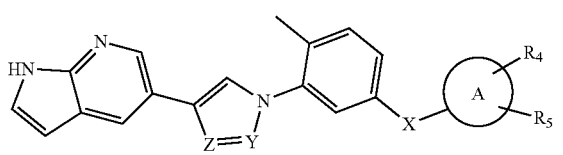

Formula (Ib)

wherein,
X is selected from the group consisting of

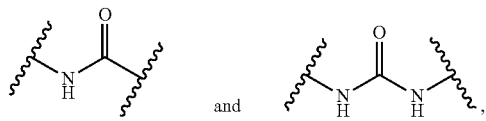 [SMILES: *NC(*)=O ; *NC(=O)N*]

and is preferably

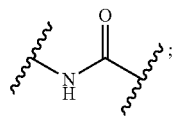 [SMILES: *NC(*)=O]

one of Y and Z is carbon and the other is nitrogen;
A ring is selected from the group consisting of

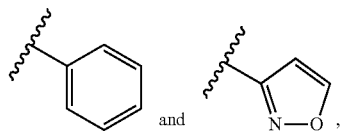 [SMILES: *c1ccccc1 ; *c1ccon1]

and is preferably

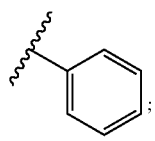

$R_4$ and $R_5$ are each independently selected from the group consisting of H, $C_{1-6}$ alkyl, $C_{1-6}$ haloalkyl, $C_{1-6}$ cyanoalkyl, piperazinyl $C_{1-6}$ alkyl optionally substituted with $R_6$, phenyl optionally substituted with $R_6$, imidazolyl optionally substituted with $R_6$, thienyl optionally substituted with $R_6$, pyridyl optionally substituted with $R_6$, and aminosulfonyl, or $R_4$ together with $R_5$ forms

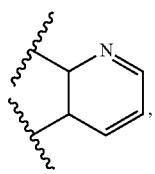

and $R_4$ and $R_5$ are not H at the same time;
$R_6$ is independently selected from the group consisting of $C_{1-6}$ alkyl and $C_{1-6}$ haloalkyl.

In another respect, the prevent invention provides a pharmaceutical composition, comprising the kinase inhibitor as described in the present invention, a pharmaceutically acceptable carrier or excipient, and optionally another therapeutic agent.

The present invention also relates to uses of the kinase inhibitor as described in the preparation of a medicament for inhibiting the activity of tyrosine kinase RAF and/or RAS, and in the preparation of a medicament for treating, preventing or ameliorating a disease, disorder or condition which is modulated or affected by, or involved in the activity of tyrosine kinase RAF and/or RAS.

DETAILED DESCRIPTION OF THE INVENTION

Terminology

Figure 1A:
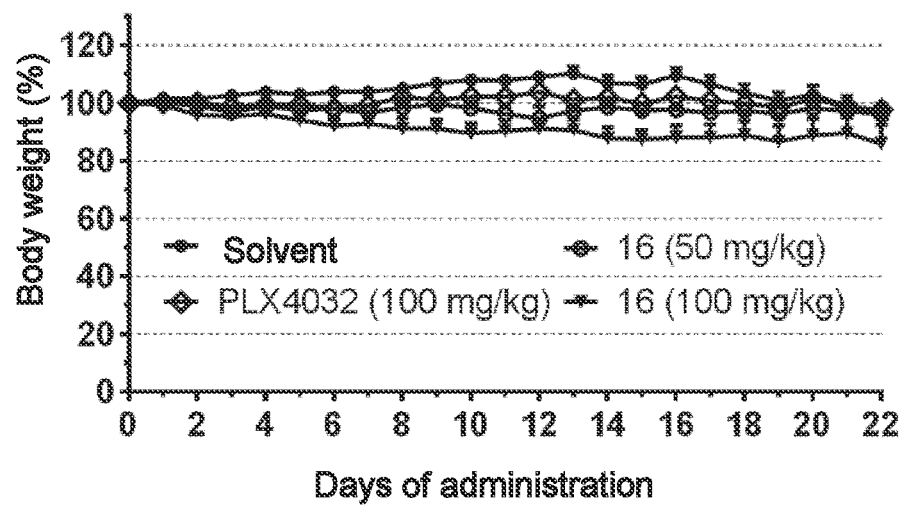
FIGS. 1a-1b illustrate the tumor inhibitory effect of the test compounds in a model of A375 cell tumor transplanted mouse.
Figure 1B:
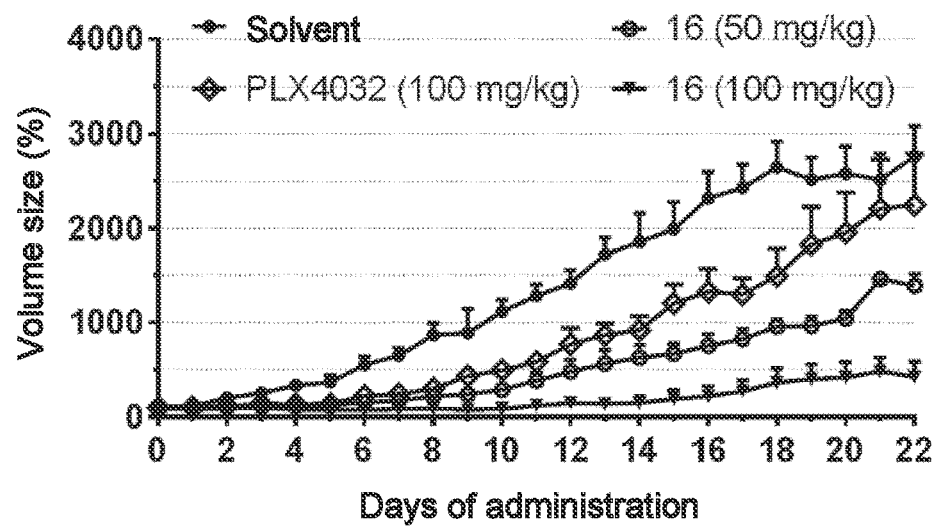
Figure 2A:
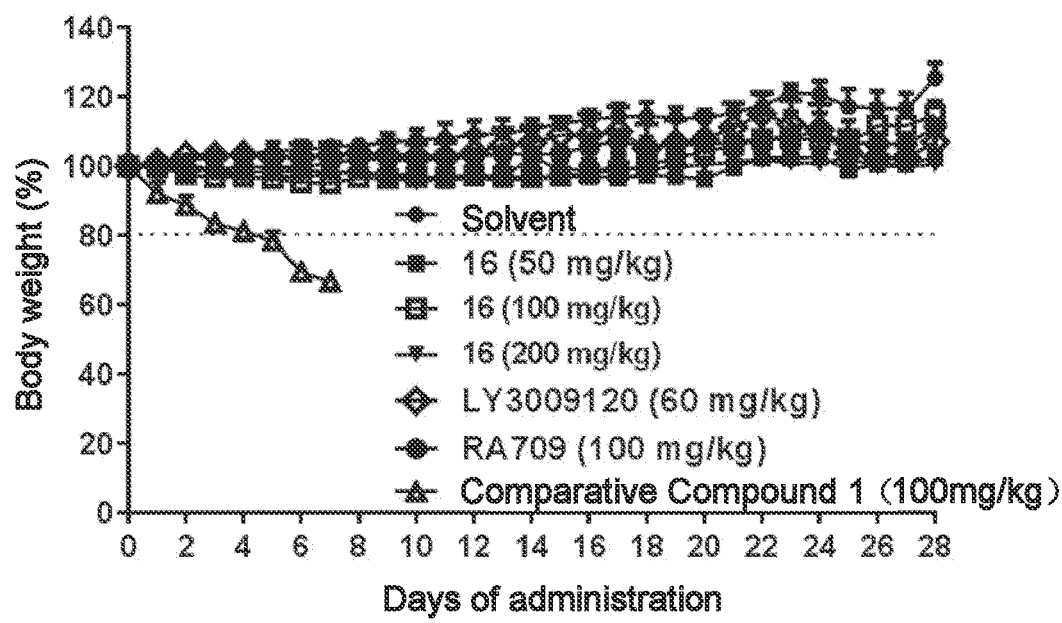
FIGS. 2a-2c illustrate the tumor inhibitory effect of the test compounds in a model of Calu-6 cell tumor transplanted mouse.
Figure 2B:
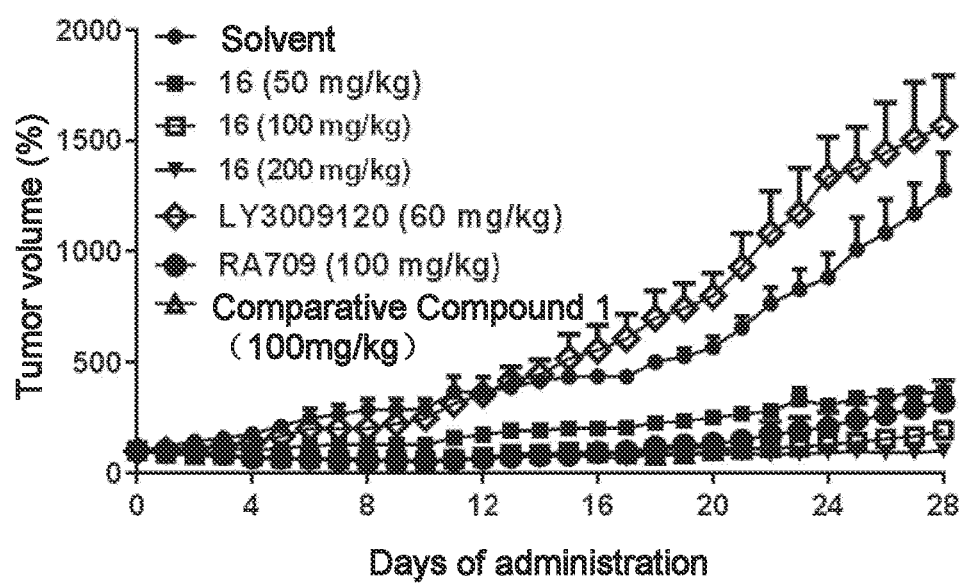
Figure 2C:
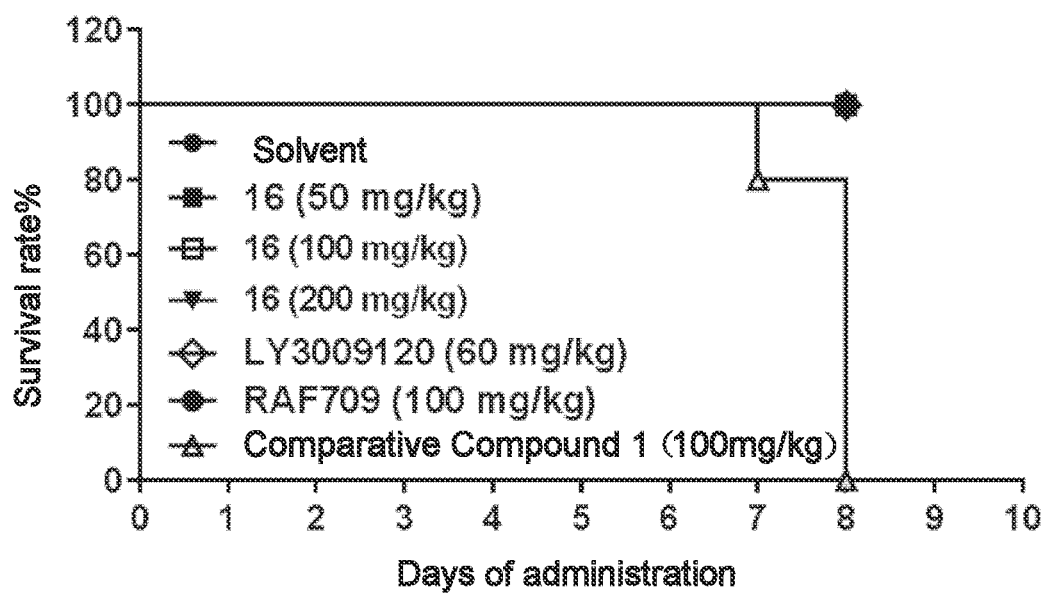
Figure 3A:
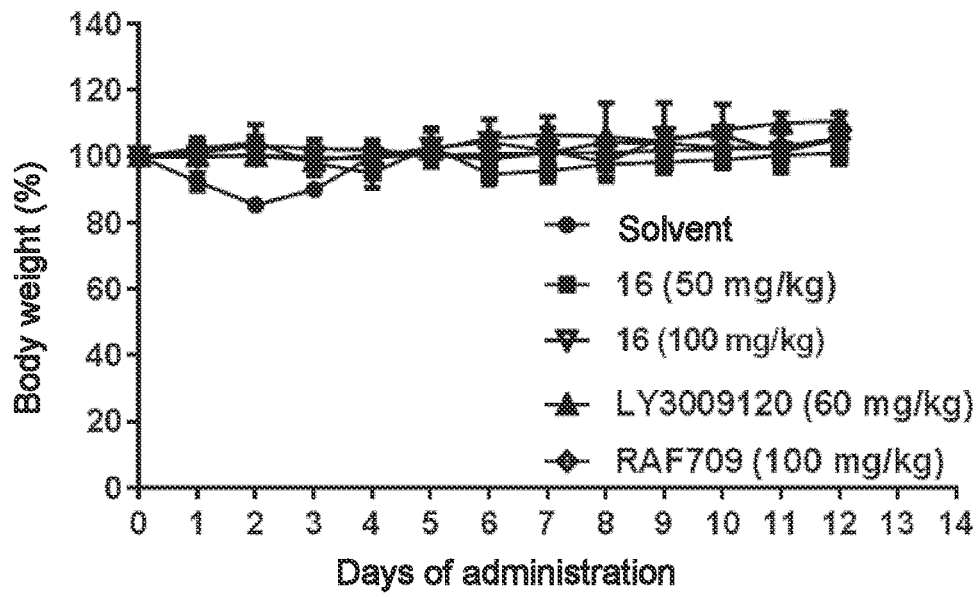
FIGS. 3a-3b illustrate the tumor inhibitory effect of the test compounds in a model of HCT116 cell tumor transplanted mouse.
Figure 3B:
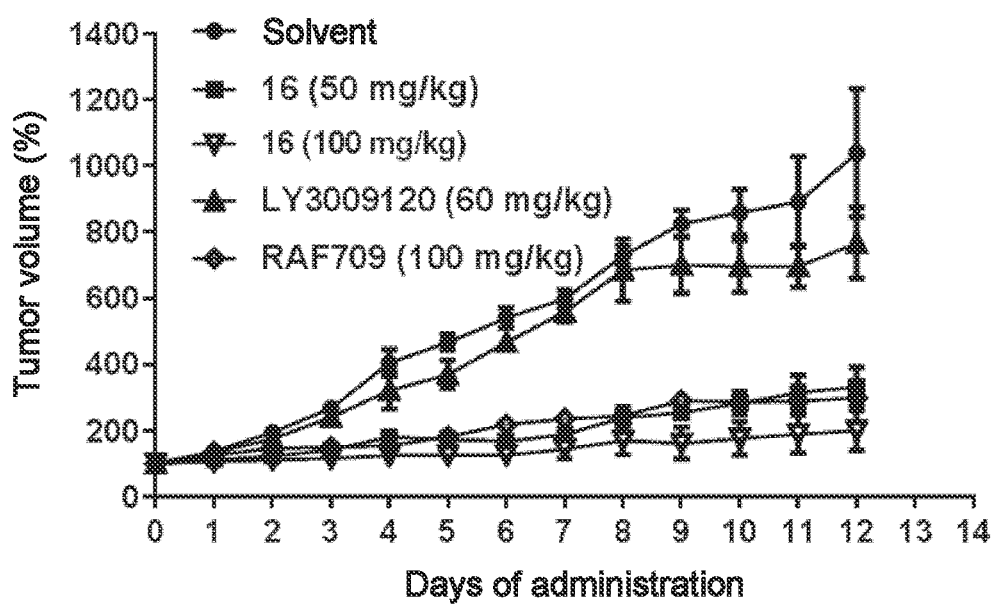
Figure 4A:
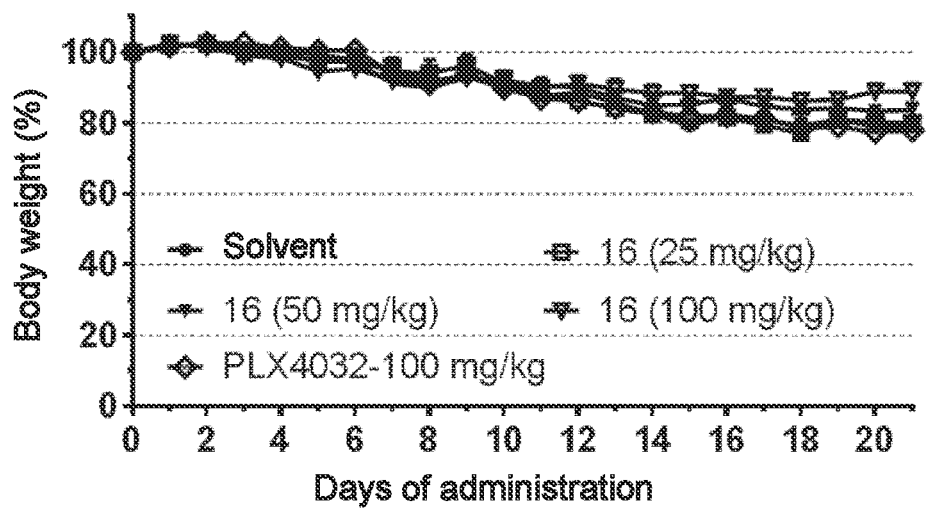
FIGS. 4a-4b illustrate the tumor inhibitory effect of the test compounds in a model of COLO205 cell tumor transplanted mouse.
Figure 4B:
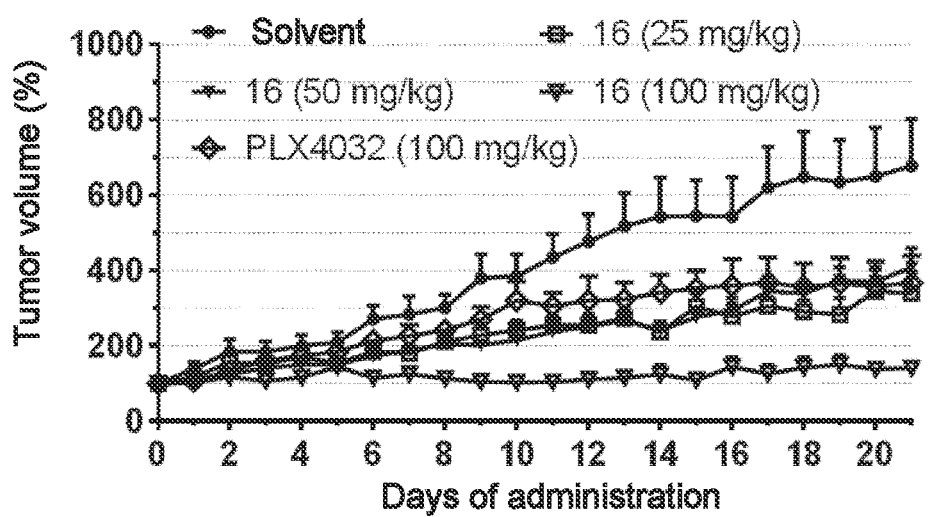
Figure 5A:
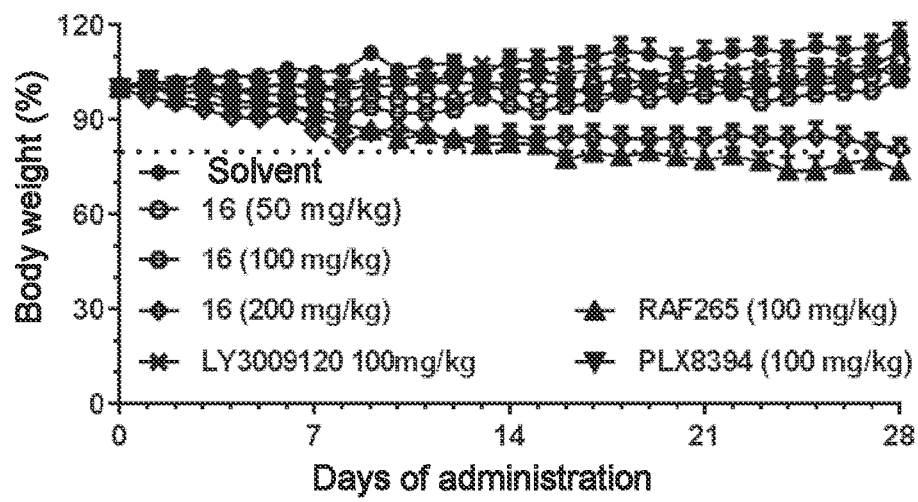
FIGS. 5a-5b illustrate the tumor inhibitory effect of the test compounds in a model of BxPC3 cell tumor transplanted mouse.
Figure 5B:
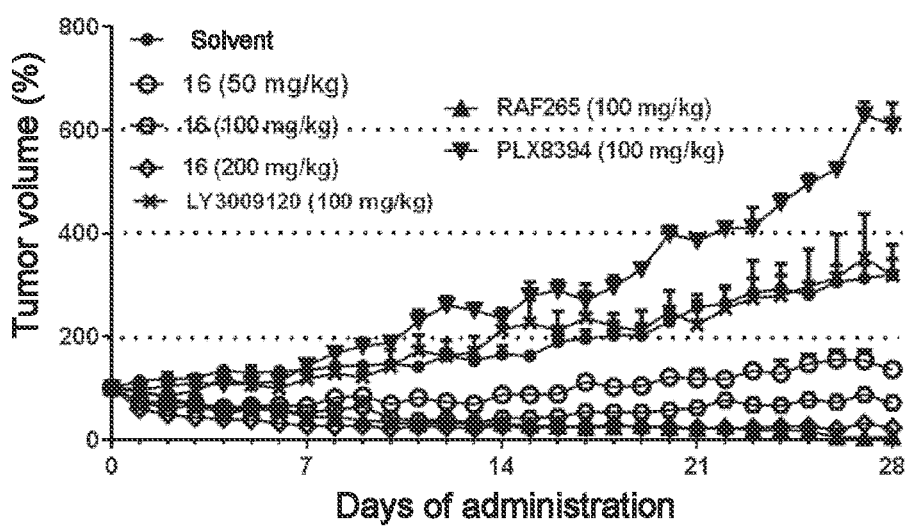

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the present disclosure.

Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed by conventional methods well known in the art and as described in various general and more specific references that are cited and discussed throughout the present specification.

The term "alkyl" refers to an aliphatic hydrocarbon group, which may have branched or straight chain. Depending on the structure, an alkyl group may be a monoradical or a diradical (i.e., an alkylene group). In the present invention, the alkyl group is preferably a "lower alkyl" having 1 to 8 carbon atoms, more preferably 1 to 6 carbon atoms, and more preferably 1 to 4 carbon atoms. Typical alkyl groups include, but are not limited to, methyl, ethyl, propyl, butyl, pentyl, hexyl, and the like. It should be understood that the "alkyl" as referred to herein includes all possible configurations and conformations of the alkyl which may be present. For example, the "propyl" as referred to herein includes n-propyl, iso-propyl. The "butyl" as referred to herein includes n-butyl, iso-butyl and tert-butyl. The "pentyl" as referred to herein includes n-pentyl, iso-pentyl, neo-pentyl, tert-butyl and pent-3-yl.

The term "alkoxy" refers to an —O-alkyl group, where alkyl is as defined herein. Typical alkoxy groups include, but are not limited to, methoxy, ethoxy, propoxy, butoxy, pentyloxy, hexyloxy, and the like.

The term "alkoxyalkyl" refers to an alkyl group, as defined herein, substituted by an alkoxy group, as defined herein.

The term "cycloalkyl" refers to a monocyclic or polycyclic radical that contains only carbon and hydrogen. Cycloalkyl groups include groups having 3 to 10 ring atoms. Depending on the structure, a cycloalkyl group can be a monoradical or a diradical (e.g., a cycloalkylene group). In the present invention, a cycloalkyl group is preferably a cycloalkyl having 3 to 8 carbon atoms, and more preferably a "lower cycloalkyl" having 3 to 6 carbon atoms. Typical cycloalkyl groups include, but are not limited to, cyclopropyl, cyclobutyl, cyclopentyl, cyclohexyl, cycloheptyl, cyclooctyl, cyclopentenyl, cyclohexenyl, cycloheptenyl and diamantanyl.

The term "alkyl(cycloalkyl)" or "cycloalkylalkyl" means an alkyl radical, as defined herein, substituted with a cycloalkyl group, as defined herein. Non-limiting cycloalkylalkyl groups include cyclopropylmethyl, cyclobutylmethyl, cyclopentylmethyl, cyclohexylmethyl, and the like.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine atoms. Aryl groups can be optionally substituted. Examples of aryl groups include, but are not limited to, phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to an —O-aryl group, wherein the aryl is as defined herein.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, a heteroaryl group may be a monoradical or a diradical (i.e., a heteroarylene group). Examples of heteroaryl groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

The term "alkyl(aryl)" or "aralkyl" refers to an alkyl group, as defined herein, substituted with an aryl group, as defined herein. Non-limiting alkyl(aryl) include benzyl, phenethyl and the like.

The term "alkyl(heteroaryl)" refers to an alkyl group, as defined herein, substituted with a heteroaryl group, as defined herein.

As used herein, the term "heteroalkyl" refers to an alkyl group, as defined herein, in which one or more skeletal chain atoms is a heteroatom, e.g., oxygen, nitrogen, sulfur, silicon, phosphorus or combinations thereof. The heteroatom(s) may be located at any position within the heteroalkyl group or at a position where the heteroalkyl group is attached to the remaining moiety of the molecule.

As used herein, the term "heterocycloalkyl" or "heterocyclic group" refers to a non-aromatic ring wherein one or more atoms forming the ring is a heteroatom selected from nitrogen, oxygen and sulfur. The heterocycloalkyl ring can be a monocyclic or polycyclic ring formed from three, four, five, six, seven, eight, nine, or more than nine atoms. The heterocycloalkyl ring can be optionally substituted.

Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" refers to an alkyl group, as defined herein, substituted with a heterocycloalkyl group, as defined herein.

The term "alkyloxy(heterocycloalkyl)" or "heterocycloalkylalkyloxy" refers to an alkyloxy group, as defined herein, substituted with a heterocycloalkyl group, as defined herein.

The term "halo" or "halogen" refers to fluoro, chloro, bromo and iodo.

The terms "haloalkyl", "haloalkoxy" and "haloheteroalkyl" include a structure of alkyl, alkoxy or heteroalkyl in which at least one hydrogen is replaced with a halogen atom. In certain embodiments, if two or more hydrogen atoms are replaced with halogen atoms, the halogen atoms are the same or different as one another.

The term "hydorxy" refers to —OH group.

The term "cyano" refers to —CN group.

The term "ester" refers to a chemical moiety with a formula —COOR, where R is selected from alkyl, cycloalkyl, aryl, heteroaryl (bonded through a ring carbon) and heterocyclic group (bonded through a ring carbon).

The term "amino" refers to —NH$_2$ group.

The term "aminocarbonyl" refers to —CO—NH$_2$ group.

The term "alkylaminocarbonyl" refers to —CO—NH—R group, wherein R is an alkyl group as defined herein.

The term "amide" or "amido" refers to —NR—CO—R', wherein R and R' are each independently hydrogen or alkyl.

The term "alkylamino" refers to an amino substituent which is further substituted with one or two alkyl groups, specifically refers to the group —NRR', wherein R and R' are each independently selected from the group consisting of hydrogen or lower alkyl, with the proviso that —NRR' is not —NH$_2$. The "alkylamino" includes a compound moiety wherein the nitrogen in —NH$_2$ is attached to at least one alkyl group. Examples of alkylamino group include, but are not limited to, methylamino, ethylamino and the like. The "dialkylamino" includes a moiety wherein the nitrogen in —NH$_2$ is attached to at least two other alkyl groups. Examples of dialkylamino group include, but are not limited to, dimethylamino, diethylamino and the like.

The term "alkylaminoalkyl" refers to an alkyl group, as defined herein, substituted with an alkylamino, as defined herein.

The term "aminoalkyl" refers to an alkyl substituted which is further substituted with one or more amino groups.

The term "aminoalkoxy" refers to an alkoxy substituted which is further substituted with one or more amino groups.

The term "hydroxyalkyl" or "hydroxylalkyl" refers to an alkyl substituent which is further substituted with one or more hydroxyl groups.

The term "cyanoalkyl" refers to an alkyl substituent which is further substituted with one or more cyano groups.

The term "acyl" refers to a monovalent group left after a hydroxyl group has been removed from an organic or inorganic oxygen acid having a general formula of R—M(O)—, where M is usually C.

The term "carbonyl" refers to an organic functional group (C=O) formed by carbon atom and oxygen atom through a double bond linkage.

The term "alkanoyl" or "alkylcarbonyl" refers to a carbonyl group which is further substituted with one alkyl group. Typical alkanoyl groups include, but are not limited to, acetyl, propionyl, butyryl, pentanoyl, hexanoyl, and the like.

The term "arylcarbonyl" refers to a carbonyl group, as defined above, substituted with an alkyl, as defined herein.

The term "alkoxycarbonyl" refers to a carbonyl group which is further substituted with one alkoxy group.

The term "heterocycloalkylcarbonyl" refers to a carbonyl group which is further substituted with one heterocycloalkyl group.

The terms "alkylaminocarbonyl", "cycloalkylaminocarbonyl", "arylaminocarbonyl", "aralkylaminocarbonyl", "heteroarylaminocarbonyl" refer to a carbonyl substituted with alkylamino, cycloalkylamino, arylamino, aralkylamino or heteroarylamino as defined herein, respectively.

The term "alkylcarbonylalkyl" or "alkylacylalkyl" refers to an alkyl group further substituted with one alkylcarbonyl.

The term "alkylcarbonylalkoxy" or "alkylacylalkoxy" refers to an alkoxy group further substituted with one alkylcarbonyl.

The term "sulfonyl" or "sulfuryl" refers to a function group left after a hydroxyl group is removed from a sulfonic acid, specifically, a —S(=O)$_2$— group.

The term "alkylsulfonyl" or "alkylsulfuryl" refers to —S(=O)$_2$—R, wherein R is an alkyl group.

The term "optional" means that one or more events described later may or may not occur, and include both events that occur and events that do not occur. The term "optionally substituted" or "substituted" means that the referenced group may be substituted with one or more additional group(s) which are each independently selected from alkyl, cycloalkyl, aryl, heteroaryl, heterocyclyl, hydroxy, alkoxy, cyano, halo, amide, nitro, haloalkyl, amino, methyl sulfonyl, alkyl carbonyl, alkoxy carbonyl, hetearyl alkyl, heterocycloalkyl alkyl, aminoacyl, amino protective group and the like. Among others, the amino protective group is preferably selected from the group consisting of pivaloyl, tert-butyloxycarbonyl, benzyloxycarbonyl, 9-fluorenylmethoxycarbonyl, benzyl, p-methoxybenzyl, allyloxycarbonyl, trifluoroacetyl, and the like.

As used herein, the term "tyrosine protein kinase" (TPK) refers to a class of kinases that catalyze the transfer of the γ-phosphate from ATP to tyrosine residue on proteins and that is capable of catalyzing the phosphorylation of tyrosine residue of various protein substrates, and thus have an important effect in cell growth, proliferation and differentiation.

As used herein, the terms "inhibit", "inhibitory", or "inhibitor" used in connection with a kinase refer to inhibition of phosphotransferase activity.

A "metabolite" of a compound as disclosed herein is a derivative of that compound that is formed when the compound is metabolized. The term "active metabolite" refers to a biologically active derivative of a compound that is formed when the compound is metabolized. The term "metabolism" as used herein, refers to the sum of the processes (including, but not limited to, hydrolysis reactions and reactions catalyzed by enzymes, such as, oxidation reactions) by which a particular substance is changed by an organism. Thus, enzymes may cause specific structural alterations. For example, cytochrome P450 catalyzes a variety of redox reactions while diphosphate glucuronyl transferases catalyze the transfer of an activated glucuronic acid molecule to aromatic alcohol, aliphatic alcohol, carboxylic acid, amine and free mercapto group. Further information on metabolism may be obtained from *The Pharmacological Basis of Therapeutics,* 9th Edition, McGraw-Hill (1996). Metabolites of the compounds as disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidation processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is tyrosine kinase RAF (wild-type or various mutants or the combination thereof), tyrosine kinase RAS (wild-type or various mutants or the combination thereof), BCR/ABL (wild-type or various mutants or the combination thereof), ABL (wild-type or various mutants or the combination thereof), KIT (wild-type or various mutants or the combination thereof), EGFR (wild-type or various mutants or the combination thereof), FLT3 (wild-type or various mutants or the combination thereof), VEGFR2 (wild-type or various mutants or the combination thereof), RET (wild-type or various mutants or the combination thereof), PDGFRα (wild-type or various mutants or the combination thereof), PDGFRβ (wild-type or various mutants or the combination thereof), FGFR1 (wild-type or various mutants or the combination thereof), FGFR2 (wild-type or various mutants or the combination thereof), FGFR3

(wild-type or various mutants or the combination thereof), FGFR4 (wild-type or various mutants or the combination thereof).

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

As used herein, $GI_{50}$ refers to a drug concentration required for 50% growth inhibition of cells, i.e., a drug concentration at which the growth of 50% cells (such as, cancer cells) can be inhibited or controlled by the drug.

The Novel Kinase Inhibitor of the Present Invention

The present invention provides a selective pan-RAF kinase inhibitor, comprising a compound of formula (I) or a pharmaceutically acceptable salt, solvate, ester, acid, metabolite or prodrug thereof:

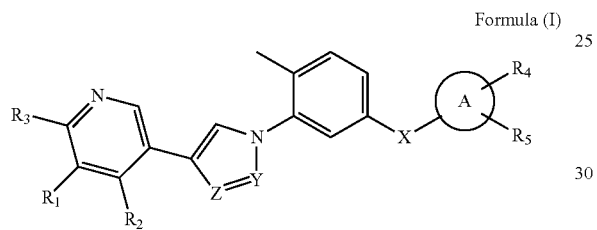

Formula (I)

wherein,
X is selected from the group consisting of

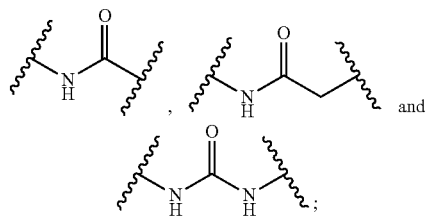

and

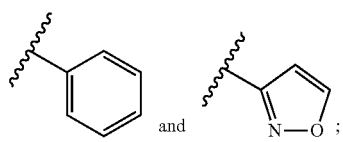 [SMILES: *c1ccccc1 ; *c1ccon1]

one of Y and Z is carbon and the other is nitrogen;
A ring is selected from the group consisting of

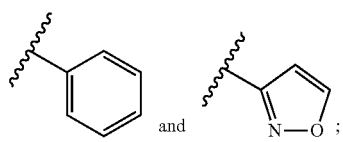 [SMILES: *c1ccccc1 ; *c1ccon1]

$R_1$, $R_2$ and $R_3$ are each independently selected from the group consisting of H, cyano, $C_{1-6}$ alkyl, $C_{1-6}$ alkoxy, $C_{1-6}$ hydroxyalkyl, $C_{1-6}$ hydroxyalkoxy, $C_{3-6}$ cycloalkyl $C_{1-6}$ alkoxy, $C_{1-6}$ alkoxy $C_{1-6}$ alkoxy, phenyl, pyridyl, phenyl $C_{1-6}$ alkoxy, furyl $C_{1-6}$ alkoxy, heterocycloalkyl optionally substituted with $R_6$, heterocycloalkylphenyl optionally substituted with $R_6$, heterocycloalkylcarbonyl optionally substituted with $R_6$, heterocycloalkyloxy optionally substituted with $R_6$, heterocycloalkyl $C_{1-6}$ alkoxy optionally substituted with $R_6$, heterocycloalkyl $C_{1-6}$ alkanoylamino optionally substituted with $R_6$, $C_{3-6}$ cycloalkyl $C_{1-6}$ alkanoylamino, and $C_{1-6}$ alkylaminocarbonyl $C_{1-6}$ alkoxy, or $R_1$ together with $R_3$ forms

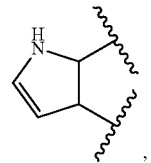

wherein $R_1$, $R_2$ and $R_3$ are not H at the same time;
$R_4$ and $R_5$ are each independently selected from the group consisting of H, $C_{1-6}$ alkyl, $C_{1-6}$ haloalkyl, $C_{1-6}$ cyanoalkyl, heterocycloalkyl $C_{1-6}$ alkyl optionally substituted with $R_6$, phenyl optionally substituted with $R_6$, heteroaryl optionally substituted with $R_6$, and aminosulfonyl, or $R_4$ together with $R_5$ forms

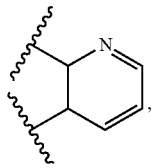 [SMILES: *C1C=CC=NC1*]

and $R_4$ and $R_5$ are not H at the same time;
$R_6$ is independently selected from the group consisting of oxo (=), $C_{1-6}$ alkyl, $C_{2-6}$ alkanoyl, $C_{1-6}$ alkylsulfonyl, $C_{1-6}$ alkylamino $C_{2-6}$ alkanoyl, and $C_{1-6}$ haloalkyl.

In a preferred aspect, in the formula (I), Y is nitrogen and Z is carbon.

In another aspect, in the formula (I), the A ring is

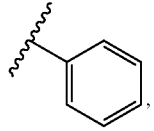 [SMILES: *c1ccccc1]

and the substituents $R_4$ and $R_5$ are located at the meta- and para-positions of the benzene ring, respectively; more preferably, $R_4$ is not H, and $R_5$ is H.

In certain embodiments, $R_2$ and $R_3$ are H; and $R_1$ is selected from the group consisting of phenyl, pyridyl, heterocycloalkyl optionally substituted with $C_{1-6}$ alkyl, heterocycloalkylphenyl optionally substituted with $C_{1-6}$ alkyl, heterocycloalkylcarbonyl optionally substituted with $C_{1-6}$ alkyl, heterocycloalkyloxy, heterocycloalkyl $C_{1-6}$ alkoxy, and $C_{1-6}$ alkylaminocarbonyl $C_{1-6}$ alkoxy.

In other embodiments, $R_1$ is H; $R_2$ is selected from the group consisting of H, cyano, $C_{1-6}$ alkyl, $C_{1-6}$ hydroxyalkoxy, $C_{3-6}$ cycloalkyl $C_{1-6}$ alkoxy, $C_{1-6}$ alkoxy $C_{1-6}$ alkoxy, phenyl $C_{1-6}$ alkoxy, furyl $C_{1-6}$ alkoxy, heterocycloalkyloxy optionally substituted with $R_6$ group, heterocycloalkyl $C_{1-6}$ alkoxy optionally substituted with $R_6$ group, heterocycloalkyl $C_{1-6}$ alkanoylamino optionally substituted with $C_{1-6}$ alkyl, and $C_{1-6}$ alkylaminocarbonyl $C_{1-6}$ alkoxy, wherein $R_6$ is independently selected from the group consisting of oxo (C=), $C_{2-6}$ alkanoyl, $C_{1-6}$ alkylsulfonyl, $C_{1-6}$ alkylamino $C_{2-6}$ alkanoyl; $R_3$ is selected from the group consisting of H and $C_{3-6}$ cycloalkyl $C_{1-6}$ alkanoylamino; and $R_2$ and $R_3$ are not H at the same time.

In the present invention, the "heterocycloalkyl" as referred to is preferably a 4- to 6-membered heterocycloalkyl containing oxygen and/or nitrogen atom(s), such as, pyrrolidinyl, morpholinyl, piperazinyl, tetrahydropyranyl, tetrahydrofuranyl, oxetanyl, azetidinyl or the like. Further, the nitrogen atom or carbon atom of those heterocycloalkyls may optionally be substituted with a $R_6$ group selected from the group consisting of oxo (=O), $C_{1-6}$ alkyl, $C_{2-6}$ alkanoyl, $C_{1-6}$ alkylsulfonyl, $C_{1-6}$ alkylamino $C_{2-6}$ alkanoyl, and $C_{1-6}$ haloalkyl.

In a preferred embodiment of the present invention, $R_1$, $R_2$ and $R_3$ are each independently selected from the group consisting of H, cyano, $C_{1-6}$ alkyl (such as, methyl, ethyl, n-propyl, iso-propyl, n-butyl, tert-butyl or the like), $C_{1-6}$ hydroxyalkoxy (such as, hydroxymethoxy, 2-hydroxyethoxy, 3-hydorxypropoxy, 4-hydroxybutoxy or the like), $C_{3-6}$ cycloalkyl $C_{1-6}$ alkoxy (such as cyclopentylmethoxy or the like), $C_{1-6}$ alkoxy $C_{1-6}$ alkoxy (such as, 2-methoxyethoxy or the like), phenyl, pyridyl (such as, 2-pyridyl, 3-pyridyl, 4-pyridyl), phenyl $C_{1-6}$ alkoxy (such as, phenyl methoxy or the like), furyl $C_{1-6}$ alkoxy (such as, furan-3-ylmethoxy or the like), heterocycloalkyl optionally substituted with $R_6$ (such as, N-morpholinyl, piperazin-1-yl, 4-methyl-piperazin-1-yl or the like), heterocycloalkylphenyl optionally substituted with $R_6$ (such as, 4-methyl-piperazin-ylphenyl or the like), heterocycloalkylcarbonyl optionally substituted with $R_6$ (such as, 4-methyl-piperizan-1-ylcarbonyl or the like), heterocycloalkyloxy optionally substituted with $R_6$ (such as, tetrahydropyran-4-yloxy, tetrahydrofuran-3-yloxy, oxetan-3-yloxy, azetidin-3-yloxy or the like), heterocycloalkyl $C_{1-6}$ alkoxy optionally substituted with $R_6$ (such as, 2-morpholinoethoxy, 3-morpholinopropoxy, tetrahydrofuran-2-ylmethoxy, tetrahydrofuran-3-ylmethoxy, tetrahydropyran-4-ylmethoxy, oxetan-3-ylmethoxy, pyrrolidin-3-ylmethoxy or the like), heterocycloalkyl $C_{1-6}$ alkanoylamino optionally substituted with $R_6$ (such as, tetrahydropyran-4-ylformylamino, tetrahydrofuran-3-ylformylamino, tetrahydropyran-4-ylacetylamino, tetrahydrofuran-3-ylacetylamino, 3-methyl-oxetan-3-ylformylamino, 3-oxadicyclo[3.1.0]hexan-6-ylformylamino or the like), $C_{3-6}$ cycloalkyl $C_{1-6}$ alkanoylamino (such as, cyclopropylformylamino or the like), and $C_{1-6}$ alkylaminocarbonyl $C_{1-6}$ alkoxy (such as, dimethylaminocarbonylmethoxy or the like), wherein $R_1$, $R_2$ and $R_3$ are not H at the same time.

In another preferred embodiment of the present invention, provided is a selective pan-RAF kinase inhibitor, comprising a compound of formula (Ia) or a pharmaceutically acceptable salt solvate, ester, acid, metabolite or prodrug thereof:

Formula (Ia)

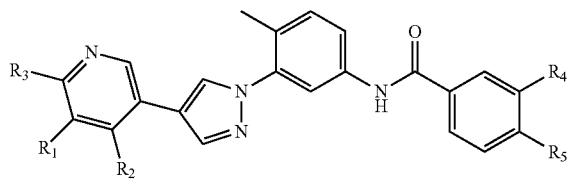

wherein, $R_1$, $R_2$, $R_3$, $R_4$ and $R_5$ are as defined as above.
In a more preferred embodiment,
$R_1$ is selected from the group consisting of H, pyridyl (such as, 3-pyridyl, 4-pyridyl), heterocycloalkyl (such as, N-morpholinyl, piperazin-1-yl), heterocycloalkylphenyl optionally substituted with $C_{1-6}$ alkyl (such as, 4-methyl-piperazin-ylphenyl), heterocycloalkyloxy (such as, tetrahydropyran-4-yloxy, oxetan-3-yloxy), heterocycloalkyl $C_{1-6}$ alkoxy (such as, 2-morpholinoethoxy, 3-morpholinopropoxy, tetrahydrofuran-3-ylmethoxy), and $C_{1-6}$ alkylaminocarbonyl $C_{1-6}$ alkoxy (such as, dimethylaminocarbonylmethoxy);

$R_2$ is selected from the group consisting of H, $C_{1-6}$ alkyl (such as, methyl), $C_{1-6}$ hydroxyalkoxy (such as, 2-hydroxyethoxy, 3-hydorxypropoxy, 4-hydroxybutoxy), $C_{1-6}$ alkoxy $C_{1-6}$ alkoxy (such as, 2-methoxyethoxy), heterocycloalkyloxy (such as, tetrahydropyran-4-yloxy, tetrahydrofuran-3-yloxy, oxetan-3-yloxy, azetidin-3-yloxy), and heterocycloalkyl $C_{1-6}$ alkoxy (such as, 2-morpholinoethoxy, tetrahydrofuran-2-ylmethoxy, tetrahydrofuran-3-ylmethoxy, tetrahydropyran-4-ylmethoxy, oxetan-3-ylmethoxy, pyrrolidin-3-ylmethoxy);

$R_3$ is selected from the group consisting of H, and $C_{3-6}$ cycloalkyl $C_{1-6}$ alkanoylamino (such as, cyclopropylformylamino);

wherein $R_1$, $R_2$ and $R_3$ are not H at the same time;

$R_4$ is selected from the group consisting of $C_{1-6}$ haloalkyl (such as, trifluoromethyl), and $C_{1-6}$ cyanoalkyl (such as, 2-cyano-eth-2-yl), 2-cyano-prop-2-yl);

$R_5$ is selected from the group consisting of H, $C_{1-6}$ alkyl (such as, methyl), and heterocycloalkyl $C_{1-6}$ alkyl optionally substituted with $C_{1-6}$ alkyl (such as, 4-methyl-piperazin-1-ylmethyl).

In a particularly preferred embodiment, $R_1$ is selected from the group consisting of 3-pyridyl, 4-pyridyl, N-morpholinyl, heterocycloalkyloxy (preferably, oxetan-3-yloxy), heterocycloalkyl $C_{1-6}$ alkoxy (preferably, 3-morpholinopropoxy, tetrahydrofuran-3-ylmethoxy), and $C_{1-6}$ alkylaminocarbonyl $C_{1-6}$ alkoxy (preferably, dimethylaminocarbonylmethoxy); $R_4$ is selected from the group consisting of $C_{1-6}$ haloalkyl (preferably, trifluoromethyl), and $C_{1-6}$ cyanoalkyl (preferably, 2-cyano-eth-2-yl), 2-cyano-prop-2-yl); each of $R_2$, $R_3$ and $R_5$ is H.

In another particularly preferred embodiment, $R_2$ is selected from the group consisting of $C_{1-6}$ hydroxyalkoxy (preferably, 3-hydorxypropoxy, 4-hydroxybutoxy), $C_{1-6}$ alkoxy $C_{1-6}$ alkoxy (preferably, 2-methoxyethoxy), heterocycloalkyloxy (preferably, tetrahydropyran-4-yloxy, tetrahydrofuran-3-yloxy, azetidin-3-yloxy), and heterocycloalkyl $C_{1-6}$ alkoxy (preferably, tetrahydropyran-4-ylmethoxy, oxetan-3-ylmethoxy); $R_4$ is selected from the group consisting of $C_{1-6}$ haloalkyl (preferably, trifluoromethyl), and $C_{1-6}$ cyanoalkyl (preferably, 2-cyano-eth-2-yl, 2-cyano-prop-2-yl); each of $R_1$, $R_3$ and $R_5$ is H.

In another preferred embodiment of the present invention, provided is a selective pan-RAF kinase inhibitor, comprising a compound of formula (Ib) or a pharmaceutically acceptable salt, solvate, ester, acid, metabolite or prodrug thereof:

Formula (Ib)

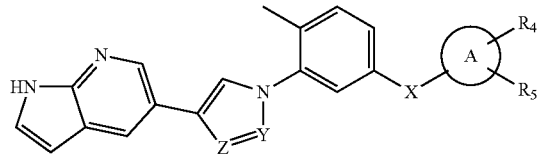

wherein,
X is selected from the group consisting of

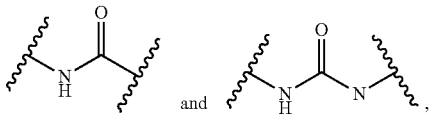 [SMILES: *NC(*)=O ; *NC(=O)N*]

and preferably is

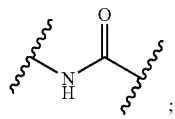

;

one of Y and Z is carbon and the other is nitrogen;
A ring is selected from the group consisting of

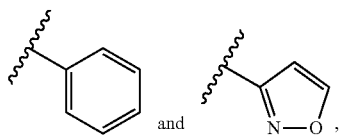 [SMILES: *c1ccccc1 ; *c1ccon1]

and preferably is

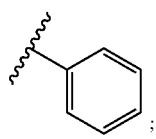 [SMILES: *c1ccccc1]

;

$R_4$ and $R_5$ are each independently selected from the group consisting of H, $C_{1-6}$ alkyl (such as, methyl, ethyl, n-propyl, iso-propyl, n-butyl, tert-butyl, and the like), $C_{1-6}$ haloalkyl (such as, trifluoromethyl), $C_{1-6}$ cyanoalkyl (such as, 2-cyano-eth-2-yl, 2-cyano-prop-2-yl), piperazinyl $C_{1-6}$ alkyl optionally substituted with $R_6$ (such as, piperazin-1-ylmethyl), phenyl optionally substituted with $R_6$, imidazolyl optionally substituted with $R_6$, thienyl optionally substituted with $R_6$, pyridyl optionally substituted with $R_6$, and aminosulfonyl, or $R_4$ together with $R_5$ forms and $R_4$ and $R_5$ are not H at the same time;
$R_6$ is independently selected from the group consisting of $C_{1-6}$ alkyl (such as, methyl, ethyl, n-propyl, iso-propyl, n-butyl, tert-butyl, and the like) and $C_{1-6}$ haloalkyl (such as, trifluoromethyl).

In a preferred embodiment, the present invention provides a following compound or a pharmaceutically acceptable salt, solvate, ester, acid, metabolite or prodrug thereof:

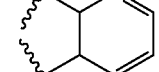

| No. | Structure |
|---|---|
| 1 | 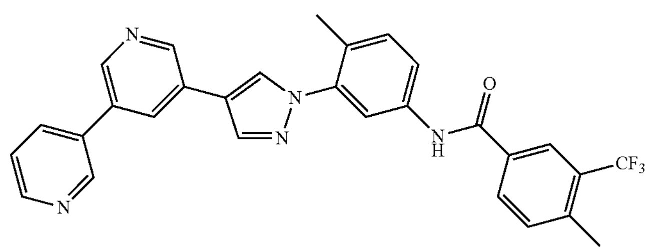 [SMILES: Cc1ccc(NC(=O)c2ccc(C)c(C(F)(F)F)c2)cc1-n1cc(-c2cncc(-c3cccnc3)c2)cn1] |
| 2 | 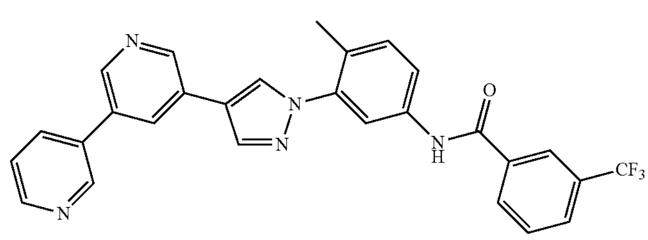 [SMILES: Cc1ccc(NC(=O)c2cccc(C(F)(F)F)c2)cc1-n1cc(-c2cncc(-c3cccnc3)c2)cn1] |

-continued

| No. | Structure |
|---|---|
| 3 | 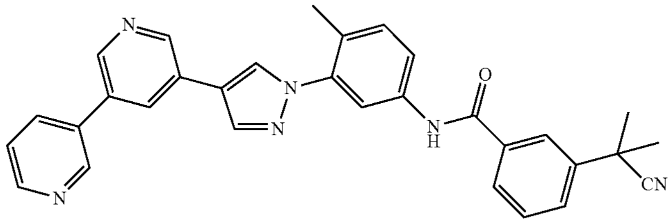 [SMILES: Cc1ccc(NC(=O)c2cccc(C(C)(C)C#N)c2)cc1-n1cc(-c2cncc(-c3cccnc3)c2)cn1] |
| 4 | 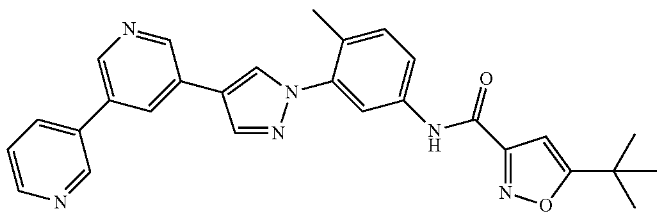 [SMILES: Cc1ccc(NC(=O)c2cc(C(C)(C)C)on2)cc1-n1cc(-c2cncc(-c3cccnc3)c2)cn1] |
| 5 | 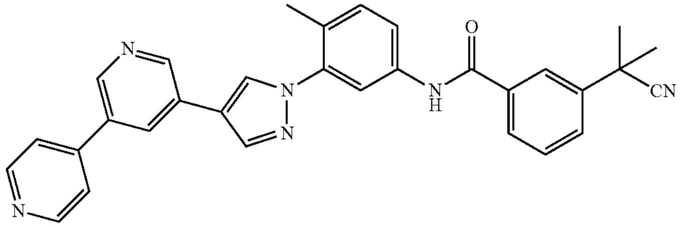 [SMILES: Cc1ccc(NC(=O)c2cccc(C(C)(C)C#N)c2)cc1-n1cc(-c2cncc(-c3ccncc3)c2)cn1] |
| 6 | 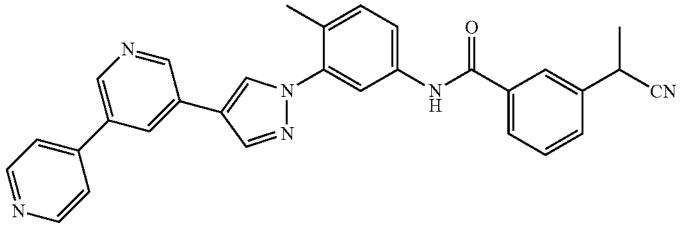 [SMILES: Cc1ccc(NC(=O)c2cccc(C(C)C#N)c2)cc1-n1cc(-c2cncc(-c3ccncc3)c2)cn1] |
| 7 | 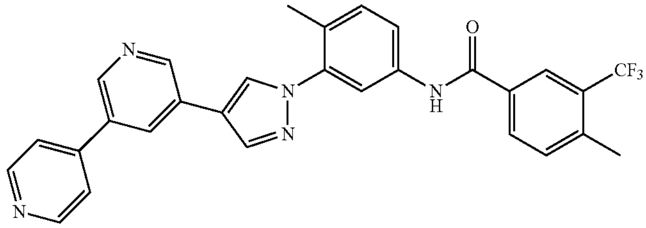 [SMILES: Cc1ccc(NC(=O)c2ccc(C)c(C(F)(F)F)c2)cc1-n1cc(-c2cncc(-c3ccncc3)c2)cn1] |
| 8 | 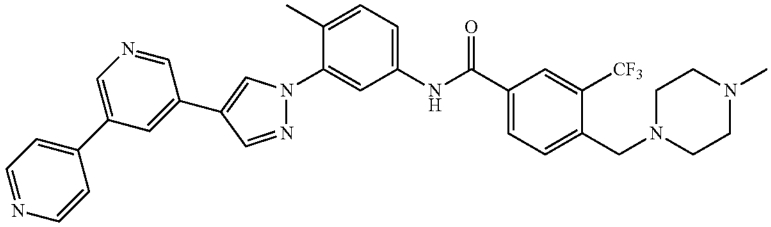 [SMILES: Cc1ccc(NC(=O)c2ccc(CN3CCN(C)CC3)c(C(F)(F)F)c2)cc1-n1cc(-c2cncc(-c3ccncc3)c2)cn1] |

-continued
| No. | Structure |
|---|---|
| 9 | 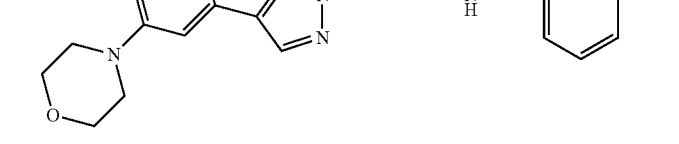 |
| 10 | 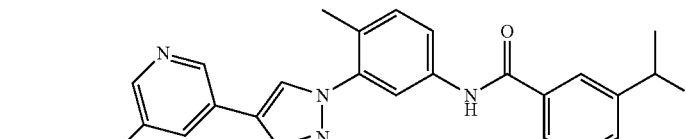 |
| 11 | 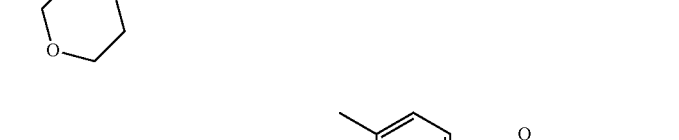 |
| 12 | 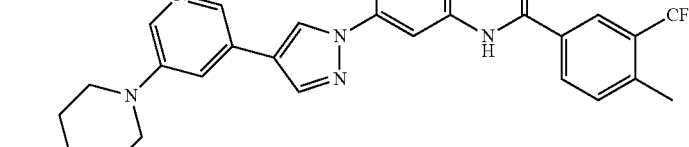 |
| 13 | 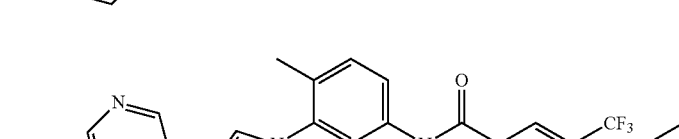 |
| 14 | 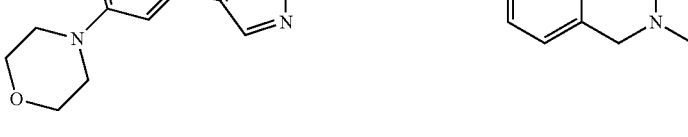 |

-continued
| No. | Structure |
|---|---|
| 15 | 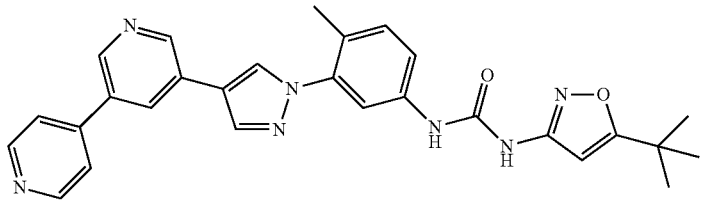 [SMILES: Cc1ccc(NC(=O)Nc2cc(C(C)(C)C)on2)cc1-n1cc(-c2cncc(-c3ccncc3)c2)cn1] |
| 16 | 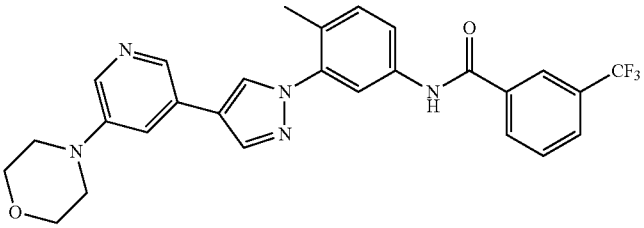 [SMILES: Cc1ccc(NC(=O)c2cccc(C(F)(F)F)c2)cc1-n1cc(-c2cncc(N3CCOCC3)c2)cn1] |
| 17 | 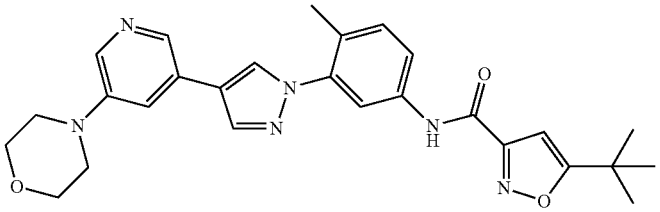 [SMILES: Cc1ccc(NC(=O)c2cc(C(C)(C)C)on2)cc1-n1cc(-c2cncc(N3CCOCC3)c2)cn1] |
| 18 | 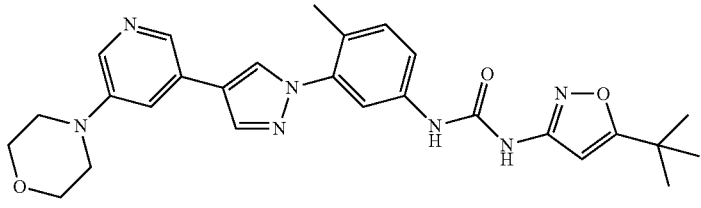 [SMILES: Cc1ccc(NC(=O)Nc2cc(C(C)(C)C)on2)cc1-n1cc(-c2cncc(N3CCOCC3)c2)cn1] |
| 19 | 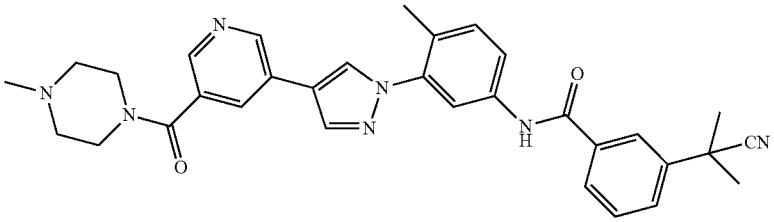 [SMILES: Cc1ccc(NC(=O)c2cccc(C(C)(C)C#N)c2)cc1-n1cc(-c2cncc(C(=O)N3CCN(C)CC3)c2)cn1] |
| 20 | 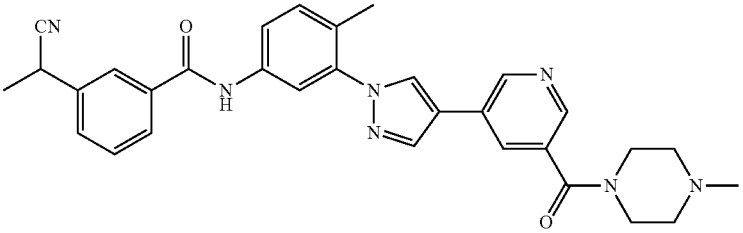 [SMILES: Cc1ccc(NC(=O)c2cccc(C(C)C#N)c2)cc1-n1cc(-c2cncc(C(=O)N3CCN(C)CC3)c2)cn1] |
| 21 | 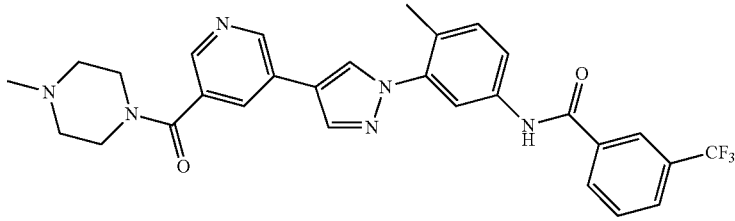 [SMILES: Cc1ccc(NC(=O)c2cccc(C(F)(F)F)c2)cc1-n1cc(-c2cncc(C(=O)N3CCN(C)CC3)c2)cn1] |

-continued
| No. | Structure |
|---|---|
| 22 | 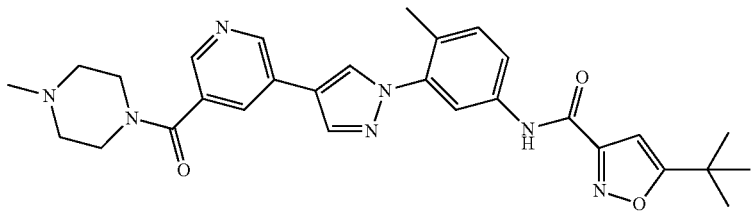 [SMILES: Cc1ccc(NC(=O)c2cc(C(C)(C)C)on2)cc1-n1cc(-c2cncc(C(=O)N3CCN(C)CC3)c2)cn1] |
| 23 | 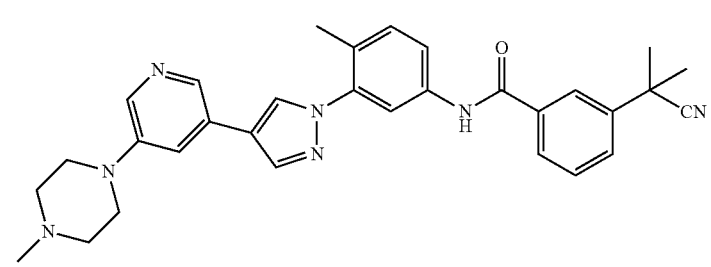 [SMILES: Cc1ccc(NC(=O)c2cccc(C(C)(C)C#N)c2)cc1-n1cc(-c2cncc(N3CCN(C)CC3)c2)cn1] |
| 24 | 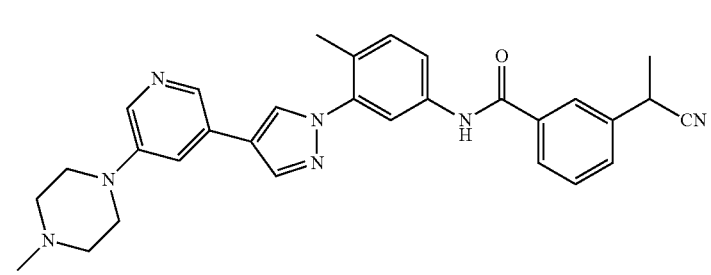 [SMILES: Cc1ccc(NC(=O)c2cccc(C(C)C#N)c2)cc1-n1cc(-c2cncc(N3CCN(C)CC3)c2)cn1] |
| 25 | 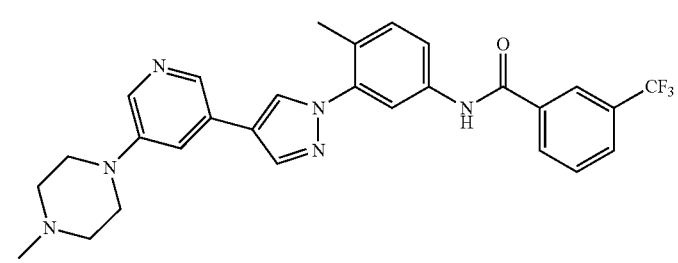 [SMILES: Cc1ccc(NC(=O)c2cccc(C(F)(F)F)c2)cc1-n1cc(-c2cncc(N3CCN(C)CC3)c2)cn1] |
| 26 | 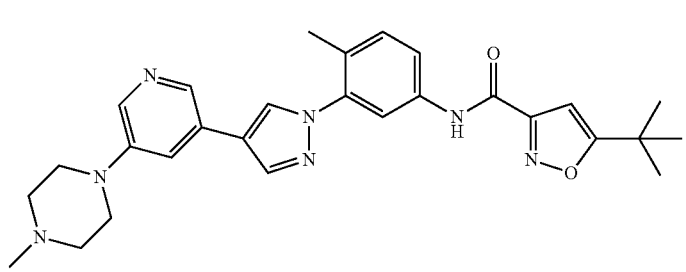 [SMILES: Cc1ccc(NC(=O)c2cc(C(C)(C)C)on2)cc1-n1cc(-c2cncc(N3CCN(C)CC3)c2)cn1] |
| 27 | 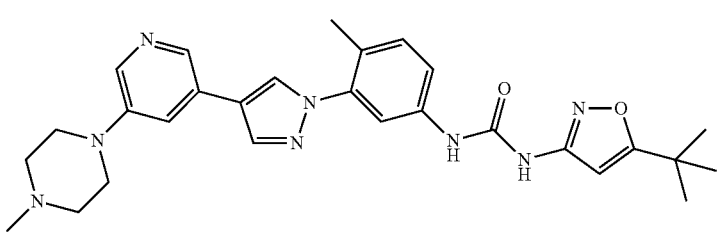 [SMILES: Cc1ccc(NC(=O)Nc2cc(C(C)(C)C)on2)cc1-n1cc(-c2cncc(N3CCN(C)CC3)c2)cn1] |

-continued
| No. | Structure |
|-----|-----------|
| 28 | 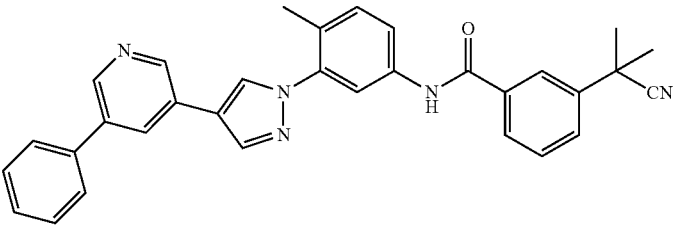 |
| 29 | 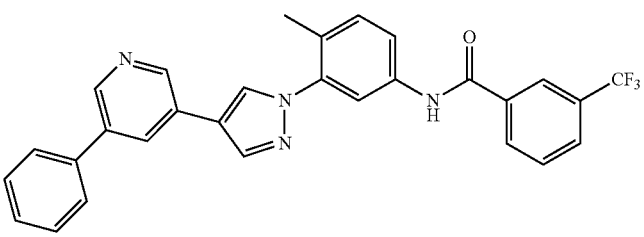 [SMILES: Cc1ccc(NC(=O)c2cccc(C(F)(F)F)c2)cc1-n1cc(-c2cncc(-c3ccccc3)c2)cn1] |
| 30 | 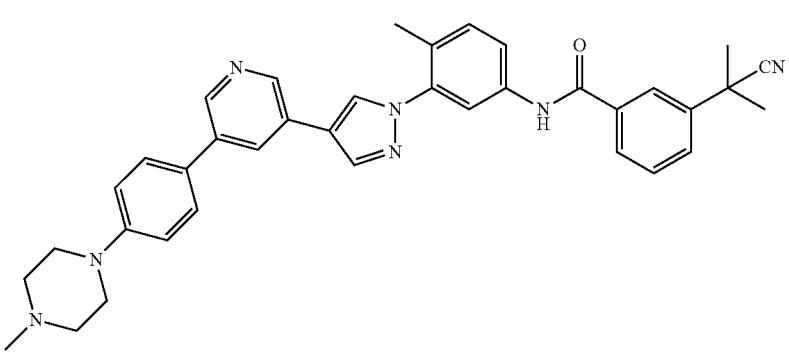 [SMILES: Cc1ccc(NC(=O)c2cccc(C(C)(C)C#N)c2)cc1-n1cc(-c2cncc(-c3ccc(N4CCN(C)CC4)cc3)c2)cn1] |
| 31 | 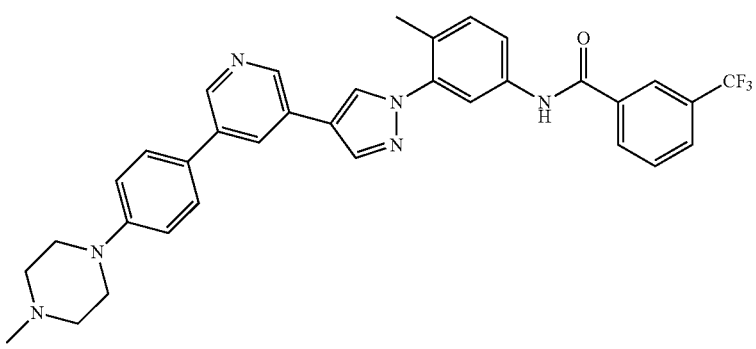 [SMILES: Cc1ccc(NC(=O)c2cccc(C(F)(F)F)c2)cc1-n1cc(-c2cncc(-c3ccc(N4CCN(C)CC4)cc3)c2)cn1] |
| 32 | 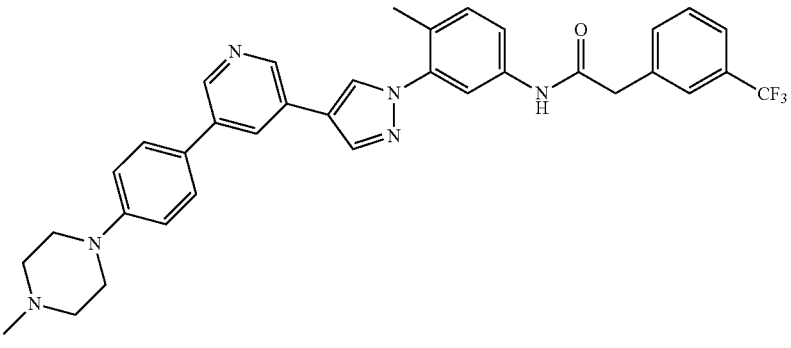 [SMILES: Cc1ccc(NC(=O)Cc2cccc(C(F)(F)F)c2)cc1-n1cc(-c2cncc(-c3ccc(N4CCN(C)CC4)cc3)c2)cn1] |

-continued

| No. | Structure |
|---|---|
| 33 | 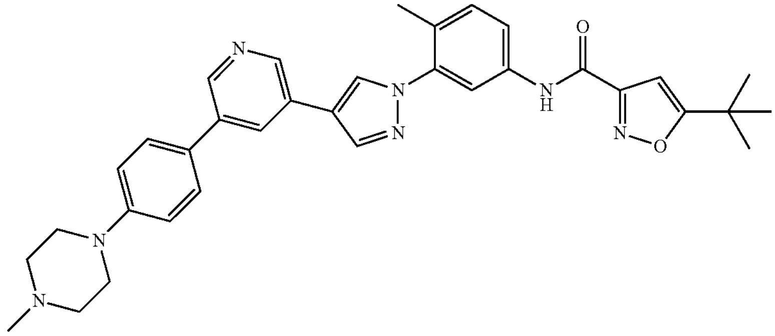 [SMILES: Cc1ccc(NC(=O)c2cc(C(C)(C)C)on2)cc1-n1cc(-c2cncc(-c3ccc(N4CCN(C)CC4)cc3)c2)cn1] |
| 34 | 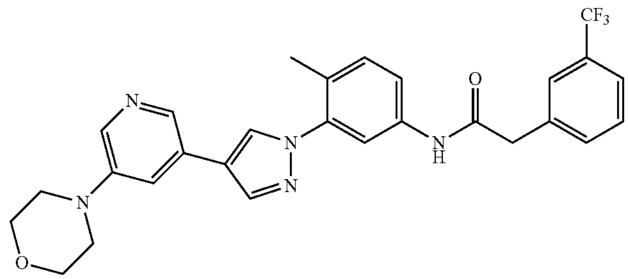 [SMILES: Cc1ccc(NC(=O)Cc2cccc(C(F)(F)F)c2)cc1-n1cc(-c2cncc(N3CCOCC3)c2)cn1] |
| 35 | 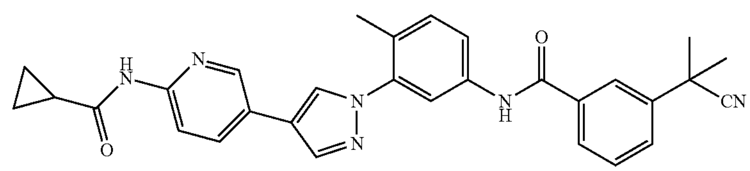 [SMILES: Cc1ccc(NC(=O)c2cccc(C(C)(C)C#N)c2)cc1-n1cc(-c2ccc(NC(=O)C3CC3)nc2)cn1] |
| 36 | 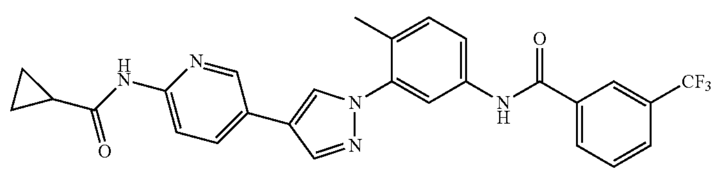 [SMILES: Cc1ccc(NC(=O)c2cccc(C(F)(F)F)c2)cc1-n1cc(-c2ccc(NC(=O)C3CC3)nc2)cn1] |
| 37 | 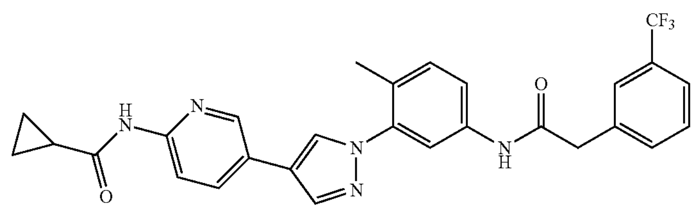 [SMILES: Cc1ccc(NC(=O)Cc2cccc(C(F)(F)F)c2)cc1-n1cc(-c2ccc(NC(=O)C3CC3)nc2)cn1] |
| 38 | 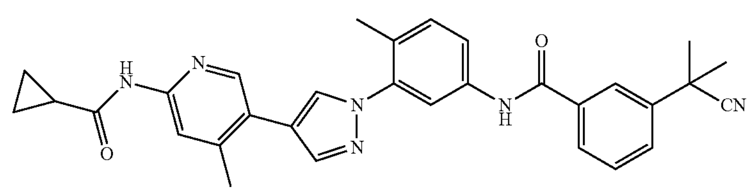 [SMILES: Cc1cc(NC(=O)C2CC2)ncc1-c1cnn(-c2cc(NC(=O)c3cccc(C(C)(C)C#N)c3)ccc2C)c1] |
| 39 | 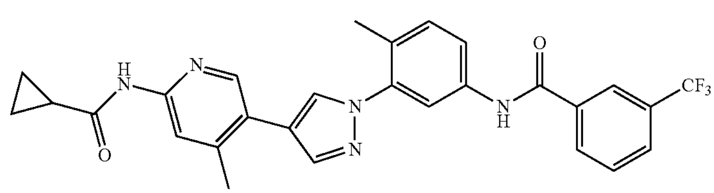 [SMILES: Cc1cc(NC(=O)C2CC2)ncc1-c1cnn(-c2cc(NC(=O)c3cccc(C(F)(F)F)c3)ccc2C)c1] |

| No. | Structure |
|---|---|
| 40 | 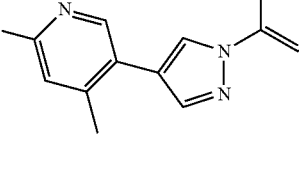 |
| 41 | 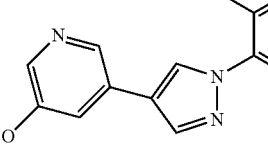 |
| 42 | 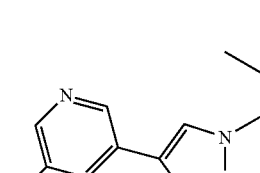 |
| 43 | 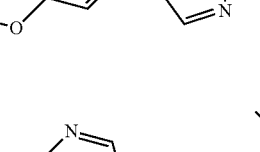 |
| 44 | 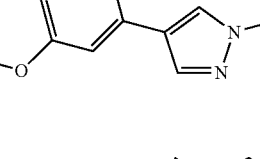 |
| 45 | 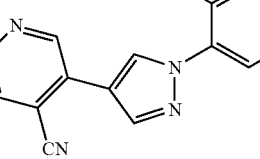 |
| 46 | 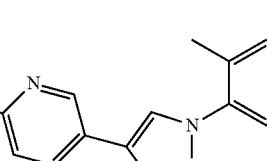 |

-continued

| No. | Structure |
|-----|-----------|
| 47 | 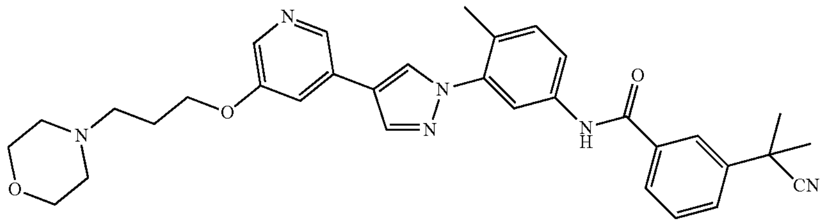 [SMILES: Cc1ccc(NC(=O)c2cccc(C(C)(C)C#N)c2)cc1-n1cc(-c2cncc(OCCCN3CCOCC3)c2)cn1] |
| 48 | 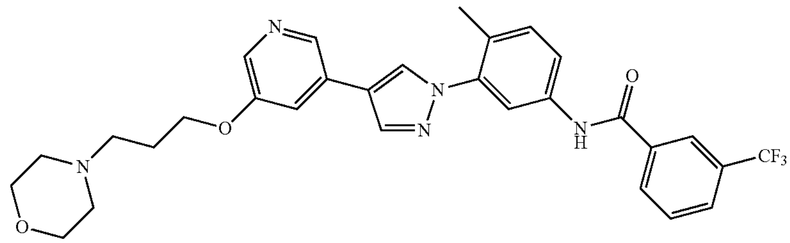 [SMILES: Cc1ccc(NC(=O)c2cccc(C(F)(F)F)c2)cc1-n1cc(-c2cncc(OCCCN3CCOCC3)c2)cn1] |
| 49 | 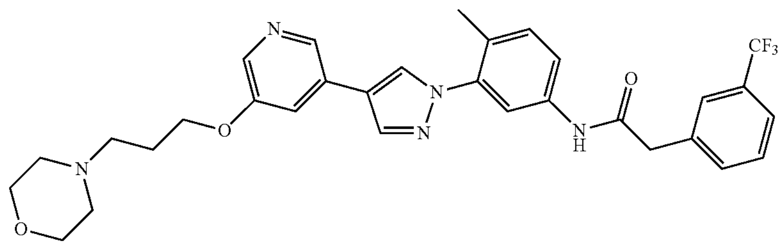 [SMILES: Cc1ccc(NC(=O)Cc2cccc(C(F)(F)F)c2)cc1-n1cc(-c2cncc(OCCCN3CCOCC3)c2)cn1] |
| 50 | 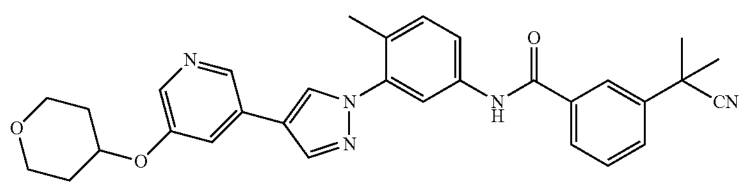 [SMILES: Cc1ccc(NC(=O)c2cccc(C(C)(C)C#N)c2)cc1-n1cc(-c2cncc(OC3CCOCC3)c2)cn1] |
| 51 | 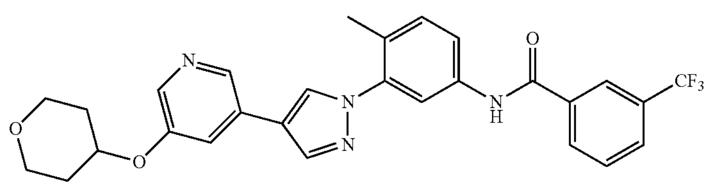 [SMILES: Cc1ccc(NC(=O)c2cccc(C(F)(F)F)c2)cc1-n1cc(-c2cncc(OC3CCOCC3)c2)cn1] |
| 52 | 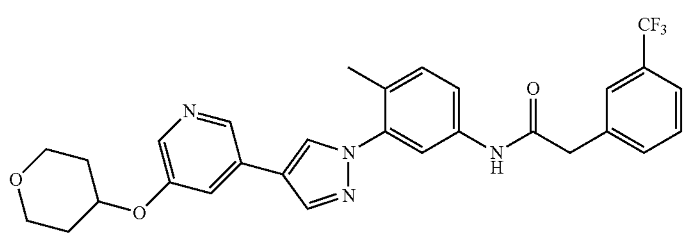 [SMILES: Cc1ccc(NC(=O)Cc2cccc(C(F)(F)F)c2)cc1-n1cc(-c2cncc(OC3CCOCC3)c2)cn1] |
| 53 | 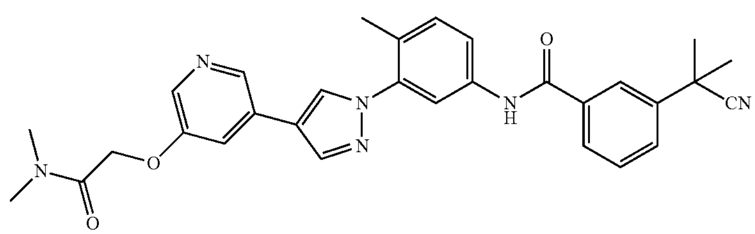 [SMILES: Cc1ccc(NC(=O)c2cccc(C(C)(C)C#N)c2)cc1-n1cc(-c2cncc(OCC(=O)N(C)C)c2)cn1] |

-continued
| No. | Structure |
|---|---|
| 54 | 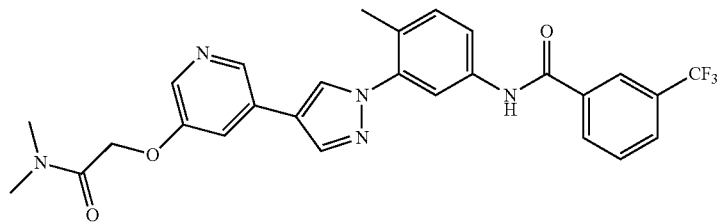 [SMILES: Cc1ccc(NC(=O)c2cccc(C(F)(F)F)c2)cc1-n1cc(-c2cncc(OCC(=O)N(C)C)c2)cn1] |
| 55 | 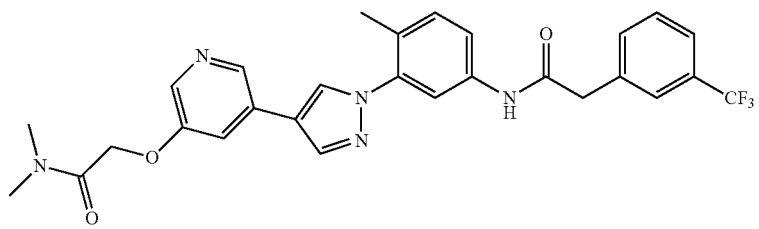 [SMILES: Cc1ccc(NC(=O)Cc2cccc(C(F)(F)F)c2)cc1-n1cc(-c2cncc(OCC(=O)N(C)C)c2)cn1] |
| 56 | 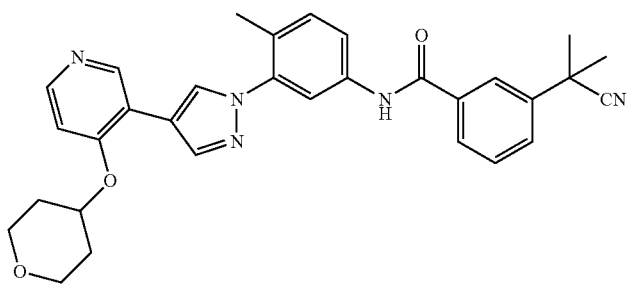 [SMILES: Cc1ccc(NC(=O)c2cccc(C(C)(C)C#N)c2)cc1-n1cc(-c2cnccc2OC2CCOCC2)cn1] |
| 57 | 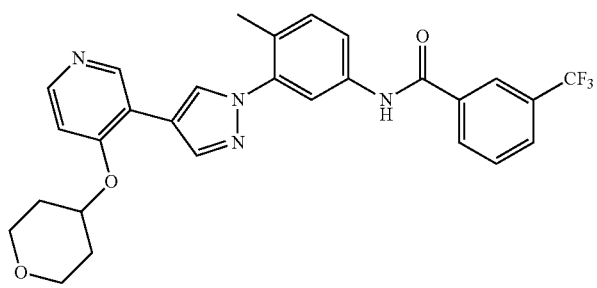 [SMILES: Cc1ccc(NC(=O)c2cccc(C(F)(F)F)c2)cc1-n1cc(-c2cnccc2OC2CCOCC2)cn1] |
| 58 | 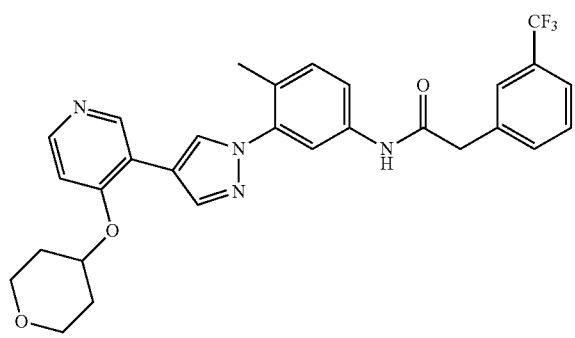 [SMILES: Cc1ccc(NC(=O)Cc2cccc(C(F)(F)F)c2)cc1-n1cc(-c2cnccc2OC2CCOCC2)cn1] |

-continued
| No. | Structure |
|---|---|
| 59 | 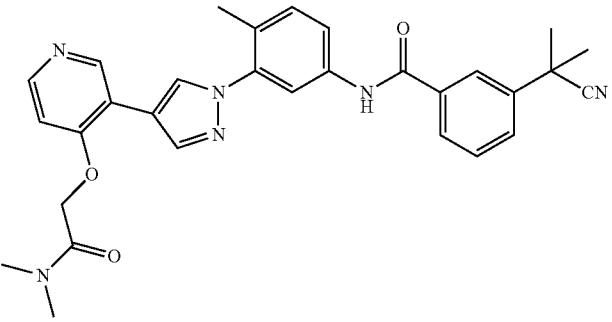 [SMILES: Cc1ccc(NC(=O)c2cccc(C(C)(C)C#N)c2)cc1-n1cc(-c2cnccc2OCC(=O)N(C)C)cn1] |
| 60 | 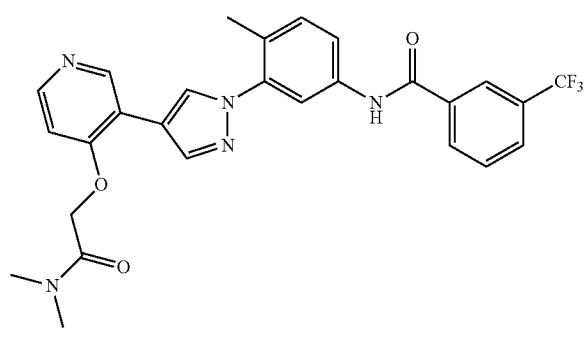 [SMILES: Cc1ccc(NC(=O)c2cccc(C(F)(F)F)c2)cc1-n1cc(-c2cnccc2OCC(=O)N(C)C)cn1] |
| 61 | 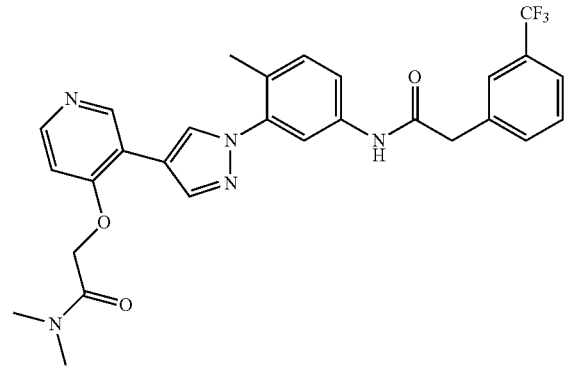 [SMILES: Cc1ccc(NC(=O)Cc2cccc(C(F)(F)F)c2)cc1-n1cc(-c2cnccc2OCC(=O)N(C)C)cn1] |
| 62 | 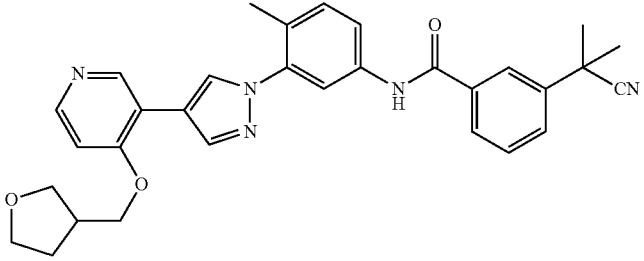 [SMILES: Cc1ccc(NC(=O)c2cccc(C(C)(C)C#N)c2)cc1-n1cc(-c2cnccc2OCC2CCOC2)cn1] |
| 63 | 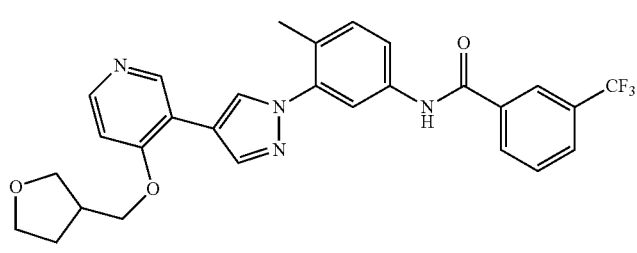 [SMILES: Cc1ccc(NC(=O)c2cccc(C(F)(F)F)c2)cc1-n1cc(-c2cnccc2OCC2CCOC2)cn1] |

-continued

| No. | Structure |
|---|---|
| 64 | 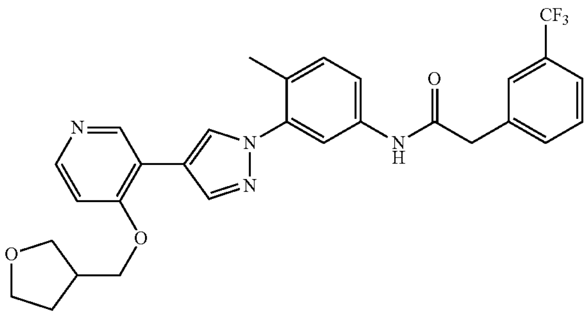 [SMILES: Cc1ccc(NC(=O)Cc2cccc(C(F)(F)F)c2)cc1-n1cc(-c2cnccc2OCC2CCOC2)cn1] |
| 65 | 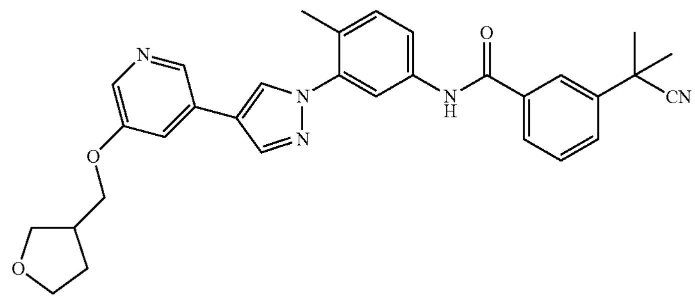 [SMILES: Cc1ccc(NC(=O)c2cccc(C(C)(C)C#N)c2)cc1-n1cc(-c2cncc(OCC3CCOC3)c2)cn1] |
| 66 | 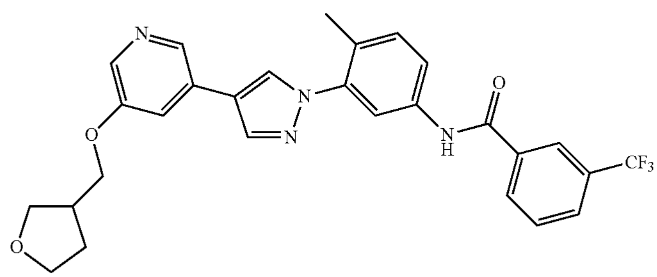 [SMILES: Cc1ccc(NC(=O)c2cccc(C(F)(F)F)c2)cc1-n1cc(-c2cncc(OCC3CCOC3)c2)cn1] |
| 67 | 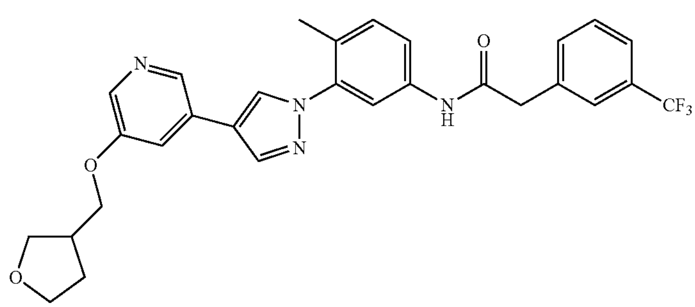 [SMILES: Cc1ccc(NC(=O)Cc2cccc(C(F)(F)F)c2)cc1-n1cc(-c2cncc(OCC3CCOC3)c2)cn1] |
| 68 | 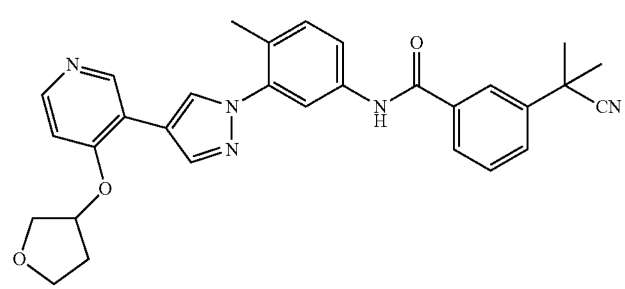 [SMILES: Cc1ccc(NC(=O)c2cccc(C(C)(C)C#N)c2)cc1-n1cc(-c2cnccc2OC2CCOC2)cn1] |

| No. | Structure |
|---|---|
| 69 | 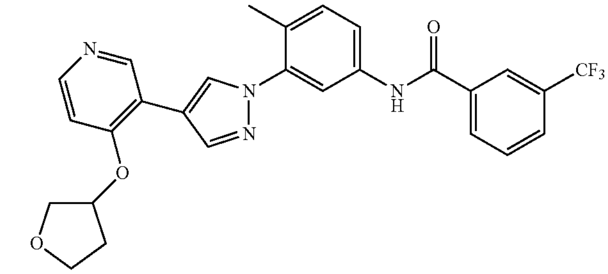 |
| 70 | 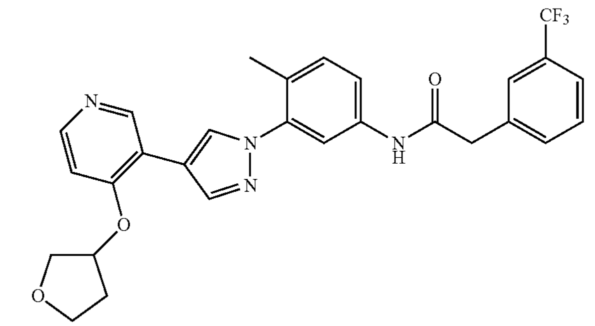 [SMILES: Cc1ccc(NC(=O)Cc2cccc(C(F)(F)F)c2)cc1-n1cc(-c2cnccc2OC2CCOC2)cn1] |
| 71 | 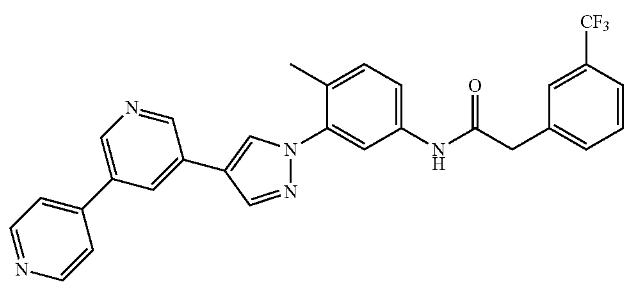 [SMILES: Cc1ccc(NC(=O)Cc2cccc(C(F)(F)F)c2)cc1-n1cc(-c2cncc(-c3ccncc3)c2)cn1] |
| 72 | 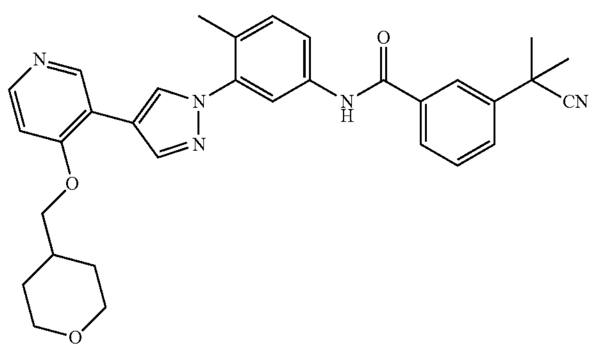 [SMILES: Cc1ccc(NC(=O)c2cccc(C(C)(C)C#N)c2)cc1-n1cc(-c2cnccc2OCC2CCOCC2)cn1] |
| 73 | 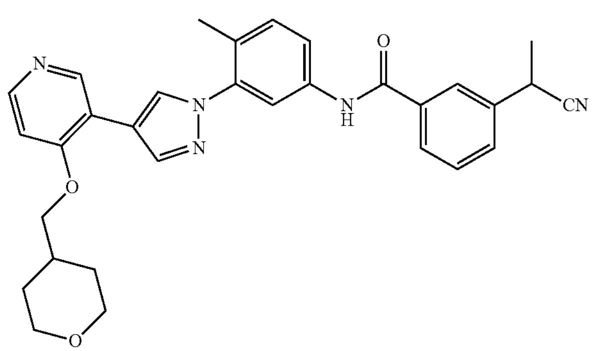 [SMILES: Cc1ccc(NC(=O)c2cccc(C(C)C#N)c2)cc1-n1cc(-c2cnccc2OCC2CCOCC2)cn1] |

| No. | Structure |
|---|---|
| 74 | 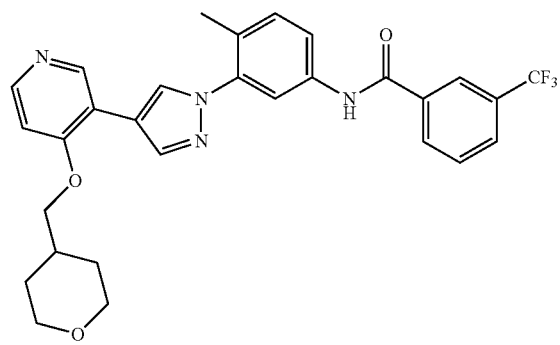 [SMILES: Cc1ccc(NC(=O)c2cccc(C(F)(F)F)c2)cc1-n1cc(-c2cnccc2OCC2CCOCC2)cn1] |
| 75 | 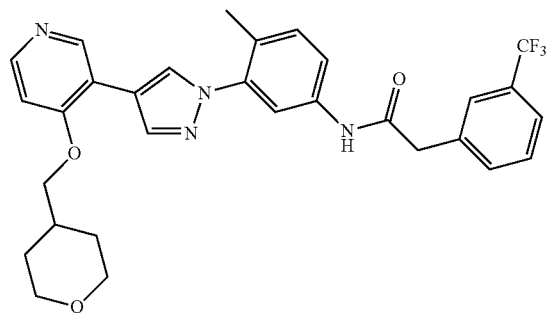 [SMILES: Cc1ccc(NC(=O)Cc2cccc(C(F)(F)F)c2)cc1-n1cc(-c2cnccc2OCC2CCOCC2)cn1] |
| 76 | 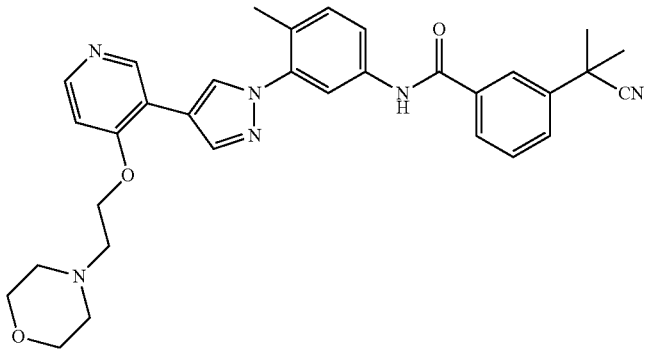 [SMILES: Cc1ccc(NC(=O)c2cccc(C(C)(C)C#N)c2)cc1-n1cc(-c2cnccc2OCCN2CCOCC2)cn1] |
| 77 | 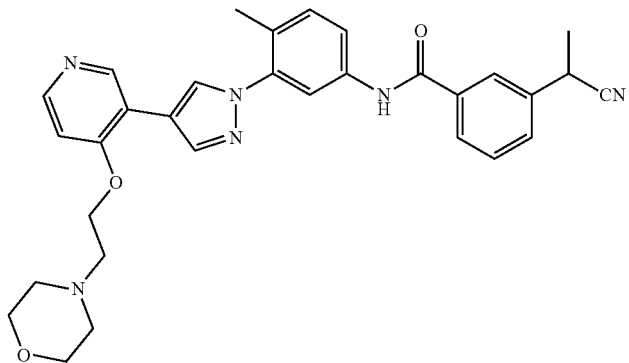 [SMILES: Cc1ccc(NC(=O)c2cccc(C(C)C#N)c2)cc1-n1cc(-c2cnccc2OCCN2CCOCC2)cn1] |

| No. | Structure |
|---|---|
| 78 | 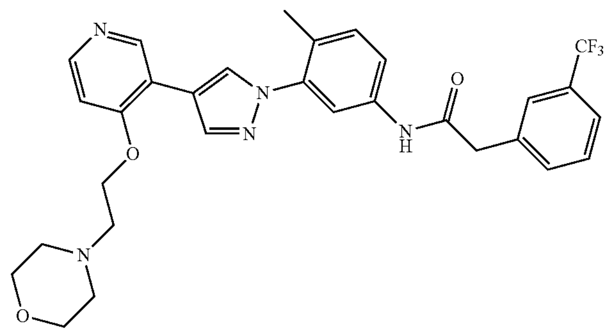 [SMILES: Cc1ccc(NC(=O)Cc2cccc(C(F)(F)F)c2)cc1-n1cc(-c2cnccc2OCCN2CCOCC2)cn1] |
| 79 | 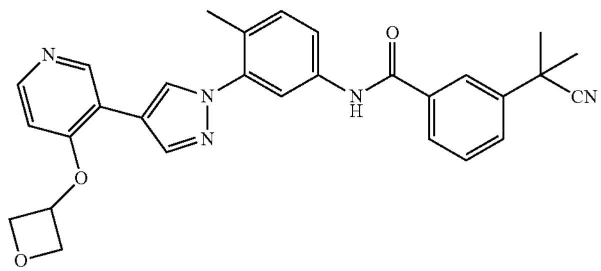 [SMILES: Cc1ccc(NC(=O)c2cccc(C(C)(C)C#N)c2)cc1-n1cc(-c2cnccc2OC2COC2)cn1] |
| 80 | 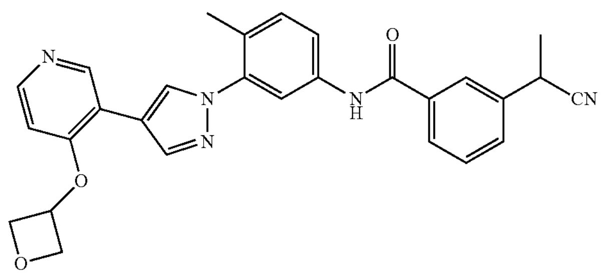 [SMILES: Cc1ccc(NC(=O)c2cccc(C(C)C#N)c2)cc1-n1cc(-c2cnccc2OC2COC2)cn1] |
| 81 | 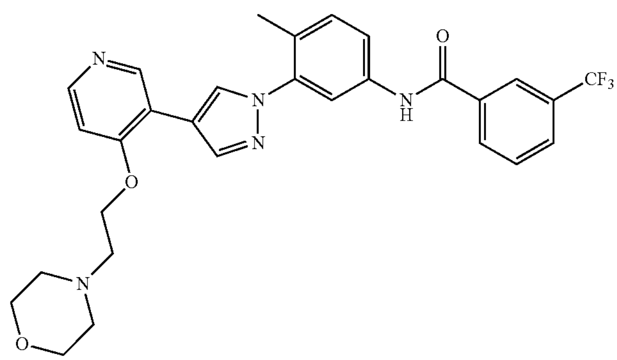 [SMILES: Cc1ccc(NC(=O)c2cccc(C(F)(F)F)c2)cc1-n1cc(-c2cnccc2OCCN2CCOCC2)cn1] |
| 82 | 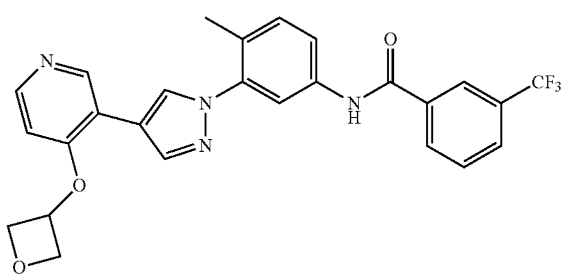 [SMILES: Cc1ccc(NC(=O)c2cccc(C(F)(F)F)c2)cc1-n1cc(-c2cnccc2OC2COC2)cn1] |

| No. | Structure |
|---|---|
| 83 | 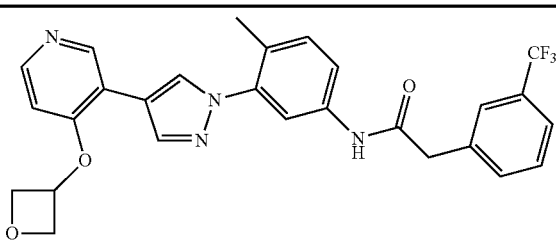 |
| 84 | 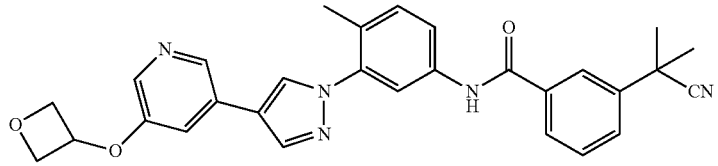 [SMILES: Cc1ccc(NC(=O)c2cccc(C(C)(C)C#N)c2)cc1-n1cc(-c2cncc(OC3COC3)c2)cn1] |
| 85 | 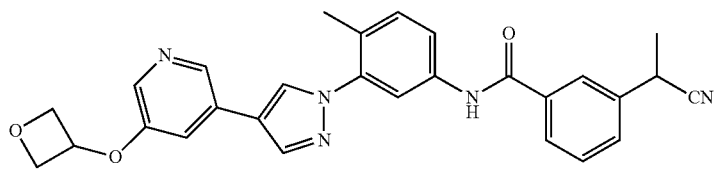 [SMILES: Cc1ccc(NC(=O)c2cccc(C(C)C#N)c2)cc1-n1cc(-c2cncc(OC3COC3)c2)cn1] |
| 86 | 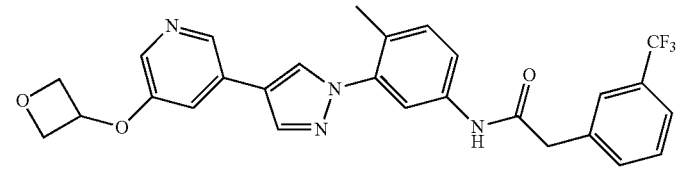 [SMILES: Cc1ccc(NC(=O)Cc2cccc(C(F)(F)F)c2)cc1-n1cc(-c2cncc(OC3COC3)c2)cn1] |
| 87 | 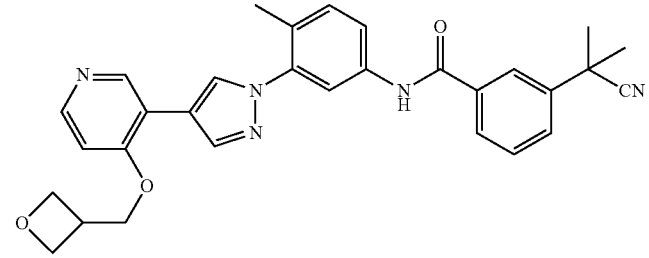 [SMILES: Cc1ccc(NC(=O)c2cccc(C(C)(C)C#N)c2)cc1-n1cc(-c2cnccc2OCC2COC2)cn1] |
| 88 | 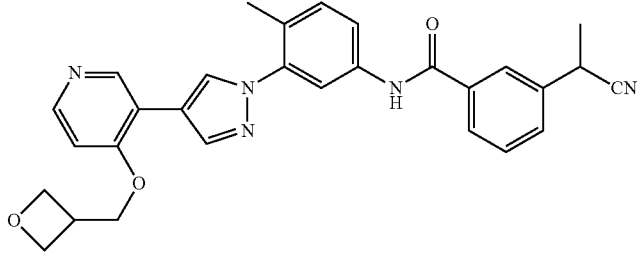 [SMILES: Cc1ccc(NC(=O)c2cccc(C(C)C#N)c2)cc1-n1cc(-c2cnccc2OCC2COC2)cn1] |
| 89 | 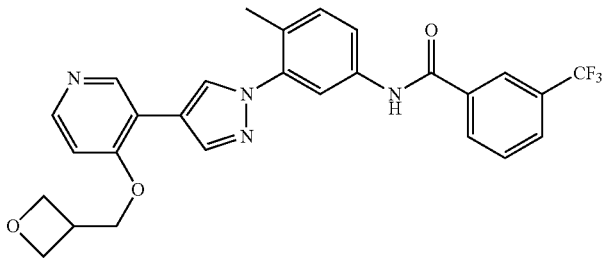 [SMILES: Cc1ccc(NC(=O)c2cccc(C(F)(F)F)c2)cc1-n1cc(-c2cnccc2OCC2COC2)cn1] |

| No. | Structure |
|---|---|
| 90 | 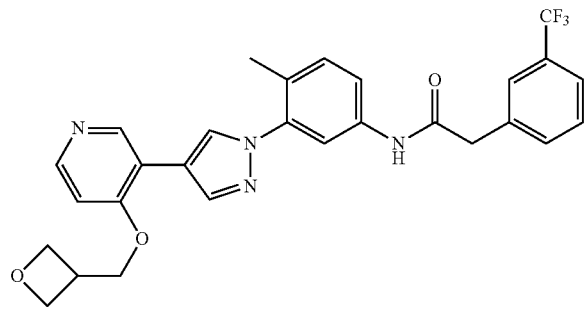 [SMILES: Cc1ccc(NC(=O)Cc2cccc(C(F)(F)F)c2)cc1-n1cc(-c2cnccc2OCC2COC2)cn1] |
| 91 | 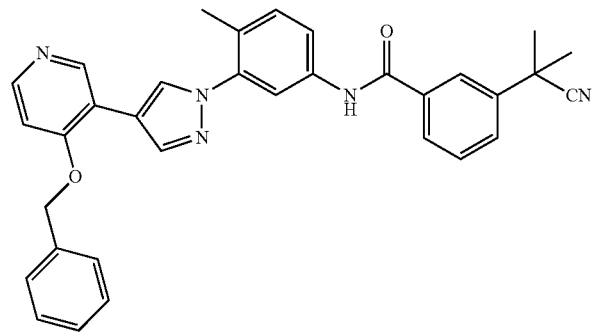 [SMILES: Cc1ccc(NC(=O)c2cccc(C(C)(C)C#N)c2)cc1-n1cc(-c2cnccc2OCc2ccccc2)cn1] |
| 92 | 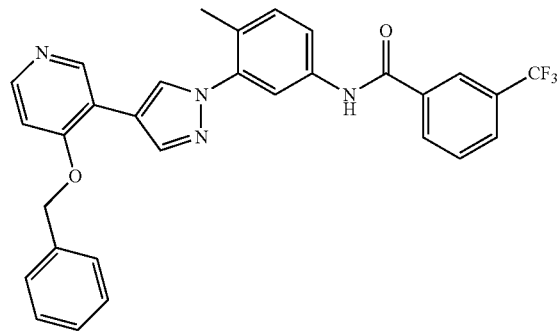 [SMILES: Cc1ccc(NC(=O)c2cccc(C(F)(F)F)c2)cc1-n1cc(-c2cnccc2OCc2ccccc2)cn1] |
| 93 | 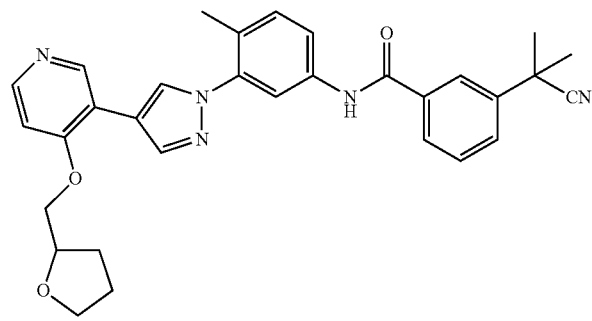 |

| No. | Structure |
|-----|-----------|
| 94 | 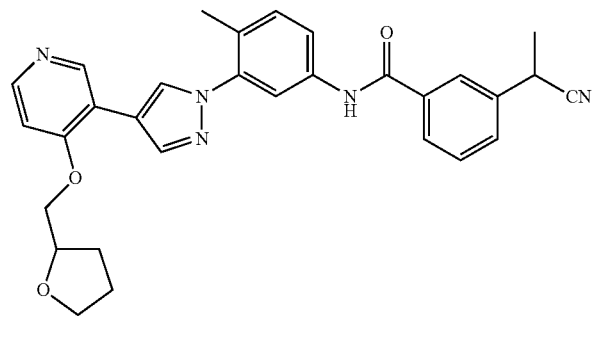 |
| 95 | 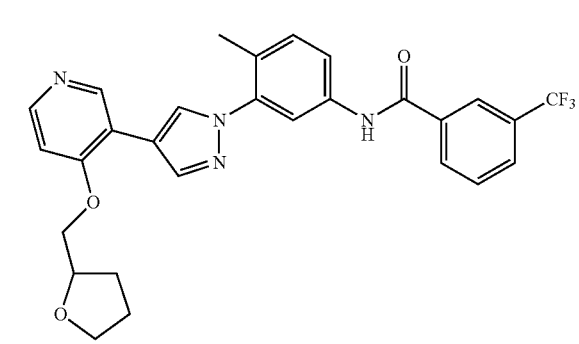 |
| 96 | 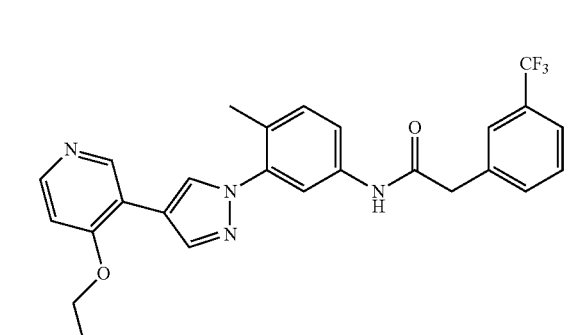 |
| 97 | 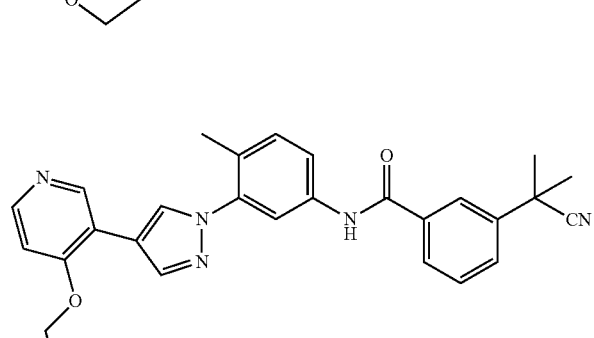 |

-continued
| No. | Structure |
|---|---|
| 98 | 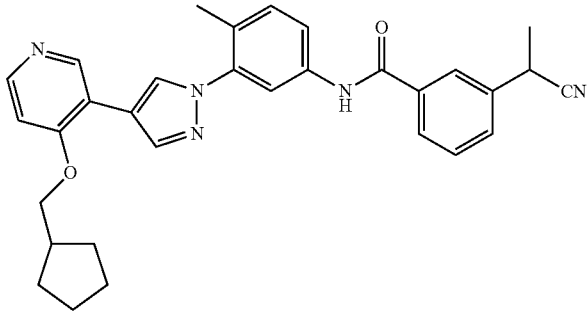 |
| 99 | 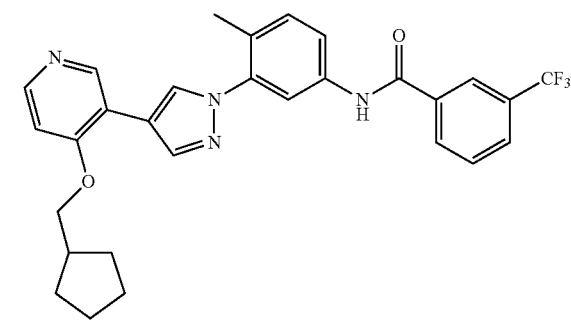 |
| 100 | 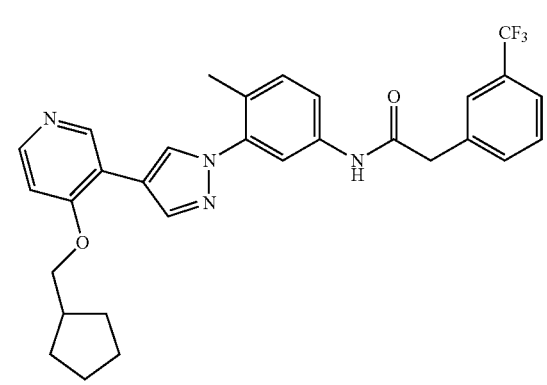 [SMILES: Cc1ccc(NC(=O)Cc2cccc(C(F)(F)F)c2)cc1-n1cc(-c2cnccc2OCC2CCCC2)cn1] |
| 101 | 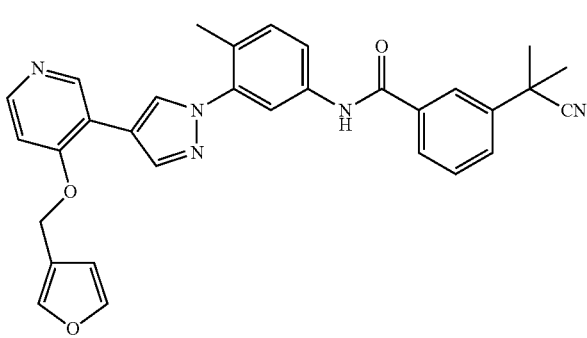 [SMILES: Cc1ccc(NC(=O)c2cccc(C(C)(C)C#N)c2)cc1-n1cc(-c2cnccc2OCc2ccoc2)cn1] |

-continued
| No. | Structure |
|---|---|
| 102 | 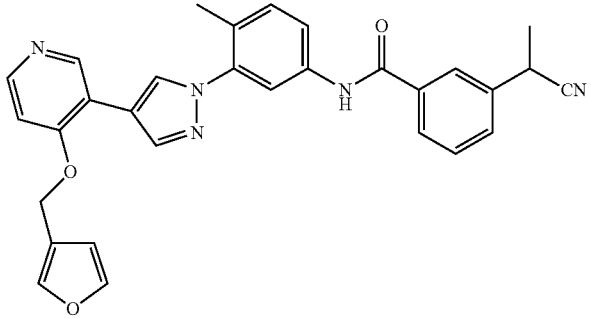 [SMILES: Cc1ccc(NC(=O)c2cccc(C(C)C#N)c2)cc1-n1cc(-c2cnccc2OCc2ccoc2)cn1] |
| 103 | 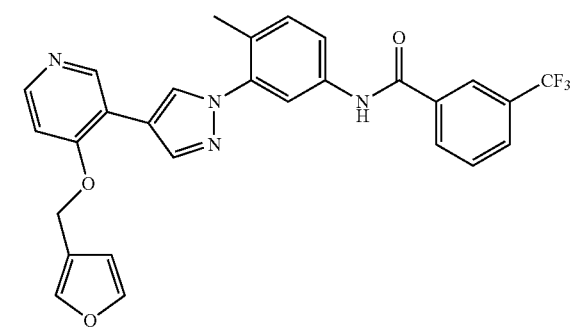 [SMILES: Cc1ccc(NC(=O)c2cccc(C(F)(F)F)c2)cc1-n1cc(-c2cnccc2OCc2ccoc2)cn1] |
| 104 | 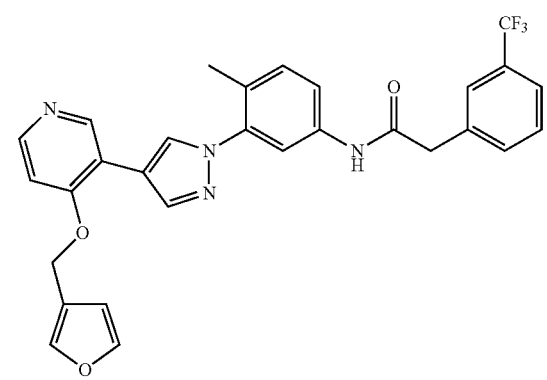 [SMILES: Cc1ccc(NC(=O)Cc2cccc(C(F)(F)F)c2)cc1-n1cc(-c2cnccc2OCc2ccoc2)cn1] |
| 105 | 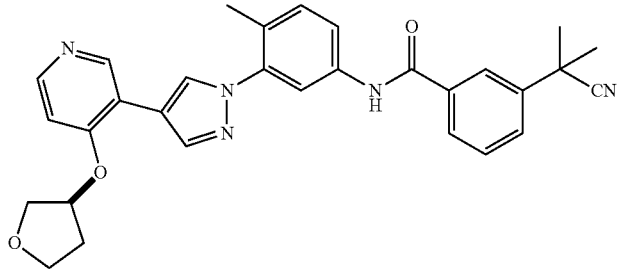 |
| 106 | 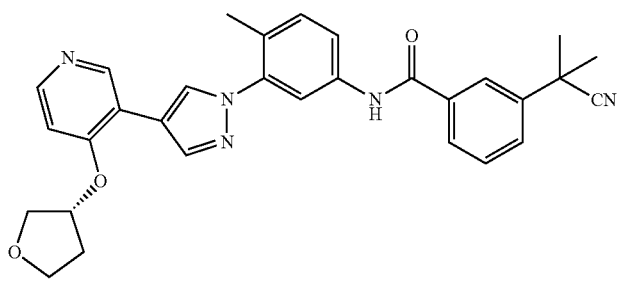 |

-continued
| No. | Structure |
|---|---|
| 107 | 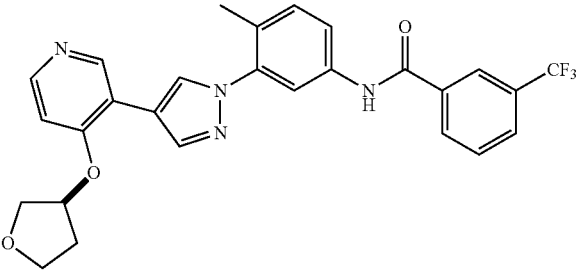 |
| 108 | 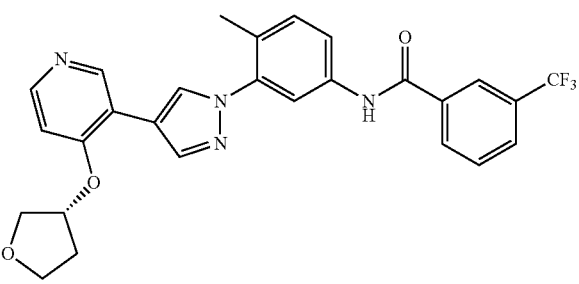 |
| 109 | 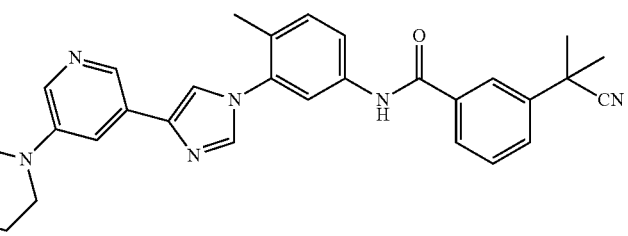 |
| 110 | 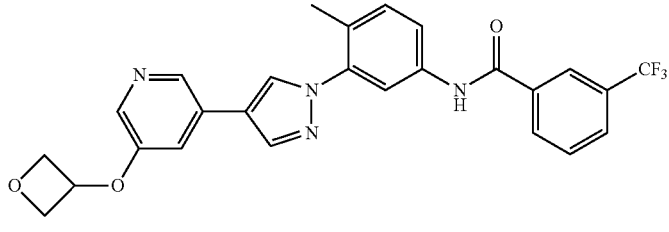 [SMILES: Cc1ccc(NC(=O)c2cccc(C(F)(F)F)c2)cc1-n1cc(-c2cncc(OC3COC3)c2)cn1] |
| 111 | 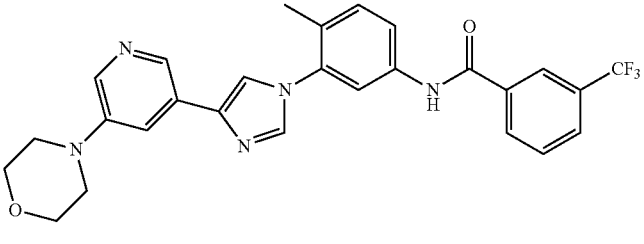 |
| 112 | 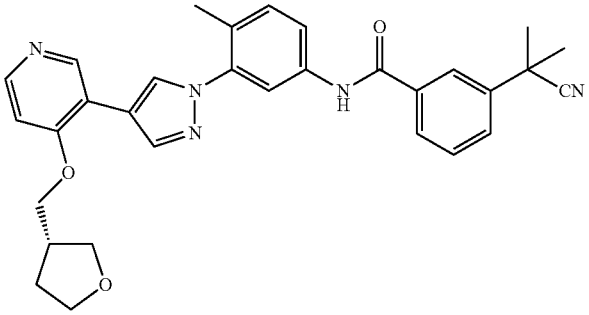 |

| No. | Structure |
|---|---|
| 113 | 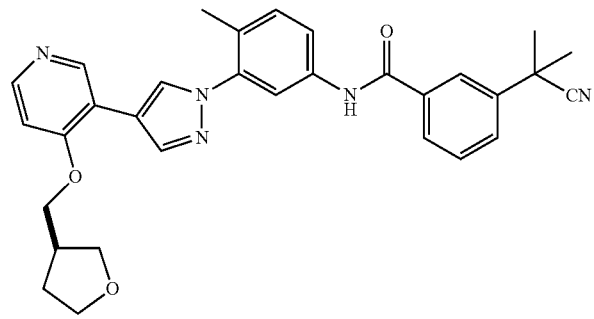 |
| 114 | 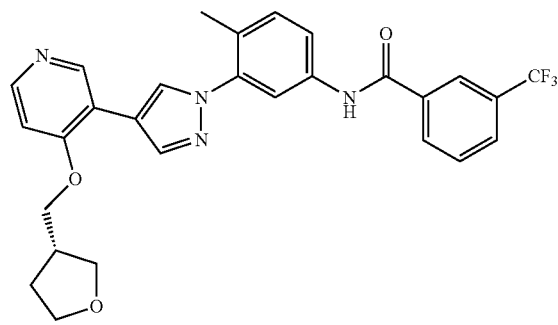 [SMILES: Cc1ccc(NC(=O)c2cccc(C(F)(F)F)c2)cc1-n1cc(-c2cnccc2OC[C@H]2CCOC2)cn1] |
| 115 | 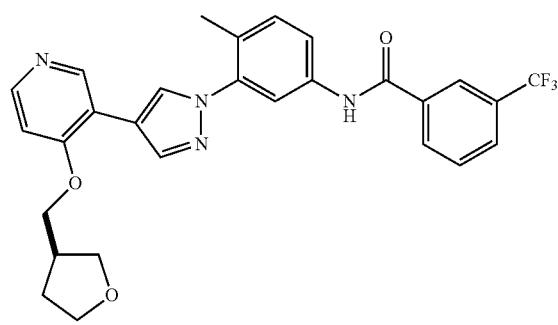 |
| 116 | 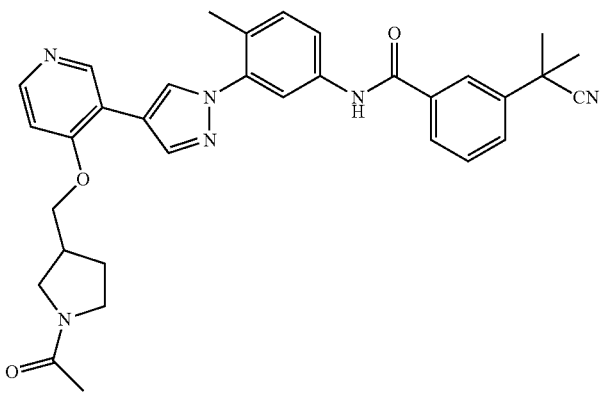 [SMILES: CC(=O)N1CCC(COc2ccncc2-c2cnn(-c3cc(NC(=O)c4cccc(C(C)(C)C#N)c4)ccc3C)c2)C1] |

| No. | Structure |
|---|---|
| 117 | 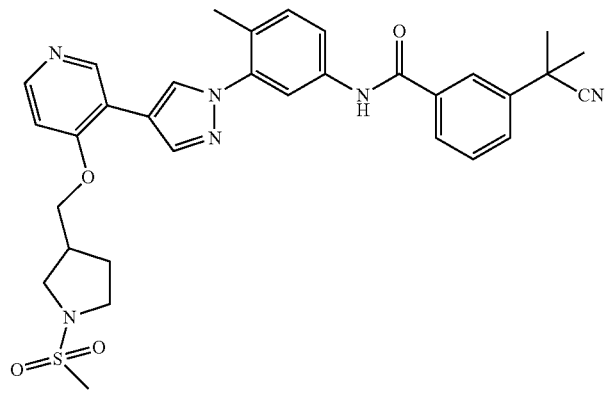 [SMILES: Cc1ccc(NC(=O)c2cccc(C(C)(C)C#N)c2)cc1-n1cc(-c2cnccc2OCC2CCN(S(C)(=O)=O)C2)cn1] |
| 118 | 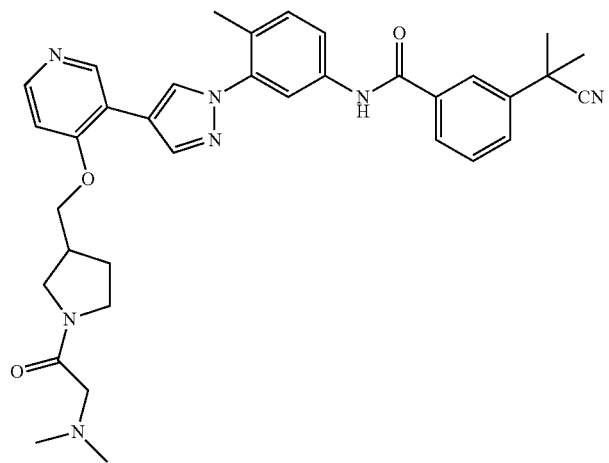 [SMILES: Cc1ccc(NC(=O)c2cccc(C(C)(C)C#N)c2)cc1-n1cc(-c2cnccc2OCC2CCN(C(=O)CN(C)C)C2)cn1] |
| 119 | 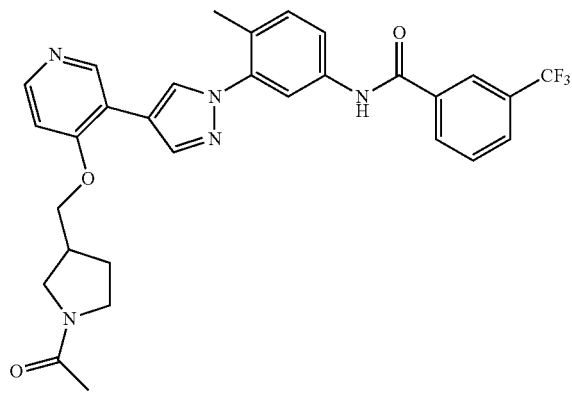 [SMILES: CC(=O)N1CCC(COc2ccncc2-c2cnn(-c3cc(NC(=O)c4cccc(C(F)(F)F)c4)ccc3C)c2)C1] |

| No. | Structure |
|---|---|
| 120 | 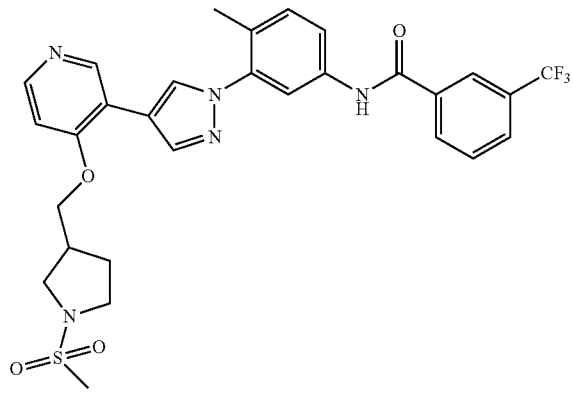 [SMILES: Cc1ccc(NC(=O)c2cccc(C(F)(F)F)c2)cc1-n1cc(-c2cnccc2OCC2CCN(S(C)(=O)=O)C2)cn1] |
| 121 | 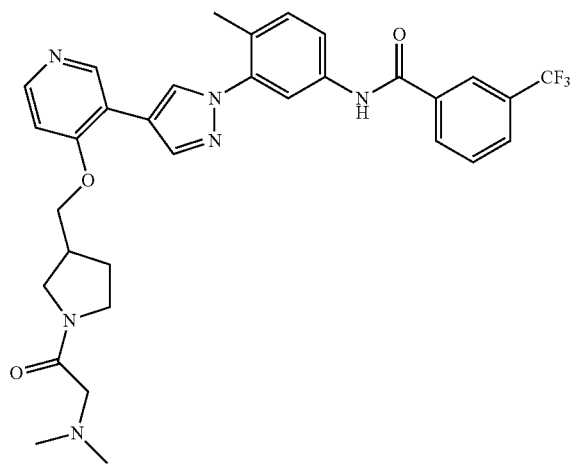 [SMILES: Cc1ccc(NC(=O)c2cccc(C(F)(F)F)c2)cc1-n1cc(-c2cnccc2OCC2CCN(C(=O)CN(C)C)C2)cn1] |
| 122 | 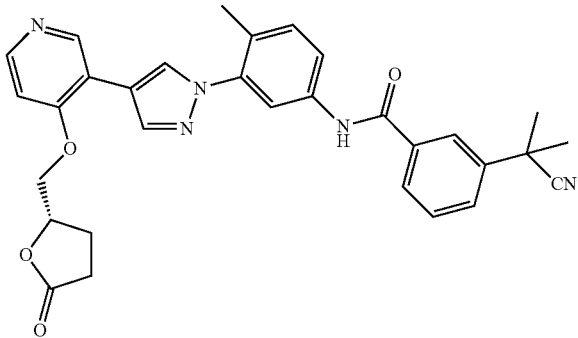 [SMILES: Cc1ccc(NC(=O)c2cccc(C(C)(C)C#N)c2)cc1-n1cc(-c2cnccc2OC[C@@H]2CCC(=O)O2)cn1] |
| 123 | 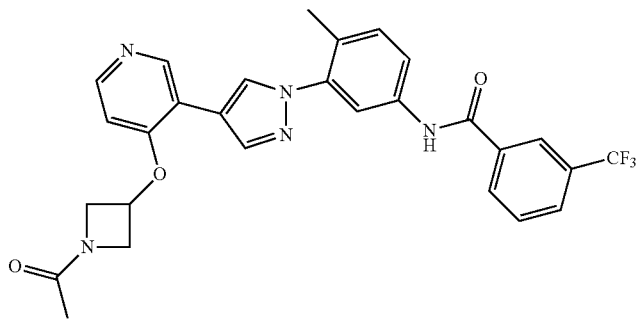 [SMILES: CC(=O)N1CC(Oc2ccncc2-c2cnn(-c3cc(NC(=O)c4cccc(C(F)(F)F)c4)ccc3C)c2)C1] |

| No. | Structure |
|---|---|
| 124 | 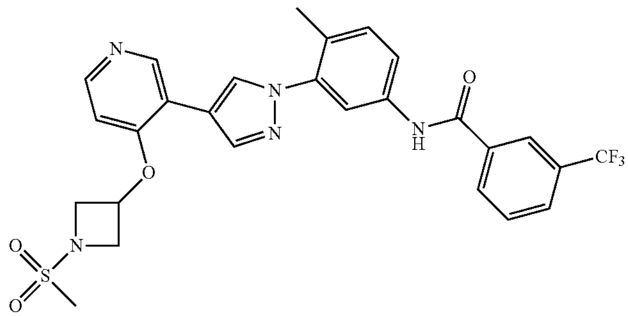 [SMILES: Cc1ccc(NC(=O)c2cccc(C(F)(F)F)c2)cc1-n1cc(-c2cnccc2OC2CN(S(C)(=O)=O)C2)cn1] |
| 125 | 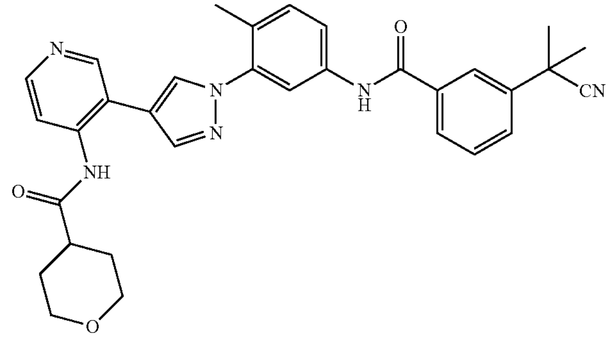 [SMILES: Cc1ccc(NC(=O)c2cccc(C(C)(C)C#N)c2)cc1-n1cc(-c2cnccc2NC(=O)C2CCOCC2)cn1] |
| 126 | 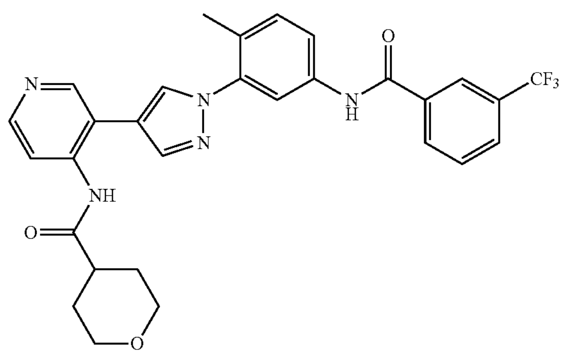 [SMILES: Cc1ccc(NC(=O)c2cccc(C(F)(F)F)c2)cc1-n1cc(-c2cnccc2NC(=O)C2CCOCC2)cn1] |
| 127 | 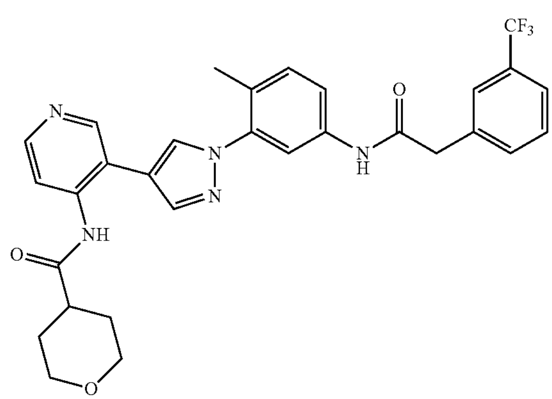 [SMILES: Cc1ccc(NC(=O)Cc2cccc(C(F)(F)F)c2)cc1-n1cc(-c2cnccc2NC(=O)C2CCOCC2)cn1] |

-continued
| No. | Structure |
|---|---|
| 128 | 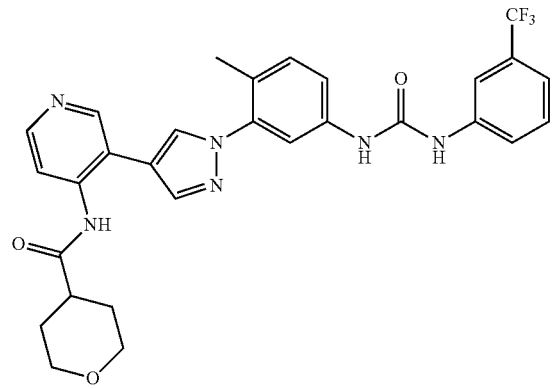 |
| 129 | 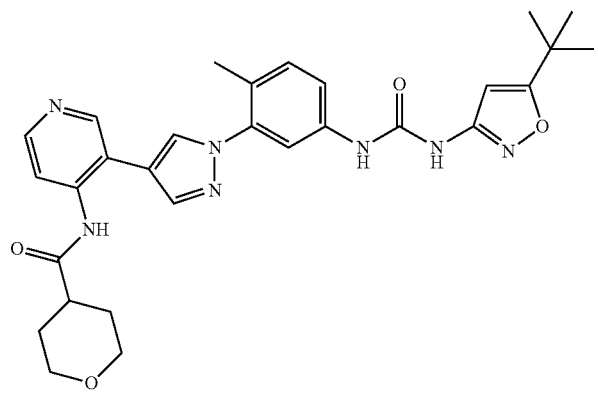 [SMILES: Cc1ccc(NC(=O)Nc2cc(C(C)(C)C)on2)cc1-n1cc(-c2cnccc2NC(=O)C2CCOCC2)cn1] |
| 130 | 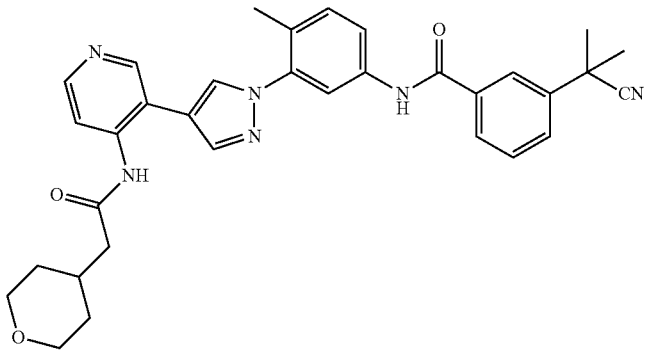 [SMILES: Cc1ccc(NC(=O)c2cccc(C(C)(C)C#N)c2)cc1-n1cc(-c2cnccc2NC(=O)CC2CCOCC2)cn1] |
| 131 | 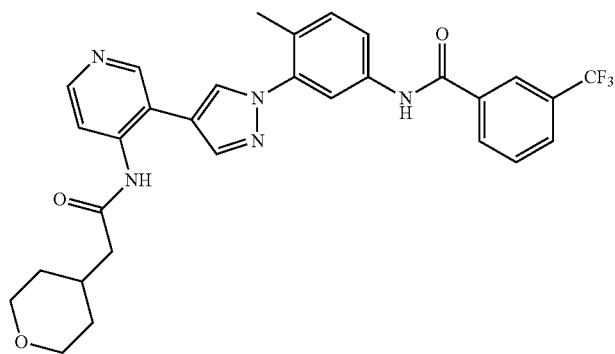 [SMILES: Cc1ccc(NC(=O)c2cccc(C(F)(F)F)c2)cc1-n1cc(-c2cnccc2NC(=O)CC2CCOCC2)cn1] |

| No. | Structure |
|-----|-----------|
| 132 | 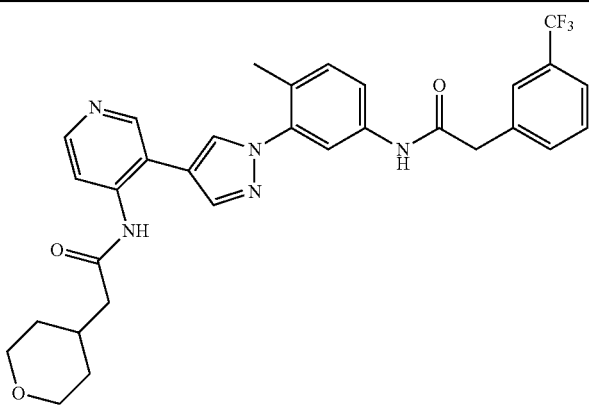 |
| 133 | 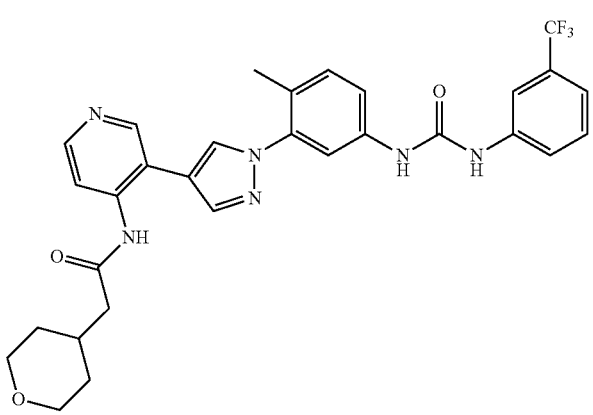 [SMILES: Cc1ccc(NC(=O)Nc2cccc(C(F)(F)F)c2)cc1-n1cc(-c2cnccc2NC(=O)CC2CCOCC2)cn1] |
| 134 | 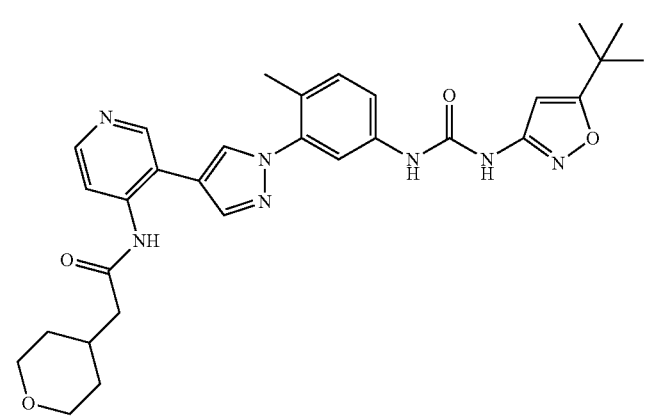 [SMILES: Cc1ccc(NC(=O)Nc2cc(C(C)(C)C)on2)cc1-n1cc(-c2cnccc2NC(=O)CC2CCOCC2)cn1] |
| 135 | 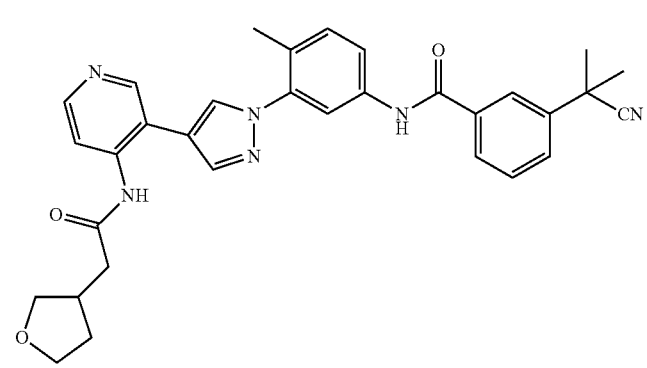 [SMILES: Cc1ccc(NC(=O)c2cccc(C(C)(C)C#N)c2)cc1-n1cc(-c2cnccc2NC(=O)CC2CCOC2)cn1] |

| No. | Structure |
|---|---|
| 136 | 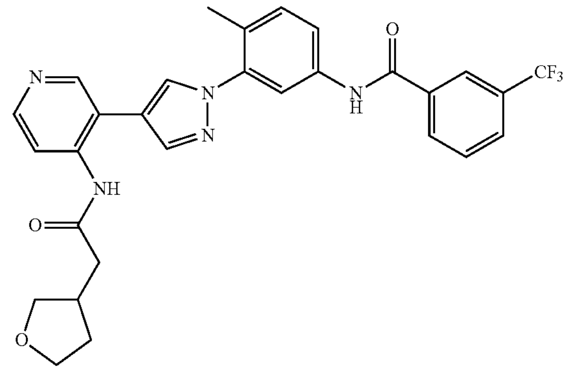 [SMILES: Cc1ccc(NC(=O)c2cccc(C(F)(F)F)c2)cc1-n1cc(-c2cnccc2NC(=O)CC2CCOC2)cn1] |
| 137 | 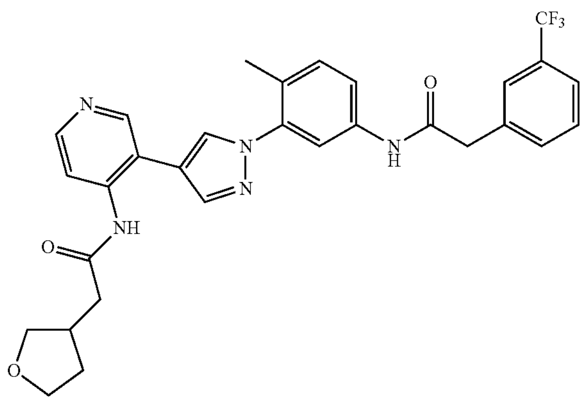 [SMILES: Cc1ccc(NC(=O)Cc2cccc(C(F)(F)F)c2)cc1-n1cc(-c2cnccc2NC(=O)CC2CCOC2)cn1] |
| 138 | 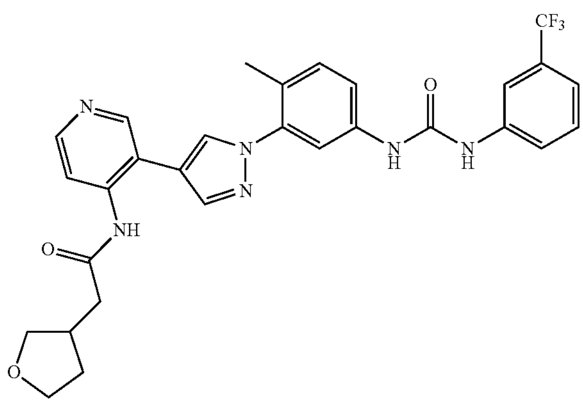 [SMILES: Cc1ccc(NC(=O)Nc2cccc(C(F)(F)F)c2)cc1-n1cc(-c2cnccc2NC(=O)CC2CCOC2)cn1] |
| 139 | 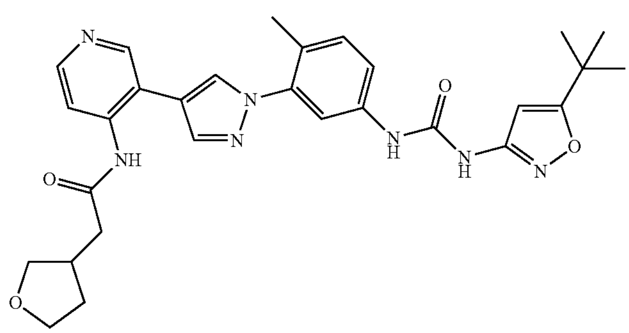 [SMILES: Cc1ccc(NC(=O)Nc2cc(C(C)(C)C)on2)cc1-n1cc(-c2cnccc2NC(=O)CC2CCOC2)cn1] |

| No. | Structure |
|---|---|
| 140 | 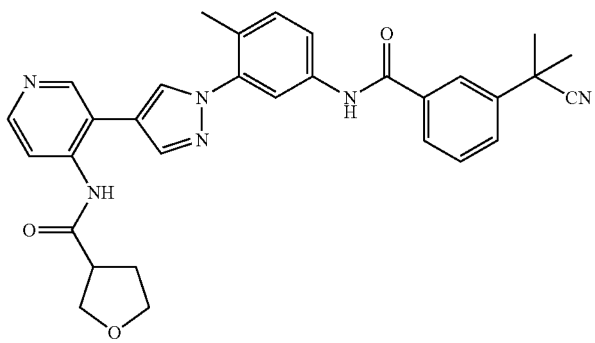 [SMILES: Cc1ccc(NC(=O)c2cccc(C(C)(C)C#N)c2)cc1-n1cc(-c2cnccc2NC(=O)C2CCOC2)cn1] |
| 141 | 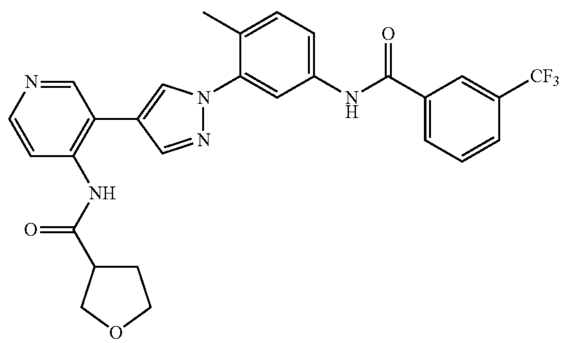 [SMILES: Cc1ccc(NC(=O)c2cccc(C(F)(F)F)c2)cc1-n1cc(-c2cnccc2NC(=O)C2CCOC2)cn1] |
| 142 | 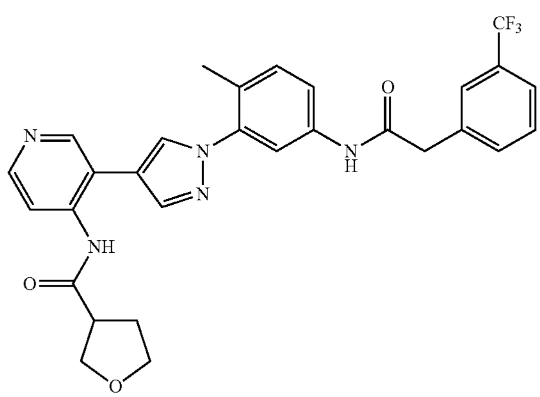 [SMILES: Cc1ccc(NC(=O)Cc2cccc(C(F)(F)F)c2)cc1-n1cc(-c2cnccc2NC(=O)C2CCOC2)cn1] |
| 143 | 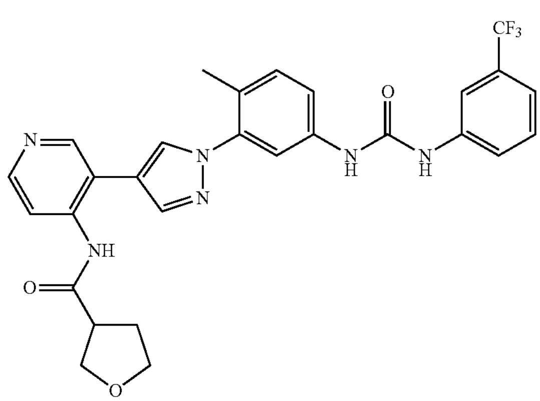 [SMILES: Cc1ccc(NC(=O)Nc2cccc(C(F)(F)F)c2)cc1-n1cc(-c2cnccc2NC(=O)C2CCOC2)cn1] |

| No. | Structure |
|---|---|
| 144 | 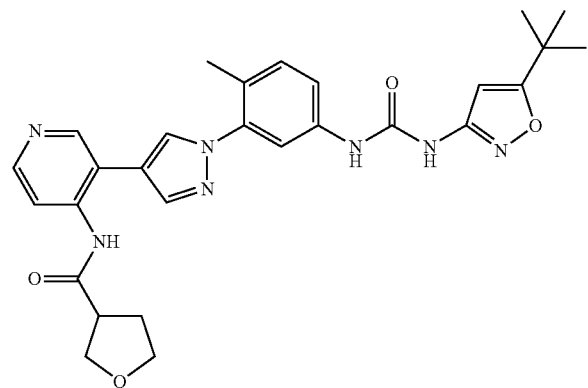 [SMILES: Cc1ccc(NC(=O)Nc2cc(C(C)(C)C)on2)cc1-n1cc(-c2cnccc2NC(=O)C2CCOC2)cn1] |
| 145 | 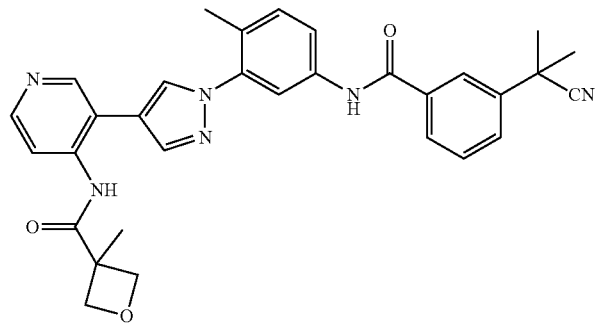 [SMILES: Cc1ccc(NC(=O)c2cccc(C(C)(C)C#N)c2)cc1-n1cc(-c2cnccc2NC(=O)C2(C)COC2)cn1] |
| 146 | 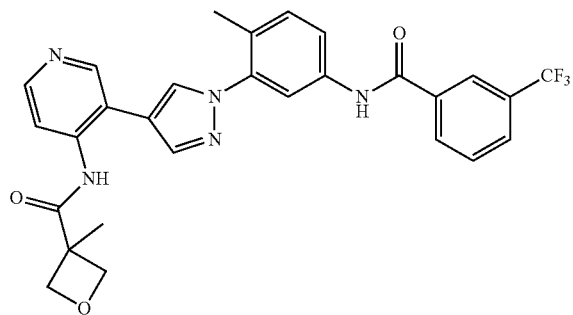 [SMILES: Cc1ccc(NC(=O)c2cccc(C(F)(F)F)c2)cc1-n1cc(-c2cnccc2NC(=O)C2(C)COC2)cn1] |
| 147 | 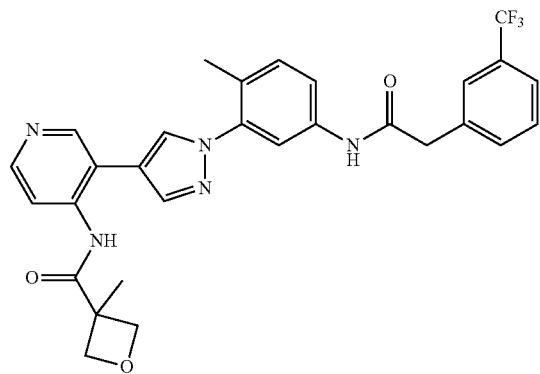 [SMILES: Cc1ccc(NC(=O)Cc2cccc(C(F)(F)F)c2)cc1-n1cc(-c2cnccc2NC(=O)C2(C)COC2)cn1] |

| No. | Structure |
|---|---|
| 148 | 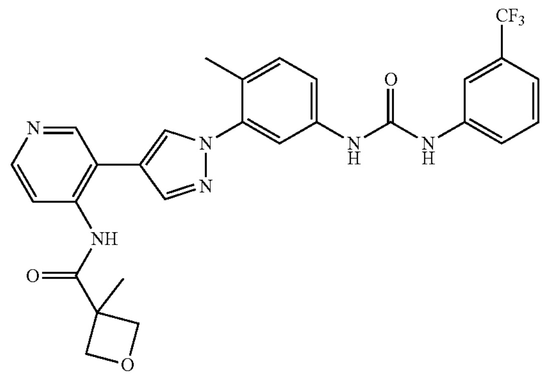 [SMILES: Cc1ccc(NC(=O)Nc2cccc(C(F)(F)F)c2)cc1-n1cc(-c2cnccc2NC(=O)C2(C)COC2)cn1] |
| 149 | 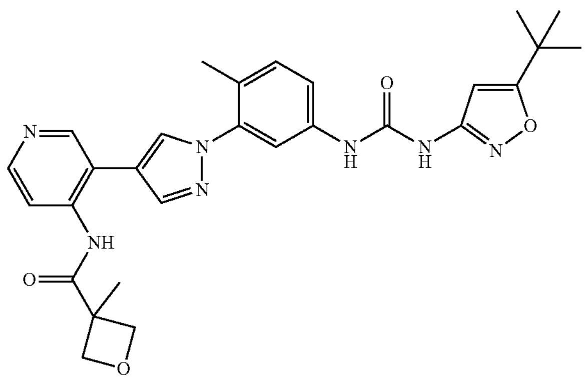 [SMILES: Cc1ccc(NC(=O)Nc2cc(C(C)(C)C)on2)cc1-n1cc(-c2cnccc2NC(=O)C2(C)COC2)cn1] |
| 150 | 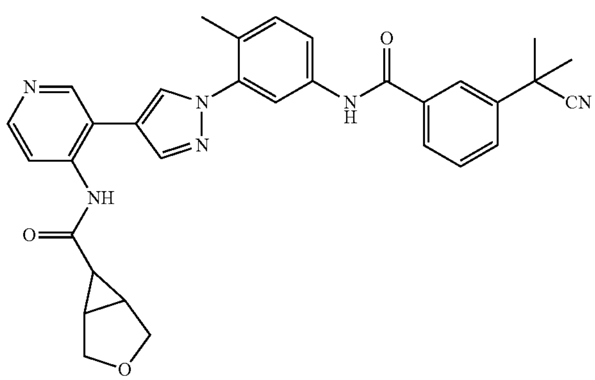 [SMILES: Cc1ccc(NC(=O)c2cccc(C(C)(C)C#N)c2)cc1-n1cc(-c2cnccc2NC(=O)C2C3COCC32)cn1] |
| 151 | 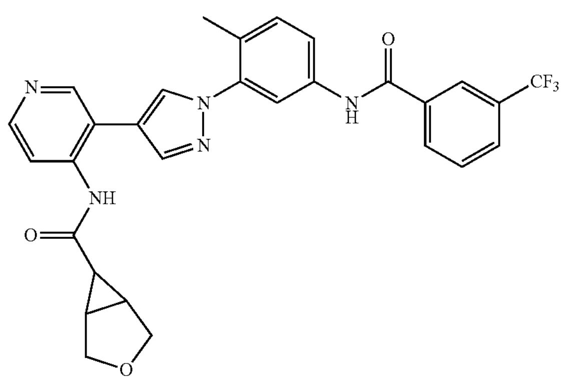 [SMILES: Cc1ccc(NC(=O)c2cccc(C(F)(F)F)c2)cc1-n1cc(-c2cnccc2NC(=O)C2C3COCC32)cn1] |

-continued
| No. | Structure |
|---|---|
| 152 | 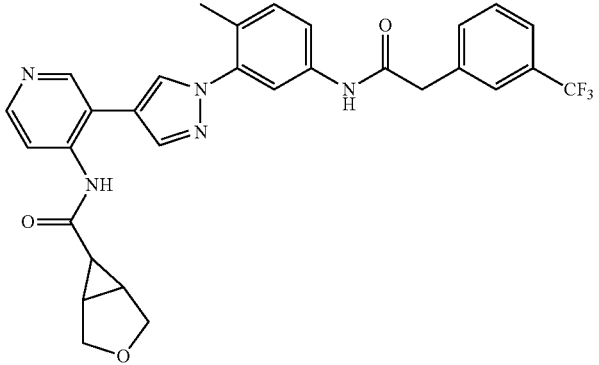 [SMILES: Cc1ccc(NC(=O)Cc2cccc(C(F)(F)F)c2)cc1-n1cc(-c2cnccc2NC(=O)C2C3COCC32)cn1] |
| 153 | 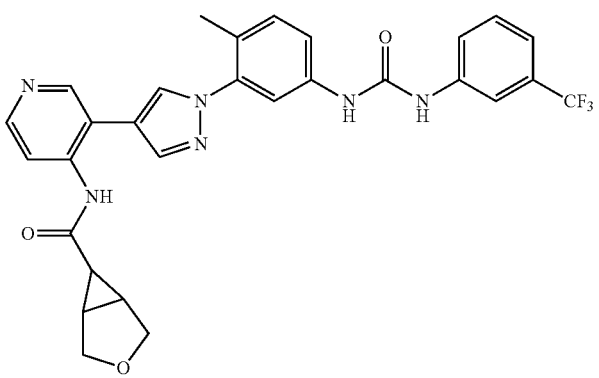 [SMILES: Cc1ccc(NC(=O)Nc2cccc(C(F)(F)F)c2)cc1-n1cc(-c2cnccc2NC(=O)C2C3COCC32)cn1] |
| 154 | 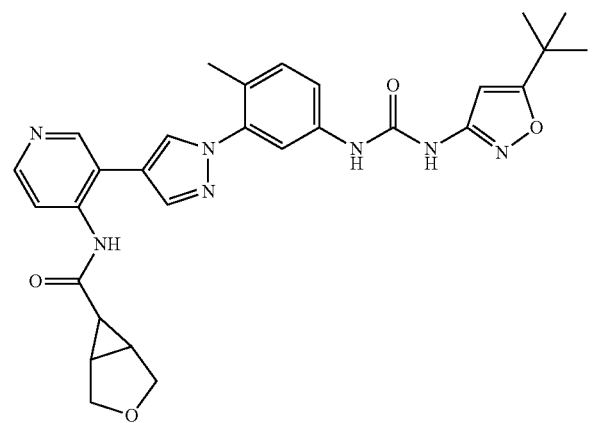 [SMILES: Cc1ccc(NC(=O)Nc2cc(C(C)(C)C)on2)cc1-n1cc(-c2cnccc2NC(=O)C2C3COCC32)cn1] |
| 155 | 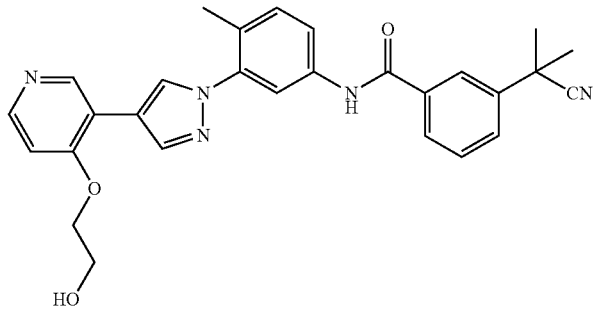 [SMILES: Cc1ccc(NC(=O)c2cccc(C(C)(C)C#N)c2)cc1-n1cc(-c2cnccc2OCCO)cn1] |

| No. | Structure |
|---|---|
| 156 | 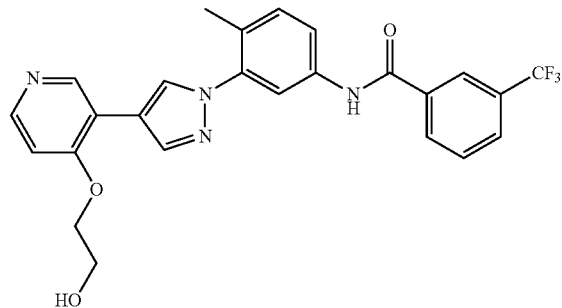 [SMILES: Cc1ccc(NC(=O)c2cccc(C(F)(F)F)c2)cc1-n1cc(-c2cnccc2OCCO)cn1] |
| 157 | 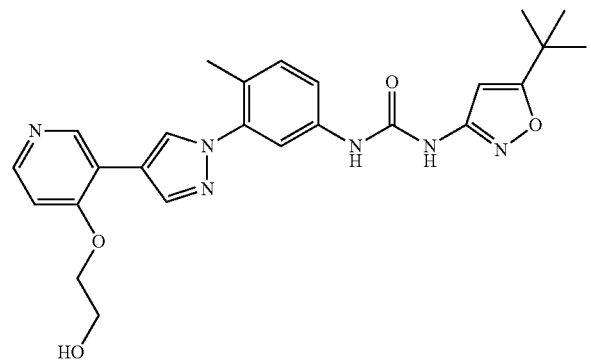 [SMILES: Cc1ccc(NC(=O)Nc2cc(C(C)(C)C)on2)cc1-n1cc(-c2cnccc2OCCO)cn1] |
| 158 | 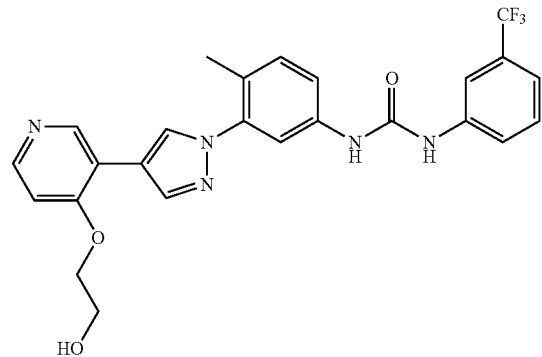 [SMILES: Cc1ccc(NC(=O)Nc2cccc(C(F)(F)F)c2)cc1-n1cc(-c2cnccc2OCCO)cn1] |
| 159 | 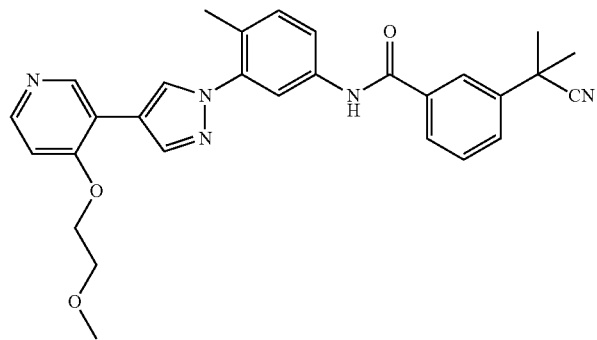 [SMILES: COCCOc1ccncc1-c1cnn(-c2cc(NC(=O)c3cccc(C(C)(C)C#N)c3)ccc2C)c1] |

-continued

| No. | Structure |
|---|---|
| 160 | 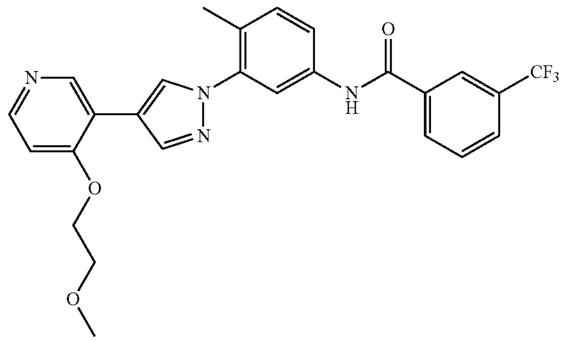 [SMILES: COCCOc1ccncc1-c1cnn(-c2cc(NC(=O)c3cccc(C(F)(F)F)c3)ccc2C)c1] |
| 161 | 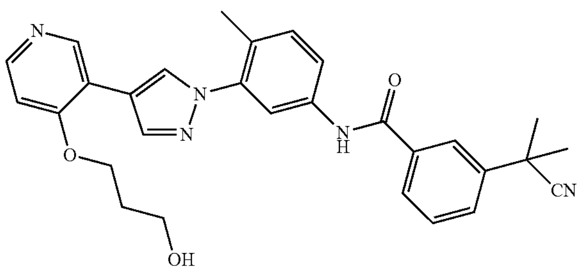 [SMILES: Cc1ccc(NC(=O)c2cccc(C(C)(C)C#N)c2)cc1-n1cc(-c2cnccc2OCCCO)cn1] |
| 162 | 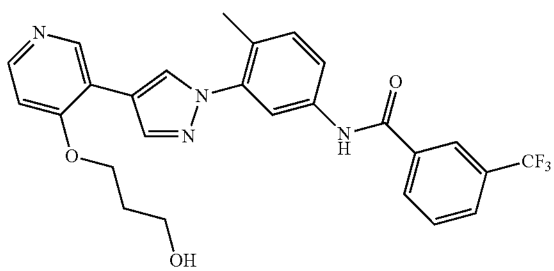 [SMILES: Cc1ccc(NC(=O)c2cccc(C(F)(F)F)c2)cc1-n1cc(-c2cnccc2OCCCO)cn1] |
| 163 | 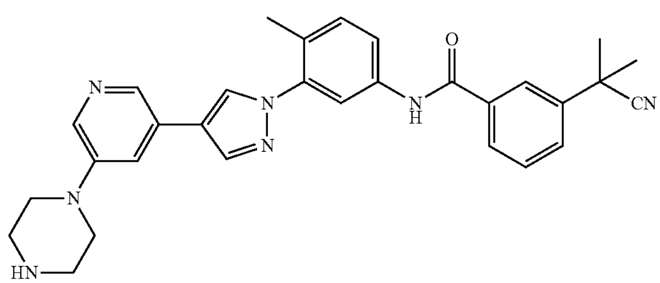 [SMILES: Cc1ccc(NC(=O)c2cccc(C(C)(C)C#N)c2)cc1-n1cc(-c2cncc(N3CCNCC3)c2)cn1] |
| 164 | 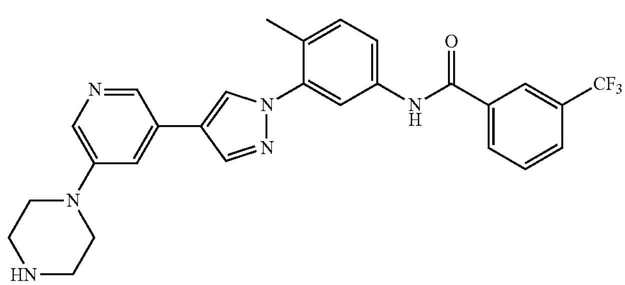 [SMILES: Cc1ccc(NC(=O)c2cccc(C(F)(F)F)c2)cc1-n1cc(-c2cncc(N3CCNCC3)c2)cn1] |

-continued

| No. | Structure |
|---|---|
| 165 | 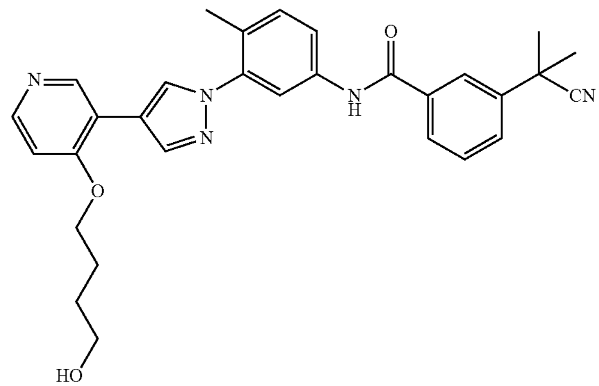 [SMILES: Cc1ccc(NC(=O)c2cccc(C(C)(C)C#N)c2)cc1-n1cc(-c2cnccc2OCCCCO)cn1] |
| 166 | 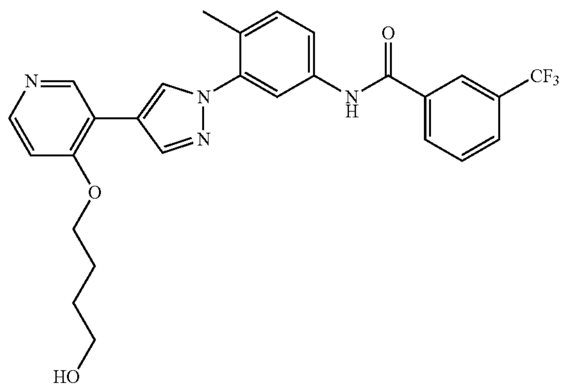 [SMILES: Cc1ccc(NC(=O)c2cccc(C(F)(F)F)c2)cc1-n1cc(-c2cnccc2OCCCCO)cn1] |
| 167 | 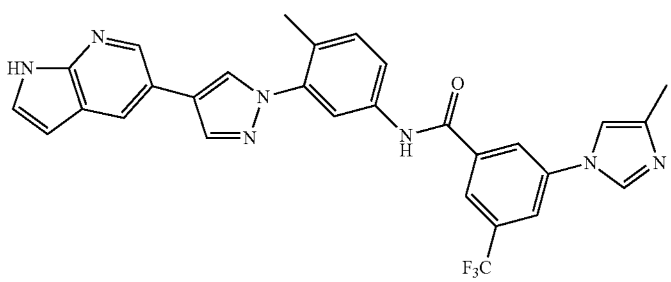 [SMILES: Cc1cn(-c2cc(C(=O)Nc3ccc(C)c(-n4cc(-c5cnc6[nH]ccc6c5)cn4)c3)cc(C(F)(F)F)c2)cn1] |
| 168 | 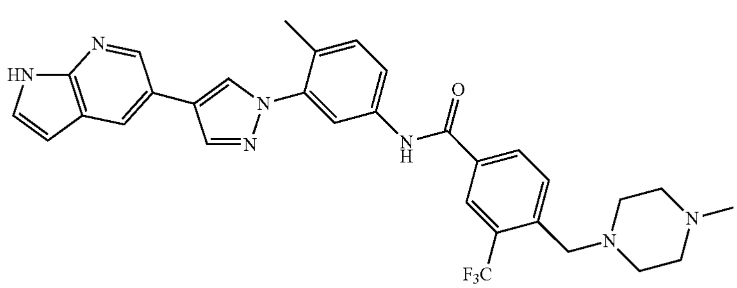 [SMILES: Cc1ccc(NC(=O)c2ccc(CN3CCN(C)CC3)c(C(F)(F)F)c2)cc1-n1cc(-c2cnc3[nH]ccc3c2)cn1] |

-continued
| No. | Structure |
|---|---|
| 169 | 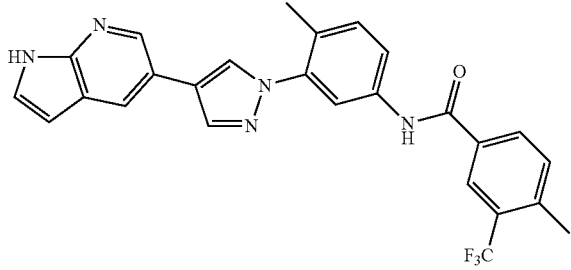 [SMILES: Cc1ccc(NC(=O)c2ccc(C)c(C(F)(F)F)c2)cc1-n1cc(-c2cnc3[nH]ccc3c2)cn1] |
| 170 | 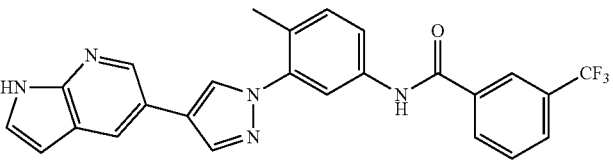 [SMILES: Cc1ccc(NC(=O)c2cccc(C(F)(F)F)c2)cc1-n1cc(-c2cnc3[nH]ccc3c2)cn1] |
| 171 | 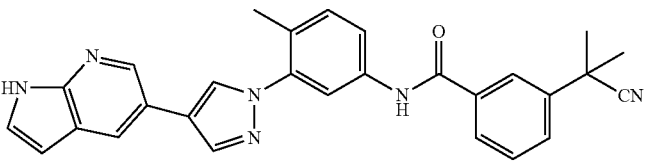 [SMILES: Cc1ccc(NC(=O)c2cccc(C(C)(C)C#N)c2)cc1-n1cc(-c2cnc3[nH]ccc3c2)cn1] |
| 172 | 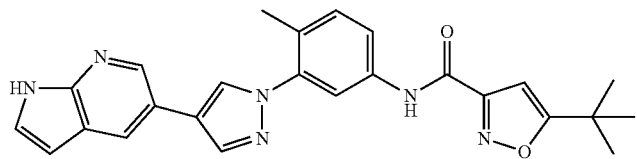 [SMILES: Cc1ccc(NC(=O)c2cc(C(C)(C)C)on2)cc1-n1cc(-c2cnc3[nH]ccc3c2)cn1] |
| 173 | 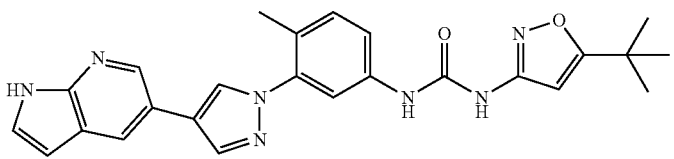 [SMILES: Cc1ccc(NC(=O)Nc2cc(C(C)(C)C)on2)cc1-n1cc(-c2cnc3[nH]ccc3c2)cn1] |
| 174 | 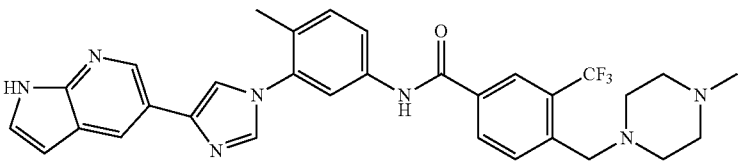 [SMILES: Cc1ccc(NC(=O)c2ccc(CN3CCN(C)CC3)c(C(F)(F)F)c2)cc1-n1cnc(-c2cnc3[nH]ccc3c2)c1] |
| 175 | 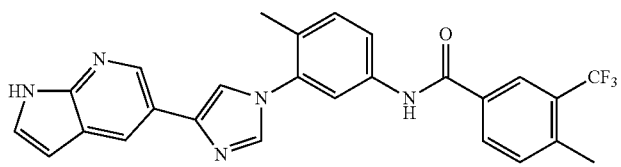 [SMILES: Cc1ccc(NC(=O)c2ccc(C)c(C(F)(F)F)c2)cc1-n1cnc(-c2cnc3[nH]ccc3c2)c1] |
| 176 | 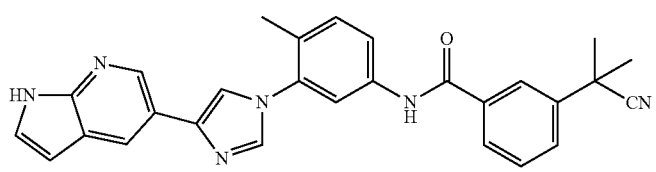 [SMILES: Cc1ccc(NC(=O)c2cccc(C(C)(C)C#N)c2)cc1-n1cnc(-c2cnc3[nH]ccc3c2)c1] |

-continued
| No. | Structure |
|---|---|
| 177 | 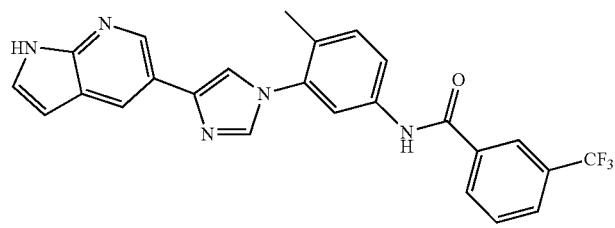 [SMILES: Cc1ccc(NC(=O)c2cccc(C(F)(F)F)c2)cc1-n1cnc(-c2cnc3[nH]ccc3c2)c1] |
| 178 | 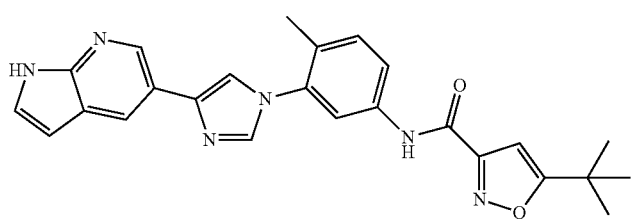 [SMILES: Cc1ccc(NC(=O)c2cc(C(C)(C)C)on2)cc1-n1cnc(-c2cnc3[nH]ccc3c2)c1] |
| 179 | 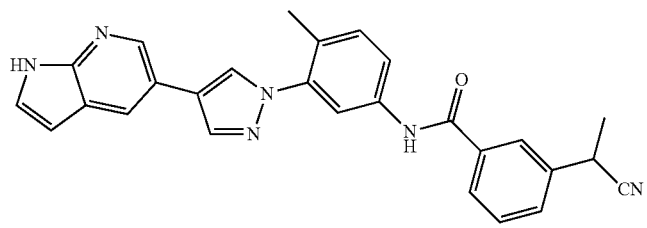 [SMILES: Cc1ccc(NC(=O)c2cccc(C(C)C#N)c2)cc1-n1cc(-c2cnc3[nH]ccc3c2)cn1] |
| 180 | 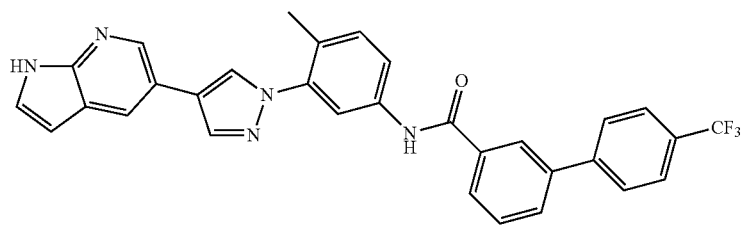 [SMILES: Cc1ccc(NC(=O)c2cccc(-c3ccc(C(F)(F)F)cc3)c2)cc1-n1cc(-c2cnc3[nH]ccc3c2)cn1] |
| 181 | 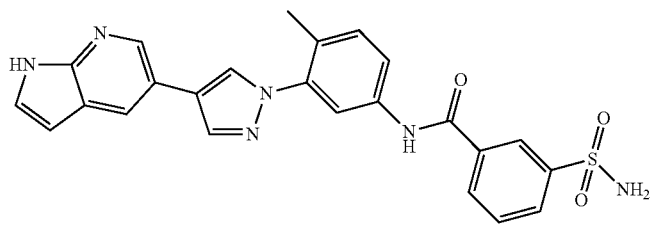 [SMILES: Cc1ccc(NC(=O)c2cccc(S(N)(=O)=O)c2)cc1-n1cc(-c2cnc3[nH]ccc3c2)cn1] |
| 182 | 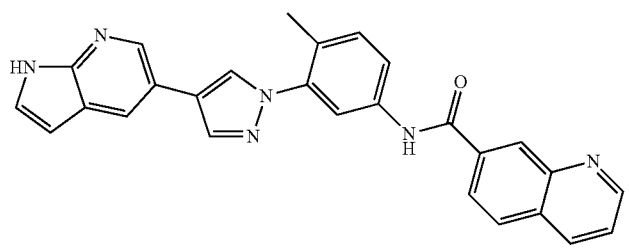 [SMILES: Cc1ccc(NC(=O)c2ccc3cccnc3c2)cc1-n1cc(-c2cnc3[nH]ccc3c2)cn1] |

| No. | Structure |
|-----|-----------|
| 183 | 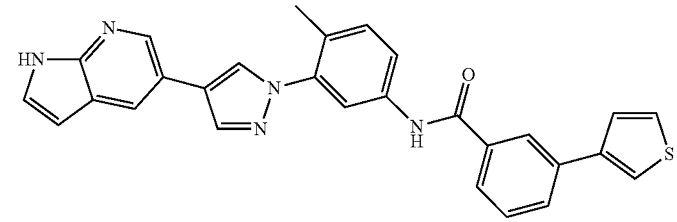 [SMILES: Cc1ccc(NC(=O)c2cccc(-c3ccsc3)c2)cc1-n1cc(-c2cnc3[nH]ccc3c2)cn1] |
| 184 | 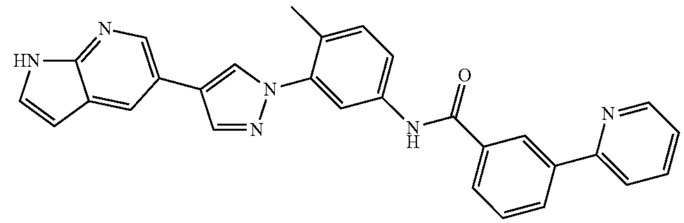 [SMILES: Cc1ccc(NC(=O)c2cccc(-c3ccccn3)c2)cc1-n1cc(-c2cnc3[nH]ccc3c2)cn1] |
| 185 | 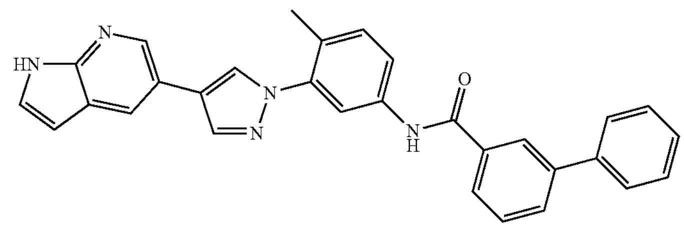 |

Any combination of the groups described above for the various variables is contemplated herein. It is understood that substituents and substitution patterns on the compounds provided herein can be selected by one of ordinary skill in the art to provide chemically stable compounds that can be synthesized by techniques known in the art, as well as those set forth herein.

Described herein is a novel kinase inhibitor. The pharmaceutically acceptable salts, solvates, esters, acids, pharmaceutically active metabolites and prodrugs of these compounds are also described herein.

In additional or further embodiments, the compounds described herein are metabolized upon administration to an organism in need thereof to produce a metabolite that is then used to produce a desirable effect, including a desirable therapeutic effect.

The compounds described herein may be formed as, and/or used as, pharmaceutically acceptable salts. Types of pharmaceutical acceptable salts, include, but are not limited to: (1) acid addition salts, formed by reacting the compound in a form of free base with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base addition salts formed when an acidic proton present in the parent compound either is replaced by a metal ion such as an alkali metal ion (such as, lithium, sodium, potassium), an alkaline earth metal ion (such as, magnesium, or calcium), or an aluminum ion; or coordinates with an organic base or an inorganic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

Corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by utilizing at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, X-ray diffraction, spectroscopy, microscopy, and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present application also provides a pharmaceutical composition comprising at least one compound of formula (I) or (Ia), or a pharmaceutically acceptable salt, solvate, ester, acid, pharmaceutically active metabolite or prodrug of the compound, and a pharmaceutically acceptable carrier or excipient, and optionally other therapeutic agents.

In the course of treatment, it may be used alone or in combination with one or more other therapeutic agents. The medicament comprising a compound of the present invention may be administered to a patient through at least one of injection, oral, inhalation, rectal and transdermal administration. Other therapeutic agents may be selected from the following: immunosuppressants (such as, tacrolimus, cyclosporin, rapamycin, methotrexate, cyclophosphamide, azathioprine, mercaptopurine, mycophenolate, or FTY720), glucocorticoids (such as, prednisone, cortisone acetate, prednisolone, methylprednisolone, dexamethasone, betamethasone, triamcinolone, hydrohydroxyprednisolone, beclomethasone, fluohydrocortisone acetate, deoxycorticosterone acetate, aldosterone), non-steroidal anti-inflammatory drugs (such as, salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (such as, mTOR inhibitors, c-Met inhibitors) or her2 antibody agents. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be for example, but not limited to, cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In embodiments of the present invention, when a patient is treated in accordance with the present invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as about 1-1500 mg per day. The desirable dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of Medicines of the Present Invention

The compound of the present invention, including a pharmaceutically acceptable salt, solvate, ester, acid, metabolite or prodrug thereof, or the pharmaceutical composition may be used for inhibiting the activity of tyrosine kinase RAF (wild-type or various mutants or the combination thereof) and/or RAS (wild-type or various mutants or the combination thereof). The compound of the present invention or a pharmaceutically acceptable salt, solvate, ester, acid, metabolite or prodrug thereof, or the pharmaceutical composition may be used for the treatment, prevention or amelioration of one or more diseases selected from the group consisting of: solid tumors (including benign or especially malignant types), especially sarcoma, Gastrointestinal Stromal Tumors (GIST), colorectal cancer, Acute Myeloblastic Leukemia (AML), Chronic Myelogenous Leukemia (CML), neoplasia, thyroid carcinoma, systemic mastocytosis, eosinophilia syndrome, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural endothelioma, hemangioblastoma, hemangioma, kidney cancer, liver cancer, adrenal carcinoma, bladder cancer, stomach cancer, rectal cancer, vaginal cancer, cervical cancer, endometrial cancer, multiple myeloma, neck and head tumors, as well as other proliferative conditions, or the like, or a combination thereof. It is especially preferred for the treatment of head and neck cancer, thyroid carcinoma, melanoma, colorectal cancer, lung cancer, breast cancer, pancreatic cancer, esophagus cancer, liver cancer, leukaemia, neoplasia or the like or a combination thereof Preparation of the Compound The compound of the present invention may be synthesized using standard synthetic techniques known to those of skill in the art or using methods known in the art in combination with methods described herein. In additions, solvents, temperatures and other reaction conditions presented herein may be varied according to techniques in the art. As a further guide the following synthetic methods may also be utilized.

The reactions can be employed in sequence to provide the compounds described herein or they may be used to synthesize building blocks which are subsequently joined by the methods described herein and/or known in the art.

In certain embodiments, provided herein are methods of preparing and methods of using tyrosine kinase inhibitor compounds described herein. In certain embodiments, the compounds described herein can be synthesized through the following synthetic schemes. The compounds may be synthesized using methodologies similar to those described below by the use of appropriate alternative starting materials.

The starting materials used for synthesis of the compounds described herein may be synthesized or can be commercially obtained. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The reaction products may be isolated and purified, if desired, using conventional techniques, including, but not limited to, filtration, distillation, crystallization, chromatography and the like. Such products may be characterized using conventional means, including physical constants and spectral data.

Example 1: N-(3-(4-([3,3'-bipyridyl]-5-yl)-1H-pyrazol-1-yl)-4-methylphenyl)-4-methyl-3-(trifluoromethyl)benzamide 1

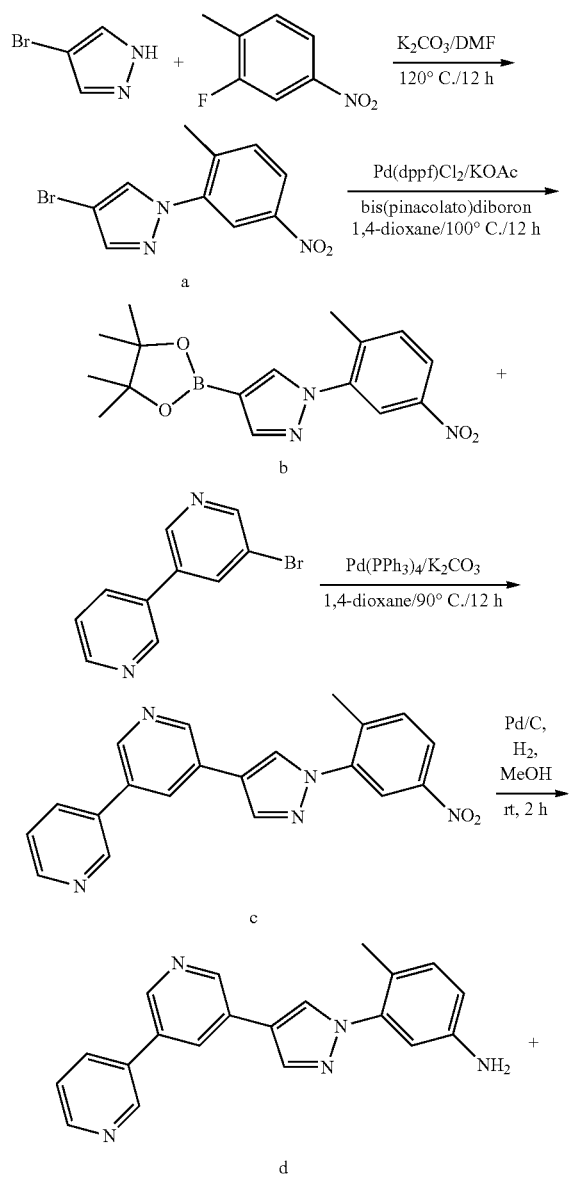

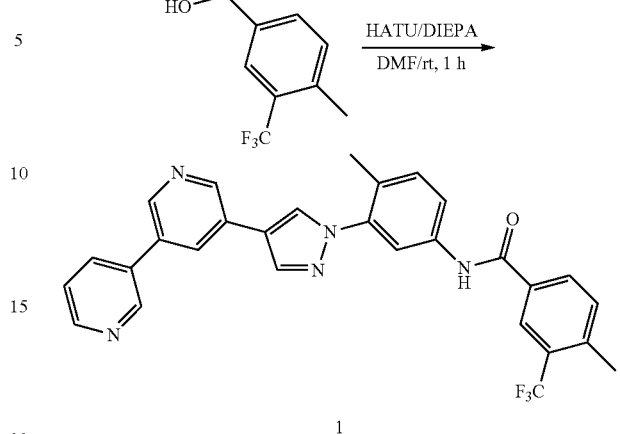

Step 1. Synthesis of 4-bromo-1-(2-methyl-5-nitrophenyl)-1H-pyrazole A

The compounds of 4-bromopyrazole (5 g, 1 eq), 2-fluoro-1-methyl-4-nitrobenzene (5.5 g, 1.05 eq) and potassium carbonate (13.1, 3 eq) were mixed in DMF (50 ml). The mixture was stirred overnight at 120° C. in a nitrogen atmosphere, then cooled and concentrated. Ethyl acetate (200 ml) was added into the concentrate. Thereafter, the resultant mixture was washed with water and saturated brine sequentially, dried over anhydrous sodium sulfate, and filtered. The filtrate was concentrated, and then separated by column chromatography to give a yellow product a (5.2 g).

Step 2. Synthesis of 1-(2-methyl-5-nitrophenyl)-4-(4,4,5,5-tetramethyl-1,3,2-dioxaborolan-2-yl)-1H-pyrazole B The compound a (5 g, 1 eq), bis(pinacolato)diboron (5.8 g, 1.3eq), potassium acetate (3.5 g, 2eq), and [1,1'-bis(diphenylphosphino)ferrocene]palladium dichloride (0.72 g, 0.05 eq) were mixed in 1,4-dioxane (50 ml). The mixture was stirred overnight at 100° C. in a nitrogen atmosphere, and then concentrated. The concentrate was separated by column chromatography to give a yellow product b (4.0 g).

Step 3. Synthesis of 5-(1-(2-methyl-5-nitrophenyl)-1H-pyrazol-4-yl)-3,3'-bipyridyl C The compound b (4.0 g, 1.1 eq), 5-bromo-3,3'-bipyridyl (2.6 g, 1 eq), potassium carbonate (3.0 g, 2eq) and tetrakis(triphenylphosphine)palladium (0.6 g, 0.05 eq) were mixed in 1,4-dioxane (40 ml) and water (4 ml). The mixture was stirred overnight at 90° C. in a nitrogen atmosphere, and then concentrated. The concentrate was separated by column chromatography to give a yellow product c (2.8 g).

Step 4. Synthesis of 3-(4-([3,3'-bipyridyl]-5-yl)-1H-pyrazol-1-yl)-4-methylaniline D The compound c (2.8 g, 1 eq) and palladium on carbon (0.5 g) were mixed in methanol (30 ml). The mixture was stirred for 2 hours at room temperature in a hydrogen atmosphere. Thereafter, dichloromethane (100 ml) was added to dilute the mixture. The resultant mixture was filtered, and concentrated to give a pale green product d (2.1 g).

Step 5. Synthesis of N-(3-(4-([3,3'-bipyridyl]-5-yl)-1H-pyrazol-1-yl)-4-methylphenyl)-4-methyl-3-(trifluoromethyl)benzamide 1

The compound d (0.05 g, 1 eq), 4-methyl-3-(trifluoromethyl)benzoic acid (0.031 g, 1 eq), HATU (0.064, 1.1 eq), and diisopropylethylamine (0.020 g, 1 eq) were mixed in DMF (2 ml). The mixture was stirred at room temperature for 0.5 hour. Thereafter, ethyl acetate (50 ml) was added to dilute the mixture. The mixture was washed with water and saturated brine sequentially, dried over anhydrous sodium sulfate, and filtered. The filtrate was concentrated, and separated by HPLC to obtain a product 1 (0.07 g). Exact Mass (calculated): 513.17; MS(ESI) m/z (M+1)+: 514.17.

Example 2: N-(3-(4-([3,3'-bipyridyl]-5-yl)-1H-pyrazol-1-yl)-4-methylphenyl)-3-(trifluoromethyl)benzamide 2

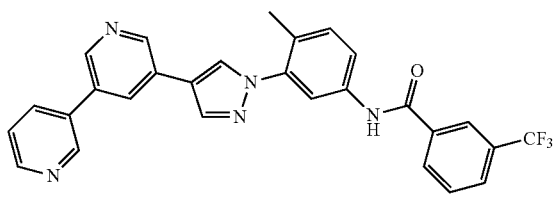 [SMILES: Cc1ccc(NC(=O)c2cccc(C(F)(F)F)c2)cc1-n1cc(-c2cncc(-c3cccnc3)c2)cn1]

Compound 2 was synthesized by employing steps similar to those described in Example 1. Exact Mass (calculated): 499.16; MS(ESI) m/z (M+1)+: 500.16.

Example 3: N-(3-(4-([3,3'-bipyridyl]-5-yl)-1H-pyrazol-1-yl)-4-methylphenyl)-3-(2-cyanoprop-2-yl)benzamide 3

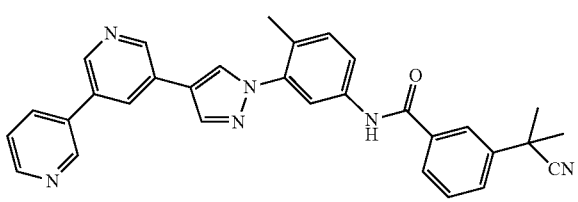 [SMILES: Cc1ccc(NC(=O)c2cccc(C(C)(C)C#N)c2)cc1-n1cc(-c2cncc(-c3cccnc3)c2)cn1]

Compound 3 was synthesized by employing steps similar to those described in Example 1. Exact Mass (calculated): 498.21; MS(ESI) m/z (M+1)+: 499.21.

Example 4: N-(3-(4-([3,3'-bipyridyl]-5-yl)-1H-pyrazol-1-yl)-4-methylphenyl)-5-(tert-butyl)isoxazole-3-carboxamide 4

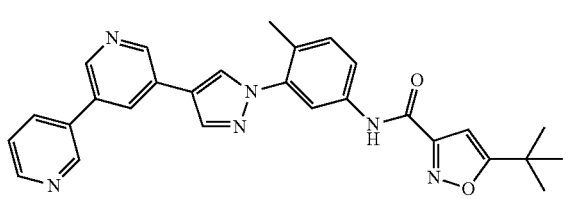

Compound 4 was synthesized by employing steps similar to those described in Example 1. Exact Mass (calculated): 478.21; MS(ESI) m/z (M+1)+: 479.21.

Example 5: N-(3-(4-([3,4'-bipyridyl]-5-yl)-1H-pyrazol-1-yl)-4-methylphenyl)-3-(2-cyanoprop-2-yl)benzamide 5

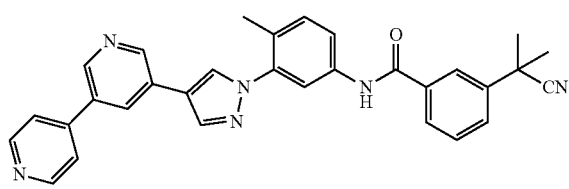 [SMILES: Cc1ccc(NC(=O)c2cccc(C(C)(C)C#N)c2)cc1-n1cc(-c2cncc(-c3ccncc3)c2)cn1]

Compound 5 was synthesized by employing steps similar to those described in Example 1. Exact Mass (calculated): 498.21; MS(ESI) m/z (M+1)+: 499.21.

Example 6: N-(3-(4-([3,4'-bipyridyl]-5-yl)-1H-pyrazol-1-yl)-4-methylphenyl)-3-(1-cyanoethyl)benzamide 6

Compound 6 was synthesized by employing steps similar to those described in Example 1. Exact Mass (calculated): 484.20; MS(ESI) m/z (M+1)+: 484.20.

Example 7: N-(3-(4-([3,4'-bipyridyl]-5-yl)-1H-pyrazol-1-yl)-4-methylphenyl)-4-methyl-3-(trifluoromethyl)benzamide 7

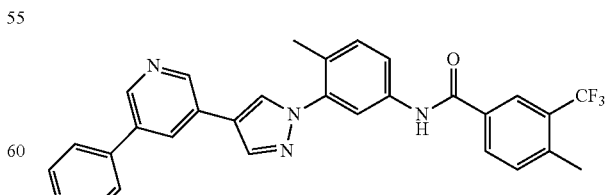

Compound 7 was synthesized by employing steps similar to those described in Example 1. Exact Mass (calculated): 513.17; MS(ESI) m/z (M+1)+: 514.17.

Example 8: N-(3-(4-([3,4'-bipyridyl]-5-yl)-1H-pyrazol-1-yl)-4-methylphenyl)-4-((4-methylpiperazin-1-yl)methyl)-3-(trifluoromethyl)benzamide 8

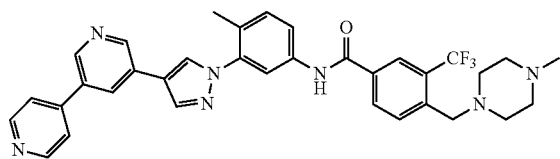 [SMILES: Cc1ccc(NC(=O)c2ccc(CN3CCN(C)CC3)c(C(F)(F)F)c2)cc1-n1cc(-c2cncc(-c3ccncc3)c2)cn1]

Compound 8 was synthesized by employing steps similar to those described in Example 1. Exact Mass (calculated): 611.26; MS(ESI) m/z (M+1)+: 612.26.

Example 9: 3-(2-cyanoprop-2-yl)-N-(4-methyl-3-(4-(5-morpholinopyrid-3-yl)-1H-pyrazol-1-yl)phenyl)benzamide 9

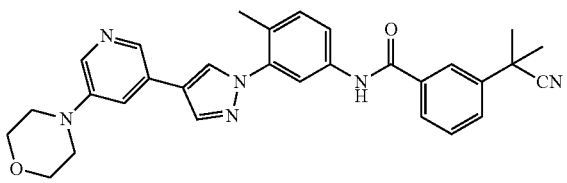 [SMILES: Cc1ccc(NC(=O)c2cccc(C(C)(C)C#N)c2)cc1-n1cc(-c2cncc(N3CCOCC3)c2)cn1]

Compound 9 was synthesized by employing steps similar to those described in Example 1. Exact Mass (calculated): 506.24; MS(ESI) m/z (M+1)+: 507.24.

Example 10: 3-(1-cyanoethyl)-N-(4-methyl-3-(4-(5-morpholinopyrid-3-yl)-1H-pyrazol-1-yl)phenyl)benzamide 10

Compound 10 was synthesized by employing steps similar to those described in Example 1. Exact Mass (calculated): 492.22; MS(ESI) m/z (M+1)+: 493.22.

Example 11: 4-methyl-N-(4-methyl-3-(4-(5-morpholinopyrid-3-yl)-1H-pyrazol-1-yl)phenyl)-3-(trifluoromethyl)benzamide 11

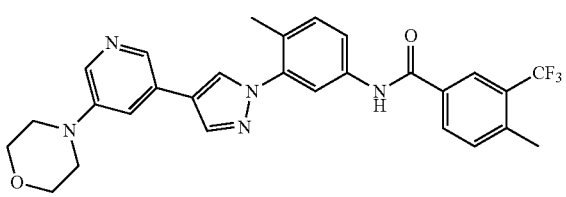 [SMILES: Cc1ccc(NC(=O)c2ccc(C)c(C(F)(F)F)c2)cc1-n1cc(-c2cncc(N3CCOCC3)c2)cn1]

Compound 11 was synthesized by employing steps similar to those described in Example 1. Exact Mass (calculated): 521.20; MS(ESI) m/z (M+1)+: 522.20.

Example 12: N-(4-methyl-3-(4-(5-morpholinopyrid-3-yl)-1H-pyrazol-1-yl)phenyl)-4-((4-methylpiperazin-1-yl)methyl)-3-(trifluoromethyl)benzamide 12

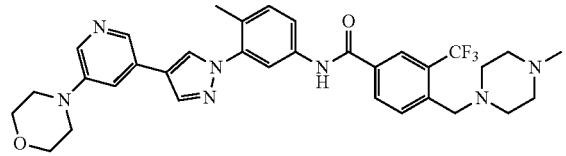 [SMILES: Cc1ccc(NC(=O)c2ccc(CN3CCN(C)CC3)c(C(F)(F)F)c2)cc1-n1cc(-c2cncc(N3CCOCC3)c2)cn1]

Compound 12 was synthesized by employing steps similar to those described in Example 1. Exact Mass (calculated): 619.28; MS(ESI) m/z (M+1)+: 620.28.

Example 13: N-(3-(4-([3,4'-bipyridyl]-5-yl)-1H-pyrazol-1-yl)-4-methylphenyl)-3-(trifluoromethyl)benzamide 13

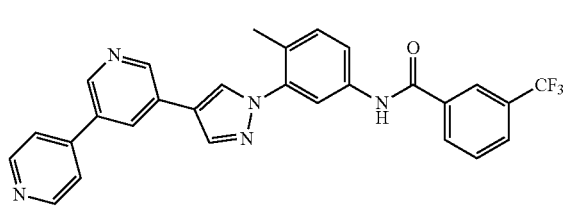 [SMILES: Cc1ccc(NC(=O)c2cccc(C(F)(F)F)c2)cc1-n1cc(-c2cncc(-c3ccncc3)c2)cn1]

Compound 13 was synthesized by employing steps similar to those described in Example 1. Exact Mass (calculated): 499.16; MS(ESI) m/z (M+1)+: 500.16.

Example 14: N-(3-(4-([3,4'-bipyridyl]-5-yl)-1H-pyrazol-1-yl)-4-methylphenyl)-5-(tert-butyl)isoxazole-3-carboxamide 14

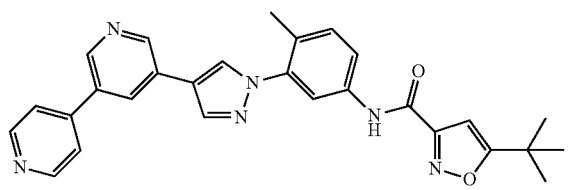 [SMILES: Cc1ccc(NC(=O)c2cc(C(C)(C)C)on2)cc1-n1cc(-c2cncc(-c3ccncc3)c2)cn1]

Compound 14 was synthesized by employing steps similar to those described in Example 1. Exact Mass (calculated): 478.21; MS(ESI) m/z (M+1)+: 479.21.

Example 15: 1-(3-(4-([3,4'-bipyridyl]-5-yl)-1H-pyrazol-1-yl)-4-methylphenyl)-3-(5-(tert-butyl)isoxazol-3-yl)urea 15

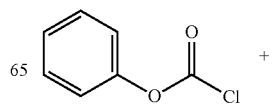

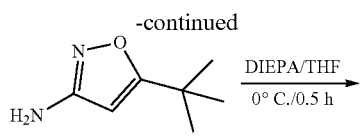

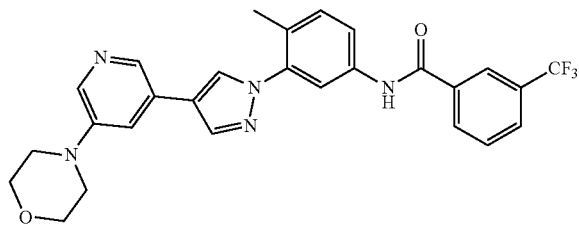 [SMILES: Cc1ccc(NC(=O)c2cccc(C(F)(F)F)c2)cc1-n1cc(-c2cncc(N3CCOCC3)c2)cn1]

Example 16: N-(4-methyl-3-(4-(5-morpholinopyrid-3-yl)-1H-pyrazol-1-yl)phenyl)-3-(trifluoromethyl)benzamide 16

Compound 16 was synthesized by employing steps similar to those described in Example 1. Exact Mass (calculated): 507.18; MS(ESI) m/z (M+1)+: 508.18.

Example 17: 5-(tert-butyl)-N-(4-methyl-3-(4-(5-morpholinopyrid-3-yl)-1H-pyrazol-1-yl)phenyl)isoxazole-3-carboxamide 17

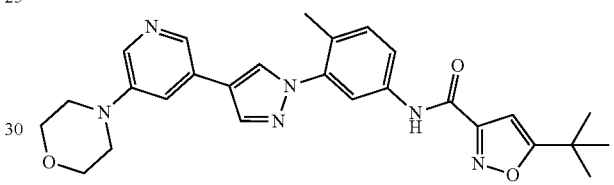

Compound 17 was synthesized by employing steps similar to those described in Example 1. Exact Mass (calculated): 486.23; MS(ESI) m/z (M+1)+: 487.23.

Example 18: 1-(5-(tert-butyl)isoxazol-3-yl)-3-(4-methyl-3-(4-(5-morpholinopyrid-3-yl)-1H-pyrazol-1-yl)phenyl)urea 18

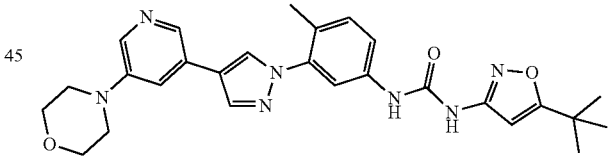

Compound 18 was synthesized by employing steps similar to those described in Examples 1 and 15. Exact Mass (calculated): 501.24; MS(ESI) m/z (M+1)+: 502.24.

Example 19: 3-(2-cyanoprop-2-yl)-N-(4-methyl-3-(4-(5-(4-methylpiperazine-1-carbonyl)pyrid-3-yl)-1H-pyrazol-1-yl)phenyl)benzamide 19

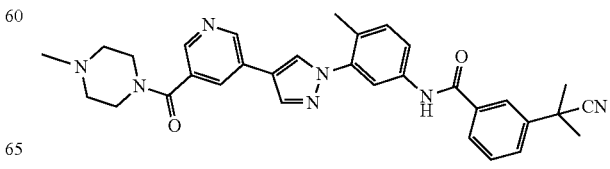

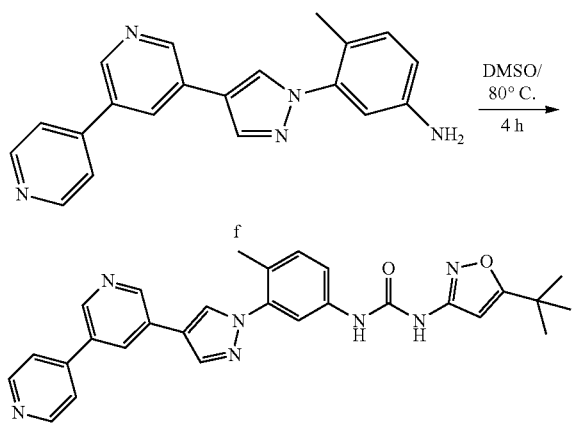

Step 1. Synthesis of phenyl (5-(tert-butyl)isoxazol-3-yl)carbamate E 5-(tert-butyl)isoxazol-3-amine (5 g, 1 eq), DIEPA (5.1 g, 1.1 eq) and THF (20 ml) were mixed at 0° C. in a nitrogen atmosphere. To the mixture was added phenyl chloroformate (5.9 g, 1.05 eq). The reaction was carried out for 0.5 hour at this temperature. Thereafter, the reaction mixture was diluted with ethyl acetate (120 ml), washed with water and saturated brine sequentially, dried over anhydrous sodium sulfate, filtered, and concentrated. The resultant solid was washed with n-hexane, and filtered to give a white solid e (7 g).

Step 2. Synthesis of 1-(3-(4-([3,4'-bipyridyl]-5-yl)-1H-pyrazol-1-yl)-4-methylphenyl)-3-(5-(tert-butyl)isoxazol-3-yl)urea 15

Compound f was synthesized by employing steps similar to those described in Example 1. Compound e (0.05 g, 1 eq), Compound f (0.055 g, 1 eq) and DMSO (2 ml) were mixed. The mixture was stirred for 4 hours at 80° C. Thereafter, ethyl acetate (50 ml) was added. The resultant mixture was washed with water and saturated brine sequentially, dried over anhydrous sodium sulfate, filtered, and concentrated. The concentrate was separated by HPLC to give Compound 12 (0.06 g). Exact Mass (calculated): 493.22; MS(ESI) m/z (M+1)+: 494.22.

Compound 19 was synthesized by employing steps similar to those described in Example 1. Exact Mass (calculated): 547.26; MS(ESI) m/z (M+1)+: 548.26.

Example 20: 3-(1-cyanoethyl)-N-(4-methyl-3-(4-(5-(4-methylpiperazine-1-carbonyl)pyrid-3-yl)-1H-pyrazol-1-yl)phenyl)benzamide 20

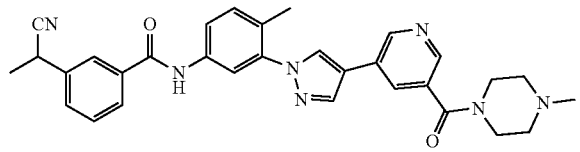 [SMILES: Cc1ccc(NC(=O)c2cccc(C(C)C#N)c2)cc1-n1cc(-c2cncc(C(=O)N3CCN(C)CC3)c2)cn1]

Compound 20 was synthesized by employing steps similar to those described in Example 1. Exact Mass (calculated): 533.25; MS(ESI) m/z (M+1)+: 534.25.

Example 21: N-(4-methyl-3-(4-(5-(4-methylpiperazine-1-carbonyl)pyrid-3-yl)-1H-pyrazol-1-yl)phenyl)-3-(trifluoromethyl)benzamide 21

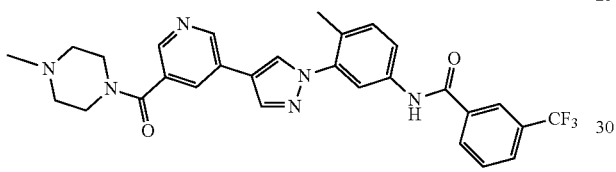

Compound 21 was synthesized by employing steps similar to those described in Example 1. Exact Mass (calculated): 548.21; MS(ESI) m/z (M+1)+: 549.21.

Example 22: 5-(tert-butyl)-N-(4-methyl-3-(4-(5-(4-methylpiperazine-1-carbonyl)pyrid-3-yl)-1H-pyrazol-1-yl)phenyl)isoxazole-3-carboxamide 22

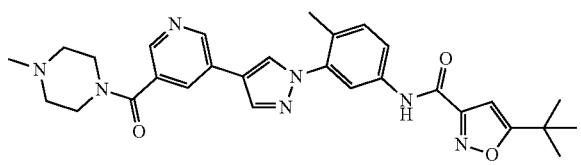 [SMILES: Cc1ccc(NC(=O)c2cc(C(C)(C)C)on2)cc1-n1cc(-c2cncc(C(=O)N3CCN(C)CC3)c2)cn1]

Example 22 was synthesized by employing steps similar to those described in Example 1. Exact Mass (calculated): 527.26; MS(ESI) m/z (M+1)+: 528.26.

Example 23: 3-(2-cyanoprop-2-yl)-N-(4-methyl-3-(4-(5-(4-methylpiperazin-1-yl)pyrid-3-yl)-1H-pyrazol-1-yl)phenyl)benzamide 23

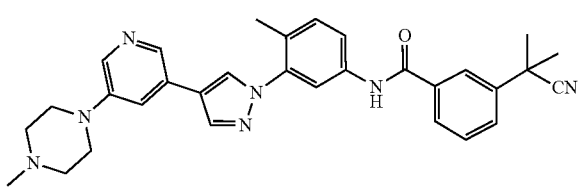 [SMILES: Cc1ccc(NC(=O)c2cccc(C(C)(C)C#N)c2)cc1-n1cc(-c2cncc(N3CCN(C)CC3)c2)cn1]

Compound 23 was synthesized by employing steps similar to those described in Example 1. Exact Mass (calculated): 519.27; MS(ESI) m/z (M+1)+: 520.27.

Example 24: 3-(1-cyanoethyl)-N-(4-methyl-3-(4-(5-(4-methylpiperazin-1-yl)pyrid-3-yl)-1H-pyrazol-1-yl)phenyl)benzamide 24

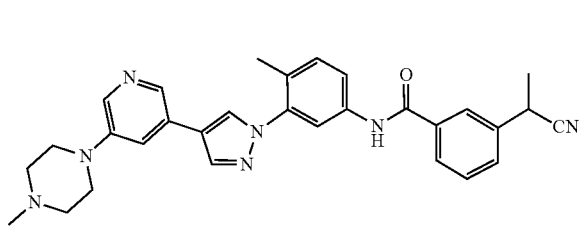 [SMILES: Cc1ccc(NC(=O)c2cccc(C(C)C#N)c2)cc1-n1cc(-c2cncc(N3CCN(C)CC3)c2)cn1]

Compound 24 was synthesized by employing steps similar to those described in Example 1. Exact Mass (calculated): 505.26; MS(ESI) m/z (M+1)+: 506.27.

Example 25: N-(4-methyl-3-(4-(5-(4-methylpiperazin-1-yl)pyrid-3-yl)-1H-pyrazol-1-yl)phenyl)-3-(trifluoromethyl)benzamide 25

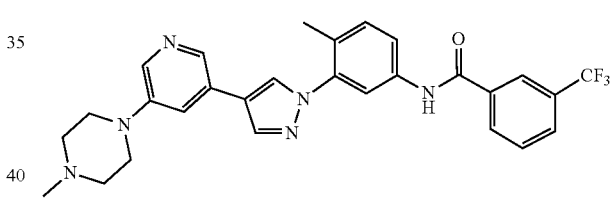

Compound 25 was synthesized by employing steps similar to those described in Example 1. Exact Mass (calculated): 520.21; MS(ESI) m/z (M+1)+: 521.21.

Example 26: 5-(tert-butyl)-N-(4-methyl-3-(4-(5-(4-methylpiperazin-1-yl)pyrid-3-yl)-1H-pyrazol-1-yl)phenyl)isoxazole-3-carboxamide 26

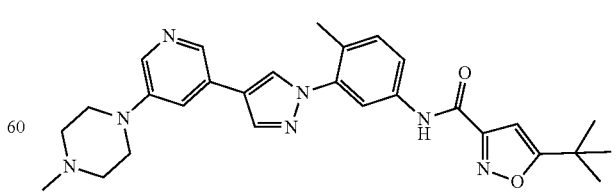

Compound 26 was synthesized by employing steps similar to those described in Example 1. Exact Mass (calculated): 499.26; MS(ESI) m/z (M+1)+: 500.26.

Example 27: 1-(5-(tert-butyl)isoxazol-3-yl)-3-(4-methyl-3-(4-(5-(4-methylpiperazin-1-yl)pyrid-3-yl)-1H-pyrazol-1-yl)phenyl)urea 27

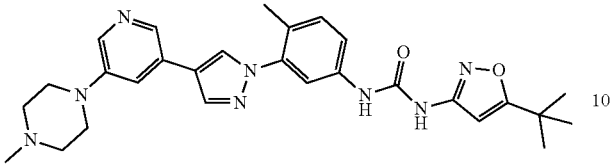

Compound 27 was synthesized by employing steps similar to those described in Examples 1 and 15. Exact Mass (calculated): 514.28; MS(ESI) m/z (M+1)+: 515.28.

Example 28: 3-(2-cyanoprop-2-yl)-N-(4-methyl-3-(4-(5-phenylpyrid-3-yl)-1H-pyrazol-1-yl)phenyl)benzamide 28

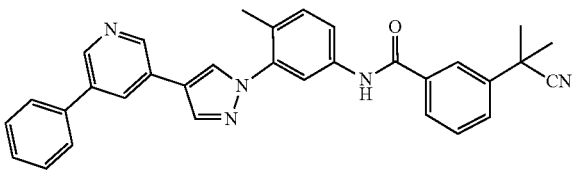 [SMILES: Cc1ccc(NC(=O)c2cccc(C(C)(C)C#N)c2)cc1-n1cc(-c2cncc(-c3ccccc3)c2)cn1]

Compound 28 was synthesized by employing steps similar to those described in Example 1. Exact Mass (calculated): 497.22; MS(ESI) m/z (M+1)+: 498.22.

Example 29: N-(4-methyl-3-(4-(5-phenylpyrid-3-yl)-1H-pyrazol-1-yl)phenyl)-3-(trifluoromethyl)benzamide 29

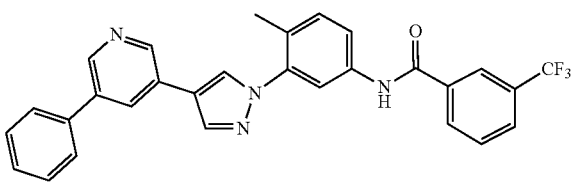 [SMILES: Cc1ccc(NC(=O)c2cccc(C(F)(F)F)c2)cc1-n1cc(-c2cncc(-c3ccccc3)c2)cn1]

Compound 29 was synthesized by employing steps similar to those described in Example 1. Exact Mass (calculated): 498.16; MS(ESI) m/z (M+1)+: 499.16.

Example 30: N-(4-methyl-3-(4-(5-(4-(4-methylpiperazin-1-yl)phenyl)pyrid-3-yl)-1H-pyrazol-1-yl)phenyl)-3-(2-cyanoprop-2-yl)benzamide 30

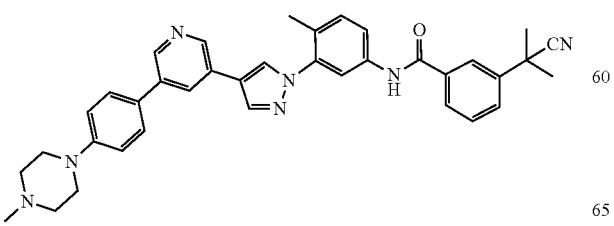

Compound 30 was synthesized by employing steps similar to those described in Example 1. Exact Mass (calculated): 595.31; MS(ESI) m/z (M+1)+: 596.31

Example 31: N-(4-methyl-3-(4-(5-(4-(4-methylpiperazin-1-yl)phenyl)pyrid-3-yl)-1H-pyrazol-1-yl)phenyl)-3-(trifluoromethyl)benzamide 31

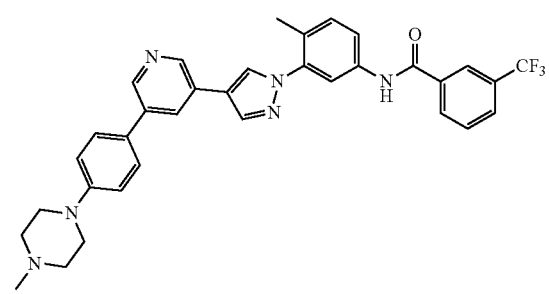 [SMILES: Cc1ccc(NC(=O)c2cccc(C(F)(F)F)c2)cc1-n1cc(-c2cncc(-c3ccc(N4CCN(C)CC4)cc3)c2)cn1]

Compound 31 was synthesized by employing steps similar to those described in Example 1. Exact Mass (calculated): 596.25; MS(ESI) m/z (M+1)+: 597.26.

Example 32: N-(4-methyl-3-(4-(5-(4-(4-methylpiperazin-1-yl)phenyl)pyrid-3-yl)-1H-pyrazol-1-yl)phenyl)-2-(3-(trifluoromethyl)phenyl)acetamide 32

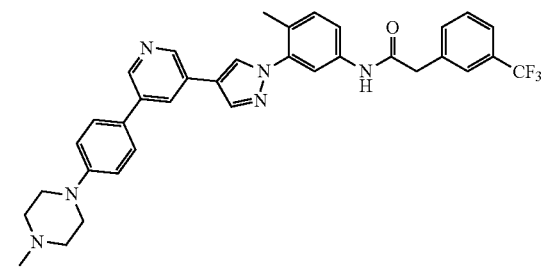 [SMILES: Cc1ccc(NC(=O)Cc2cccc(C(F)(F)F)c2)cc1-n1cc(-c2cncc(-c3ccc(N4CCN(C)CC4)cc3)c2)cn1]

Compound 32 was synthesized by employing steps similar to those described in Example 1. Exact Mass (calculated): 610.26; MS(ESI) m/z (M+1)+: 611.26.

Example 33: 5-(tert-butyl)-N-(4-methyl-3-(4-(5-(4-(4-methylpiperazin-1-yl)phenyl)pyrid-3-yl)-1H-pyrazol-1-yl)phenyl)isoxazole-3-carboxamide 33

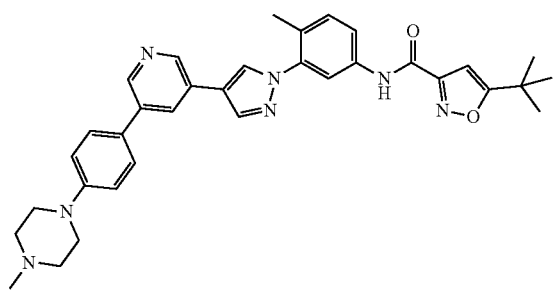 [SMILES: Cc1ccc(NC(=O)c2cc(C(C)(C)C)on2)cc1-n1cc(-c2cncc(-c3ccc(N4CCN(C)CC4)cc3)c2)cn1]

Compound 33 was synthesized by employing steps similar to those described in Example 1. Exact Mass (calculated): 575.30; MS(ESI) m/z (M+1)+: 576.30.

Example 34: N-(4-methyl-3-(4-(5-morpholinopyrid-3-yl)-1H-pyrazol-1-yl)phenyl)-2-(3-(trifluoromethyl)phenyl)acetamide 54

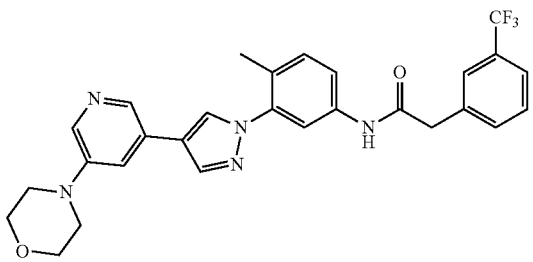 [SMILES: Cc1ccc(NC(=O)Cc2cccc(C(F)(F)F)c2)cc1-n1cc(-c2cncc(N3CCOCC3)c2)cn1]

Compound 34 was synthesized by employing steps similar to those described in Example 1. Exact Mass (calculated): 521.20; MS(ESI) m/z (M+1)+: 522.20.

Example 35: 3-(2-cyanoprop-2-yl)-N-(3-(4-(6-(cyclopropylformylamino)pyrid-3-yl)-1H-pyrazol-1-yl)-4-methylphenyl)benzamide 35

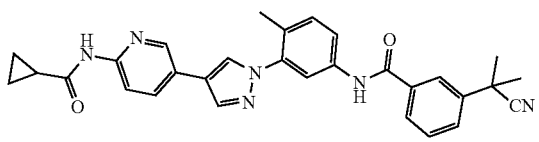 [SMILES: Cc1ccc(NC(=O)c2cccc(C(C)(C)C#N)c2)cc1-n1cc(-c2ccc(NC(=O)C3CC3)nc2)cn1]

Compound 35 was synthesized by employing steps similar to those described in Example 1. Exact Mass (calculated): 504.22; MS(ESI) m/z (M+1)+: 505.22.

Example 36: N-(3-(4-(6-(cyclopropylformylamino)pyrid-3-yl)-1H-pyrazol-1-yl)-4-methylphenyl)-3-(trifluoromethyl)benzamide 36

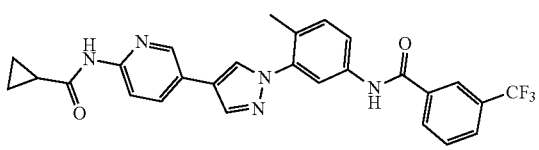 [SMILES: Cc1ccc(NC(=O)c2cccc(C(F)(F)F)c2)cc1-n1cc(-c2ccc(NC(=O)C3CC3)nc2)cn1]

Compound 36 was synthesized by employing steps similar to those described in Example 1. Exact Mass (calculated): 505.17; MS(ESI) m/z (M+1)+: 506.17.

Example 37: N-(5-(1-(2-methyl-5-(2-(3-(trifluoromethyl)phenyl)acetylamino)phenyl)-1H-pyrazol-4-yl)pyrid-2-yl)cyclopropane carboxamide 37

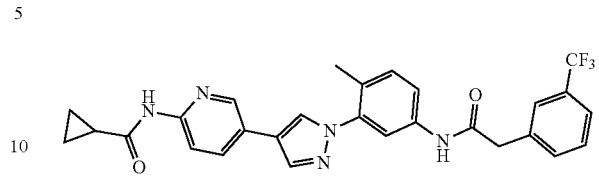

Compound 37 was synthesized by employing steps similar to those described in Example 1. Exact Mass (calculated): 519.18; MS(ESI) m/z (M+1)+: 520.18.

Example 38: 3-(2-cyanoprop-2-yl)-N-(3-(4-(6-(cyclopropylformylamino)-4-methylpyrid-3-yl)-1H-pyrazol-1-yl)-4-methylphenyl)benzamide 38

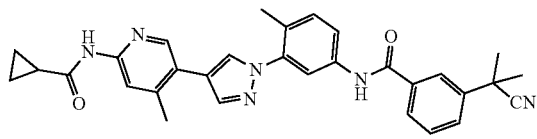 [SMILES: Cc1cc(NC(=O)C2CC2)ncc1-c1cnn(-c2cc(NC(=O)c3cccc(C(C)(C)C#N)c3)ccc2C)c1]

Compound 38 was synthesized by employing steps similar to those described in Example 1. Exact Mass (calculated): 518.24; MS(ESI) m/z (M+1)+: 519.24.

Example 39: N-(3-(4-(6-(cyclopropylformylamino)-4-methylpyrid-3-yl)-1H-pyrazol-1-yl)-4-methylphenyl)-3-(trifluoromethyl)benzamide 39

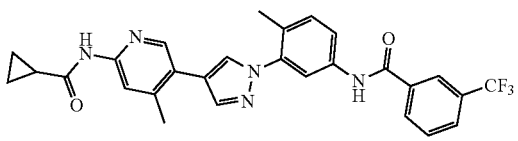 [SMILES: Cc1cc(NC(=O)C2CC2)ncc1-c1cnn(-c2cc(NC(=O)c3cccc(C(F)(F)F)c3)ccc2C)c1]

Compound 39 was synthesized by employing steps similar to those described in Example 1. Exact Mass (calculated): 519.18; MS(ESI) m/z (M+1)+: 520.18.

Example 40: N-(4-methyl-5-(1-(2-methyl-5-(2-(3-(trifluoromethyl)phenyl)acetylamino)phenyl)-1H-pyrazol-4-yl)pyrid-2-yl)cyclopropane carboxamide 40

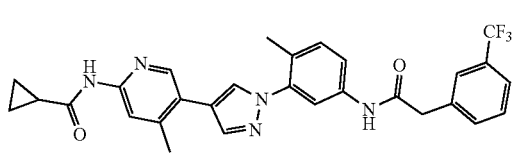 [SMILES: Cc1cc(NC(=O)C2CC2)ncc1-c1cnn(-c2cc(NC(=O)Cc3cccc(C(F)(F)F)c3)ccc2C)c1]

Compound 40 was synthesized by employing steps similar to those described in Example 1. Exact Mass (calculated): 533.20; MS(ESI) m/z (M+1)+: 534.20.

Example 41: 3-(2-cyanoprop-2-yl)-N-(4-methyl-3-(4-(5-(2-morpholino ethoxy)pyrid-3-yl)-1H-pyrazol-1-yl)phenyl)benzamide 41

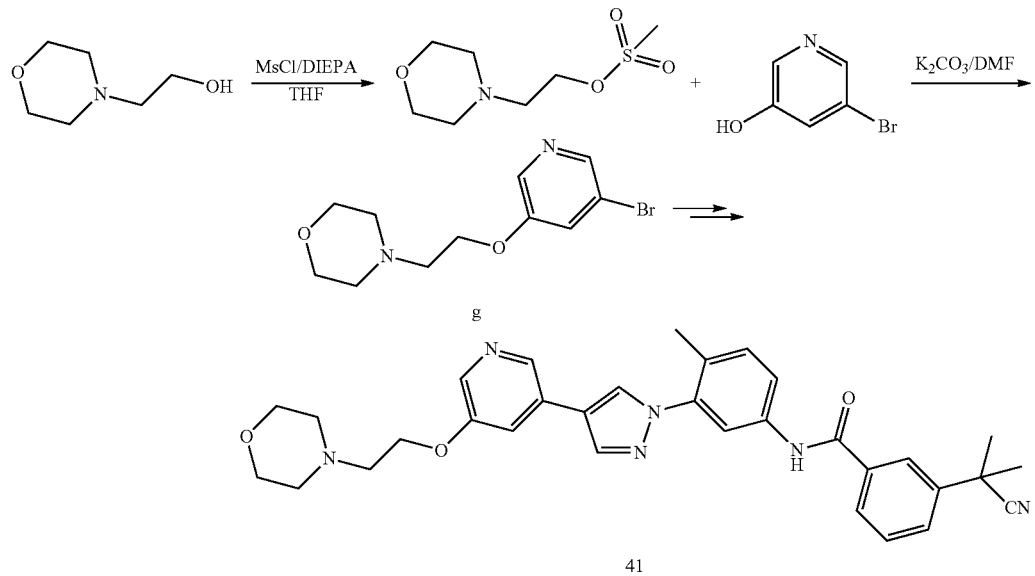

Step 1. Synthesis of 4-(2-((5-bromopyrid-3-yl)oxy)ethyl) morpholine G 2-morpholinoethanol (3 g, 1 eq), DIEPA (3.2 g, 1.1 eq) and THF (15 ml) were mixed. To the mixture was added methylsufonyl chloride (2.7 g, 1.1 eq) dropwise at 0° C. The resultant mixture was stirred at the temperature for 6 hours. The reaction solution was concentrated, eluted with ethyl acetate (100 ml), washed with water and saturated brine sequentially, dried over anhydrous sodium sulfate, and filtered. The filtrate was concentrated to give a product 2-morpholinoethylmethanesulfonate (3.8 g, 1 eq). The product was mixed with 5-bromopyrid-3-ol (2.8 g, 0.9eq), potassium carbonate (3.7 g, 2eq). The mixture was stirred in DMF (30 ml) at 70° C. for 5 hours. Thereafter, the resultant mixture was concentrated, eluted with ethyl acetate (150 ml), washed with water and saturated brine sequentially, dried over anhydrous sodium sulfate, and filtered. The filtrate was concentrated to give a product 4-(2-((5-bromopyrid-3-yl)oxy)ethyl) morpholine g (3.2 g).

Step 2. Compound 41 was synthesized by employing steps similar to those described in Example 1. Exact Mass (calculated): 550.26; MS(ESI) m/z (M+1)+: 551.26.

Example 42: N-(4-methyl-3-(4-(5-(2-morpholino-ethoxy)pyrid-3-yl)-1H-pyrazol-1-yl)phenyl)-3-(trifluoromethyl)benzamide 42

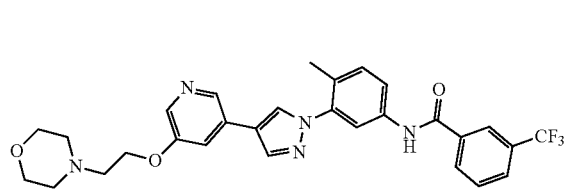 [SMILES: Cc1ccc(NC(=O)c2cccc(C(F)(F)F)c2)cc1-n1cc(-c2cncc(OCCN3CCOCC3)c2)cn1]

Compound 42 was synthesized by employing steps similar to those described in Example 41. Exact Mass (calculated): 551.21; MS(ESI) m/z (M+1)+: 552.21.

Example 43: N-(4-methyl-3-(4-(5-(2-morpholino-ethoxy)pyrid-3-yl)-1H-pyrazol-1-yl)phenyl)-2-(3-(trifluoromethyl)phenyl)acetamide 43

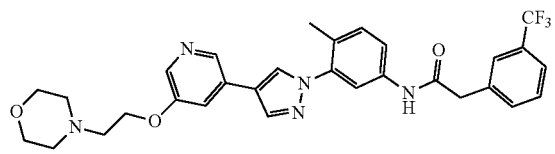 [SMILES: Cc1ccc(NC(=O)Cc2cccc(C(F)(F)F)c2)cc1-n1cc(-c2cncc(OCCN3CCOCC3)c2)cn1]

Compound 43 was synthesized by employing steps similar to those described in Example 41. Exact Mass (calculated): 565.23; MS(ESI) m/z (M+1)+: 566.23.

Example 44: N-(3-(4-(4-cyano-6-(cyclopropyl-formylamino)pyrid-3-yl)-1H-pyrazol-1-yl)-4-methylphenyl)-3-(2-cyanoprop-2-yl)benzamide 44

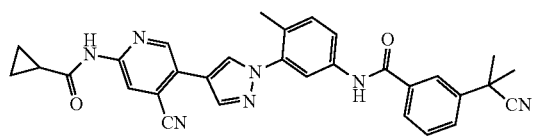 [SMILES: Cc1ccc(NC(=O)c2cccc(C(C)(C)C#N)c2)cc1-n1cc(-c2cnc(NC(=O)C3CC3)cc2C#N)cn1]

Compound 44 was synthesized by employing steps similar to those described in Example 1. Exact Mass (calculated): 529.22; MS(ESI) m/z (M+1)+: 530.22.

Example 45: N-(3-(4-(4-cyano-6-(cyclopropyl-formylamino)pyrid-3-yl)-1H-pyrazol-1-yl)-4-methylphenyl)-3-(trifluoromethyl)benzamide 45

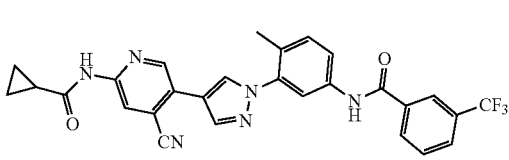 [SMILES: Cc1ccc(NC(=O)c2cccc(C(F)(F)F)c2)cc1-n1cc(-c2cnc(NC(=O)C3CC3)cc2C#N)cn1]

Compound 45 was synthesized by employing steps similar to those described in Example 1. Exact Mass (calculated): 530.16; MS(ESI) m/z (M+1)+: 531.16.

Example 46: N-(4-cyano-5-(1-(2-methyl-5-(2-(3-(trifluoromethyl)phenyl)acetylamino)phenyl)-1H-pyrazol-4-yl)pyrid-2-yl)cyclopropane carboxamide 46

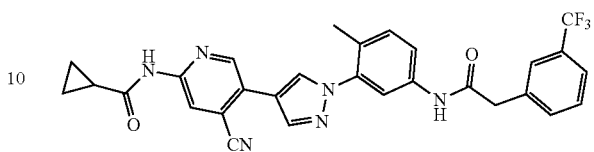

Compound 46 was synthesized by employing steps similar to those described in Example 1. Exact Mass (calculated): 544.18; MS(ESI) m/z (M+1)+: 545.18.

Example 47: 3-(2-cyanoprop-2-yl)-N-(4-methyl-3-(4-(5-(3-morpholino propoxy)pyrid-3-yl)-1H-pyrazol-1-yl)phenyl)benzamide 47

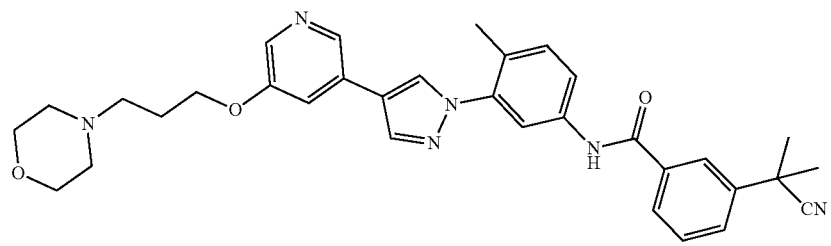 [SMILES: Cc1ccc(NC(=O)c2cccc(C(C)(C)C#N)c2)cc1-n1cc(-c2cncc(OCCCN3CCOCC3)c2)cn1]

Compound 47 was synthesized by employing steps similar to those described in Example 41. Exact Mass (calculated): 564.28; MS(ESI) m/z (M+1)+: 565.28.

Example 48: N-(4-methyl-3-(4-(5-(3-morpholino propoxy)pyrid-3-yl)-1H-pyrazol-1-yl)phenyl)-3-(trifluoromethyl)benzamide 48

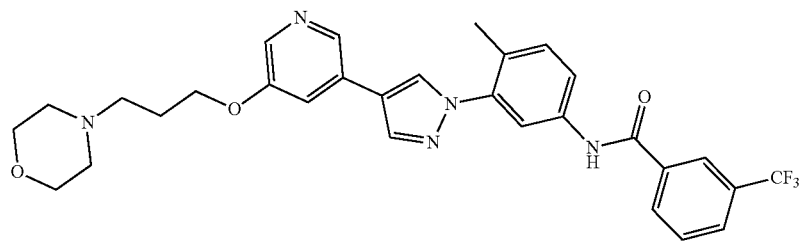 [SMILES: Cc1ccc(NC(=O)c2cccc(C(F)(F)F)c2)cc1-n1cc(-c2cncc(OCCCN3CCOCC3)c2)cn1]

Compound 48 was synthesized by employing steps similar to those described in Example 41. Exact Mass (calculated): 565.23; MS(ESI) m/z (M+1)+: 566.23.

Example 49: N-(4-methyl-3-(4-(5-(3-morpholino propoxy)pyrid-3-yl)-1H-pyrazol-1-yl)phenyl)-2-(3-(trifluoromethyl)phenyl)acetamide 49

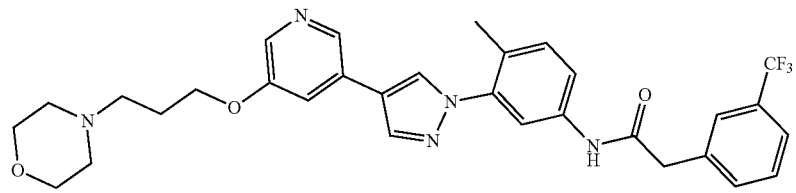 [SMILES: Cc1ccc(NC(=O)Cc2cccc(C(F)(F)F)c2)cc1-n1cc(-c2cncc(OCCCN3CCOCC3)c2)cn1]

Compound 49 was synthesized by employing steps similar to those described in Example 41. Exact Mass (calculated): 579.24; MS(ESI) m/z (M+1)+: 580.24.

Example 50: 3-(2-cyanoprop-2-yl)-N-(4-methyl-3-(4-(5-((tetrahydro-2H-pyran-4-yl)oxy)pyrid-3-yl)-1H-pyrazol-1-yl)phenyl)benzamide 50

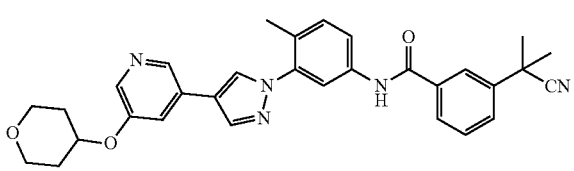 [SMILES: Cc1ccc(NC(=O)c2cccc(C(C)(C)C#N)c2)cc1-n1cc(-c2cncc(OC3CCOCC3)c2)cn1]

Compound 50 was synthesized by employing steps similar to those described in Example 41. Exact Mass (calculated): 521.24; MS(ESI) m/z (M+1)+: 522.24.

Example 51: N-(4-methyl-3-(4-(5-((tetrahydro-2H-pyran-4-yl)oxy)pyrid-3-yl)-1H-pyrazol-1-yl)phenyl)-3-(trifluoromethyl)benzamide 51

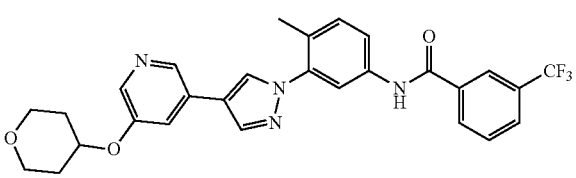 [SMILES: Cc1ccc(NC(=O)c2cccc(C(F)(F)F)c2)cc1-n1cc(-c2cncc(OC3CCOCC3)c2)cn1]

Compound 51 was synthesized by employing steps similar to those described in Example 41. Exact Mass (calculated): 522.18; MS(ESI) m/z (M+1)+: 523.18.

Example 52: N-(4-methyl-3-(4-(5-((tetrahydro-2H-pyran-4-yl)oxy)pyrid-3-yl)-1H-pyrazol-1-yl)phenyl)-2-(3-(trifluoromethyl)phenyl)acetamide 52

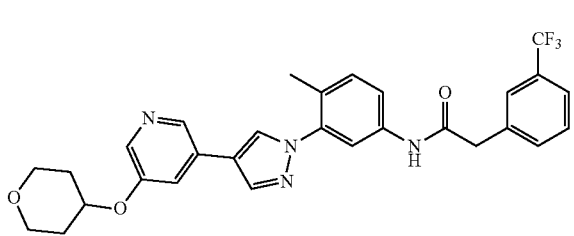 [SMILES: Cc1ccc(NC(=O)Cc2cccc(C(F)(F)F)c2)cc1-n1cc(-c2cncc(OC3CCOCC3)c2)cn1]

Compound 52 was synthesized by employing steps similar to those described in Example 41. Exact Mass (calculated): 536.20; MS(ESI) m/z (M+1)+: 537.20.

Example 53: 3-(2-cyanoprop-2-yl)-N-(3-(4-(5-(2-(dimethylamino)-2-oxoethoxy)pyrid-3-yl)-11H-pyrazol-1-yl)-4-methylphenyl)benzamide 53

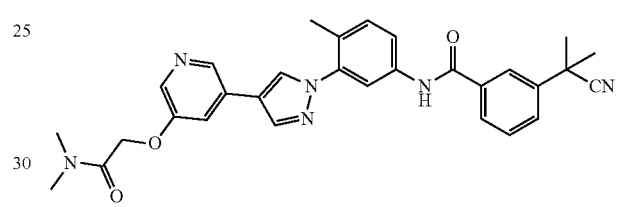

Compound 53 was synthesized by employing steps similar to those described in Example 41. Exact Mass (calculated): 522.23; MS(ESI) m/z (M+1)+: 523.23.

Example 54: N-(3-(4-(5-(2-(dimethylamino)-2-oxoethoxy)pyrid-3-yl)-1H-pyrazol-1-yl)-4-methylphenyl)-3-(trifluoromethyl)benzamide 54

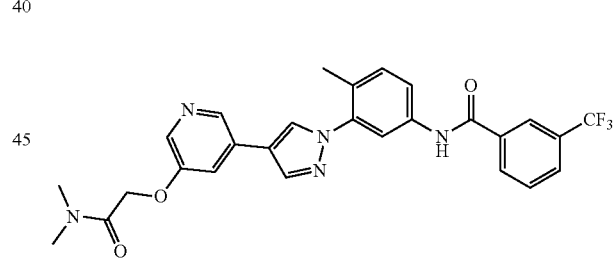

Compound 54 was synthesized by employing steps similar to those described in Example 41. Exact Mass (calculated): 523.18; MS(ESI) m/z (M+1)+: 524.18.

Example 55: N,N-dimethyl-2-((5-(1-(2-methyl-5-(2-(3-(trifluoromethyl)phenyl)acetylamino)phenyl)-1H-pyrazol-4-yl)pyrid-3-yl)oxy)acetamide 55

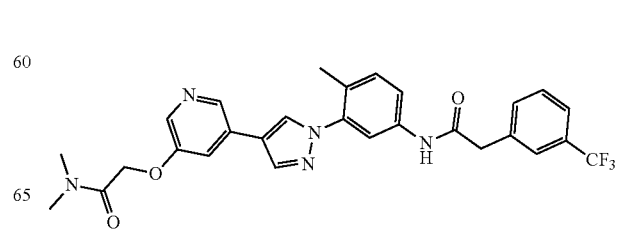

Compound 55 was synthesized by employing steps similar to those described in Example 41. Exact Mass (calculated): 537.19; MS(ESI) m/z (M+1)+: 538.19.

Example 56: 3-(2-cyanoprop-2-yl)-N-(4-methyl-3-(4-(4-((tetrahydro-2H-pyran-4-yl)oxy)pyrid-3-yl)-1H-pyrazol-1-yl)phenyl)benzamide 56

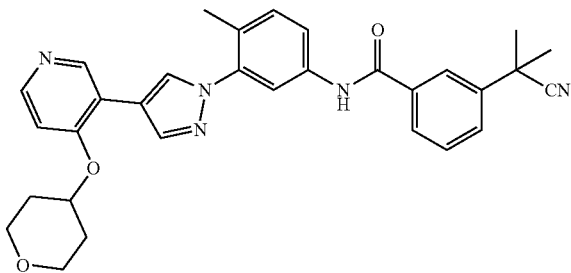 [SMILES: Cc1ccc(NC(=O)c2cccc(C(C)(C)C#N)c2)cc1-n1cc(-c2cnccc2OC2CCOCC2)cn1]

Compound 56 was synthesized by employing steps similar to those described in Example 41. Exact Mass (calculated): 521.24; MS(ESI) m/z (M+1)+: 522.24.

Example 57: N-(4-methyl-3-(4-(4-((tetrahydro-2H-pyran-4-yl)oxy)pyrid-3-yl)-1H-pyrazol-1-yl)phenyl)-3-(trifluoromethyl)benzamide 57

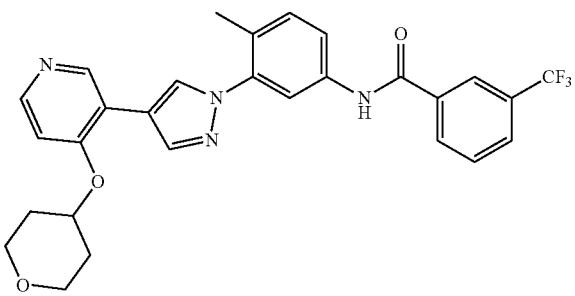 [SMILES: Cc1ccc(NC(=O)c2cccc(C(F)(F)F)c2)cc1-n1cc(-c2cnccc2OC2CCOCC2)cn1]

Compound 57 was synthesized by employing steps similar to those described in Example 41. Exact Mass (calculated): 522.19; MS(ESI) m/z (M+1)+: 523.20.

Example 58: N-(4-methyl-3-(4-(4-((tetrahydro-2H-pyran-4-yl)oxy)pyrid-3-yl)-1H-pyrazol-1-yl)phenyl)-2-(3-(trifluoromethyl)phenyl)acetamide 58

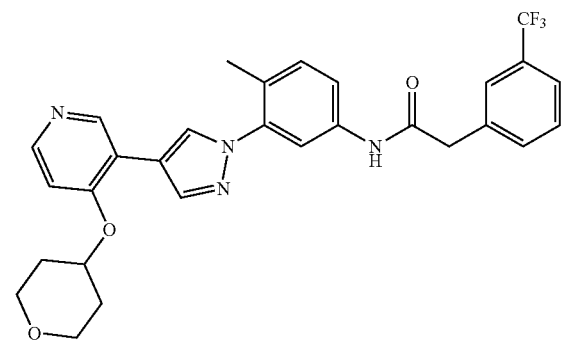 [SMILES: Cc1ccc(NC(=O)Cc2cccc(C(F)(F)F)c2)cc1-n1cc(-c2cnccc2OC2CCOCC2)cn1]

Compound 58 was synthesized by employing steps similar to those described in Example 41. Exact Mass (calculated): 536.20; MS(ESI) m/z (M+1)+: 537.20.

Example 59: 3-(2-cyanoprop-2-yl)-N-(3-(4-(4-(2-(dimethylamino)-2-oxoethoxy)pyrid-3-yl)-1H-pyrazol-1-yl)-4-methylphenyl)benzamide 59

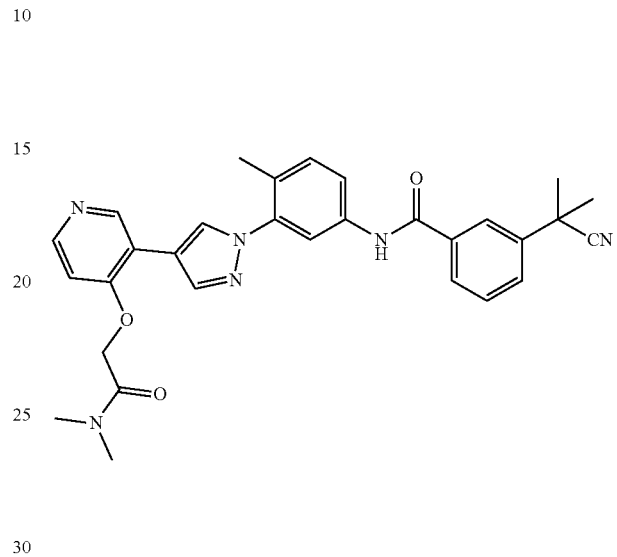

Compound 59 was synthesized by employing steps similar to those described in Example 41. Exact Mass (calculated): 522.23; MS(ESI) m/z (M+1)+: 523.23.

Example 60: N-(3-(4-(4-(2-(dimethylamino)-2-oxoethoxy)pyrid-3-yl)-1H-pyrazol-1-yl)-4-methylphenyl)-3-(trifluoromethyl)benzamide 60

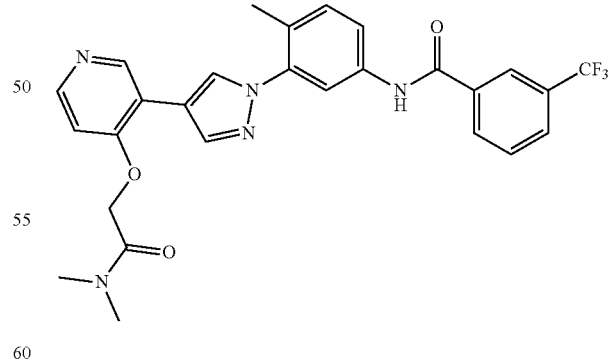

Compound 60 was synthesized by employing steps similar to those described in Example 41. Exact Mass (calculated): 522.23; MS(ESI) m/z (M+1)+: 523.23.

Example 61: N,N-dimethyl-2-((3-(1-(2-methyl-5-(2-(3-(trifluoromethyl)phenyl) acetylamino)phenyl)-1H-pyrazol-4-yl)pyrid-4-yl)oxy)acetamide 61

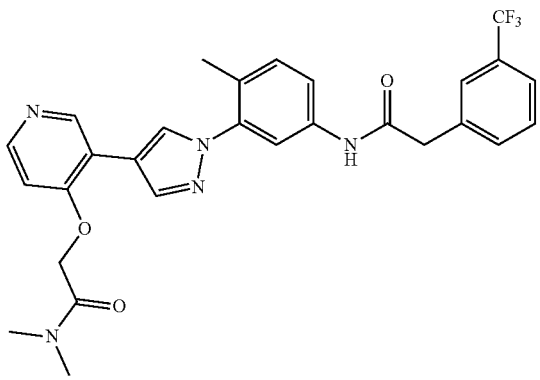 [SMILES: Cc1ccc(NC(=O)Cc2cccc(C(F)(F)F)c2)cc1-n1cc(-c2cnccc2OCC(=O)N(C)C)cn1]

Compound 61 was synthesized by employing steps similar to those described in Example 61. Exact Mass (calculated): 537.19; MS(ESI) m/z (M+1)+: 538.19.

Example 62: 3-(2-cyanoprop-2-yl)-N-(4-methyl-3-(4-(4-((tetrahydrofuran-3-yl)methoxy)pyrid-3-yl)-1H-pyrazol-1-yl)phenyl)benzamide 62

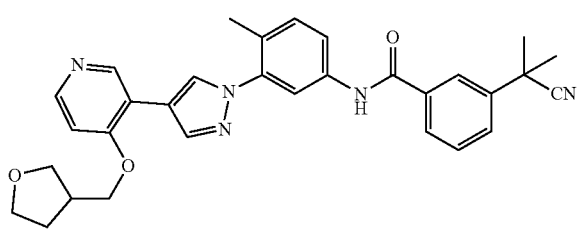 [SMILES: Cc1ccc(NC(=O)c2cccc(C(C)(C)C#N)c2)cc1-n1cc(-c2cnccc2OCC2CCOC2)cn1]

Compound 62 was synthesized by employing steps similar to those described in Example 41. Exact Mass (calculated): 521.24; MS(ESI) m/z (M+1)+: 522.24.

Example 63: N-(4-methyl-3-(4-(4-((tetrahydrofuran-3-yl)methoxy)pyrid-3-yl)-1H-pyrazol-1-yl)phenyl)-3-(trifluoromethyl)benzamide 63

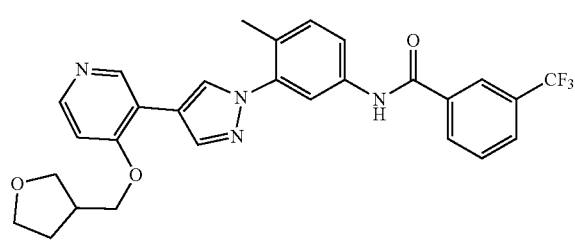 [SMILES: Cc1ccc(NC(=O)c2cccc(C(F)(F)F)c2)cc1-n1cc(-c2cnccc2OCC2CCOC2)cn1]

Compound 63 was synthesized by employing steps similar to those described in Example 41. Exact Mass (calculated): 522.18; MS(ESI) m/z (M+1)+: 523.18.

Example 64: N-(4-methyl-3-(4-(4-((tetrahydrofuran-3-yl)methoxy)pyrid-3-yl)-1H-pyrazol-1-yl)phenyl)-2-(3-(trifluoromethyl)phenyl)acetamide 64

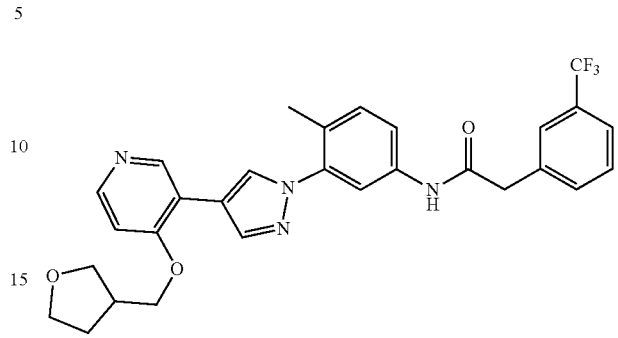

Compound 64 was synthesized by employing steps similar to those described in Example 41. Exact Mass (calculated): 536.20; MS(ESI) m/z (M+1)+: 537.20.

Example 65: 3-(2-cyanoprop-2-yl)-N-(4-methyl-3-(4-(5-((tetrahydrofuran-3-yl)methoxy)pyrid-3-yl)-1H-pyrazol-1-yl)phenyl)benzamide 65

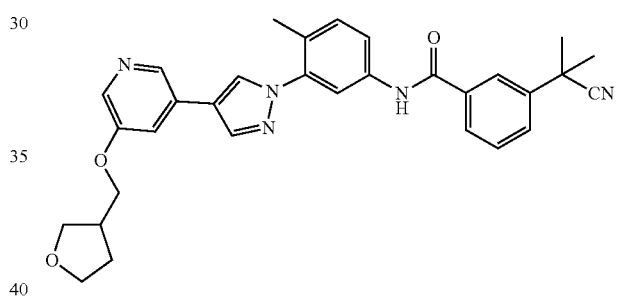

Compound 65 was synthesized by employing steps similar to those described in Example 41. Exact Mass (calculated): 521.24; MS(ESI) m/z (M+1)+: 522.24.

Example 66: N-(4-methyl-3-(4-(5-((tetrahydrofuran-3-yl)methoxy)pyrid-3-yl)-1H-pyrazol-1-yl)phenyl)-3-(trifluoromethyl)benzamide 66

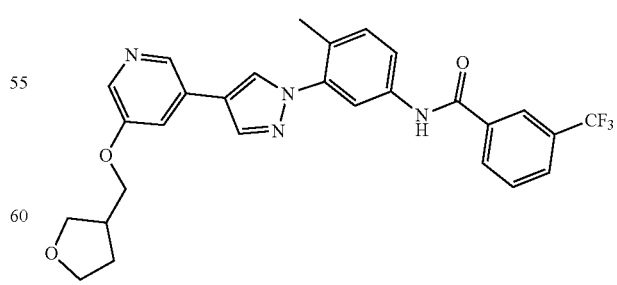

Compound 66 was synthesized by employing steps similar to those described in Example 41. Exact Mass (calculated): 522.18; MS(ESI) m/z (M+1)+: 523.18.

Example 67: N-(4-methyl-3-(4-(5-((tetrahydrofuran-3-yl)methoxy)pyrid-3-yl)-1H-pyrazol-1-yl)phenyl)-2-(3-(trifluoromethyl)phenyl)acetamide 67

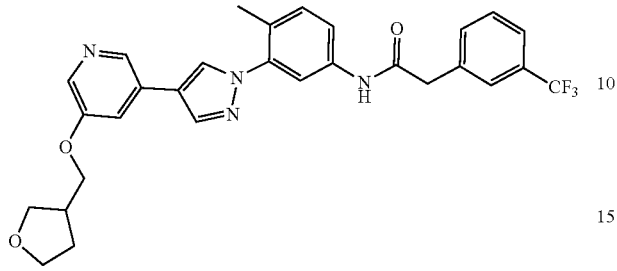

Compound 67 was synthesized by employing steps similar to those described in Example 41. Exact Mass (calculated): 536.20; MS(ESI) m/z (M+1)+: 537.20.

Example 68: 3-(2-cyanoprop-2-yl)-N-(4-methyl-3-(4-(4-((tetrahydrofuran-3-yl)oxy)pyrid-3-yl)-1H-pyrazol-1-yl)phenyl)benzamide 68

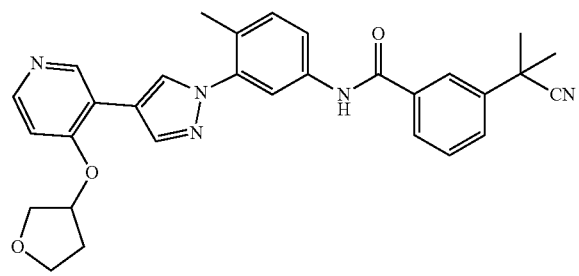 [SMILES: Cc1ccc(NC(=O)c2cccc(C(C)(C)C#N)c2)cc1-n1cc(-c2cnccc2OC2CCOC2)cn1]

Compound 68 was synthesized by employing steps similar to those described in Example 41. Exact Mass (calculated): 507.22; MS(ESI) m/z (M+1)+: 508.22.

Example 69: N-(4-methyl-3-(4-(4-((tetrahydrofuran-3-yl)oxy)pyrid-3-yl)-1H-pyrazol-1-yl)phenyl)-3-(trifluoromethyl)benzamide 69

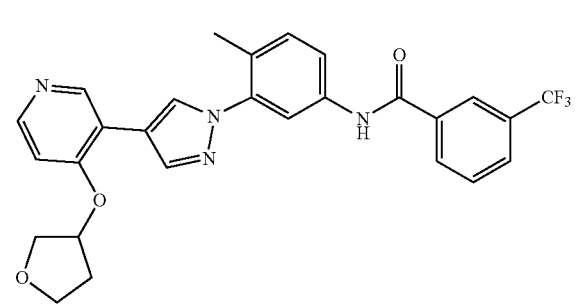 [SMILES: Cc1ccc(NC(=O)c2cccc(C(F)(F)F)c2)cc1-n1cc(-c2cnccc2OC2CCOC2)cn1]

Compound 69 was synthesized by employing steps similar to those described in Example 41. Exact Mass (calculated): 508.17; MS(ESI) m/z (M+1)+: 509.17.

Example 70: N-(4-methyl-3-(4-(4-((tetrahydrofuran-3-yl)oxy)pyrid-3-yl)-1H-pyrazol-1-yl)phenyl)-2-(3-(trifluoromethyl)phenyl)acetamide 70

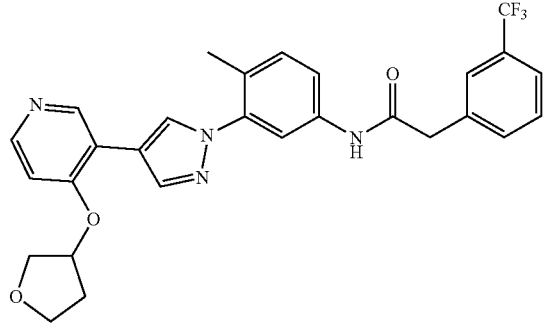 [SMILES: Cc1ccc(NC(=O)Cc2cccc(C(F)(F)F)c2)cc1-n1cc(-c2cnccc2OC2CCOC2)cn1]

Compound 70 was synthesized by employing steps similar to those described in Example 41. Exact Mass (calculated): 522.18; MS(ESI) m/z (M+1)+: 523.18.

Example 71: N-(3-(4-([3,4'-bipyrid]-5-yl)-1H-pyrazol-1-yl)-4-methylphenyl)-2-(3-(trifluoromethyl)phenyl)acetamide 71

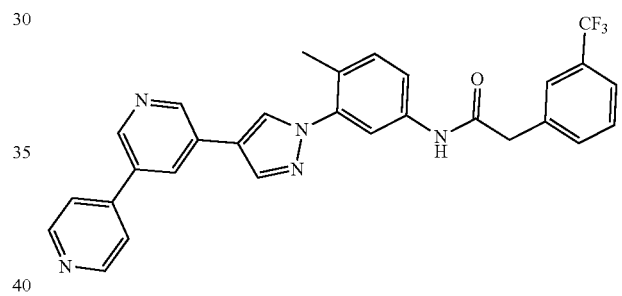

Compound 71 was synthesized by employing steps similar to those described in Example 1. Exact Mass (calculated): 513.17; MS(ESI) m/z (M+1)+: 514.17.

Example 72: 3-(2-cyanoprop-2-yl)-N-(4-methyl-3-(4-(4-((tetrahydro-2H-pyran-4-yl)methoxy)pyrid-3-yl)-1H-pyrazol-1-yl)phenyl)benzamide 72

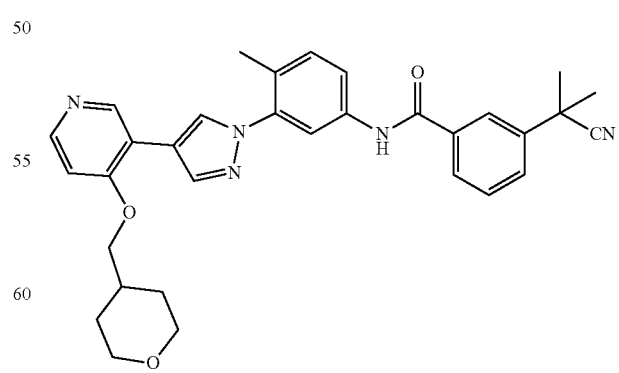

Compound 72 was synthesized by employing steps similar to those described in Example 41. Exact Mass (calculated): 535.25; MS(ESI) m/z (M+1)+: 536.25.

Example 73: 3-(1-cyanoethyl)-N-(4-methyl-3-(4-(4-((tetrahydro-2H-pyran-4-yl)methoxy)pyrid-3-yl)-1H-pyrazol-1-yl)phenyl)benzamide 73

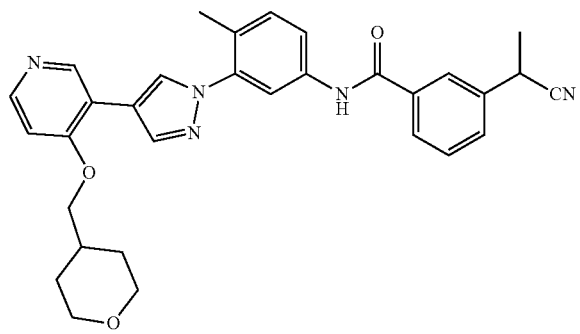 [SMILES: Cc1ccc(NC(=O)c2cccc(C(C)C#N)c2)cc1-n1cc(-c2cnccc2OCC2CCOCC2)cn1]

Compound 73 was synthesized by employing steps similar to those described in Example 41. Exact Mass (calculated): 521.24; MS(ESI) m/z (M+1)+: 522.25.

Example 74: N-(4-methyl-3-(4-(4-((tetrahydro-2H-pyran-4-yl)methoxy)pyrid-3-yl)-1H-pyrazol-1-yl)phenyl)-3-(trifluoromethyl)benzamide 74

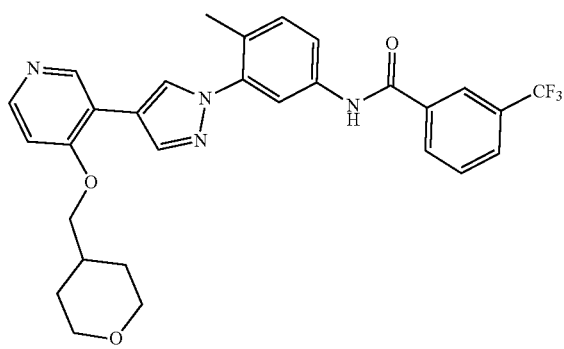 [SMILES: Cc1ccc(NC(=O)c2cccc(C(F)(F)F)c2)cc1-n1cc(-c2cnccc2OCC2CCOCC2)cn1]

Compound 74 was synthesized by employing steps similar to those described in Example 41. Exact Mass (calculated): 536.20; MS(ESI) m/z (M+1)+: 537.20.

Example 75: N-(4-methyl-3-(4-(4-((tetrahydro-2H-pyran-4-yl)methoxy)pyrid-3-yl)-1H-pyrazol-1-yl)phenyl)-2-(3-(trifluoromethyl)phenyl)acetamide 75

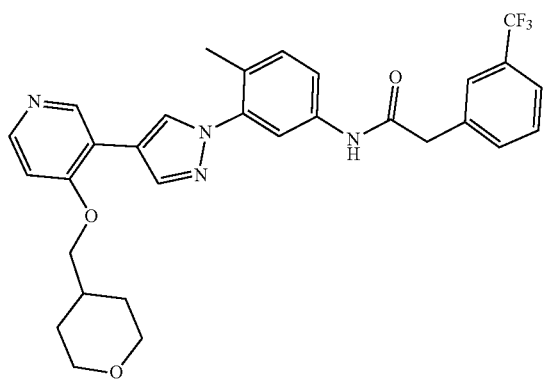 [SMILES: Cc1ccc(NC(=O)Cc2cccc(C(F)(F)F)c2)cc1-n1cc(-c2cnccc2OCC2CCOCC2)cn1]

Compound 75 was synthesized by employing steps similar to those described in Example 41. Exact Mass (calculated): 550.21; MS(ESI) m/z (M+1)+: 551.21.

Example 76: 3-(2-cyanoprop-2-yl)-N-(4-methyl-3-(4-(4-(2-morpholinoethoxy)pyrid-3-yl)-1H-pyrazol-1-yl)phenyl)benzamide 76

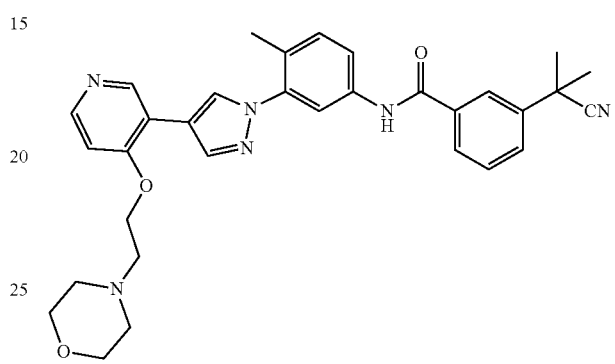

Compound 76 was synthesized by employing steps similar to those described in Example 41. Exact Mass (calculated): 550.26; MS(ESI) m/z (M+1)+: 551.26.

Example 77: 3-(1-cyanoethyl)-N-(4-methyl-3-(4-(4-(2-morpholinoethoxy)pyrid-3-yl)-1H-pyrazol-1-yl)phenyl)benzamide 77

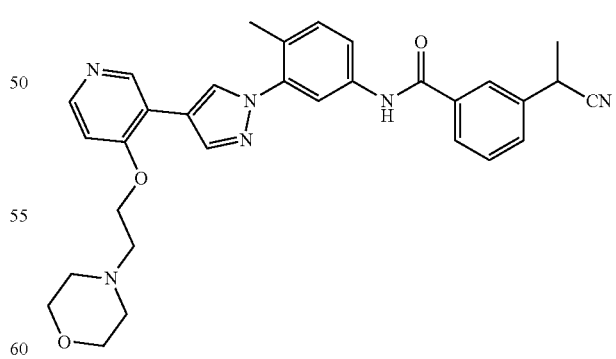

Compound 77 was synthesized by employing steps similar to those described in Example 41. Exact Mass (calculated): 536.25; MS(ESI) m/z (M+1)+: 537.25.

Example 78: N-(4-methyl-3-(4-(4-(2-morpholino ethoxy)pyrid-3-yl)-1H-pyrazol-1-yl)phenyl)-2-(3-(trifluoromethyl)phenyl)acetamide 78

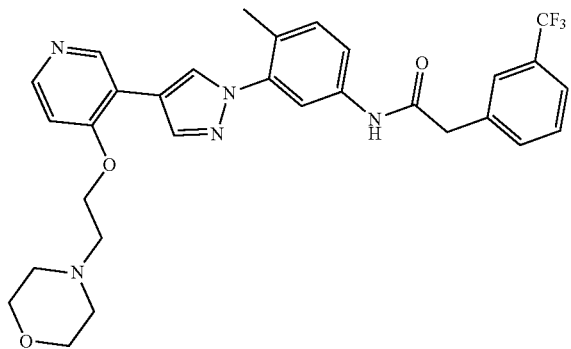 [SMILES: Cc1ccc(NC(=O)Cc2cccc(C(F)(F)F)c2)cc1-n1cc(-c2cnccc2OCCN2CCOCC2)cn1]

Compound 78 was synthesized by employing steps similar to those described in Example 41. Exact Mass (calculated): 565.23; MS(ESI) m/z (M+1)+: 566.23.

Example 79: 3-(2-cyanoprop-2-yl)-N-(4-methyl-3-(4-(4-(oxetan-3-yloxy)pyrid-3-yl)-1H-pyrazol-1-yl)phenyl)benzamide 79

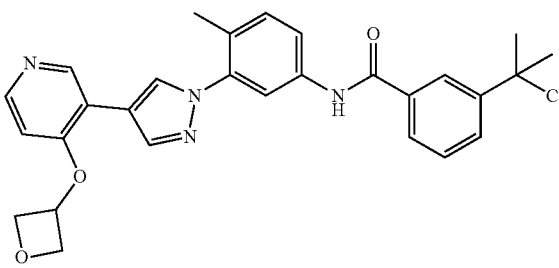

Compound 79 was synthesized by employing steps similar to those described in Example 41. Exact Mass (calculated): 493.21; MS(ESI) m/z (M+1)+: 494.21.

Example 80: 3-(1-cyanoethyl)-N-(4-methyl-3-(4-(4-(oxetan-3-yloxy)pyrid-3-yl)-1H-pyrazol-1-yl)phenyl)benzamide 80

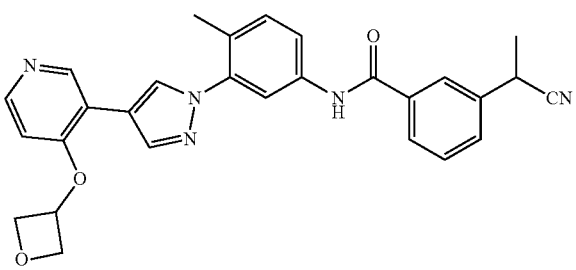 [SMILES: Cc1ccc(NC(=O)c2cccc(C(C)C#N)c2)cc1-n1cc(-c2cnccc2OC2COC2)cn1]

Compound 80 was synthesized by employing steps similar to those described in Example 41. Exact Mass (calculated): 479.19; MS(ESI) m/z (M+1)+: 480.19.

Example 81: N-(4-methyl-3-(4-(4-(2-morpholino-ethoxy)pyrid-3-yl)-1H-pyrazol-1-yl)phenyl)-3-(trifluoromethyl)benzamide 81

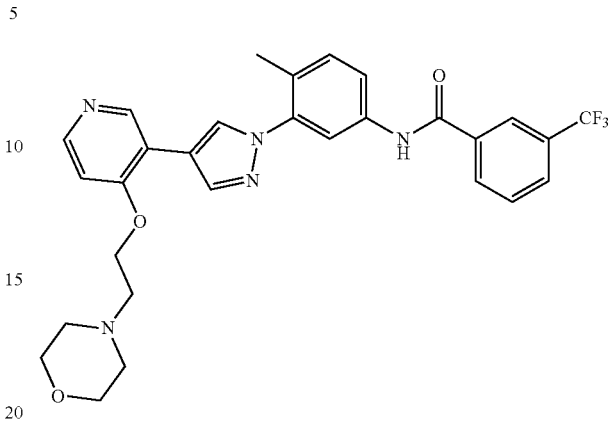

Compound 81 was synthesized by employing steps similar to those described in Example 41. Exact Mass (calculated): 521.21; MS(ESI) m/z (M+1)+: 522.22.

Example 82: N-(4-methyl-3-(4-(4-(oxetan-3-yloxy)pyrid-3-yl)-1H-pyrazol-1-yl)phenyl)-3-(trifluoromethyl)benzamide 82

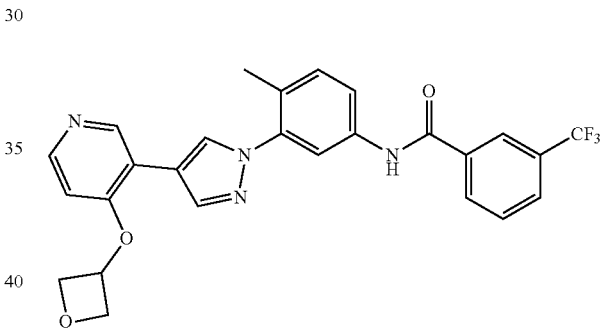

Compound 82 was synthesized by employing steps similar to those described in Example 41. Exact Mass (calculated): 494.15; MS(ESI) m/z (M+1)+: 495.15.

Example 83: N-(4-methyl-3-(4-(4-(oxetan-3-yloxy) pyrid-3-yl)-1H-pyrazol-1-yl)phenyl)-2-(3-(trifluoromethyl)phenyl)acetamide 83

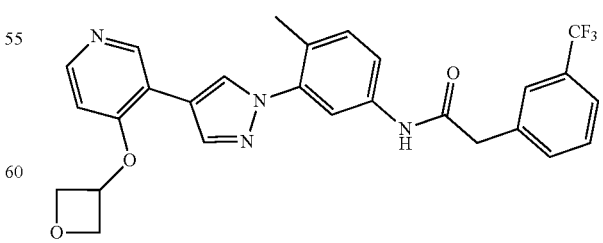

Compound 83 was synthesized by employing steps similar to those described in Example 41. Exact Mass (calculated): 508.17; MS(ESI) m/z (M+1)+: 509.18.

Example 84: 3-(2-cyanoprop-2-yl)-N-(4-methyl-3-(4-(5-(oxetan-3-yloxy)pyrid-3-yl)-1H-pyrazol-1-yl)phenyl)benzamide 84

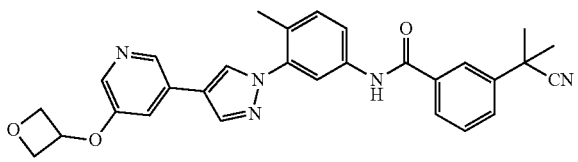 [SMILES: Cc1ccc(NC(=O)c2cccc(C(C)(C)C#N)c2)cc1-n1cc(-c2cncc(OC3COC3)c2)cn1]

Compound 84 was synthesized by employing steps similar to those described in Example 41. Exact Mass (calculated): 493.21; MS(ESI) m/z (M+1)+: 494.21.

Example 85: 3-(1-cyanoethyl)-N-(4-methyl-3-(4-(5-(oxetan-3-yloxy)pyrid-3-yl)-1H-pyrazol-1-yl)phenyl)benzamide 85

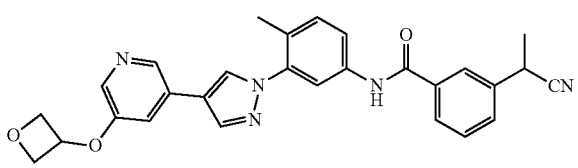 [SMILES: Cc1ccc(NC(=O)c2cccc(C(C)C#N)c2)cc1-n1cc(-c2cncc(OC3COC3)c2)cn1]

Compound 85 was synthesized by employing steps similar to those described in Example 41. Exact Mass (calculated): 479.19; MS(ESI) m/z (M+1)+: 480.19.

Example 86: N-(4-methyl-3-(4-(5-(oxetan-3-yloxy)pyrid-3-yl)-1H-pyrazol-1-yl)phenyl)-2-(3-(trifluoromethyl)phenyl)acetamide 86

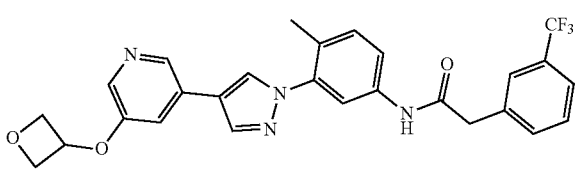 [SMILES: Cc1ccc(NC(=O)Cc2cccc(C(F)(F)F)c2)cc1-n1cc(-c2cncc(OC3COC3)c2)cn1]

Compound 86 was synthesized by employing steps similar to those described in Example 41. Exact Mass (calculated): 508.17; MS(ESI) m/z (M+1)+: 509.17.

Example 87: 3-(2-cyanoprop-2-yl)-N-(4-methyl-3-(4-(4-(oxetan-3-ylmethoxy)pyrid-3-yl)-1H-pyrazol-1-yl)phenyl)benzamide 87

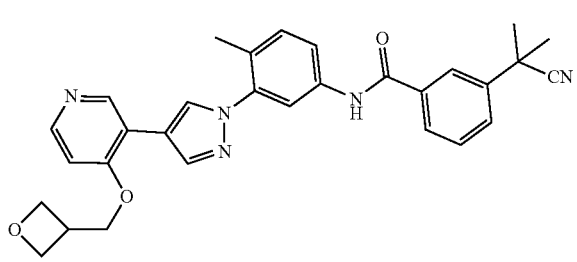 [SMILES: Cc1ccc(NC(=O)c2cccc(C(C)(C)C#N)c2)cc1-n1cc(-c2cnccc2OCC2COC2)cn1]

Compound 87 was synthesized by employing steps similar to those described in Example 41. Exact Mass (calculated): 507.22; MS(ESI) m/z (M+1)+: 508.22.

Example 88: 3-(1-cyanoethyl)-N-(4-methyl-3-(4-(4-(oxetan-3-ylmethoxy)pyrid-3-yl)-1H-pyrazol-1-yl)phenyl)benzamide 88

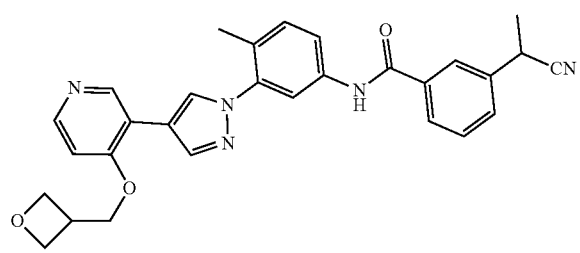 [SMILES: Cc1ccc(NC(=O)c2cccc(C(C)C#N)c2)cc1-n1cc(-c2cnccc2OCC2COC2)cn1]

Compound 88 was synthesized by employing steps similar to those described in Example 41. Exact Mass (calculated): 493.21; MS(ESI) m/z (M+1)+: 494.21.

Example 89: N-(4-methyl-3-(4-(4-(oxetan-3-ylmethoxy)pyrid-3-yl)-1H-pyrazol-1-yl)phenyl)-3-(trifluoromethyl)benzamide 89

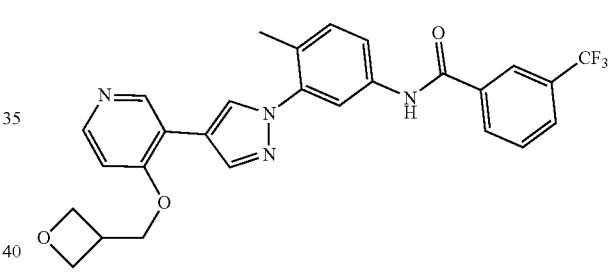

Compound 89 was synthesized by employing steps similar to those described in Example 41. Exact Mass (calculated): 508.17; MS(ESI) m/z (M+1)+: 509.17.

Example 90: N-(4-methyl-3-(4-(4-(oxetan-3-ylmethoxy)pyrid-3-yl)-1H-pyrazol-1-yl)phenyl)-2-(3-(trifluoromethyl)phenyl)acetamide 90

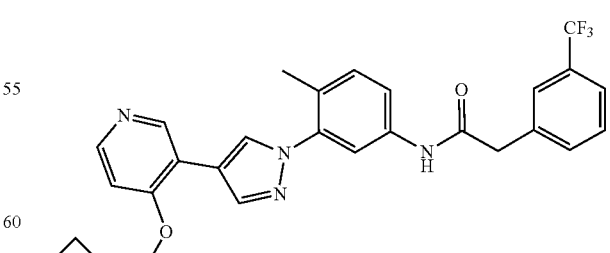

Compound 90 was synthesized by employing steps similar to those described in Example 41. Exact Mass (calculated): 522.18; MS(ESI) m/z (M+1)+: 523.18.

Example 91: N-(3-(4-(4-(benzyloxy)pyrid-3-yl)-1H-pyrazol-1-yl)-4-methylphenyl)-3-(2-cyanoprop-2-yl)benzamide 91

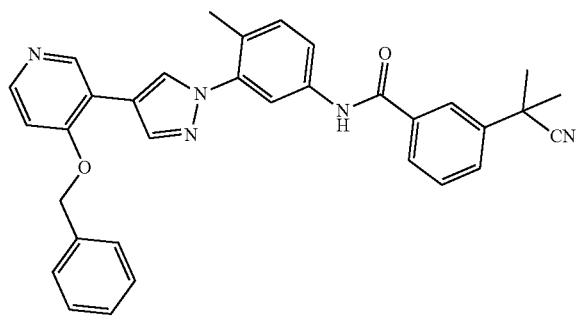 [SMILES: Cc1ccc(NC(=O)c2cccc(C(C)(C)C#N)c2)cc1-n1cc(-c2cnccc2OCc2ccccc2)cn1]

Compound 91 was synthesized by employing steps similar to those described in Example 41. Exact Mass (calculated): 527.23; MS(ESI) m/z (M+1)+: 528.24.

Example 92: N-(3-(4-(4-(benzyloxy)pyrid-3-yl)-1H-pyrazol-1-yl)-4-methylphenyl)-3-(trifluoromethyl)benzamide 92

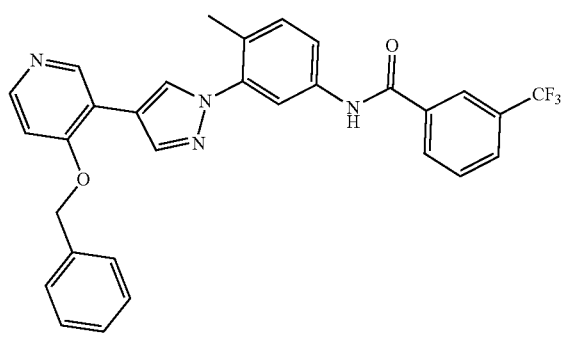 [SMILES: Cc1ccc(NC(=O)c2cccc(C(F)(F)F)c2)cc1-n1cc(-c2cnccc2OCc2ccccc2)cn1]

Compound 92 was synthesized by employing steps similar to those described in Example 41. Exact Mass (calculated): 528.17; MS(ESI) m/z (M+1)+: 529.17.

Example 93: 3-(2-cyanoprop-2-yl)-N-(4-methyl-3-(4-(4-((tetrahydrofuran-2-yl)methoxy)pyrid-3-yl)-1H-pyrazol-1-yl)phenyl)benzamide 93

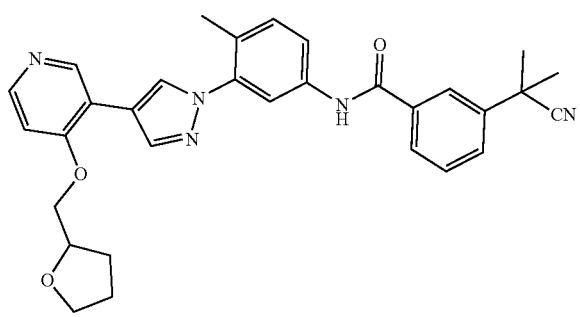 [SMILES: Cc1ccc(NC(=O)c2cccc(C(C)(C)C#N)c2)cc1-n1cc(-c2cnccc2OCC2CCCO2)cn1]

Compound 93 was synthesized by employing steps similar to those described in Example 41. Exact Mass (calculated): 521.24; MS(ESI) m/z (M+1)+: 522.24.

Example 94: 3-(1-cyanoethyl)-N-(4-methyl-3-(4-(4-((tetrahydrofuran-2-yl)methoxy)pyrid-3-yl)-1H-pyrazol-1-yl)phenyl)benzamide 94

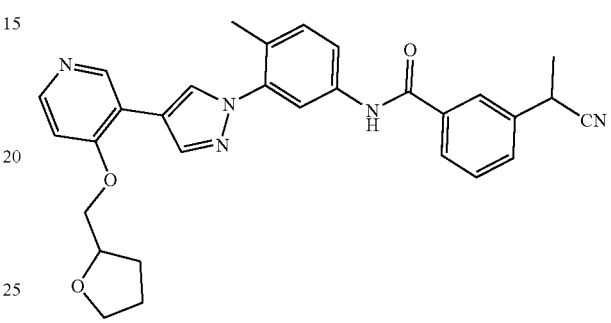

Compound 94 was synthesized by employing steps similar to those described in Example 41. Exact Mass (calculated): 507.22; MS(ESI) m/z (M+1)+: 508.22.

Example 95: N-(4-methyl-3-(4-(4-((tetrahydrofuran-2-yl)methoxy)pyrid-3-yl)-1H-pyrazol-1-yl)phenyl)-3-(trifluoromethyl)benzamide 95

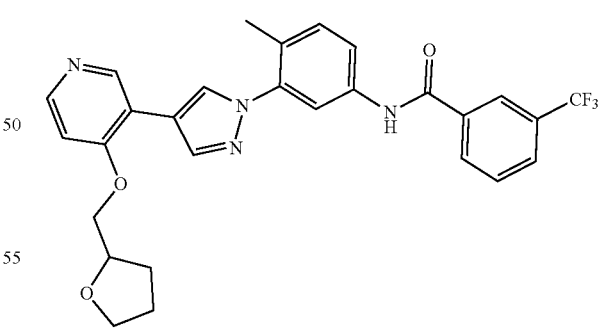

Compound 95 was synthesized by employing steps similar to those described in Example 41. Exact Mass (calculated): 522.18; MS(ESI) m/z (M+1)+: 523.18.

Example 96: N-(4-methyl-3-(4-(4-((tetrahydrofuran-2-yl)methoxy)pyrid-3-yl)-1H-pyrazol-1-yl)phenyl)-2-(3-(trifluoromethyl)phenyl)acetamide 96

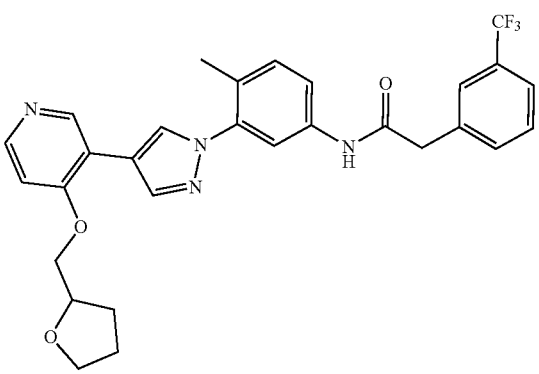 [SMILES: Cc1ccc(NC(=O)Cc2cccc(C(F)(F)F)c2)cc1-n1cc(-c2cnccc2OCC2CCCO2)cn1]

Compound 96 was synthesized by employing steps similar to those described in Example 41. Exact Mass (calculated): 536.20; MS(ESI) m/z (M+1)+: 537.20.

Example 97: 3-(2-cyanoprop-2-yl)-N-(3-(4-(4-(cyclopentylmethoxy)pyrid-3-yl)-1H-pyrazol-1-yl)-4-methylphenyl)benzamide 97

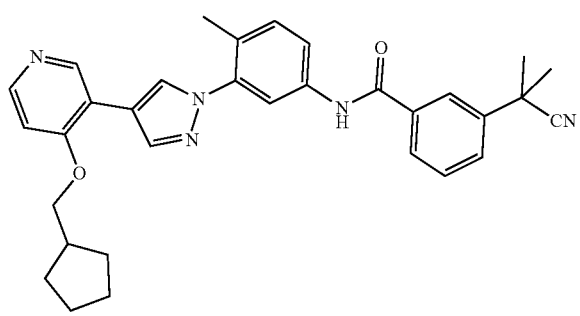 [SMILES: Cc1ccc(NC(=O)c2cccc(C(C)(C)C#N)c2)cc1-n1cc(-c2cnccc2OCC2CCCC2)cn1]

Compound 97 was synthesized by employing steps similar to those described in Example 41. Exact Mass (calculated): 519.26; MS(ESI) m/z (M+1)+: 520.26.

Example 98: 3-(1-cyanoethyl)-N-(3-(4-(4-(cyclopentylmethoxy)pyrid-3-yl)-1H-pyrazol-1-yl)-4-methylphenyl)benzamide 98

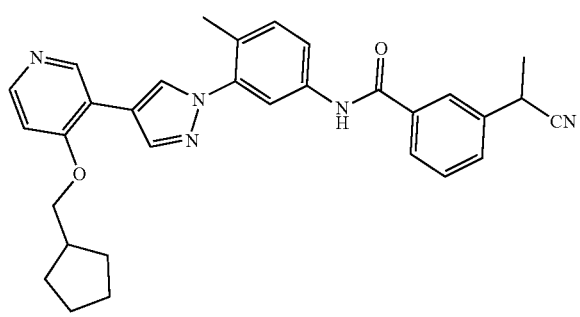 [SMILES: Cc1ccc(NC(=O)c2cccc(C(C)C#N)c2)cc1-n1cc(-c2cnccc2OCC2CCCC2)cn1]

Compound was synthesize by employing steps similar to those described in Example 41. Exact Mass (calculated): 505.24; MS(ESI) m/z (M+1)+: 506.24.

Example 99: N-(3-(4-(4-(cyclopentylmethoxy)pyrid-3-yl)-1H-pyrazol-1-yl)-4-methylphenyl)-3-(trifluoromethyl)benzamide 99

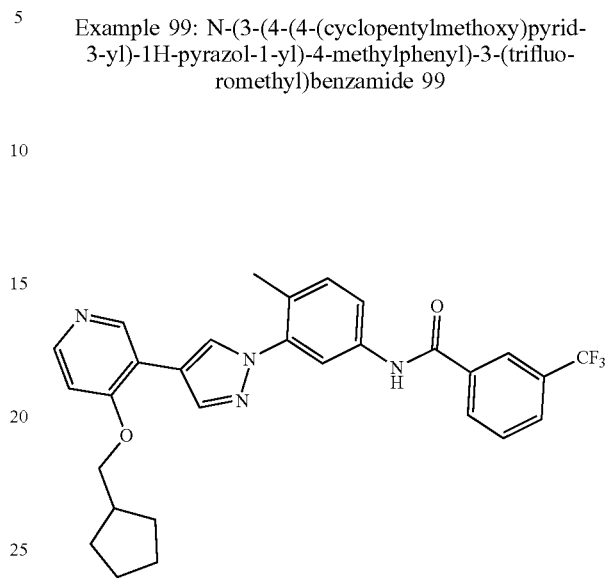

Compound 99 was synthesized by employing steps similar to those described in Example 41. Exact Mass (calculated): 520.20; MS(ESI) m/z (M+1)+: 521.20.

Example 100: N-(3-(4-(4-(cyclopentylmethoxy)pyrid-3-yl)-1H-pyrazol-1-yl)-4-methylphenyl)-2-(3-(trifluoromethyl)phenyl)acetamide 100

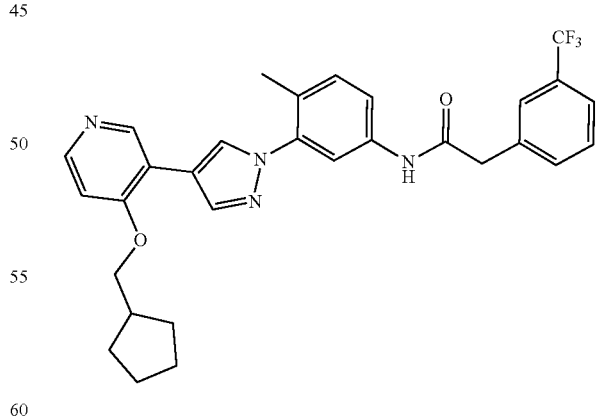

Compound 100 was synthesized by employing steps similar to those described in Example 41. Exact Mass (calculated): 534.22; MS(ESI) m/z (M+1)+: 535.22.

Example 101: 3-(2-cyanoprop-2-yl)-N-(3-(4-(4-(furan-3-ylmethoxy)pyrid-3-yl)-1H-pyrazol-1-yl)-4-methylphenyl)benzamide 101

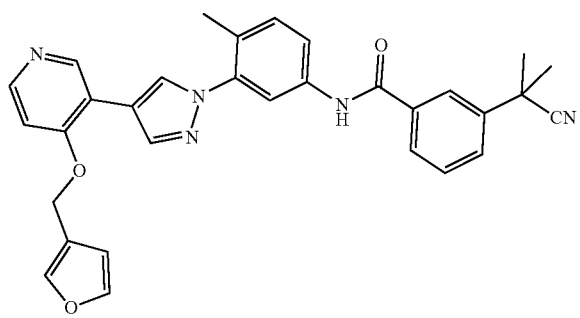 [SMILES: Cc1ccc(NC(=O)c2cccc(C(C)(C)C#N)c2)cc1-n1cc(-c2cnccc2OCc2ccoc2)cn1]

Compound 101 was synthesized by employing steps similar to those described in Example 41. Exact Mass (calculated): 517.21; MS(ESI) m/z (M+1)+: 518.21.

Example 102: 3-(1-cyanoethyl)-N-(3-(4-(4-(furan-3-ylmethoxy)pyrid-3-yl)-1H-pyrazol-1-yl)-4-methylphenyl)benzamide 102

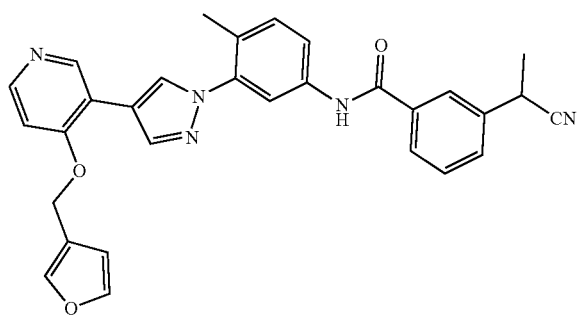 [SMILES: Cc1ccc(NC(=O)c2cccc(C(C)C#N)c2)cc1-n1cc(-c2cnccc2OCc2ccoc2)cn1]

Compound 102 was synthesized by employing steps similar to those described in Example 41. Exact Mass (calculated): 503.19; MS(ESI) m/z (M+1)+: 504.19.

Example 103: N-(3-(4-(4-(furan-3-ylmethoxy)pyrid-3-yl)-1H-pyrazol-1-yl)-4-methylphenyl)-3-(trifluoromethyl)benzamide 103

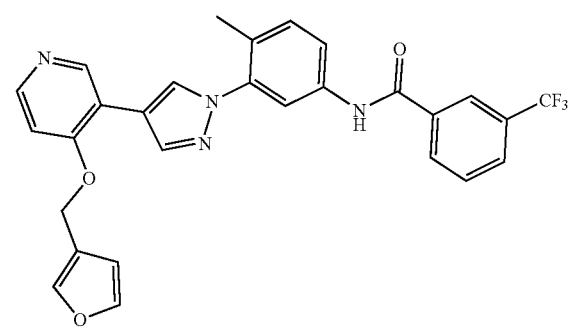 [SMILES: Cc1ccc(NC(=O)c2cccc(C(F)(F)F)c2)cc1-n1cc(-c2cnccc2OCc2ccoc2)cn1]

Compound 103 was synthesized by employing steps similar to those described in Example 41. Exact Mass (calculated): 518.15; MS(ESI) m/z (M+1)+: 519.15.

Example 104: N-(3-(4-(4-(furan-3-ylmethoxy)pyrid-3-yl)-1H-pyrazol-1-yl)-4-methylphenyl)-2-(3-(trifluoromethyl)phenyl)acetamide 104

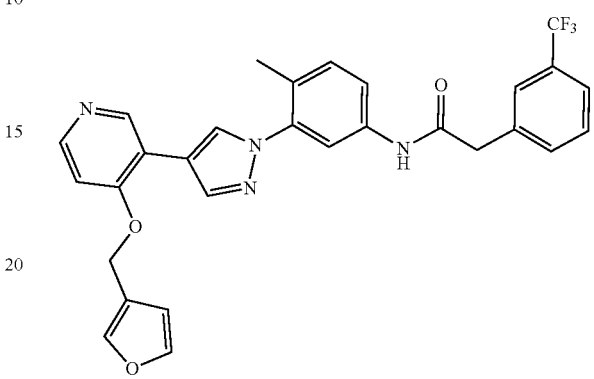

Compound 104 was synthesized by employing steps similar to those described in Example 41. Exact Mass (calculated): 532.17; MS(ESI) m/z (M+1)+: 533.17.

Example 105: (S)-3-(2-cyanoprop-2-yl)-N-(4-methyl-3-(4-(4-((tetrahydrofuran-3-yl)oxy)pyrid-3-yl)-1H-pyrazol-1-yl)phenyl)benzamide 105

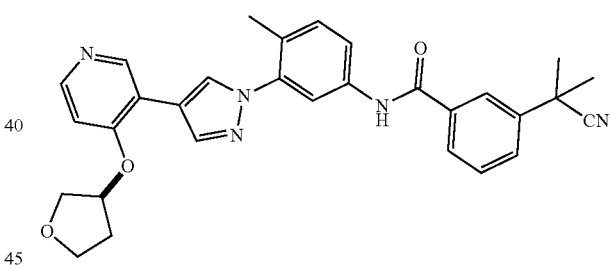

Compound 105 was synthesized by employing steps similar to those described in Example 41. Exact Mass (calculated): 507.22; MS(ESI) m/z (M+1)+: 508.22.

Example 106: (R)-3-(2-cyanoprop-2-yl)-N-(4-methyl-3-(4-(4-((tetrahydrofuran-3-yl)oxy)pyrid-3-yl)-1H-pyrazol-1-yl)phenyl)benzamide 106

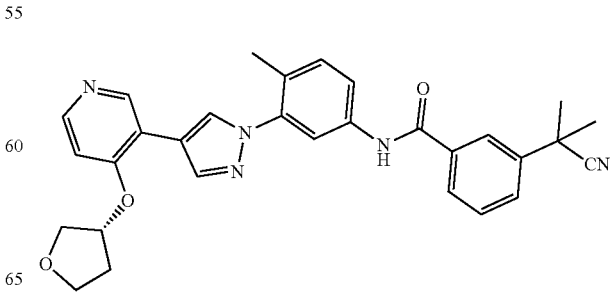

Compound 106 was synthesized by employing steps similar to those described in Example 41. Exact Mass (calculated): 507.22; MS(ESI) m/z (M+1)+: 508.22.

Example 107: (S)—N-(4-methyl-3-(4-(4-((tetrahydrofuran-3-yl)oxy)pyrid-3-yl)-1H-pyrazol-1-yl)phenyl)-3-(trifluoromethyl)benzamide 107

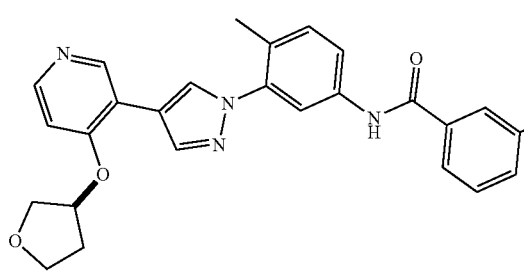

Compound 107 was synthesized by employing steps similar to those described in Example 41. Exact Mass (calculated): 508.17; MS(ESI) m/z (M+1)+: 509.17.

Example 108: (R)—N-(4-methyl-3-(4-(4-((tetrahydrofuran-3-yl)oxy)pyrid-3-yl)-1H-pyrazol-1-yl)phenyl)-3-(trifluoromethyl)benzamide 108

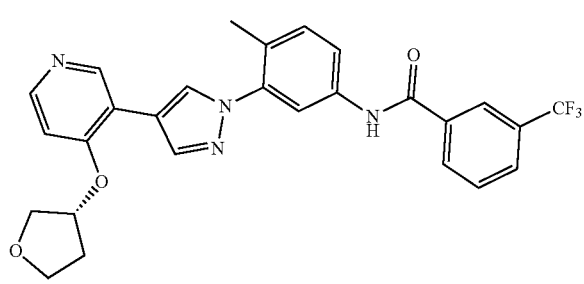 [SMILES: Cc1ccc(NC(=O)c2cccc(C(F)(F)F)c2)cc1-n1cc(-c2cnccc2O[C@@H]2CCOC2)cn1]

Compound 108 was synthesized by employing steps similar to those described in Example 41. Exact Mass (calculated): 508.17; MS(ESI) m/z (M+1)+: 509.17.

Example 109: 3-(2-cyanoprop-2-yl)-N-(4-methyl-3-(4-(5-morpholino pyrid-3-yl)-1H-imidazol-1-yl)phenyl)benzamide 109

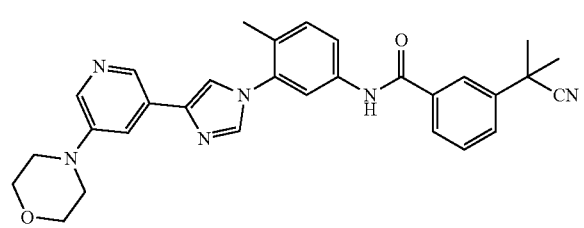 [SMILES: Cc1ccc(NC(=O)c2cccc(C(C)(C)C#N)c2)cc1-n1cnc(-c2cncc(N3CCOCC3)c2)c1]

Compound 109 was synthesized by employing steps similar to those described in Example 1. Exact Mass (calculated): 506.24; MS(ESI) m/z (M+1)+: 507.24.

Example 110: N-(4-methyl-3-(4-(5-(oxetan-3-yloxy)pyrid-3-yl)-1H-pyrazol-1-yl)phenyl)-3-(trifluoromethyl)benzamide 110

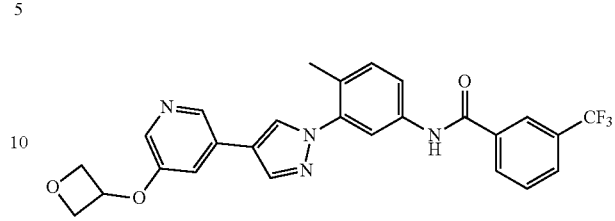

Compound 110 was synthesized by employing steps similar to those described in Example 41. Exact Mass (calculated): 506.24; MS(ESI) m/z (M+1)+: 507.24.

Example 111: N-(4-methyl-3-(4-(5-morpholinopyrid-3-yl)-1H-imidazol-1-yl)phenyl)-3-(trifluoromethyl)benzamide 111

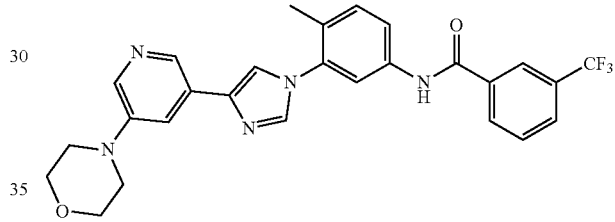

Compound 111 was synthesized by employing steps similar to those described in Example 1. Exact Mass (calculated): 507.18; MS(ESI) n/z (M+1)+: 508.18.

Example 112: (S)-3-(2-cyanoprop-2-yl)-N-(4-methyl-3-(4-(4-((tetrahydrofuran-3-yl)methoxy)pyrid-3-yl)-1H-pyrazol-1-yl)phenyl)benzamide 112

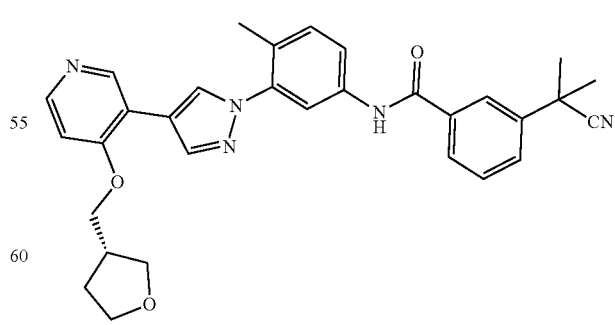

Compound 112 was synthesized by employing steps similar to those described in Example 41. Exact Mass (calculated): 521.24; MS(ESI) m/z (M+1)+: 522.24.

Example 113: (R)-3-(2-cyanoprop-2-yl)-N-(4-methyl-3-(4-(4-((tetrahydrofuran-3-yl)methoxy)pyrid-3-yl)-1H-pyrazol-1-yl)phenyl)benzamide 113

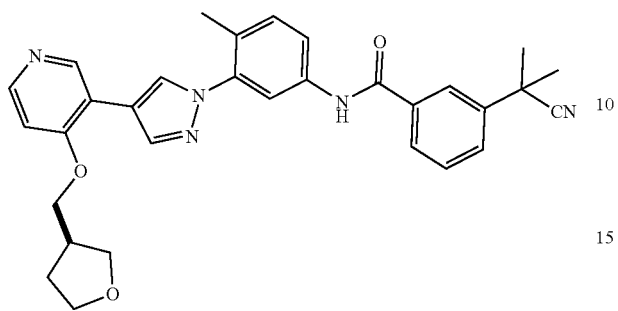

Compound 113 was synthesized by employing steps similar to those described in Example 41. Exact Mass (calculated): 521.24; MS(ESI) m/z (M+1)+: 522.24.

Example 114: (S)—N-(4-methyl-3-(4-(4-((tetrahydrofuran-3-yl)methoxy)pyrid-3-yl)-1H-pyrazol-1-yl)phenyl)-3-(trifluoromethyl)benzamide 114

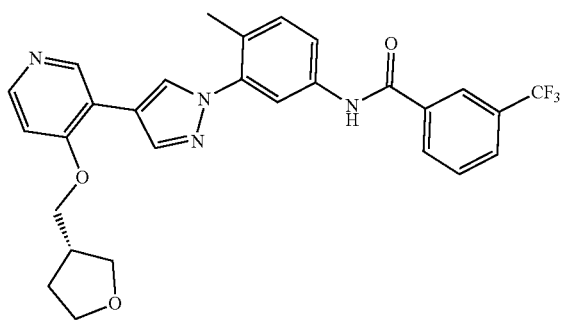 [SMILES: Cc1ccc(NC(=O)c2cccc(C(F)(F)F)c2)cc1-n1cc(-c2cnccc2OC[C@H]2CCOC2)cn1]

Compound 114 was synthesized by employing steps similar to those described in Example 41. Exact Mass (calculated): 522.18; MS(ESI) m/z (M+1)+: 523.18.

Example 115: (R)—N-(4-methyl-3-(4-(4-((tetrahydrofuran-3-yl)methoxy)pyrid-3-yl)-1H-pyrazol-1-yl)phenyl)-3-(trifluoromethyl)benzamide 115

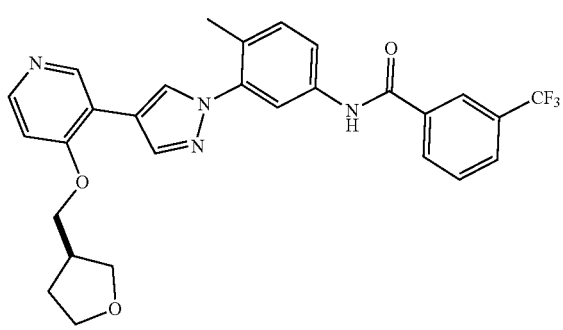

Compound 115 was synthesized by employing steps similar to those described in Example 41. Exact Mass (calculated): 522.18; MS(ESI) m/z (M+1)+: 523.18.

Example 116: N-(3-(4-(4-((1-acetylpyrrolidin-3-yl)methoxy)pyrid-3-yl)-1H-pyrazol-1-yl)-4-methylphenyl)-3-(2-cyanoprop-2-yl)benzamide 116

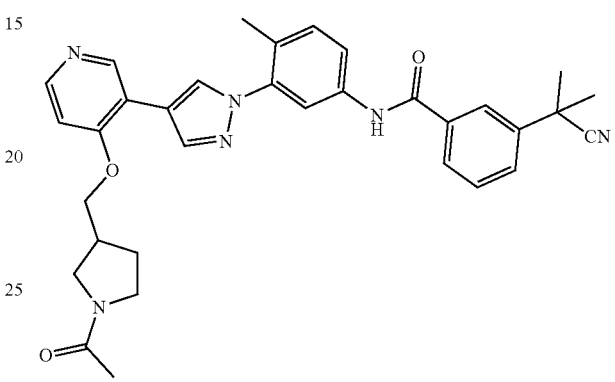

Compound 116 was synthesized by employing steps similar to those described in Example 41. Exact Mass (calculated): 562.26; MS(ESI) m/z (M+1)+: 563.26.

Example 117: 3-(2-cyanoprop-2-yl)-N-(4-methyl-3-(4-(4-((1-(methylsulfonyl)pyrrolidin-3-yl)methoxy)pyrid-3-yl)-1H-pyrazol-1-yl)phenyl)benzamide 117

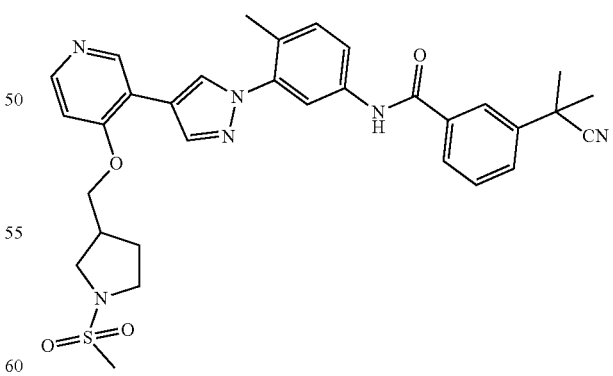

Compound 117 was synthesized by employing steps similar to those described in Example 41. Exact Mass (calculated): 598.23; MS(ESI) m/z (M+1)+: 599.23.

Example 118: 3-(2-cyanoprop-2-yl)-N-(3-(4-(4-((1-(2-(dimethylamino)acetyl)pyrrolidin-3-yl)methoxy)pyrid-3-yl)-1H-pyrazol-1-yl)-4-methylphenyl)benzamide 118

Example 120: N-(4-methyl-3-(4-(4-((1-(methylsulfonyl)pyrrolidin-3-yl)methoxy)pyrid-3-yl)-1H-pyrazol-1-yl)phenyl)-3-(trifluoromethyl)benzamide 120

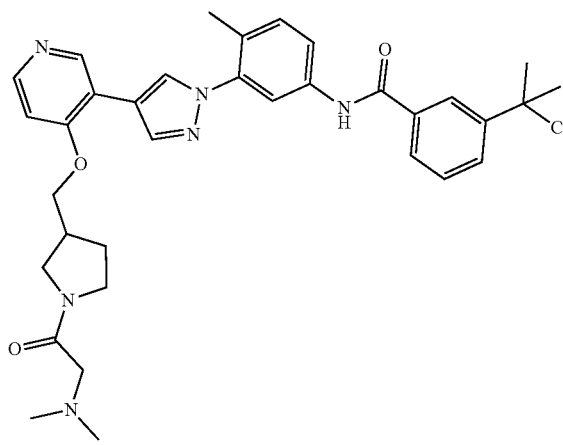

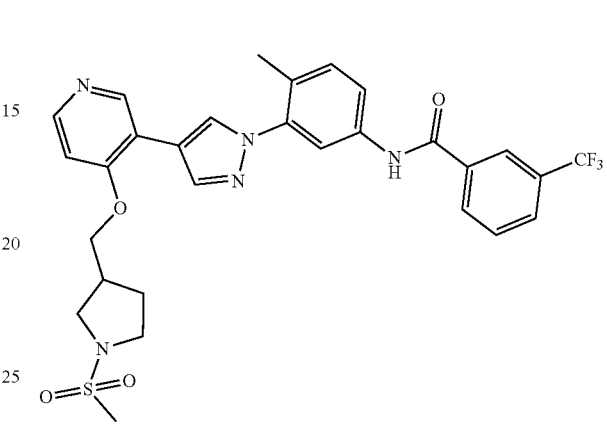

Compound 118 was synthesized by employing steps similar to those described in Example 41. Exact Mass (calculated): 605.31; MS(ESI) m/z (M+1)+: 606.31.

Compound 120 was synthesized by employing steps similar to those described in Example 41. Exact Mass (calculated): 599.18; MS(ESI) m/z (M+1)+: 600.18.

Example 119: N-(3-(4-(4-((1-acetylpyrrolidin-3-yl)methoxy)pyrid-3-yl)-1H-pyrazol-1-yl)-4-methylphenyl)-3-(trifluoromethyl)benzamide 119

Example 121: N-(3-(4-(4-((1-(2-(dimethylamino)acetyl)pyrrolidin-3-yl)methoxy)pyrid-3-yl)-1H-pyrazol-1-yl)-4-methylphenyl)-3-(trifluoromethyl)benzamide 121

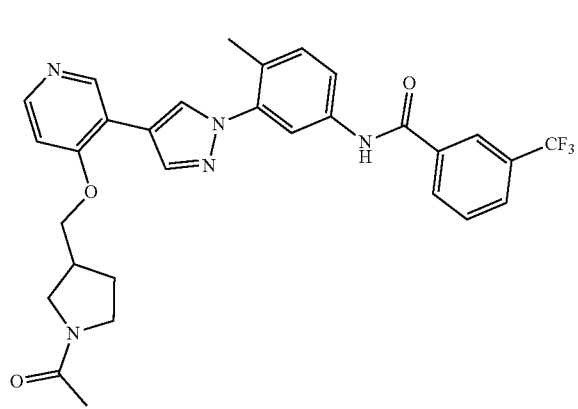 [SMILES: CC(=O)N1CCC(COc2ccncc2-c2cnn(-c3cc(NC(=O)c4cccc(C(F)(F)F)c4)ccc3C)c2)C1]

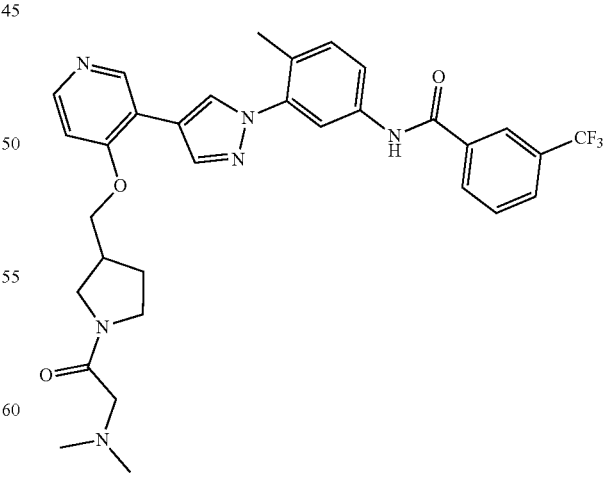

Compound 119 was synthesized by employing steps similar to those described in Example 41. Exact Mass (calculated): 563.21; MS(ESI) m/z (M+1)+: 564.21.

Compound 121 was synthesized by employing steps similar to those described in Example 41. Exact Mass (calculated): 606.25; MS(ESI) m/z (M+1)+: 607.25.

Example 122: (S)-3-(2-cyanoprop-2-yl)-N-(4-methyl-3-(4-(4-((5-oxotetrahydrofuran-2-yl)methoxy)pyrid-3-yl)-H-pyrazol-1-yl)phenyl)benzamide 122

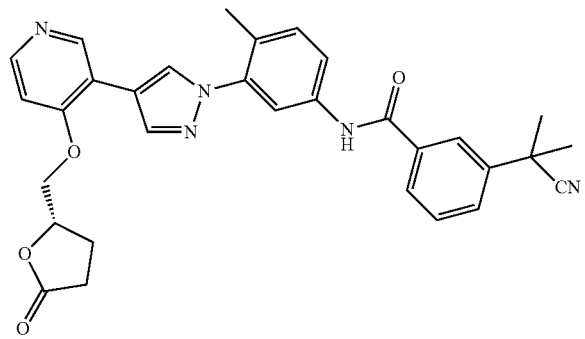 [SMILES: Cc1ccc(NC(=O)c2cccc(C(C)(C)C#N)c2)cc1-n1cc(-c2cnccc2OC[C@@H]2CCC(=O)O2)cn1]

Compound 122 was synthesized by employing steps similar to those described in Example 41. Exact Mass (calculated): 535.22; MS(ESI) m/z (M+1)+: 536.22.

Example 123: N-(3-(4-(4-((1-acetylazetidin-3-yl)oxy)pyrid-3-yl)-1H-pyrazol-1-yl)-4-methylphenyl))-3-(trifluoromethyl)benzamide 123

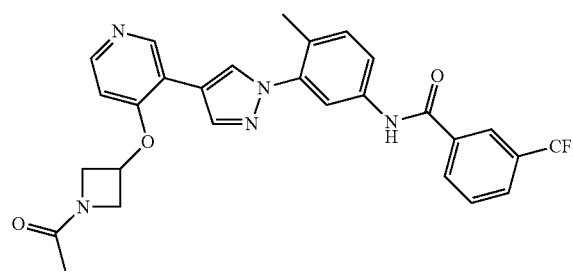

Compound 123 was synthesized by employing steps similar to those described in Example 41. Exact Mass (calculated): 535.18; MS(ESI) m/z (M+1)+: 536.18.

Example 124: N-(4-methyl-3-(4-(4-((1-(methylsulfonyl)azetidin-3-yl)oxy)pyrid-3-yl)-1H-pyrazol-1-yl)phenyl)-3-(trifluoromethyl)benzamide 124

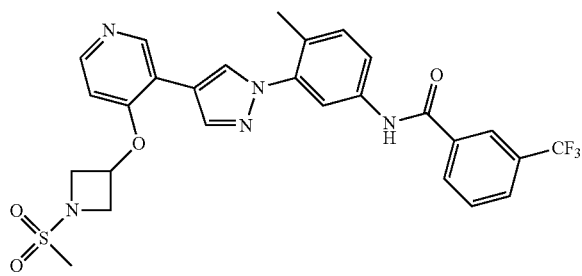 [SMILES: Cc1ccc(NC(=O)c2cccc(C(F)(F)F)c2)cc1-n1cc(-c2cnccc2OC2CN(S(C)(=O)=O)C2)cn1]

Compound 124 was synthesized by employing steps similar to those described in Example 41. Exact Mass (calculated): 571.15; MS(ESI) m/z (M+1)+: 572.15.

Example 125: N-(3-(1-(5-(3-(2-cyanoprop-2-yl)benzoylamino)-2-methylphenyl)-1H-pyrazol-4-yl)pyrid-4-yl)tetrahydro-2H-pyran-4-carboxamide 125

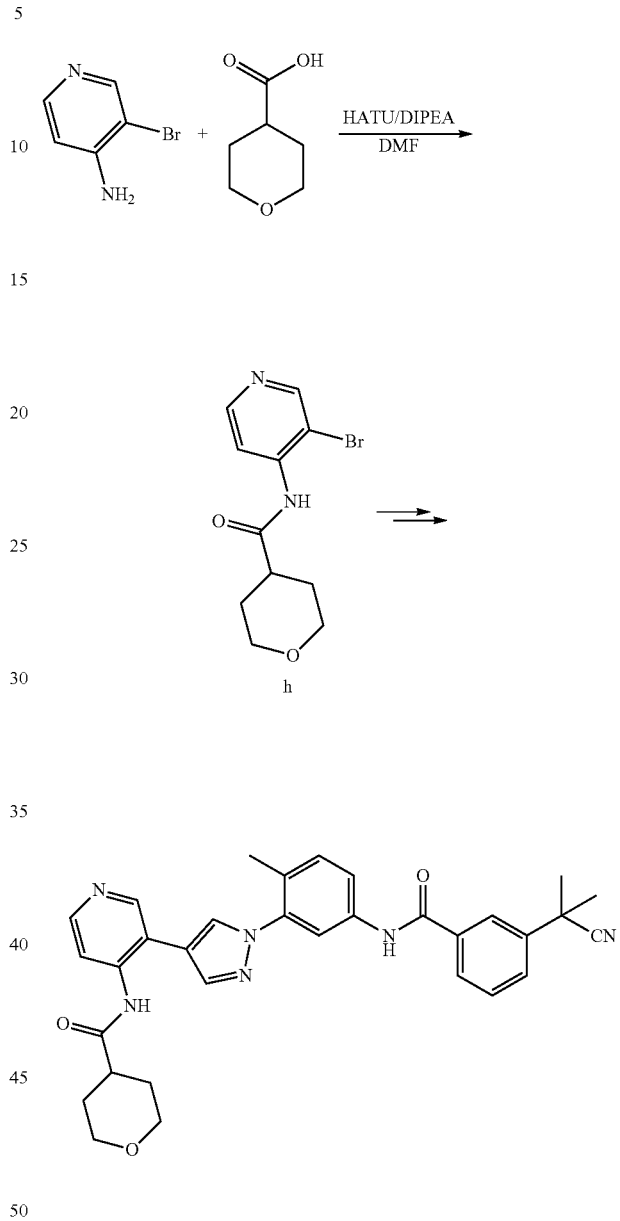

Step 1. Synthesis of N-(3-bromopyrid-4-yl)tetrahydro-2H-pyran-4-carboxamide H 3-bromopyrid-4-ylamine (1.0 g, 1 eq), tetrahydro-2H-pyran-4-carboxylic acid (0.75 g, 1 eq), HATU (2.4 g, 1.1 eq), DIPEA (0.75) and DMF (5 mL) were mixed, and stirred at the room temperature for 0.5 hour. Thereafter, the resultant mixture was eluted with ethyl acetate (150 mL), washed with water and saturated brine sequentially, dried over anhydrous sodium sulfate, and filtered. The filtrate was concentrated to give the product h (1.3 g) to be directly used in the next step.

Step 2. The final product Compound 125 was synthesized by employing steps similar to those described in Example 1. Exact Mass (calculated): 548.25; MS(ESI) m/z (M+1)+: 549.25.

Example 126: N-(3-(1-(2-methyl-5-(3-(trifluoromethyl)benzoylamino)phenyl)-1H-pyrazol-4-yl)pyrid-4-yl)tetrahydro-2H-pyran-4-carboxamide 126

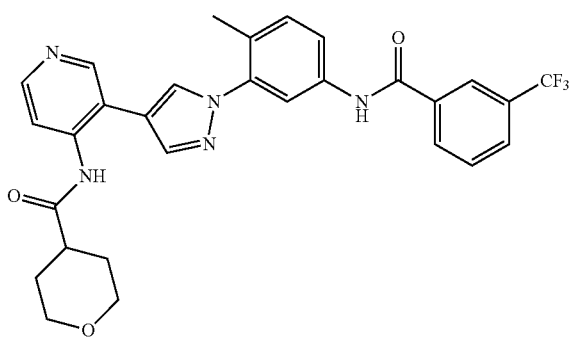 [SMILES: Cc1ccc(NC(=O)c2cccc(C(F)(F)F)c2)cc1-n1cc(-c2cnccc2NC(=O)C2CCOCC2)cn1]

Compound 126 was synthesized by employing steps similar to those described in Examples 1 and 125. Exact Mass (calculated): 549.19; MS(ESI) m/z (M+1)+: 550.19.

Example 127: N-(3-(1-(2-methyl-5-(2-(3-(trifluoromethyl)phenyl)acetylamino)phenyl)-1H-pyrazol-4-yl)pyrid-4-yl)tetrahydro-2H-pyran-4-carboxamide 127

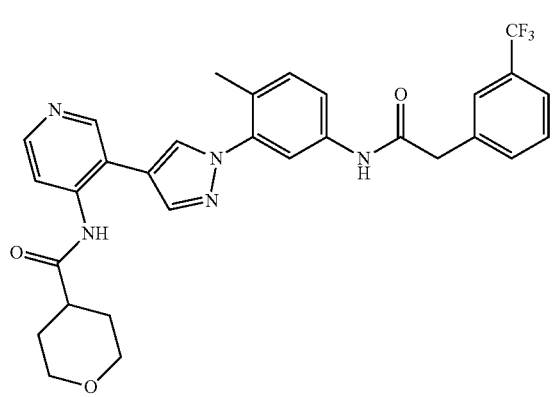 [SMILES: Cc1ccc(NC(=O)Cc2cccc(C(F)(F)F)c2)cc1-n1cc(-c2cnccc2NC(=O)C2CCOCC2)cn1]

Compound 127 was synthesized by employing steps similar to those described in Examples 1 and 125. Exact Mass (calculated): 563.24; MS(ESI) m/z (M+1)+: 564.24.

Example 128: N-(3-(1-(2-methyl-5-(3-(3-(trifluoromethyl)phenyl)ureido)phenyl)-1H-pyrazol-4-yl)pyrid-4-yl)tetrahydro-2H-pyran-4-carboxamide 128

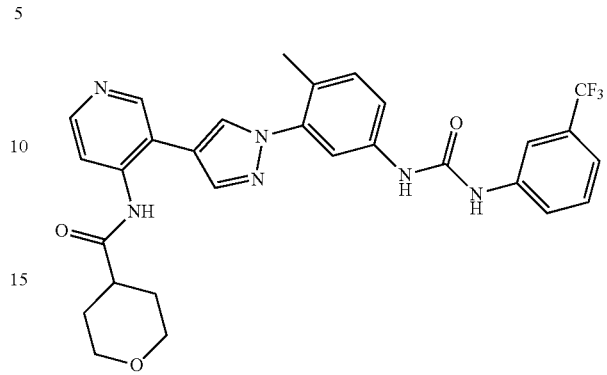

Compound 128 was synthesized by employing steps similar to those described in Examples 1, 125 and 15. Exact Mass (calculated): 564.20; MS(ESI) m/z (M+1)+: 565.20.

Example 129: N-(3-(1-(5-(3-(5-(tert-butyl)isoxazol-3-yl)ureido)-2-methylphenyl)-1H-pyrazol-4-yl)pyrid-4-yl)tetrahydro-2H-pyran-4-carboxamide 129

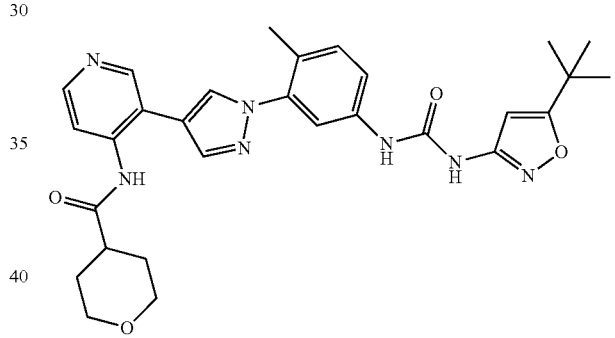

Compound 129 was synthesized by employing steps similar to those described in Examples 1, 125 and 15. Exact Mass (calculated): 543.25; MS(ESI) m/z (M+1)+: 544.25.

Example 130: 3-(2-cyanoprop-2-yl)-N-(4-methyl-3-(4-(4-(2-(tetrahydro-2H-pyran-4-yl)acetylamino)pyrid-3-yl)-1H-pyrazol-1-yl)phenyl)benzamide 130

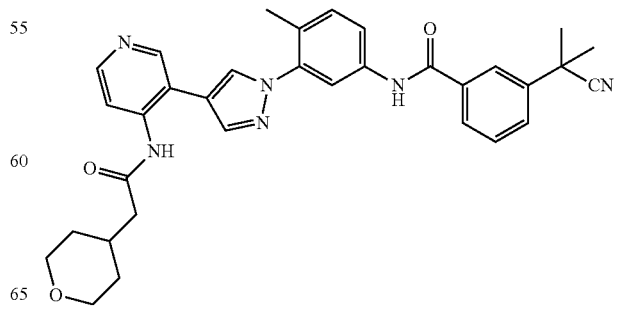

Compound 130 was synthesized by employing steps similar to those described in Examples 1 and 125. Exact Mass (calculated): 562.26; MS(ESI) m/z (M+1)+: 563.26.

Example 131: N-(4-methyl-3-(4-(4-(2-(tetrahydro-2H-pyran-4-yl)acetylamino)pyrid-3-yl)-1H-pyrazol-1-yl)phenyl)-3-(trifluoromethyl)benzamide 131

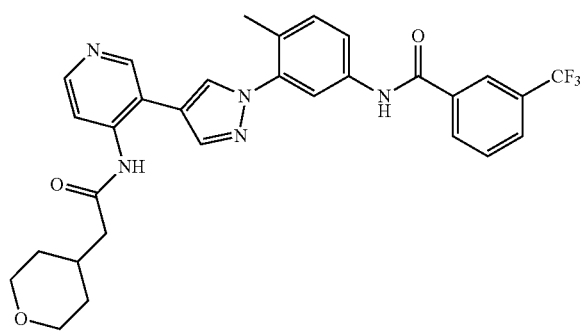 [SMILES: Cc1ccc(NC(=O)c2cccc(C(F)(F)F)c2)cc1-n1cc(-c2cnccc2NC(=O)CC2CCOCC2)cn1]

Compound 131 was synthesized by employing steps similar to those described in Examples 1 and 125. Exact Mass (calculated): 563.21; MS(ESI) m/z (M+1)+: 564.21.

Example 132: N-(4-methyl-3-(4-(4-(2-(tetrahydro-2H-pyran-4-yl)acetylamino)pyrid-3-yl)-1H-pyrazol-1-yl)phenyl)-2-(3-(trifluoromethyl)phenyl)acetamide 132

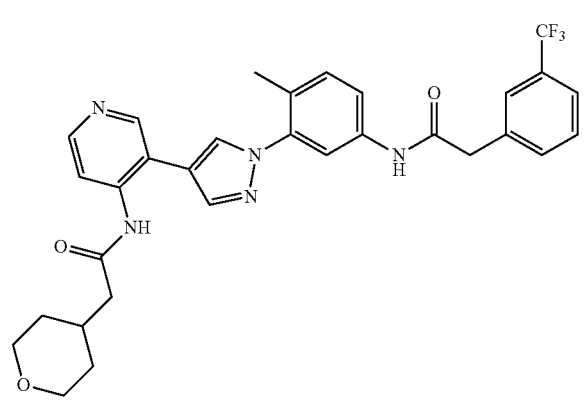 [SMILES: Cc1ccc(NC(=O)Cc2cccc(C(F)(F)F)c2)cc1-n1cc(-c2cnccc2NC(=O)CC2CCOCC2)cn1]

Compound 132 was synthesized by employing steps similar to those described in Examples 1 and 125. Exact Mass (calculated): 577.23; MS(ESI) m/z (M+1)+: 578.23.

Example 133: N-(3-(1-(2-methyl-5-(3-(3-(trifluoromethyl)phenyl)ureido)phenyl)-1H-pyrazol-4-yl)pyrid-4-yl)-2-(tetrahydro-2H-pyran-4-yl)acetamide 133

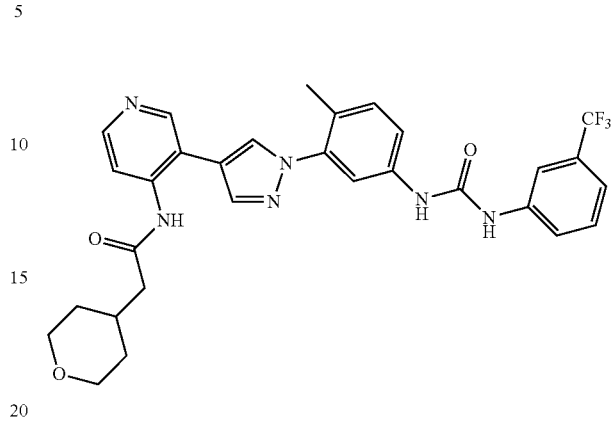

Compound 133 was synthesized by employing steps similar to those described in Examples 1, 125 and 15. Exact Mass (calculated): 578.22; MS(ESI) m/z (M+1)+: 579.22.

Example 134: N-(3-(1-(5-(3-(5-(tert-butyl)isoxazol-3-yl)ureido)-2-methylphenyl)-1H-pyrazol-4-yl)pyrid-4-yl)-2-(tetrahydro-2H-pyran-4-yl)acetamide 134

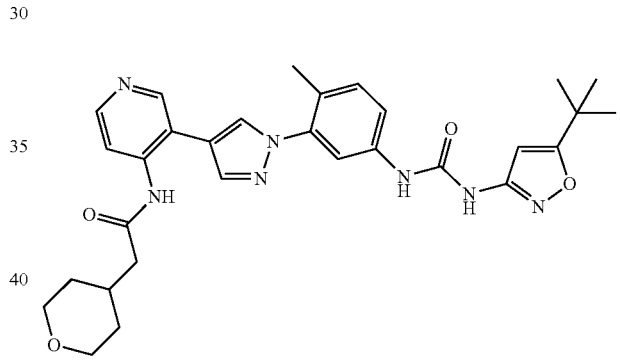

Compound 134 was synthesized by employing steps similar to those described in Examples 1, 125 and 15. Exact Mass (calculated): 557.27; MS(ESI) m/z (M+1)+: 558.27.

Example 135: 3-(2-cyanoprop-2-yl)-N-(4-methyl-3-(4-(4-(2-(tetrahydrofuran-3-yl)acetylamino)pyrid-3-yl)-1H-pyrazol-1-yl)phenyl)benzamide 135

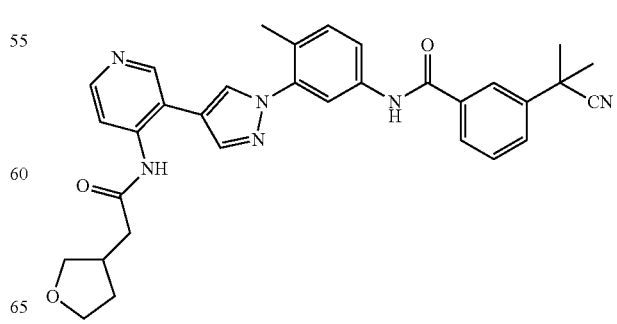

Compound 135 was synthesized by employing steps similar to those described in Examples 1 and 125. Exact Mass (calculated): 548.25; MS(ESI) m/z (M+1)+: 549.25.

Example 136: N-(4-methyl-3-(4-(4-(2-(tetrahydrofuran-3-yl)acetylamino)pyrid-3-yl)-1H-pyrazol-1-yl)phenyl)-3-(trifluoromethyl)benzamide 136

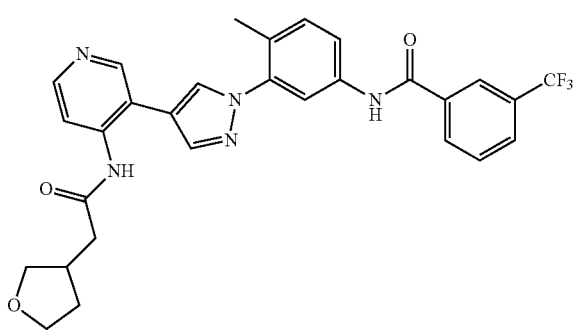 [SMILES: Cc1ccc(NC(=O)c2cccc(C(F)(F)F)c2)cc1-n1cc(-c2cnccc2NC(=O)CC2CCOC2)cn1]

Compound 136 was synthesized by employing steps similar to those described in Examples 1 and 125. Exact Mass (calculated): 549.19; MS(ESI) m/z (M+1)+: 550.19.

Example 137: N-(4-methyl-3-(4-(4-(2-(tetrahydrofuran-3-yl)acetylamino)pyrid-3-yl)-1H-pyrazol-1-yl)phenyl)-2-(3-(trifluoromethyl)phenyl)acetamide 137

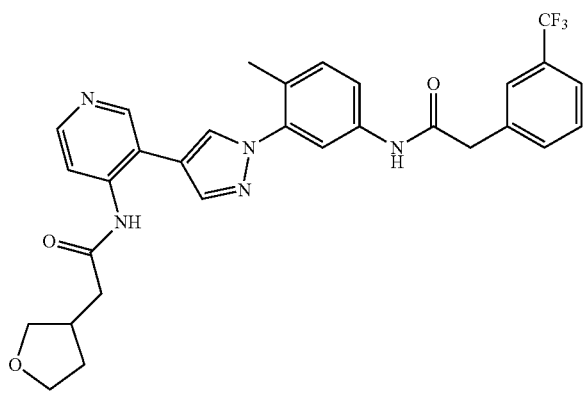 [SMILES: Cc1ccc(NC(=O)Cc2cccc(C(F)(F)F)c2)cc1-n1cc(-c2cnccc2NC(=O)CC2CCOC2)cn1]

Compound 137 was synthesized by employing steps similar to those described in Examples 1 and 125. Exact Mass (calculated): 563.21; MS(ESI) m/z (M+1)+: 564.21.

Example 138: N-(3-(1-(2-methyl-5-(3-(3-(trifluoromethyl)phenyl)ureido)phenyl)-1H-pyrazol-4-yl)pyrid-4-yl)-2-(tetrahydrofuran-3-yl)acetamide 138

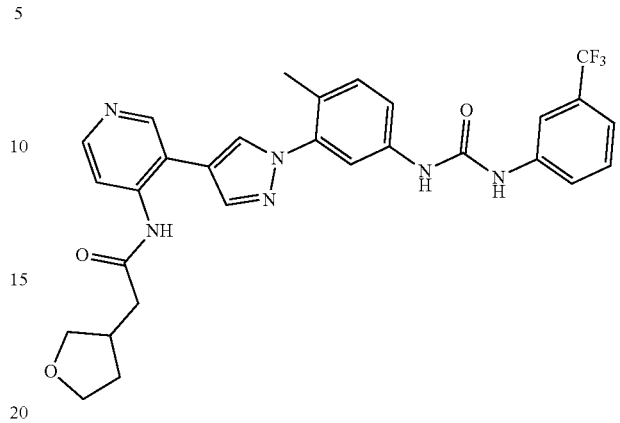

Compound 138 was synthesized by employing steps similar to those described in Examples 1, 125 and 15. Exact Mass (calculated): 564.20; MS(ESI) m/z (M+1)+: 565.20.

Example 139: N-(3-(1-(5-(3-(5-(tert-butyl)isoxazol-3-yl)ureido)-2-methylphenyl)-1H-pyrazol-4-yl)pyrid-4-yl)-2-(tetrahydrofuran-3-yl)acetamide 139

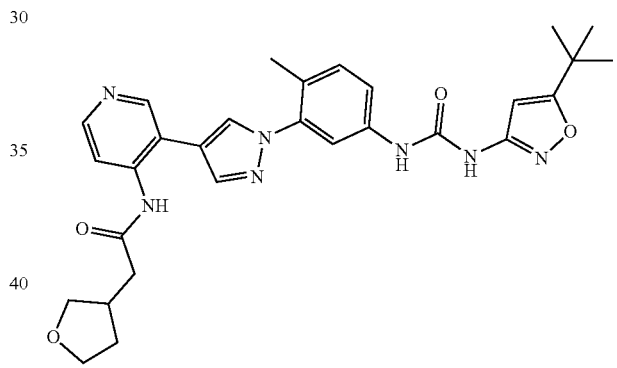

Compound 139 was synthesized by employing steps similar to those described in Examples 1, 125 and 15. Exact Mass (calculated): 543.25; MS(ESI) m/z (M+1)+: 544.25.

Example 140: N-(3-(1-(5-(3-(2-cyanoprop-2-yl)benzoylamino)-2-methylphenyl)-1H-pyrazol-4-yl)pyrid-4-yl)tetrahydrofuran-3-carboxamide 140

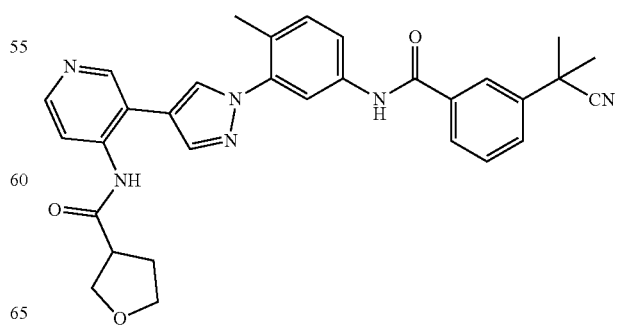

Compound 140 was synthesized by employing steps similar to those described in Examples 1 and 125. Exact Mass (calculated): 534.23; MS(ESI) m/z (M+1)+: 535.23.

Example 141: N-(3-(1-(2-methyl-5-(3-(trifluoromethyl)benzoylamino)phenyl)-1H-pyrazol-4-yl)pyrid-4-yl)tetrahydrofuran-3-carboxamide 141

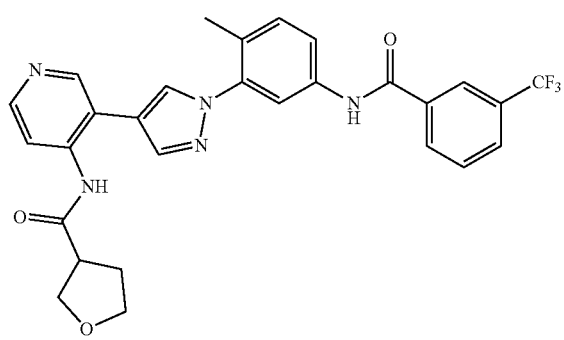 [SMILES: Cc1ccc(NC(=O)c2cccc(C(F)(F)F)c2)cc1-n1cc(-c2cnccc2NC(=O)C2CCOC2)cn1]

Compound 141 was synthesized by employing steps similar to those described in Examples 1 and 125. Exact Mass (calculated): 535.18; MS(ESI) m/z (M+1)+: 536.18.

Example 142: N-(3-(1-(2-methyl-5-(2-(3-(trifluoromethyl)phenyl)acetylamino)phenyl)-1H-pyrazol-4-yl)pyrid-4-yl)tetrahydrofuran-3-carboxamide 142

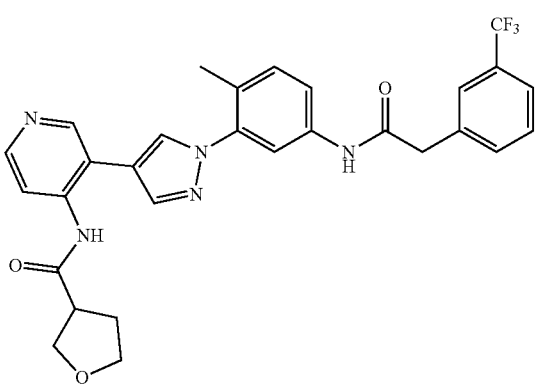 [SMILES: Cc1ccc(NC(=O)Cc2cccc(C(F)(F)F)c2)cc1-n1cc(-c2cnccc2NC(=O)C2CCOC2)cn1]

Compound 142 was synthesized by employing steps similar to those described in Examples 1 and 125. Exact Mass (calculated): 549.19; MS(ESI) m/z (M+1)+: 550.19.

Example 143: N-(3-(1-(2-methyl-5-(3-(3-(trifluoromethyl)phenyl)ureido)phenyl)-1H-pyrazol-4-yl)pyrid-4-yl)-3-tetrahydrofuran carboxamide 143

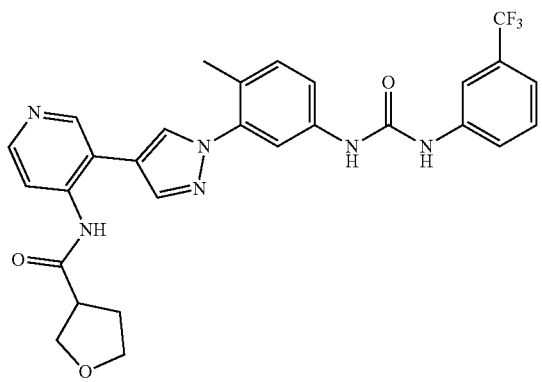 [SMILES: Cc1ccc(NC(=O)Nc2cccc(C(F)(F)F)c2)cc1-n1cc(-c2cnccc2NC(=O)C2CCOC2)cn1]

Compound 143 was synthesized by employing steps similar to those described in Examples 1, 125 and 15. Exact Mass (calculated): 550.19; MS(ESI) m/z (M+1)+: 551.19.

Example 144: N-(3-(1-(5-(3-(5-(tert-butyl)isoxazol-3-yl)ureido)-2-methylphenyl)-1H-pyrazol-4-yl)pyrid-4-yl)tetrahydrofuran-3-carboxamide 144

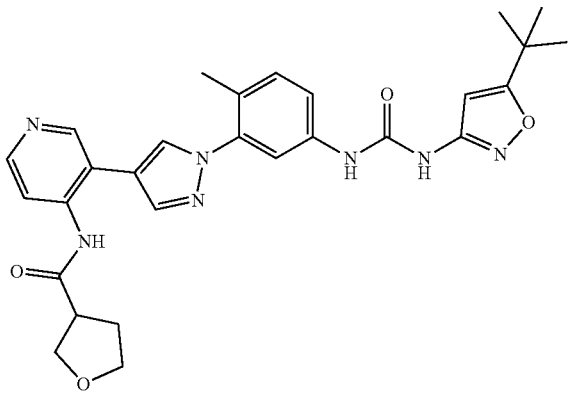 [SMILES: Cc1ccc(NC(=O)Nc2cc(C(C)(C)C)on2)cc1-n1cc(-c2cnccc2NC(=O)C2CCOC2)cn1]

Compound 144 was synthesized by employing steps similar to those described in Examples 1, 125 and 15. Exact Mass (calculated): 529.24; MS(ESI) m/z (M+1)+: 530.24.

Example 145: N-(3-(1-(5-(3-(2-cyanoprop-2-yl)benzoylamino)-2-methylphenyl)-1H-pyrazol-4-yl)pyrid-4-yl)-3-methyloxetane-3-carboxamide 145

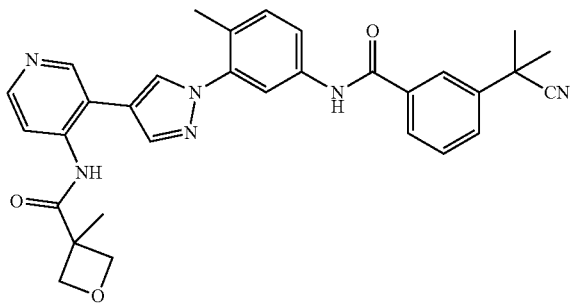 [SMILES: Cc1ccc(NC(=O)c2cccc(C(C)(C)C#N)c2)cc1-n1cc(-c2cnccc2NC(=O)C2(C)COC2)cn1]

Compound 145 was synthesized by employing steps similar to those described in Examples 1 and 125. Exact Mass (calculated): 534.23; MS(ESI) m/z (M+1)+: 535.23.

Example 146: 3-methyl-N-(3-(1-(2-methyl-5-(3-(trifluoromethyl)benzoylamino)phenyl)-1H-pyrazol-4-yl)pyrid-4-yl) oxetane-3-carboxamide 146

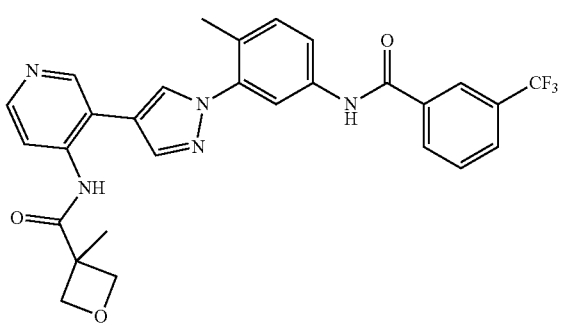 [SMILES: Cc1ccc(NC(=O)c2cccc(C(F)(F)F)c2)cc1-n1cc(-c2cnccc2NC(=O)C2(C)COC2)cn1]

Compound 146 was synthesized by employing steps similar to those described in Examples 1 and 125. Exact Mass (calculated): 535.18; MS(ESI) m/z (M+1)+: 536.18.

Example 147: 3-methyl-N-(3-(1-(2-methyl-5-(2-(3-(trifluoromethyl)phenyl)acetylamino)phenyl)-1H-pyrazol-4-yl)pyrid-4-yl) oxetane-3-carboxamide 147

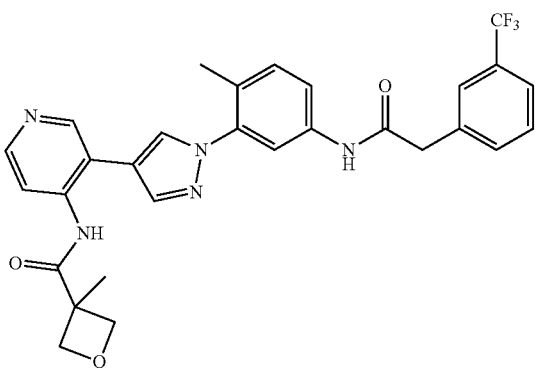 [SMILES: Cc1ccc(NC(=O)Cc2cccc(C(F)(F)F)c2)cc1-n1cc(-c2cnccc2NC(=O)C2(C)COC2)cn1]

Compound 147 was synthesized by employing steps similar to those described in Examples 1 and 125. Exact Mass (calculated): 549.19; MS(ESI) m/z (M+1)+: 550.19.

Example 148: 3-methyl-N-(3-(1-(2-methyl-5-(3-(3-(trifluoromethyl)phenyl)ureido)phenyl)-1H-pyrazol-4-yl)pyrid-4-yl)oxetane-3-carboxamide 148

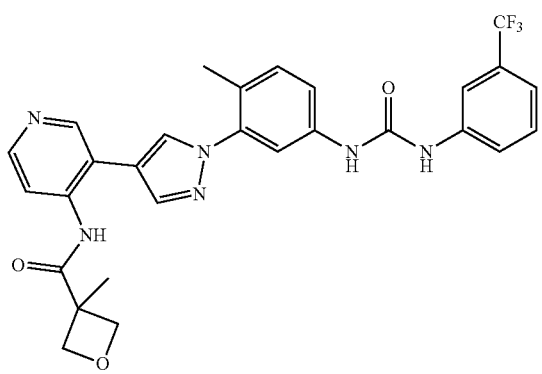 [SMILES: Cc1ccc(NC(=O)Nc2cccc(C(F)(F)F)c2)cc1-n1cc(-c2cnccc2NC(=O)C2(C)COC2)cn1]

Compound 148 was synthesized by employing steps similar to those described in Examples 1, 125 and 15. Exact Mass (calculated): 550.19; MS(ESI) m/z (M+1)+: 551.19.

Example 149: N-(3-(1-(5-(3-(5-(tert-butyl)isoxazol-3-yl)ureido)-2-methylphenyl)-1H-pyrazol-4-yl)pyrid-4-yl)-3-methyloxetane-3-carboxamide 149

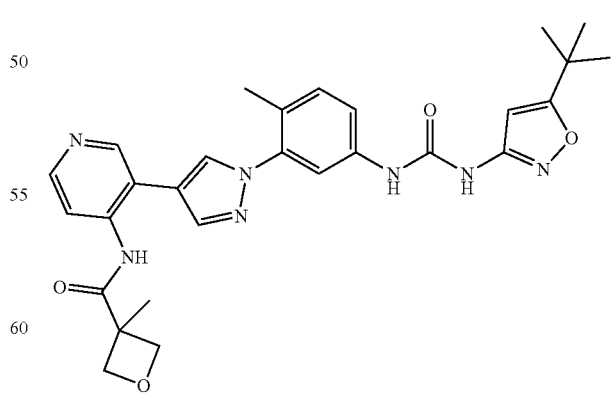

Compound 149 was synthesized by employing steps similar to those described in Examples 1, 125 and 15. Exact Mass (calculated): 529.24; MS(ESI) m/z (M+1)+: 530.24.

Example 150: N-(3-(1-(5-(3-(2-cyanoprop-2-yl)benzoylamino)-2-methylphenyl)-1H-pyrazol-4-yl)pyrid-4-yl)-3-oxadicyclo[3.1.0]hexane-6-carboxamide 150

Example 152: N-(3-(1-(2-methyl-5-(2-(3-(trifluoromethyl)phenyl)acetylamino)phenyl)-1H-pyrazol-4-yl)pyrid-4-yl)-3-oxadicyclo[3.1.0]hexane-6-carboxamide 152

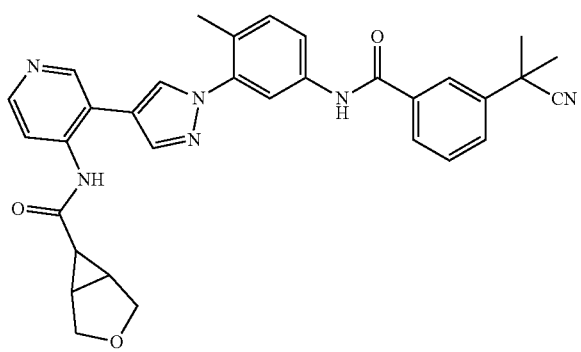 [SMILES: Cc1ccc(NC(=O)c2cccc(C(C)(C)C#N)c2)cc1-n1cc(-c2cnccc2NC(=O)C2C3COCC32)cn1]

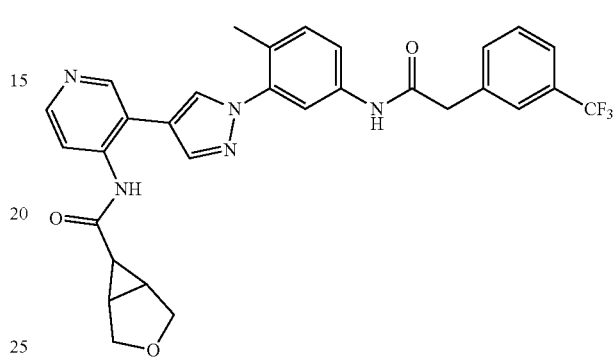

Compound 150 was synthesized by employing steps similar to those described in Examples 1 and 125. Exact Mass (calculated): 546.23; MS(ESI) m/z (M+1)+: 547.23.

Compound 152 was synthesized by employing steps similar to those described in Examples 1 and 125. Exact Mass (calculated): 561.19; MS(ESI) m/z (M+1)+: 562.19.

Example 151: N-(3-(1-(2-methyl-5-(3-(trifluoromethyl)benzoylamino)phenyl)-1H-pyrazol-4-yl)pyrid-4-yl)-3-oxadicyclo[3.1.0]hexane-6-carboxamide 151

Example 153: N-(3-(1-(2-methyl-5-(3-(3-(trifluoromethyl)phenyl)ureido)phenyl)-1H-pyrazol-4-yl)pyrid-4-yl)-3-oxadicyclo[3.1.0]hexane-6-carboxamide 153

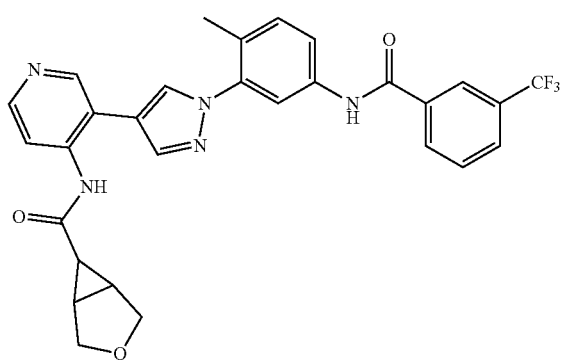 [SMILES: Cc1ccc(NC(=O)c2cccc(C(F)(F)F)c2)cc1-n1cc(-c2cnccc2NC(=O)C2C3COCC32)cn1]

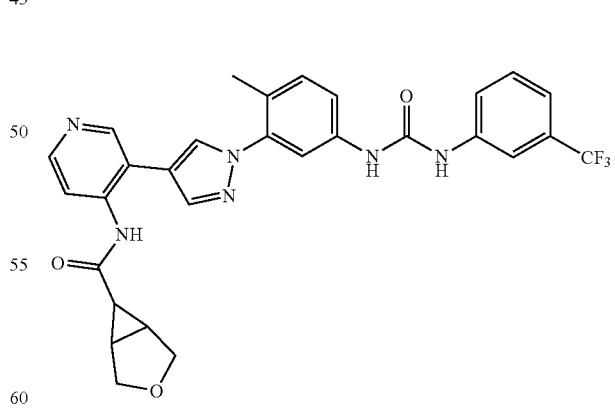

Compound 151 was synthesized by employing steps similar to those described in Examples 1 and 125. Exact Mass (calculated): 547.18; MS(ESI) m/z (M+1)+: 548.18.

Compound 153 was synthesized by employing steps similar to those described in Examples 1, 125 and 15. Exact Mass (calculated): 562.19; MS(ESI) m/z (M+1)+: 563.19.

Example 154: N-(3-(1-(5-(3-(5-(tert-butyl)isoxazol-3-yl)ureido)2-methylphenyl)-1H-pyrazol-4-yl)pyrid-4-yl)-3-oxadicyclo[3.1.0]hexane-6-carboxamide 154

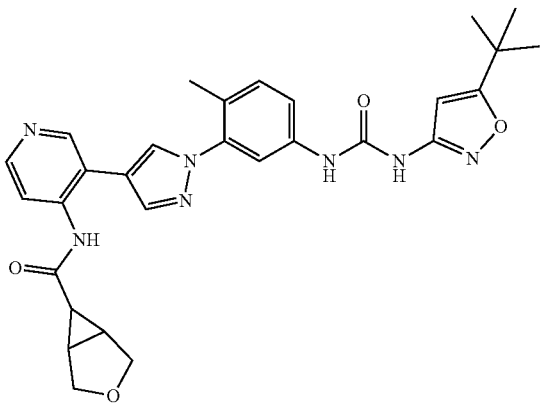 [SMILES: Cc1ccc(NC(=O)Nc2cc(C(C)(C)C)on2)cc1-n1cc(-c2cnccc2NC(=O)C2C3COCC32)cn1]

Compound 154 was synthesized by employing steps similar to those described in Examples 1, 125 and 15. Exact Mass (calculated): 541.24; MS(ESI) m/z (M+1)+: 542.24.

Example 155: 3-(2-cyanoprop-2-yl)-N-(3-(4-(4-(2-hydroxyethoxy)pyrid-3-yl)-1H-pyrazol-1-yl)-4-methylphenyl)benzamide 155

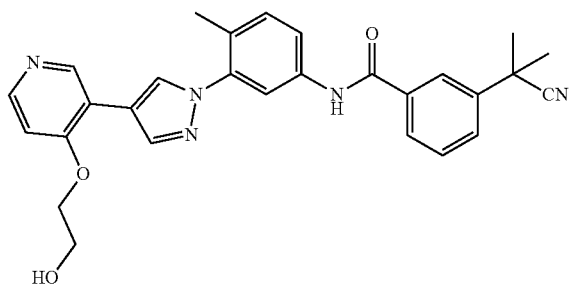 [SMILES: Cc1ccc(NC(=O)c2cccc(C(C)(C)C#N)c2)cc1-n1cc(-c2cnccc2OCCO)cn1]

Compound 155 was synthesized by employing steps similar to those described in Examples 1 and 125. Exact Mass (calculated): 481.21; MS(ESI) m/z (M+1)+: 482.21.

Example 156: N-(3-(4-(4-(2-hydroxyethoxy)pyrid-3-yl)-1H-pyrazol-1-yl)-4-methylphenyl)-3-(trifluoromethyl)benzamide 156

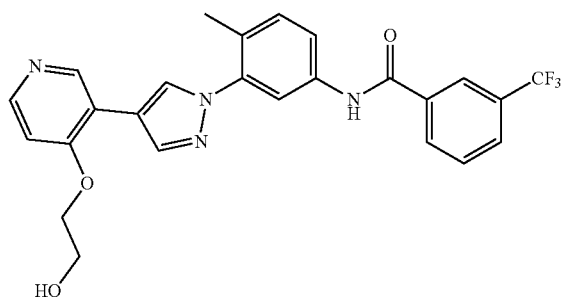 [SMILES: Cc1ccc(NC(=O)c2cccc(C(F)(F)F)c2)cc1-n1cc(-c2cnccc2OCCO)cn1]

Compound 156 was synthesized by employing steps similar to those described in Example 41. Exact Mass (calculated): 482.15; MS(ESI) m/z (M+1)+: 483.15.

Example 157: 1-(5-(tert-butyl)isoxazol-3-yl)-3-(3-(4-(4-(2-hydroxyethoxy)pyrid-3-yl)-1H-pyrazol-1-yl)-4-methylphenyl)urea 157

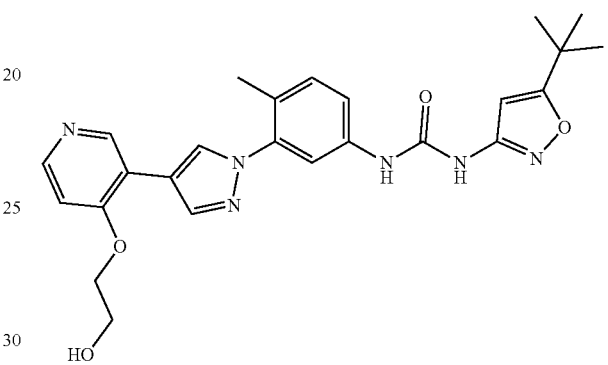

Compound 157 was synthesized by employing steps similar to those described in Examples 1 and 41. Exact Mass (calculated): 476.21; MS(ESI) m/z (M+1)+: 477.21.

Example 158: 1-(3-(4-(4-(2-hydroxyethoxy)pyrid-3-yl)-1H-pyrazol-1-yl)-4-methylphenyl)-3-(3-(trifluoromethyl)phenyl)urea 158

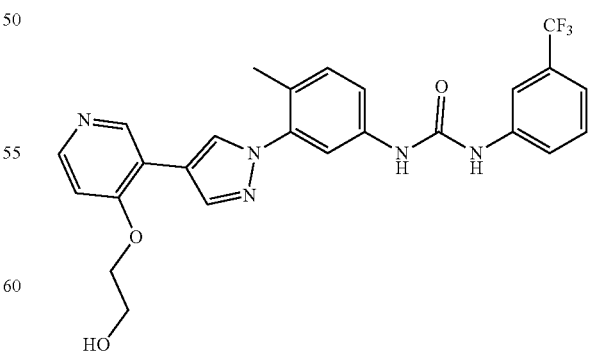

Compound 158 was synthesized by employing steps similar to those described in Example 41. Exact Mass (calculated): 497.16; MS(ESI) m/z (M+1)+: 498.16.

Example 159: 3-(2-cyanoprop-2-yl)-N-(3-(4-(4-(2-methoxyethoxy)pyrid-3-yl)-1H-pyrazol-1-yl)-4-methylphenyl)benzamide 159

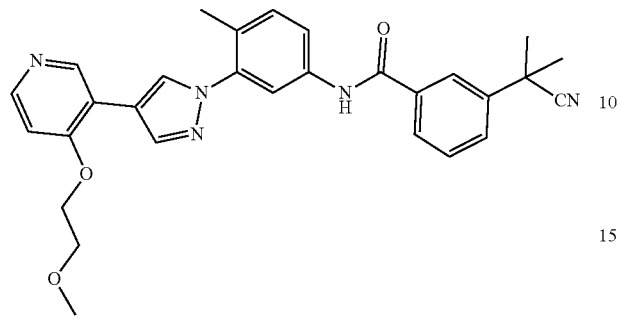

Compound 159 was synthesized by employing steps similar to those described in Example 41. Exact Mass (calculated): 495.22; MS(ESI) m/z (M+1)+: 496.22.

Example 160: N-(3-(4-(4-(2-methoxyethoxy)pyrid-3-yl)-1H-pyrazol-1-yl)-4-methylphenyl)-3-(trifluoromethyl)benzamide 160

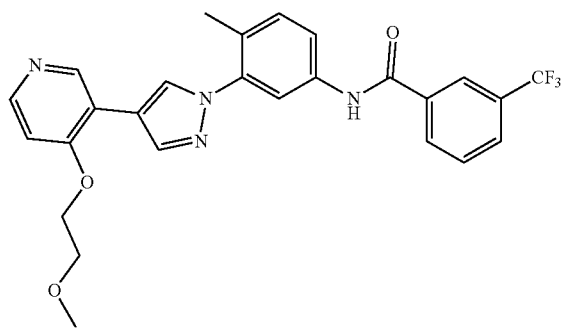 [SMILES: COCCOc1ccncc1-c1cnn(-c2cc(NC(=O)c3cccc(C(F)(F)F)c3)ccc2C)c1]

Compound 160 was synthesized by employing steps similar to those described in Example 41. Exact Mass (calculated): 496.17; MS(ESI) m/z (M+1)+: 497.17.

Example 161: 3-(2-cyanoprop-2-yl)-N-(3-(4-(4-(3-hydorxypropoxy)pyrid-3-yl)-1H-pyrazol-1-yl)-4-methylphenyl)benzamide 161

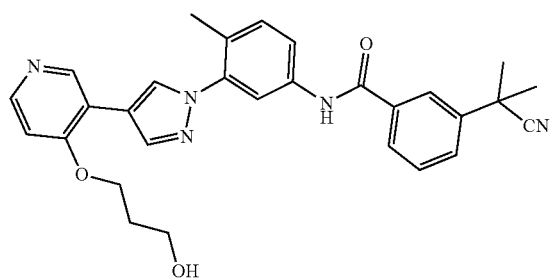 [SMILES: Cc1ccc(NC(=O)c2cccc(C(C)(C)C#N)c2)cc1-n1cc(-c2cnccc2OCCCO)cn1]

Compound 161 was synthesized by employing steps similar to those described in Example 41. Exact Mass (calculated): 495.22; MS(ESI) m/z (M+1)+: 496.22.

Example 162: N-(3-(4-(4-(3-hydoxypropoxy)pyrid-3-yl)-1H-pyrazol-1-yl)-4-methylphenyl)-3-(trifluoromethyl)benzamide 162

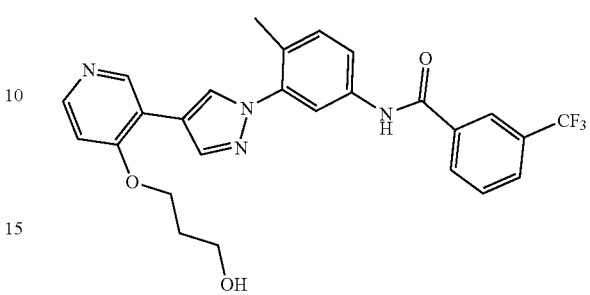

Compound 162 was synthesized by employing steps similar to those described in Example 41. Exact Mass (calculated): 496.17; MS(ESI) m/z (M+1)+: 497.17.

Example 163: 3-(2-cyanoprop-2-yl)-N-(4-methyl-3-(4-(5-(piperizan-1-yl)pyrid-3-yl)1H-pyrazol-1-yl)phenyl)benzamide 163

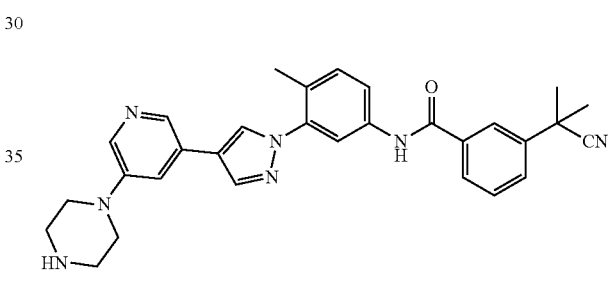

Compound 163 was synthesized by employing steps similar to those described in Example 1. Exact Mass (calculated): 505.25; MS(ESI) m/z (M+1)+: 506.25.

Example 164: N-(4-methyl-3-(4-(5-(piperizan-1-yl)pyrid-3-yl)-1H-pyrazol-1-yl)phenyl)-3-(trifluoromethyl)benzamide 164

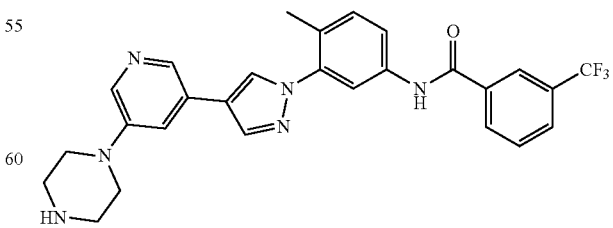

Compound 164 was synthesized by employing steps similar to those described in Example 1. Exact Mass (calculated): 506.20; MS(ESI) m/z (M+1)+: 507.20.

Example 165: 3-(2-cyanoprop-2-yl)-N-(3-(4-(4-(4-hydroxybutoxy)pyrid-3-yl)-1H-pyrazol-1-yl)-4-methylphenyl)benzamide 165

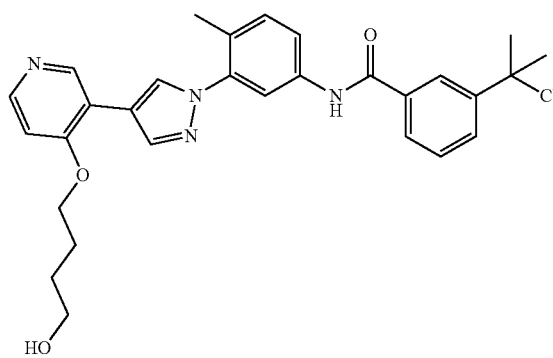

Compound 165 was synthesized by employing steps similar to those described in Example 41. Exact Mass (calculated): 509.24; MS(ESI) m/z (M+1)+: 510.24.

Example 166: N-(3-(4-(4-(4-hydroxybutoxy)pyrid-3-yl)-1H-pyrazol-1-yl)-4-methylphenyl)-3-(trifluoromethyl)benzamide 166

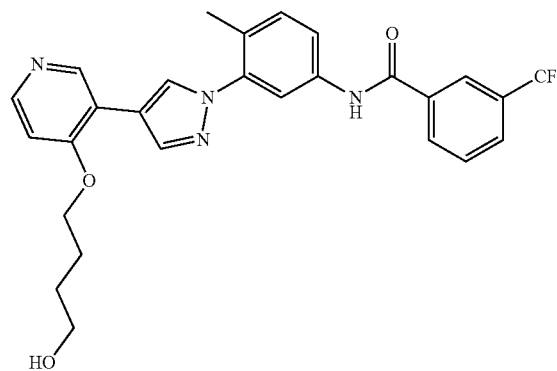

Compound 166 was synthesized by employing steps similar to those described in Example 41. Exact Mass (calculated): 510.18; MS(ESI) m/z (M+1)+: 511.18.

Example 167: N-(3-(4-(1H-pyrrolo[2,3-b]pyrid-5-yl)-1H-pyrazol-1-yl)-4-methylphenyl)-3-(4-methyl-1H-imidazol-1-yl)-5-(trifluoromethyl)benzamide 167

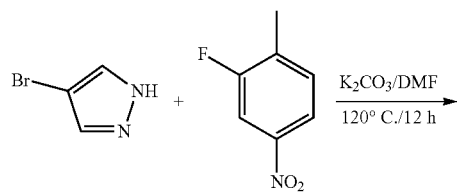

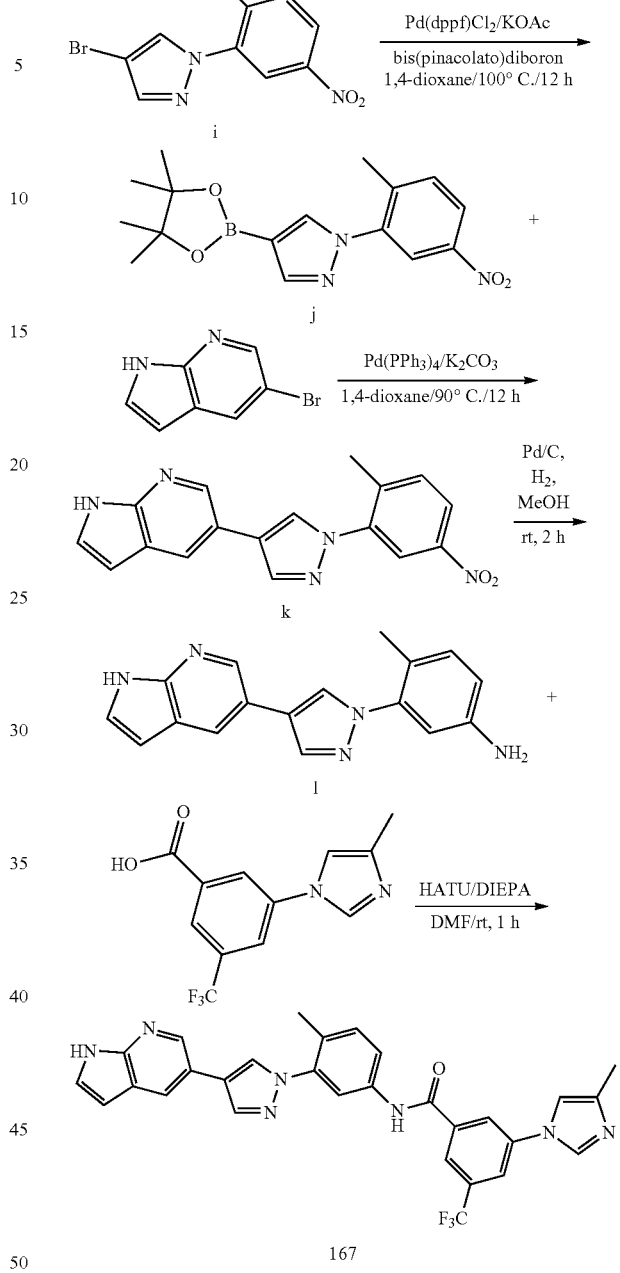

Step 1. Synthesis of 4-bromo-1-(2-methyl-5-nitrophenyl)-1H-pyrazole I 4-bromopyrazole (5 g, 1 eq), 2-fluoro-1-methyl-4-nitrobenzene (5.5 g, 1.05 eq), potassium carbonate (13.1, 3eq) were mixed in DMF (50 ml), and stirred overnight at 100° C. in a nitrogen atmosphere, and then cooled and concentrated. To the concentrate was added ethyl acetate (200 ml). The resultant mixture was washed with water and saturated brine sequentially, dried over anhydrous sodium sulfate, and filtered. The filtrate was concentrated, and then separated by column chromatography to give a yellow product i (5.2 g).

Step 2. Synthesis of 1-(2-methyl-5-nitrophenyl)-4-(4,4,5,5-tetramethyl-1,3,2-dioxaborolan-2-yl)-1H-pyrazole J The compound i (5 g, 1 eq), bis(pinacolato)diboron (5.8 g, 1.3eq), potassium acetate (3.5 g, 2eq), and [1,1'-bis(diphenylphosphino)ferrocene]palladium dichloride (0.72 g, 0.05 eq) were mixed in 1,4-dioxane (50 ml). The mixture was stirred overnight at 100° C. in a nitrogen atmosphere, and then concentrated. The concentrate was separated by column chromatography to give a yellow product j (4.0 g).

Step 3. 5-(1-(2-methyl-5-nitrophenyl)-11H-pyrazol-4-yl)1H-pyrrolo[2,3-b]pyridine K The compound j (4.0 g, 1.1 eq), 5-bromo-1H-pyrrolo[2,3-b]pyridine (2.2 g, 1 eq), potassium carbonate (3.0 g, 2eq) and tetrakis(triphenylphosphine)palladium (0.6 g, 0.05 eq) were mixed in 1,4-dioxane (40 ml) and water (4 ml). The mixture was stirred overnight at 90° C. in a nitrogen atmosphere, and then concentrated. The concentrate was separated by column chromatography to give a yellow product k (2.8 g).

Step 4. Synthesis of 3-(4-(1H-pyrrolo[2,3-b]pyrid-5-yl)-1H-pyrazol-1-yl)-4-methylaniline L The compound k (2.8 g, 1 eq) and palladium on carbon (0.5 g) were mixed in methanol (30 ml). The mixture was stirred for 2 hours at room temperature in a hydrogen atmosphere. Thereafter, dichloromethane (100 ml) was added to dilute the mixture. The resultant mixture was filtered, and concentrated to give a pale green product 1 (2.1 g).

Step 5. Synthesis of N-(3-(4-(1H-pyrrolo[2,3-b]pyrid-5-yl)-1H-pyrazol-1-yl)-4-methylphenyl)-3-(4-methyl-1H-imidazol-1-yl)-5-(trifluorornethyl)benzamide 167

The compound 1 (0.05 g, 1 eq), 3-(4-methyl-1H-imidazol-1-yl)-5-(trifluoromethyl) benzoic acid (0.46 g, 1 eq), HATU (0.072, 1.1 eq), and diisopropylethylenediamine (0.22 g, 1 eq) were mixed in DMF (2 ml). The mixture was stirred at room temperature for 1 hour. Thereafter, ethyl acetate (50 ml) was added to dilute the mixture. The mixture was washed with water and saturated brine sequentially, dried over anhydrous sodium sulfate, and filtered. The filtrate was concentrated, and separated by HPLC to give Compound 167 (0.07 g). Exact Mass (calculated): 541.18; MS(ESI) m/z (M+1)+: 542.19.

Example 168: N-(3-(4-(1H-pyrrolo[2,3-b]pyrid-5-yl)-1H-pyrazol-1-yl)-4-methylphenyl)-4-((4-methylpiperazin-1-yl)methyl)-3-(trifluoromethyl)benzamide 168

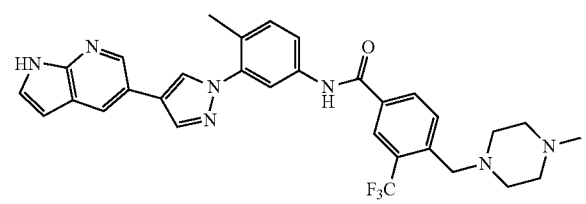 [SMILES: Cc1ccc(NC(=O)c2ccc(CN3CCN(C)CC3)c(C(F)(F)F)c2)cc1-n1cc(-c2cnc3[nH]ccc3c2)cn1]

Compound 168 was synthesized by employing steps similar to those described in Example 167. Exact Mass (calculated): 573.24; MS(ESI) m/z (M+1)+: 574.25.

Example 169: N-(3-(4-(1H-pyrrolo[2,3-b]pyrid-5-yl)-1H-pyrazol-1-yl)-4-methylphenyl)-4-methyl-3-(trifluoromethyl)benzamide 169

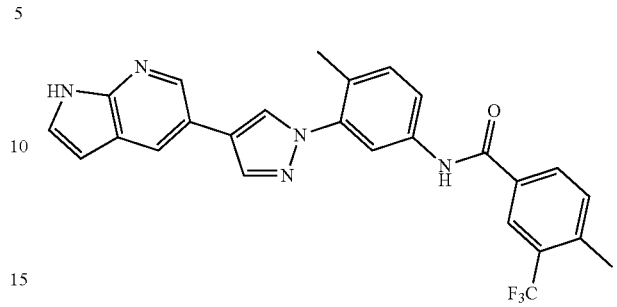

Compound 169 was synthesized by employing steps similar to those described in Example 167. Exact Mass (calculated): 475.16; MS(ESI) m/z (M+1)+: 476.16.

Example 170: N-(3-(4-(1H-pyrrolo[2,3-b]pyrid-5-yl)-1H-pyrazol-1-yl)-4-methylphenyl)-3-(trifluoromethyl)benzamide 170

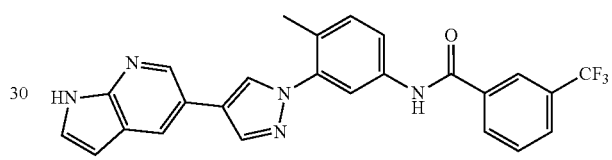

Compound 170 was synthesized by employing steps similar to those described in Example 167. Exact Mass (calculated): 461.14; MS(ESI) m/z (M+1)+: 462.14.

Example 171: N-(3-(4-(1H-pyrrolo[2,3-b]pyrid-5-yl)-1H-pyrazol-1-yl)-4-methylphenyl)-3-(2-cyanoprop-2-yl)benzamide 171

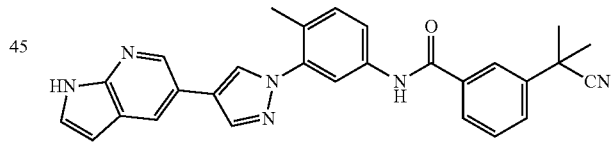

Compound 171 was synthesized by employing steps similar to those described in Example 167. Exact Mass (calculated): 460.20; MS(ESI) m/z (M+1)+: 461.20.

Example 172: N-(3-(4-(1H-pyrrolo[2,3-b]pyrid-5-yl)-1H-pyrazol-1-yl)-4-methylphenyl)-5-(tert-butyl)isoxazole-3-carboxamide 172

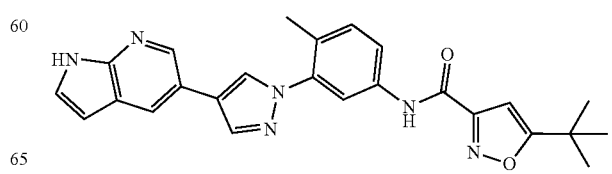

Compound 172 was synthesized by employing steps similar to those described in Example 167. Exact Mass (calculated): 440.19; MS(ESI) m/z (M+1)+: 441.19.

Example 173: 1-(3-(4-(1H-pyrrolo[2,3-b]pyrid-5-yl)-1H-pyrazol-1-yl)-4-methylphenyl)-3-(5-(tert-butyl)isoxazol-3-yl)urea 173

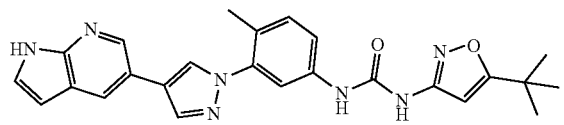 [SMILES: Cc1ccc(NC(=O)Nc2cc(C(C)(C)C)on2)cc1-n1cc(-c2cnc3[nH]ccc3c2)cn1]

Compound 173 was synthesized by employing steps similar to those described in Examples 15 and 167. Exact Mass (calculated): 455.20; MS(ESI) m/z (M+1)+: 456.20.

Example 174: N-(3-(4-(1H-pyrrolo[2,3-b]pyrid-5-yl)-1H-imidazol-1-yl)-4-methylphenyl)-4-((4-methylpiperazin-1-yl)methyl)-3-(trifluoromethyl)benzamide 174

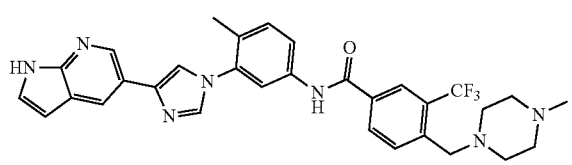 [SMILES: Cc1ccc(NC(=O)c2ccc(CN3CCN(C)CC3)c(C(F)(F)F)c2)cc1-n1cnc(-c2cnc3[nH]ccc3c2)c1]

Compound 174 was synthesized by employing steps similar to those described in Example 167. Exact Mass (calculated): 573.24; MS(ESI) m/z (M+1)+: 574.24.

Example 175: N-(3-(4-(1H-pyrrolo[2,3-b]pyrid-5-yl)-1H-imidazol-1-yl)-4-methylphenyl)-4-methyl-3-(trifluoromethyl)benzamide 175

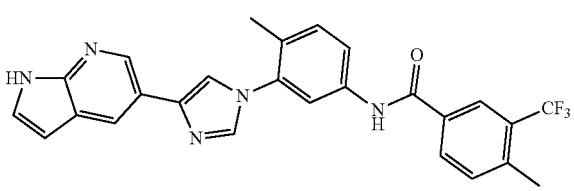 [SMILES: Cc1ccc(NC(=O)c2ccc(C)c(C(F)(F)F)c2)cc1-n1cnc(-c2cnc3[nH]ccc3c2)c1]

Compound 175 was synthesized by employing steps similar to those described in Example 167. Exact Mass (calculated): 475.16; MS(ESI) m/z (M+1)+: 476.16.

Example 176: N-(3-(4-(1H-pyrrolo[2,3-b]pyrid-5-yl)-1H-imidazol-1-yl)-4-methylphenyl)-3-(2-cyanoprop-2-yl)benzamide 176

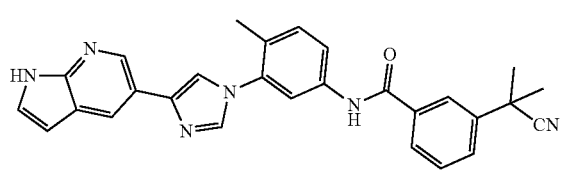 [SMILES: Cc1ccc(NC(=O)c2cccc(C(C)(C)C#N)c2)cc1-n1cnc(-c2cnc3[nH]ccc3c2)c1]

Compound 176 was synthesized by employing steps similar to those described in Example 167. Exact Mass (calculated): 460.20; MS(ESI) m/z (M+1)+: 461.20.

Example 177: N-(3-(4-(1H-pyrrolo[2,3-b]pyrid-5-yl)-1H-imidazol-1-yl)-4-methylphenyl)-3-(trifluoromethyl)benzamide 177

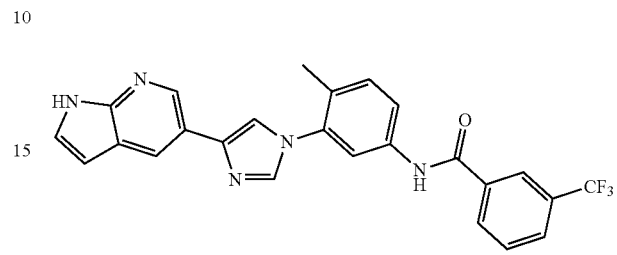

Compound 177 was synthesized by employing steps similar to those described in Example 167. Exact Mass (calculated): 461.14; MS(ESI) m/z (M+1)+: 462.14.

Example 178: N-(3-(4-(1H-pyrrolo[2,3-b]pyrid-5-yl)-1H-imidazol-1-yl)-4-methylphenyl)-5-(tert-butyl)isoxazole-3-carboxamide 178

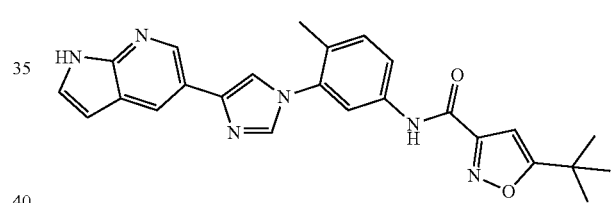

Compound 178 was synthesized by employing steps similar to those described in Example 167. Exact Mass (calculated): 440.19; MS(ESI) m/z (M+1)+: 441.19.

Example 179: N-(3-(4-(1H-pyrrolo[2,3-b]pyrid-5-yl)-1H-pyrazol-1-yl)-4-methylphenyl)-3-(1-cyanoethyl)benzamide 179

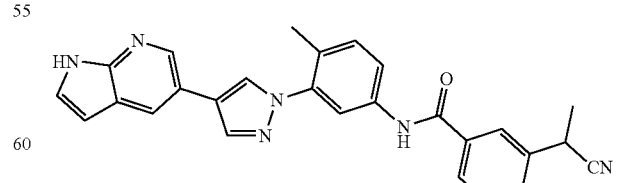

Compound 179 was synthesized by employing steps similar to those described in Example 167. Exact Mass (calculated): 466.18; MS(ESI) m/z (M+1)+: 467.18.

Example 180: N-(3-(4-(1H-pyrrolo[2,3-b]pyrid-5-yl)-1H-pyrazol-1-yl)-4-methylphenyl)-3-(4-trifluoromethylphenyl)benzamide 180

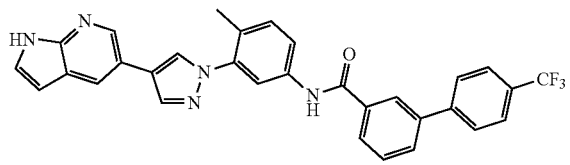 [SMILES: Cc1ccc(NC(=O)c2cccc(-c3ccc(C(F)(F)F)cc3)c2)cc1-n1cc(-c2cnc3[nH]ccc3c2)cn1]

Compound 180 was synthesized by employing steps similar to those described in Example 167. Exact Mass (calculated): 537.17; MS(ESI) m/z (M+1)+: 538.17.

Example 181: N-(3-(4-(1H-pyrrolo[2,3-b]pyrid-5-yl)-1H-pyrazol-1-yl)-4-methylphenyl)-3-aminosulfonyl-benzamide 181

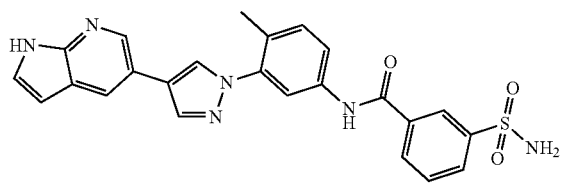 [SMILES: Cc1ccc(NC(=O)c2cccc(S(N)(=O)=O)c2)cc1-n1cc(-c2cnc3[nH]ccc3c2)cn1]

Compound 181 was synthesized by employing steps similar to those described in Example 167. Exact Mass (calculated): 472.13; MS(ESI) m/z (M+1)+: 473.13.

Example 182: N-(3-(4-(1H-pyrrolo[2,3-b]pyrid-5-yl)-1H-pyrazol-1-yl)-4-methylphenyl)quinoline-7-carboxamide 182

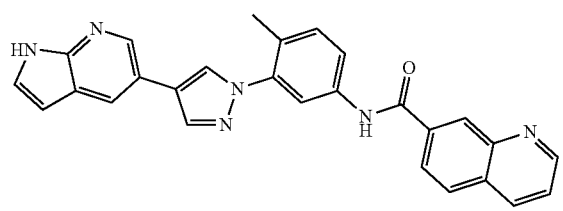 [SMILES: Cc1ccc(NC(=O)c2ccc3cccnc3c2)cc1-n1cc(-c2cnc3[nH]ccc3c2)cn1]

Compound 182 was synthesized by employing steps similar to those described in Example 167. Exact Mass (calculated): 444.16; MS(ESI) m/z (M+1)+: 445.16.

Example 183: N-(3-(4-(1H-pyrrolo[2,3-b]pyrid-5-yl)-1H-pyrazol-1-yl)-4-methylphenyl)-3-(thien-3-yl)benzamide 183

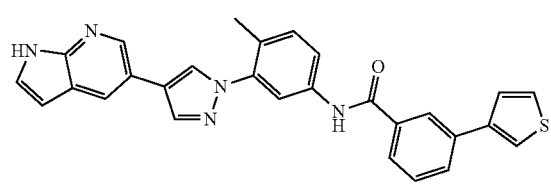 [SMILES: Cc1ccc(NC(=O)c2cccc(-c3ccsc3)c2)cc1-n1cc(-c2cnc3[nH]ccc3c2)cn1]

Compound 183 was synthesized by employing steps similar to those described in Example 167. Exact Mass (calculated): 475.14; MS(ESI) m/z (M+1)+: 476.14.

Example 184: N-(3-(4-(1H-pyrrolo[2,3-b]pyrid-5-yl)-1H-pyrazol-1-yl)-4-methylphenyl)-3-(pyrid-2-yl)benzamide 184

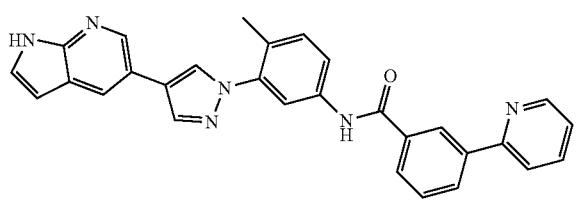 [SMILES: Cc1ccc(NC(=O)c2cccc(-c3ccccn3)c2)cc1-n1cc(-c2cnc3[nH]ccc3c2)cn1]

Compound 184 was synthesized by employing steps similar to those described in Example 167. Exact Mass (calculated): 470.18; MS(ESI) m/z (M+1)+: 471.18.

Example 185: N-(3-(4-(1H-pyrrolo[2,3-b]pyrid-5-yl)-1H-pyrazol-1-yl)-4-methylphenyl)-[1,1'-biphenyl]-3-carboxamide 185

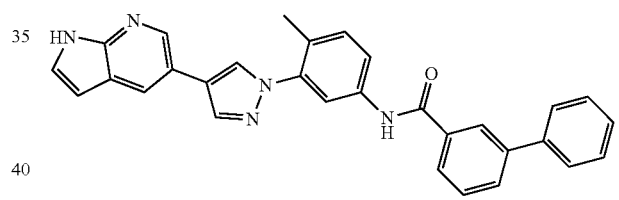

Compound 185 was synthesized by employing steps similar to those described in Example 167. Exact Mass (calculated): 469.19; MS(ESI) m/z (M+1)+: 470.19.

Comparative Example 1: 3-trifluoromethyl-N-(4-methyl-3-(4-(pyrid-3-yl)-1H-pyrazol-1-yl)phenyl)benzamide

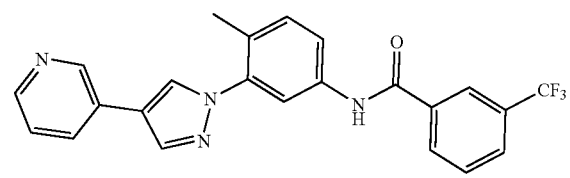 [SMILES: Cc1ccc(NC(=O)c2cccc(C(F)(F)F)c2)cc1-n1cc(-c2cccnc2)cn1]

Comparative Compound 1 was synthesized by employing steps similar to those described in Example 1. Exact Mass (calculated): 422.14; MS(ESI) m/z (M+1)+: 423.14.

Comparative Example 2: 3-chloro-N-(4-methyl-3-(4-(pyrid-3-yl)-1H-pyrazol-1-yl)phenyl)benzamide

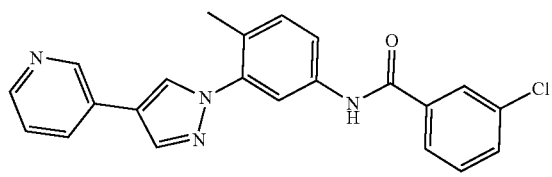 [SMILES: Cc1ccc(NC(=O)c2cccc(Cl)c2)cc1-n1cc(-c2cccnc2)cn1]

Comparative Compound 2 was synthesized by employing steps similar to those described in Example 1. Exact Mass (calculated): 388.11; MS(ESI) m/z (M+1)+: 389.12.

Example 186: Effect on Proliferation of Cancer Cells

The compounds of the present invention were tested for their effect on growth of cancer cells (Table 2), to further evaluate the compounds herein for their inhibitory effect on proliferation of cancer cells and their selectivity in inhibiting proliferation of cancer cells.

In the present example, mouse primary B cell BaF3 (purchased from ATCC), mouse BaF3-FL-BRAF-V600E (stably expressing full-length BRAF-V600E mutant kinase), melanoma cell A375 (expressing BRAF-V600E mutant kinase, purchased from Cobioer Biosciences Co., Ltd., Nanjing, China), colorectal cancer cell COL0205 (expressing BRAF-V600E mutant kinase, purchased from ATCC, USA), human acute leukemia cell OCI-AML-3 (expressing NRAS-Q61 L mutant kinase, purchased from Cobioer Biosciences Co., Ltd., Nanjing, China), and human acute leukemia cell NB4 (expressing KRAS-A18D mutant kinase, purchased from ATCC, USA) were used. The above-mentioned BaF3-FL-BRAF-V600E mutant cell line was constructed by the method as follows. The sequence of human full-length BRAF-V600E mutant kinase region was amplified by PCR, inserted into a MSCV-Puro vector (purchased from Clontech), and stably transfected into mouse BaF3 cells by the retroviral method, and the growth factor IL-3 was removed. Eventually, a cell line dependent on a full-length BRAF-V600E protein having various mutation transferred was obtained.

In the example, solutions of the test compound in DMSO at different concentrations (0.000508 µM, 0.00152 µM, 0.00457 µM, 0.0137 µM, 0.0411 µM, 0.123 µM, 0.370 µM, 1.11 µM, 3.33 µM, 10 µM) was added to the above cells respectively. The cells were incubated for 72 hours. The number of viable cells was detected with a Cell Titer-Glo (Promega, USA) Cell Viability Assay Kit by quantifying the ATP in viable cells. The values of $GI_{50}$ (unit) of the compounds of the present invention against each of the test cells were determined. The experimental results were shown in Table 2.

TABLE 2

| Example No. | BaF3 (µM) | BaF3-FL-BRAF-V600E (µM) | A375 (µM) | COLO205 (µM) | AML-3 (µM) | NB4 (µM) |
|---|---|---|---|---|---|---|
| 2 | 1.7 | | | 0.036 | 0.048 | |
| 3 | 1 | <0.0003 | 0.021 | 0.01 | | |
| 5 | 0.51 | 0.0019 | 0.019 | 0.017 | | |
| 6 | 0.78 | 0.0075 | 0.057 | 0.053 | | |
| 7 | 2.4 | 0.012 | 0.086 | 0.15 | | |
| 8 | 0.31 | 0.01 | 0.027 | 0.028 | | |
| 12 | 0.21 | 0.0074 | 0.097 | 0.045 | | |
| 13 | 1.3 | | 0.081 | 0.062 | | |
| 16 | >10 | 0.02 | 0.077 | 0.088 | 0.021 | 0.027 |
| 30 | | 0.01 | 0.047 | 0.052 | | |
| 31 | | | 0.1 | 0.098 | | |
| 47 | 0.6 | 0.0013 | 0.017 | 0.015 | | |
| 48 | 0.52 | 0.0041 | 0.014 | 0.032 | | |
| 49 | 0.5 | 0.0072 | 0.041 | 0.052 | | |
| 56 | 4.1 | <0.0003 | 0.077 | 0.119 | | |
| 65 | 1.7 | 0.0013 | 0.016 | 0.035 | | |
| 66 | 3 | 0.018 | 0.071 | 0.23 | | |
| 68 | 1.8 | 0.0043 | 0.027 | 0.066 | | |
| 69 | 1.2 | 0.016 | 0.035 | 0.061 | | |
| 71 | 1.1 | 0.028 | 0.079 | 0.056 | | |
| 72 | 5.8 | 0.0056 | 0.034 | 0.1 | | |
| 79 | 4.8 | <0.0003 | 0.061 | 0.057 | | |
| 82 | 3.2 | 0.004 | 0.097 | 0.083 | | |
| 84 | 8.6 | <0.0003 | 0.099 | 0.13 | | |
| 87 | 2.5 | <0.0003 | 0.036 | 0.065 | | |
| 109 | 3.8 | | 0.06 | 0.11 | | |
| 159 | 5.2 | 0.0066 | 0.022 | 0.036 | 0.023 | 0.16 |
| 161 | 3.6 | 0.0023 | 0.014 | 0.055 | 0.012 | 0.095 |
| 162 | 5 | 0.0039 | 0.032 | 0.039 | 0.011 | 0.061 |
| 163 | 1.6 | 0.018 | 0.16 | 0.039 | 0.01 | 0.044 |
| 164 | 1.6 | 0.004 | 0.12 | 0.071 | 0.0091 | 0.035 |
| 165 | 1.8 | <0.0003 | 0.04 | 0.19 | 0.014 | 0.075 |
| 166 | 2.6 | 0.001 | 0.077 | 0.094 | 0.019 | 0.069 |
| 167 | 3.9 | | 0.33 | 0.67 | | |
| 168 | 3.3 | | 0.046 | 0.028 | | |
| 170 | 4.8 | | 0.27 | 0.28 | | |
| 171 | 2.6 | | 0.11 | 0.36 | | |
| 174 | 0.96 | | 0.16 | 0.11 | | |
| 175 | 1.6 | | 0.1 | 0.15 | | |
| 176 | 0.92 | | 0.089 | 0.13 | | |
| 177 | 2.7 | | 0.12 | 0.065 | | |
| 178 | 3.7 | | 0.14 | 0.3 | | |
| 179 | 3.6 | | 0.25 | 0.14 | | |
| 182 | 2 | | 0.5 | 0.4 | | |
| 183 | 3.4 | | 0.3 | 0.15 | | |
| Comp. Example 1 | 3.3 | 0.017 | 0.085 | 0.15 | 0.02 | 0.083 |
| Comp. Example 2 | 9.3 | 0.24 | 1.6 | 3.3 | | |

It has been experimentally demonstrated that the compounds of the present invention could have a comparable or even better inhibitory activity against the cell lines of BaF3-FL-BRAF-V600E, A375 and COL0205 expressing BRAF-V600E as compared with that of the Comparative Compound 1, and have a better inhibitory activity as compared with that of the Comparative Compound 2. In the OCI-AML-3 and NB34 cells expressing a NRAS mutation or KRAS mutation, the compounds of the present invention also exhibited a comparable or better inhibitory activity as compared with the Comparative Compound 1 and Comparative Compound 2.

Example 187: Protease Activity Assay

The activity of Compound 16 and the control compound PLX4032 (MedChem Express, China) against the BRAF, BRAF V599E and RAF 1 (cRAF) Y340 target sites was tested by Invitrogen (Carlsbad, USA).

It was shown from the data that Compound 16 of the present invention had a strong inhibitory effect against each of BRAF protein, BRAF-V600E protein and RAF1 (CRAF) Y340D protein in vitro, which was better than the control compound PLX4032.

TABLE 3

In vitro enzymatic activity assay of Compound 16 and the control compound PLX4032 against proteins BRAF, BRAF-V600E, RAF1 (CRAF) Y340D

| $IC_{50}$ (nM) | Compound 16 | PLX4032 |
|---|---|---|
| BRAF | 5.9 | 17.5 |
| BRAF-V600E | 5.89 | 41.7 |
| RAF1 (CRAF) Y340D | 3.55 | 23.5 |

Example 188: Study on Pharmacokinetic Parameters in Rats

In the example, SD rats (180-220 g, male) (purchased from Experimental Animal Center of Anhui Medical University, China) were used. The animals were kept in cages ventilated independently with 6 rats per cage. The feeding was performed at a temperature of 20~26° C. and a humidity of 35-75%. The light condition was 12 hours of lighting/12 hours of darkness. The corncob bedding was refreshed once a week. The rats were fed with foods and drinking water on an ad libitum basis. The rats were marked with a number on the tails. During the experiment, the breeding and use of animals strictly follow the regulations of Association for Assessment and Accreditation of Laboratory Animal Care International.

Solutions of Compound 16 and Comparative Compound 1 were prepared as follows. 10 mg of the compound to be tested was precisely weighed into a sterile vial, and was dissolved with a small amount of DMSO, and then was made to a constant volume of 5 ml with 5% glucose solution, to give a gavage test solution at a concentration of 2 mg/mL. 0.5 ml of the above gavage test solution at a concentration of 2 mg/mL was precisely taken, and was made to constant volume of 5 ml with 4.5 ml of 5% glucose solution, to give an intravenous injection test solution at a concentration of 0.2 mg/mL. The solution was prepared immediately before being used in the experiment.

6 SD rats were randomly divided into two groups, and the synthesized compounds were administered by gavage and tail vein injection, respectively. About 0.3 mL of blood samples were collected from the retro-orbital venous plexus at 0 h before administration and at 5 min, 15 min, 30 min, 1 h, 1.5 h, 2 h, 4 h, 6 h, 9 h, 12 h, 24 h after administration for the gavage group; and at 0 h before administration and at 2 min, 5 min, 15 min, 30 min, 1 h, 2 h, 4 h, 6 h, 9 h, and 12 h after administration for the tail vein group. Each of the collected blood samples was put in a 1.5 mL centrifuge tube with heparin (Sigma, USA). The sample was centrifuged at 6000 rpm for 3 min to separate the plasma. 100 μL of plasma in the upper layer was placed into a new 1.5 mL centrifuge tube, and stored at −80° C. for determination. 10 mg of a standard for the compound to be tested was precisely weighed into a 10 mL volumetric flask, and was dissolved by adding methanol to make a constant volume and mixed uniformly, to give a 1 mg/mL stock solution. The stock solution was then diluted gradually with methanol to give a series of working solutions at concentrations of 0.01, 0.02, 0.05, 0.1, 0.2, 0.5, 1, 2, 5, 10, 20 μg/mL. The working solutions were placed in a refrigerator at 4° C. for later use. 11 centrifuge tubes were used. 10 μL of the above working solutions was respectively added to each of the centrifuge tubes, and then 90 μL of blank rat plasma was respectively added therein. The mixtures were mixed uniformly, so that the concentration of the compound in the rat plasma was 1, 2, 5, 10, 20, 50, 100, 200, 500, 1000, 2000 ng/mL. Then, 20 μL of a solution of caffeine as the internal standard (200 ng/mL) (National Institutes for Food and Drug Control, China) was added therein, and the resultant mixtures were vortexed for 10 s. Next, 400 μL of methanol was added. The resultant mixtures were vortexed for 10 min, and centrifuged at 16000 rpm for 5 min. Thereafter, 70 μL of the supernatant was placed into the inserted pipe of a sampling bottle. 5 μL of the sample was introduced for a LC-MS/MS analysis. A standard curve of the compound in the rat plasma was obtained by means of a linear regression performed by taking the ratio of the peak area of the sample to that of the internal standard As/Ais as the vertical ordinate, taking the concentration C (μg/mL) as the horizontal ordinate, and taking $1/C^2$ was taken as a weighting coefficient.

To 100 μL of the rat plasma to be tested stored at −80° C., 20 μL of a caffeine solution (200 ng/mL) as the internal standard was added. The resultant mixture was vortexed for 10 s. Next, 400 μL of methanol was added. The resultant mixture was vortexed for 10 min, and centrifuged at 16000 rpm for 5 min. Thereafter, 70 μL of the supernatant was placed into the inserted pipe of a sampling bottle. 5 μL of the sample was introduced for LC-MS/MS analysis.

The LC-MS/MS analysis was performed by the procedure as follows. The experimental instrument was API 4000 Triple Quad detector (AB SCIEX, USA); the operating software was Analyst 1.5.1 (Applied Biosystems Co., Ltd., USA); a Shimadzu LC-30AD liquid pump, a Shimadzu DGU-20A degassing unit, a Shimadzu CTO-30A column oven, and a SIL-30AC autosampler (Shimadzu Corporation, Japan) were used. The chromatographic conditions were as follows. The chromatographic column was Hanbon *Hedera* ODS-2 (Jiangsu Hanbon Science & Technology Co., Ltd., China), Dim. (mm): 150×2.1, Pro. No: H18100205.15; Ser. No: C981210513; the column temperature was 40° C.; a mobile phase A was aqueous phase (containing 0.1% formic acid), and a mobile phase B was methanol for a gradient elution: 0-0.5 min, B 10%; 0.5-1.0 min, B 90%; 1.0-5.0 min, B 90%; 5.0-5.5 min, B 10%; 5.5-7 min, B 10%. The flow rate was 0.3 mL/min. The injection volume was 5 μL. The Mass spectrometry conditions were as follows. The ion source was Turbo Spray source; the CAD was 10; the curtain gas (CUR) was 25; the heating temperature was 500° C.; the ion source gas GS1 was 45; the ion source gas GS2 was 45; the spray voltage was 5500V; and the source temperature was 500° C.

The results were shown in Table 4-7 below. The results showed that the highest concentration Cmax of Compound 16 in blood was higher than that of Comparative Compound 1, whether administered by intravenous injection or administrated by gavage. When administered by gavage, the maximum drug absorption of Compound 16 in vivo in rats was 1482 ng/ml, the cumulative drug concentration in vivo $AUC_{0-t}$ was 10930 hr*ng/ml, and the oral bioavailability F % was 144.1%. On the other hand, the maximum drug absorption of Comparative Compound 1 in vivo in rats was 575.7 ng/ml, the cumulative drug concentration in vivo $AUC_{0-t}$ was 1012 hr*ng/ml, and the oral bioavailability F % was 110.7%. Therefore, by introducing a substituent group on the pyridyl group, the compound of the present invention can have a greatly improved absorption in rats, and a considerably improved oral bioavailability.

TABLE 4

Intravenous injection of Compound 16 at 1 mg/kg (n = 3)

| Parameter | Unit | #1 | #2 | #3 | Average | SD |
|---|---|---|---|---|---|---|
| T½ | hr | 3.59 | 2.62 | 2.84 | 3.01 | 0.51 |
| Tmax | hr | 0.033 | 0.033 | 0.033 | 0.033 | 0.000 |
| Cmax | ng/ml | 1020 | 796 | 925 | 914 | 112 |
| $C_0$ | ng/ml | 1308 | 933 | 1116 | 1119 | 187 |
| $AUC_{0-t}$ | hr*ng/ml | 822 | 680 | 723 | 742 | 73 |
| $AUC_{0-\infty}$ | hr*ng/ml | 861 | 694 | 742 | 765 | 86 |
| Vz | ml/kg | 6010 | 5441 | 5521 | 5657 | 308 |
| Cl | ml/hr/kg | 1162 | 1442 | 1348 | 1317 | 142 |
| $AUMC_{0-t}$ | hr*hr*ng/ml | 1708 | 1207 | 1326 | 1413 | 262 |
| $AUMC_{0-\infty}$ | hr*hr*ng/ml | 2368 | 1418 | 1630 | 1805 | 499 |
| $MRT_{0-t}$ | hr | 2.08 | 1.77 | 1.83 | 1.89 | 0.16 |
| $MRT_{0-\infty}$ | hr | 2.75 | 2.04 | 2.20 | 2.33 | 0.37 |

TABLE 5

Oral administration of Compound 16 at 10 mg/kg (n = 3)

| Parameter | Unit | #1 | #2 | #3 | Average | SD |
|---|---|---|---|---|---|---|
| T½ | hr | 3.19 | 2.86 | 3.01 | 3.02 | 0.17 |
| Tmax | hr | 0.5 | 0.5 | 1 | 0.67 | 0.29 |
| Cmax | ng/ml | 2090 | 1710 | 645 | 1482 | 749 |
| $AUC_{0-t}$ | hr*ng/ml | 13357 | 11999 | 7435 | 10930 | 3103 |
| $AUC_{0-\infty}$ | hr*ng/ml | 13475 | 12067 | 7520 | 11021 | 3112 |
| Vz | ml/kg | 3418 | 3420 | 5773 | 4204 | 1359 |
| Cl | ml/hr/kg | 742 | 829 | 1330 | 967 | 317 |
| $AUMC_{0-t}$ | hr*hr*ng/ml | 80004 | 72172 | 58480 | 70219 | 10894 |
| $AUMC_{0-\infty}$ | hr*hr*ng/ml | 83364 | 74076 | 60891 | 72777 | 11293 |
| $MRT_{0-t}$ | hr | 5.99 | 6.01 | 7.87 | 6.62 | 1.08 |
| $MRT_{0-\infty}$ | hr | 6.19 | 6.14 | 8.10 | 6.81 | 1.12 |
| F | | 176.1% | 157.7% | 98.3% | 144.1% | 40.7% |

TABLE 6

Intravenous injection of Comparative Compound 1 at 1 mg/kg (n = 3)

| Parameter | Unit | #1 | #2 | #3 | Average | SD |
|---|---|---|---|---|---|---|
| T½ | hr | 0.646 | 0.906 | 0.592 | 0.715 | 0.168 |
| Tmax | hr | 0.033 | 0.033 | 0.033 | 0.033 | 0 |
| Cmax | ng/ml | 200.0 | 285.0 | 300.0 | 261.7 | 53.9 |
| $C_0$ | ng/ml | 260.5 | 402.4 | 380.8 | 347.9 | 76.5 |
| $AUC_{0-t}$ | hr*ng/ml | 83.29 | 71.86 | 119.59 | 91.58 | 24.92 |
| $AUC_{0-\infty}$ | hr*ng/ml | 84.00 | 73.08 | 120.51 | 92.53 | 24.84 |
| Vz | ml/kg | 11101 | 17886 | 7085 | 12024 | 5459 |
| Cl | ml/hr/kg | 11905 | 13684 | 8298 | 11296 | 2744 |
| $AUMC_{0-t}$ | hr*hr*ng/ml | 50.39 | 31.52 | 78.58 | 53.50 | 23.68 |
| $AUMC_{0-\infty}$ | hr*hr*ng/ml | 53.89 | 37.99 | 83.06 | 58.31 | 22.86 |
| $MRT_{0-t}$ | hr | 0.605 | 0.439 | 0.657 | 0.567 | 0.114 |
| $MRT_{0-\infty}$ | hr | 0.642 | 0.520 | 0.689 | 0.617 | 0.087 |

TABLE 7

Oral administration of Comparative Compound 1 at 10 mg/kg (n = 3)

| Parameter | Unit | #1 | #2 | #3 | Average | SD |
|---|---|---|---|---|---|---|
| T½ | hr | 1.004 | 0.821 | 0.894 | 0.906 | 0.092 |
| Tmax | hr | 0.5 | 0.5 | 0.5 | 0.5 | 0 |
| Cmax | ng/ml | 138 | 579 | 1010 | 575.7 | 436.0 |
| $AUC_{0-t}$ | hr*ng/ml | 285.6 | 1217 | 1532 | 1012 | 648 |
| $AUC_{0-\infty}$ | hr*ng/ml | 289.0 | 1236 | 1547 | 1024 | 655 |
| Vz | ml/kg | 50104 | 9579 | 8334 | 22672 | 23764 |
| Cl | ml/hr/kg | 34606 | 8089 | 6465 | 16387 | 15799 |
| $AUMC_{0-t}$ | hr*hr*ng/ml | 518.7 | 1889 | 2013 | 1474 | 829 |
| $AUMC_{0-\infty}$ | hr*hr*ng/ml | 554.4 | 2023 | 2121 | 1566 | 878 |
| $MRT_{0-t}$ | hr | 1.816 | 1.552 | 1.314 | 1.561 | 0.251 |
| $MRT_{0-\infty}$ | hr | 1.919 | 1.637 | 1.371 | 1.642 | 0.274 |
| F | | 31.2% | 133.6% | 167.2% | 110.7% | 70.8% |

Example 189: Drug Efficacy Experiment on Animals

In the present Example, the experimental results of Compound 16, Comparative Compound 1, and control compounds LY30019120 (purchased from MedChemExpress, China), PLX4032 (purchased from MedChemExpress, China), RAF709 (purchased from MedChemExpress, China), RAF265 (purchased from MedChemExpress, China), and PLX8394 (purchased from MedChemExpress, China) in the mouse models of human degenerative lung cancer Calu-6 (expressing KRAS Q61K mutant kinase, purchased from Cobioer Biosciences Co., Ltd., Nanjing, China), melanoma cell A375 (expressing BRAF-V600E mutant kinase, purchased from Cobioer Biosciences Co., Ltd., Nanjing, China), pancreatic cancer cell BxPC3 (expressing KRAS wild-; type, BRAF V487-P492>A deletion mutant kinase, purchased from Cobioer Biosciences Co., Ltd., Nanjing, China), colorectal cancer cell HCT116 (expressing KRAS G13D mutant kinase, purchased from ATCC, USA), colorectal cancer cell COL0205 (expressing BRAF-V600E mutant kinase, purchased from ATCC, USA) were tested respectively.

The experimental steps were as follows:
(1) 4-6 weeks old female SCID mice (A375/COL0205) and nude mice (HCT116/Calu-6/BxPC) purchased from Beijing Vital River Laboratory Animal Technology Co., Ltd. were raised at SPF level in the laboratory. The drinking water and the bedding had been sterilized by autoclaving. All the operations on mice were performed under aseptic conditions.
(2) On Day 0, about $5 \times 10^6$ of non-small cell lung cancer Calu-6, colorectal cancer HCT116, colorectal cancer COLO205, melanoma A375 and pancreatic cancer BxPC3 cells were injected subcutaneously into the left back of the mouse. (3) Starting from Day 14, the respective mice were orally administered with a solvent of castor oil:ethanol:water (1:1:6) every day (5 mice); Compound 16 at a dose of 50 mg/kg, 100 mg/kg and PLX4032 at a dose of 100 g/kg for the A375 transplanted tumor; Compound 16 at a dose of 50 mg/kg, 100 mg/kg and 200 mg/kg, RAF709 at a dose of 100 g/kg, LY30019120 at a dose of 60 mg/kg and Comparative Compound 1 at a dose of 100 mg/kg for the Calu-6 transplanted tumor; Compound 16 at a dose of 50 mg/kg, 100 mg/kg, RAF709 at a dose of 100 mg/kg and LY30019120 at a dose of 60 mg/kg for the HCT116 transplanted tumor; Compound 16 at a dose of 25 mg/kg, 50 mg/kg, 100 mg/kg, PLX4032 at a dose of 100 mg/kg for the COL0205 transplanted tumor; Compound 16 at a dose of 50 mg/kg, 100 mg/kg, 200 mg/kg, LY3009120 at a dose of 100 mg/kg, RAF265 at a dose of 100 mg/kg and PLX8394 at 100 mg/kg for the BxPC3 transplanted tumor. Starting from Day 15, the respective mice were orally administered with the solvent of castor oil:ethanol:water (1:1:6) every day.
(4) Starting from Day 15, the length/width of the subcutaneous tumors was measured with a vernier calliper every day, and the weight of the mouse was recorded every day to determine the effect of Compound 16 on the weight of the mouse.

(5) For each of the model groups, the mice were sacrificed on Day 36, Day 42, Day 26, Day 35 or Day 42.

(6) The growth trend of the subendothelialtumors was statistically analyzed. The tumor volume was calculated as follows: length×width×width/2 mm$^3$.

It has been experimentally demonstrated that Compound 16 of the present invention had an inhibitory effect superior to the control compounds in mouse transplanted tumor models of different cancer cells expressing KRAS, BRAF or NRAS mutations. As Compared with Comparative Compound 1, in the calu6 cell transplanted tumor model, Comparative Compound 1 had a very strong toxicity as all mice died on Day 8, while Compound 16 did not exhibit any toxicity. It has also been proven that the compound of the present invention having introduced a morpholinyl substituent would produce unexpected pharmaceutical effects in vivo in mice without producing significant toxicity.

INDUSTRIAL APPLICABILITY

The invention provides a novel pan-RAF kinase inhibitor, comprising a compound of formula (I) or a pharmaceutically acceptable salt, solvate, ester, acid, metabolite or prodrug thereof. The present invention also provides a use or method of the compound of formula (I) in the treatment or prevention of a disorder related to the activity of RAF and/or RAS kinase. Therefore, the above inhibitor can be prepared as corresponding medicament and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A kinase inhibitor, comprising a compound of formula (I) or a pharmaceutically acceptable salt, solvate, ester, acid, metabolite or prodrug thereof:

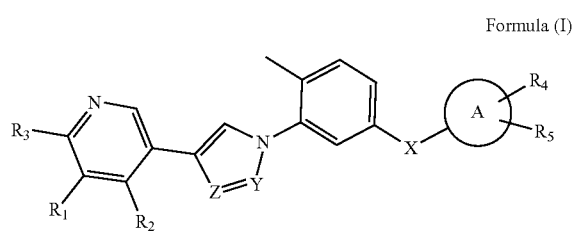

Formula (I)

wherein,
X is selected from the group consisting of

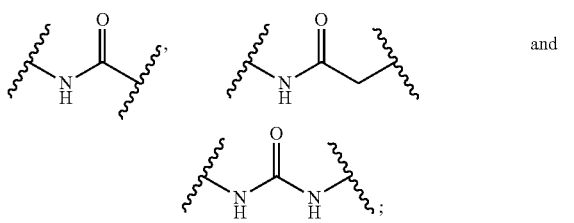

one of Y and Z is carbon and the other is nitrogen;
A ring is selected from the group consisting of

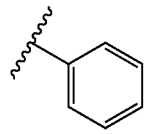 and 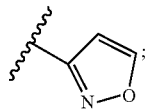;

$R_1$, $R_2$ and $R_3$ are each independently selected from the group consisting of H, cyano, $C_{1-6}$ alkyl, $C_{1-6}$ alkoxy, $C_{1-6}$ hydroxyalkyl, $C_{1-6}$ hydroxyalkoxy, $C_{3-6}$ cycloalkyl $C_{1-6}$ alkoxy, $C_{1-6}$ alkoxy $C_{1-6}$ alkoxy, phenyl, pyridyl, phenyl $C_{1-6}$ alkoxy, furyl $C_{1-6}$ alkoxy, heterocycloalkyl optionally substituted with $R_6$, heterocycloalkylphenyl optionally substituted with $R_6$, heterocycloalkylcarbonyl optionally substituted with $R_6$, heterocycloalkyloxy optionally substituted with $R_6$, heterocycloalkyl $C_{1-6}$ alkoxy optionally substituted with $R_6$, heterocycloalkyl $C_{1-6}$ alkanoylamino optionally substituted with $R_6$, $C_{3-6}$ cycloalkyl $C_{1-6}$ alkanoylamino, and $C_{1-6}$ alkylaminocarbonyl $C_{1-6}$ alkoxy, or $R_1$ together with $R_3$ forms

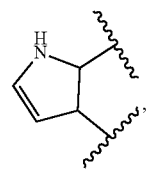

wherein $R_1$, $R_2$ and $R_3$ are not H at the same time;
$R_4$ and $R_5$ are each independently selected from the group consisting of H, $C_{1-6}$ alkyl, $C_{1-6}$ haloalkyl, $C_{1-6}$ cyanoalkyl, heterocycloalkyl $C_{1-6}$ alkyl optionally substituted with $R_6$, phenyl optionally substituted with $R_6$, heteroaryl optionally substituted with $R_6$, and aminosulfonyl, or
$R_4$ together with $R_5$ forms

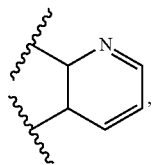

and $R_4$ and $R_5$ are not H at the same time;
$R_6$ is independently selected from the group consisting of oxo, $C_{1-6}$ alkyl, $C_{2-6}$ alkanoyl, $C_{1-6}$ alkylsulfonyl, $C_{1-6}$ alkylamino $C_{2-6}$ alkanoyl, and $C_{1-6}$ haloalkyl.

2. The kinase inhibitor according to claim 1, wherein Y is nitrogen and Z is carbon.

3. The kinase inhibitor according to claim 1, wherein the A ring is

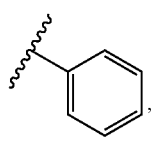 [SMILES: *c1ccccc1], and the substituents $R_4$ and $R_5$ are located at the meta- and para-positions of the benzene ring, respectively.

4. The kinase inhibitor according to claim 1, wherein $R_2$ and $R_3$ are H; and $R_1$ is selected from the group consisting of phenyl, pyridyl, heterocycloalkyl optionally substituted with $C_{1-6}$ alkyl, heterocycloalkylphenyl optionally substituted with $C_{1-6}$ alkyl, heterocycloalkylcarbonyl optionally substituted with $C_{1-6}$ alkyl, heterocycloalkyloxy, heterocycloalkyl $C_{1-6}$ alkoxy, and $C_{1-6}$ alkylaminocarbonyl $C_{1-6}$ alkoxy.

5. The kinase inhibitor according to claim 1, wherein $R_1$ is H; $R_2$ is selected from the group consisting of H, cyano, $C_{1-6}$ alkyl, $C_{1-6}$ hydroxyalkoxy, $C_{3-6}$ cycloalkyl $C_{1-6}$ alkoxy, $C_{1-6}$ alkoxy $C_{1-6}$ alkoxy, phenyl $C_{1-6}$ alkoxy, furyl $C_{1-6}$ alkoxy, heterocycloalkyloxy optionally substituted with $R_6$ group, heterocycloalkyl $C_{1-6}$ alkoxy optionally substituted with $R_6$ group, heterocycloalkyl $C_{1-6}$ alkanoylamino optionally substituted with $C_{1-6}$ alkyl, and $C_{1-6}$ alkylaminocarbonyl $C_{1-6}$ alkoxy, wherein $R_6$ is independently selected from the group consisting of oxo, $C_{2-6}$ alkanoyl, $C_{1-6}$ alkylsulfonyl, $C_{1-6}$ alkylamino $C_{2-6}$ alkanoyl; $R_3$ is selected from the group consisting of H and $C_{3-6}$ cycloalkyl $C_{1-6}$ alkanoylamino; and $R_2$ and $R_3$ are not H at the same time.

6. The kinase inhibitor of claim 1, comprising a compound of formula (Ia) or a pharmaceutically acceptable salt, solvate, ester, acid, metabolite or prodrug thereof:

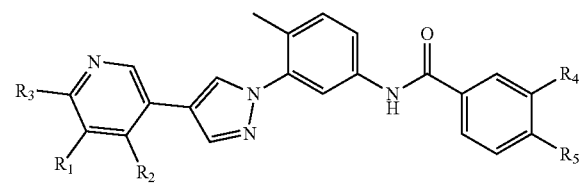

Formula (Ia)

wherein, $R_1$, $R_2$, $R_3$, $R_4$ and $R_5$ are as defined as in claim 1.

7. The kinase inhibitor according to claim 6, wherein
$R_1$ is selected from the group consisting of H, pyridyl, heterocycloalkyl, heterocycloalkylphenyl optionally substituted with $C_{1-6}$ alkyl, heterocycloalkyloxy, heterocycloalkyl $C_{1-6}$ alkoxy, and $C_{1-6}$ alkylaminocarbonyl $C_{1-6}$ alkoxy;
$R_2$ is selected from the group consisting of H, $C_{1-6}$ alkyl, $C_{1-6}$ hydroxyalkoxy, $C_{1-6}$ alkoxy $C_{1-6}$ alkoxy, heterocycloalkyloxy, and heterocycloalkyl $C_{1-6}$ alkoxy;
$R_3$ is selected from the group consisting of H, and $C_{3-6}$ cycloalkyl $C_{1-6}$ alkanoylamino;
wherein $R_1$, $R_2$ and $R_3$ are not H at the same time;
$R_4$ is selected from the group consisting of $C_{1-6}$ haloalkyl, and $C_{1-6}$ cyanoalkyl;
$R_5$ is selected from the group consisting of H, $C_{1-6}$ alkyl, and heterocycloalkyl $C_{1-6}$ alkyl optionally substituted with $C_{1-6}$ alkyl.

8. The kinase inhibitor according to claim 6, wherein
$R_1$ is selected from the group consisting of H, 3-pyridyl, 4-pyridyl, N-morpholinyl, piperazin-1-yl, 4-methyl-piperazin-1-ylphenyl, tetrahydropyran-4-yloxy, oxetan-3-yloxy, 2-morpholinoethoxy, 3-morpholinopropoxy, tetrahydrofuran-3-ylmethoxy, and dimethylaminocarbonylmethoxy;
$R_2$ is selected from the group consisting of H, methyl, 2-hydroxyethoxy, 3-hydroxypropoxy, 4-hydroxybutoxy, 2-methoxyethoxy, tetrahydropyran-4-yloxy, tetrahydrofuran-3-yloxy, oxetan-3-yloxy, azetidin-3-yloxy, 2-morpholinoethoxy, tetrahydrofuran-2-ylmethoxy, tetrahydrofuran-3-ylmethoxy, tetrahydropyran-4-ylmethoxy, oxetan-3-ylmethoxy, and pyrrolidin-3-ylmethoxy;
$R_3$ is selected from the group consisting of H, and cyclopropylformamido;
wherein $R_1$, $R_2$ and $R_3$ are not H at the same time;
$R_4$ is selected from the group consisting of trifluoromethyl, 2-cyanoethan-2-yl, and 2-cyanoprop-2-yl;
$R_5$ is selected from the group consisting of H, methyl, and 4-methyl-piperazin-1-ylmethyl.

9. The kinase inhibitor according to claim 6, wherein $R_1$ is selected from the group consisting of 3-pyridyl, 4-pyridyl, N-morpholinyl, heterocycloalkyloxy, heterocycloalkyl $C_{1-6}$ alkoxy, and $C_{1-6}$ alkylaminocarbonyl $C_{1-6}$ alkoxy; $R_4$ is selected from the group consisting of $C_{1-6}$ haloalkyl and $C_{1-6}$ cyanoalkyl; each of $R_2$, $R_3$ and $R_5$ is H.

10. The kinase inhibitor according to claim 6, wherein $R_2$ is selected from the group consisting of $C_{1-6}$ hydroxyalkoxy, $C_{1-6}$ alkoxy $C_{1-6}$ alkoxy, heterocycloalkyloxy, and heterocycloalkyl $C_{1-6}$ alkoxy; $R_4$ is selected from the group consisting of $C_{1-6}$ haloalkyl and $C_{1-6}$ cyanoalkyl; each of $R_1$, $R_3$ and $R_5$ is H.

11. The kinase inhibitor claim 1, comprising a compound of formula (Ib) or a pharmaceutically acceptable salt, solvate, ester, acid, metabolite or prodrug thereof:

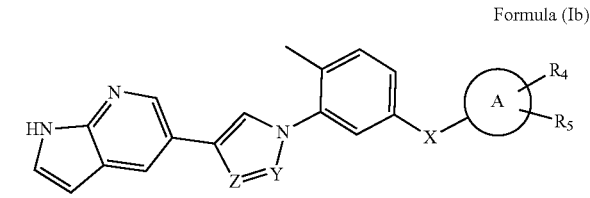

Formula (Ib)

wherein,
X is selected from the group consisting of

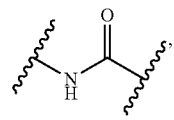 and 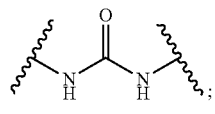;

one of Y and Z is carbon and the other is nitrogen;
A ring is selected from the group consisting of

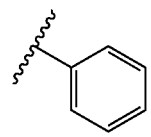 and 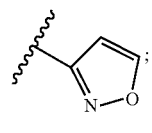;

$R_4$ and $R_5$ are each independently selected from the group consisting of H, $C_{1-6}$ alkyl, $C_{1-6}$ haloalkyl, $C_{1-6}$ cyanoalkyl, piperazinyl $C_{1-6}$ alkyl optionally substituted with $R_6$, phenyl optionally substituted with $R_6$, imidazolyl optionally substituted with $R_6$, thienyl optionally substituted with $R_6$, pyridyl optionally substituted with $R_6$, and aminosulfonyl, or $R_4$ together with $R_5$ forms

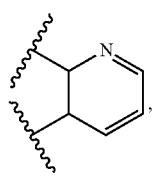 [SMILES: *C1C=CC=NC1*],
and R$_4$ and R$_5$ are not H at the same time;
R$_6$ is independently selected from the group consisting of C$_{1-6}$ alkyl and C$_{1-6}$ haloalkyl.
12. The kinase inhibitor according to claim 1, comprising a following compound or a pharmaceutically acceptable salt, solvate, ester, acid, metabolite or prodrug thereof:
| No. | Structure |
|---|---|
| 1 | 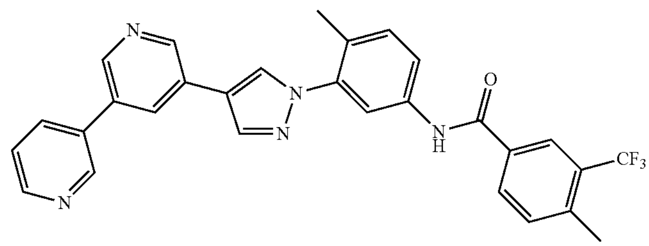 [SMILES: Cc1ccc(NC(=O)c2ccc(C)c(C(F)(F)F)c2)cc1-n1cc(-c2cncc(-c3cccnc3)c2)cn1] |
| 2 | 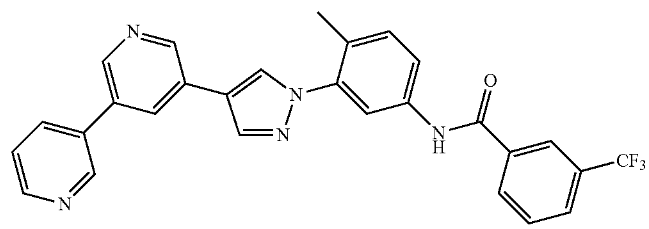 [SMILES: Cc1ccc(NC(=O)c2cccc(C(F)(F)F)c2)cc1-n1cc(-c2cncc(-c3cccnc3)c2)cn1] |
| 3 | 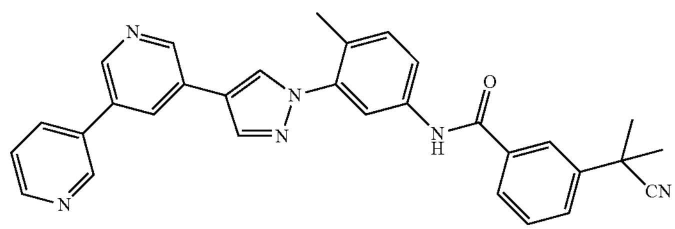 [SMILES: Cc1ccc(NC(=O)c2cccc(C(C)(C)C#N)c2)cc1-n1cc(-c2cncc(-c3cccnc3)c2)cn1] |
| 4 | 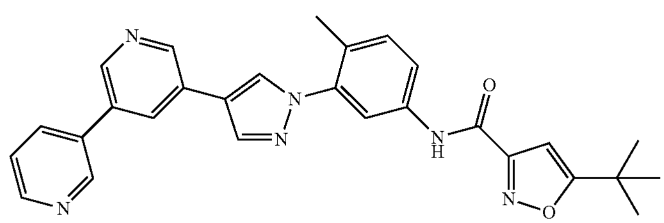 [SMILES: Cc1ccc(NC(=O)c2cc(C(C)(C)C)on2)cc1-n1cc(-c2cncc(-c3cccnc3)c2)cn1] |
| 5 | 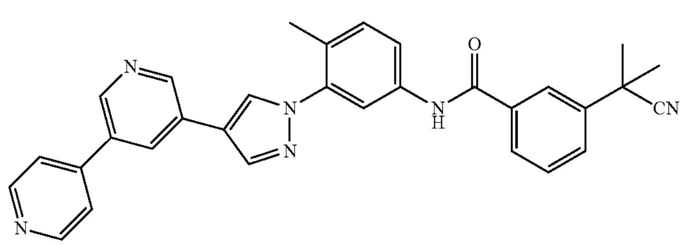 |

-continued

| No. | Structure |
|---|---|
| 6 | 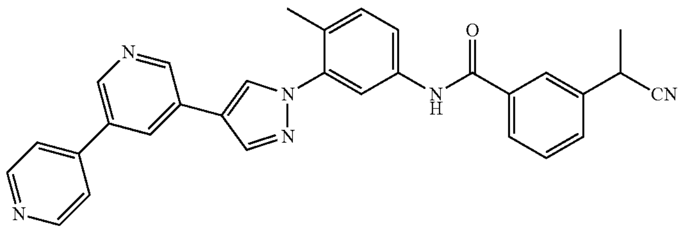 [SMILES: Cc1ccc(NC(=O)c2cccc(C(C)C#N)c2)cc1-n1cc(-c2cncc(-c3ccncc3)c2)cn1] |
| 7 | 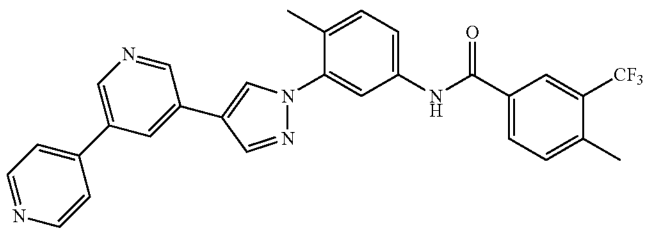 [SMILES: Cc1ccc(NC(=O)c2ccc(C)c(C(F)(F)F)c2)cc1-n1cc(-c2cncc(-c3ccncc3)c2)cn1] |
| 8 | 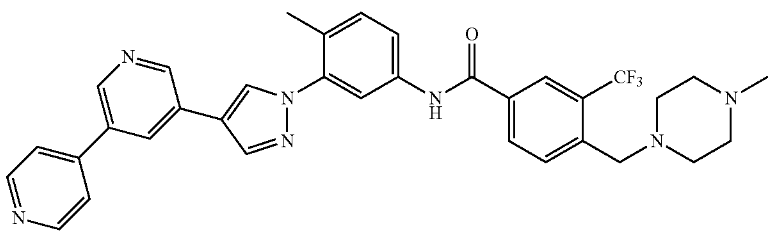 [SMILES: Cc1ccc(NC(=O)c2ccc(CN3CCN(C)CC3)c(C(F)(F)F)c2)cc1-n1cc(-c2cncc(-c3ccncc3)c2)cn1] |
| 9 | 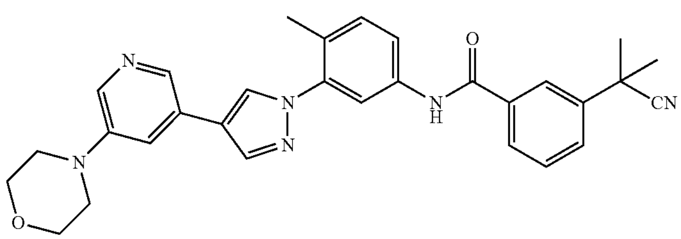 [SMILES: Cc1ccc(NC(=O)c2cccc(C(C)(C)C#N)c2)cc1-n1cc(-c2cncc(N3CCOCC3)c2)cn1] |
| 10 | 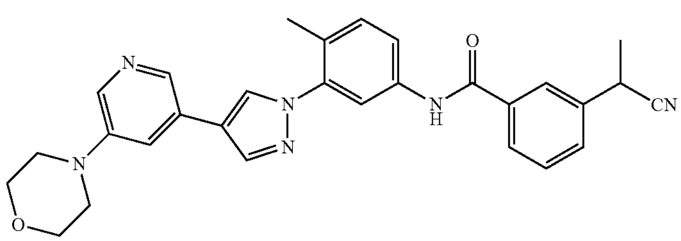 [SMILES: Cc1ccc(NC(=O)c2cccc(C(C)C#N)c2)cc1-n1cc(-c2cncc(N3CCOCC3)c2)cn1] |
| 11 | 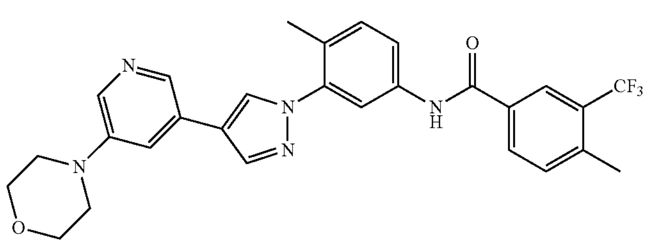 [SMILES: Cc1ccc(NC(=O)c2ccc(C)c(C(F)(F)F)c2)cc1-n1cc(-c2cncc(N3CCOCC3)c2)cn1] |

| No. | Structure |
|---|---|
| 12 | 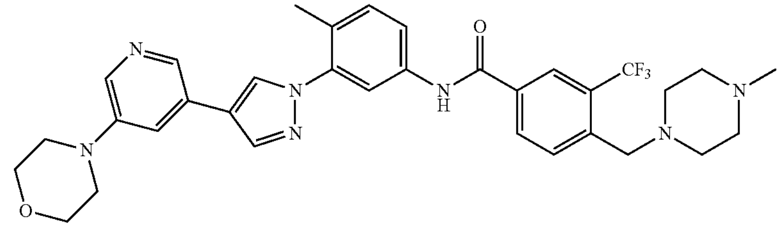 [SMILES: Cc1ccc(NC(=O)c2ccc(CN3CCN(C)CC3)c(C(F)(F)F)c2)cc1-n1cc(-c2cncc(N3CCOCC3)c2)cn1] |
| 13 | 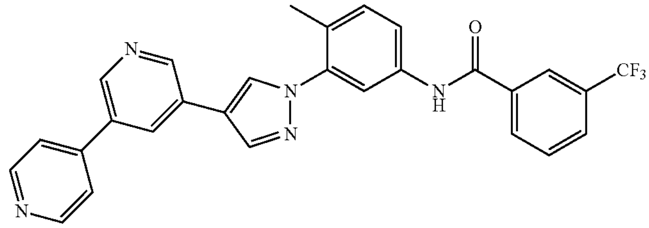 |
| 14 | 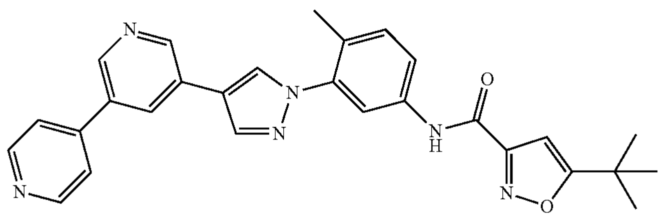 [SMILES: Cc1ccc(NC(=O)c2cc(C(C)(C)C)on2)cc1-n1cc(-c2cncc(-c3ccncc3)c2)cn1] |
| 15 | 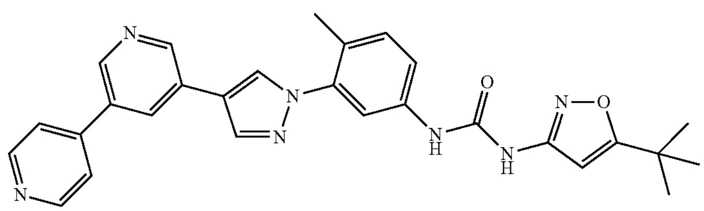 [SMILES: Cc1ccc(NC(=O)Nc2cc(C(C)(C)C)on2)cc1-n1cc(-c2cncc(-c3ccncc3)c2)cn1] |
| 16 | 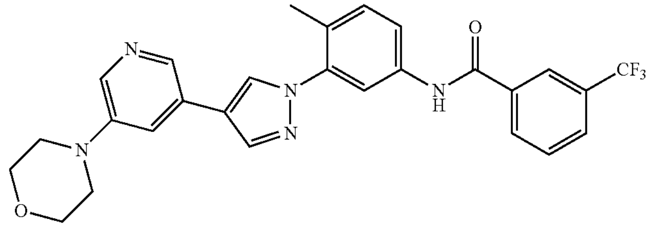 [SMILES: Cc1ccc(NC(=O)c2cccc(C(F)(F)F)c2)cc1-n1cc(-c2cncc(N3CCOCC3)c2)cn1] |
| 17 | 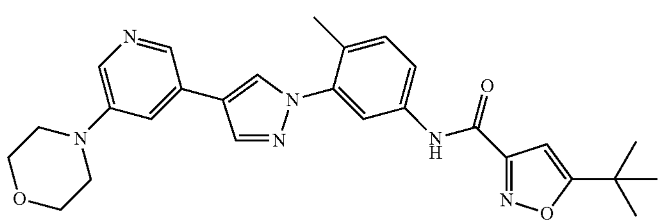 [SMILES: Cc1ccc(NC(=O)c2cc(C(C)(C)C)on2)cc1-n1cc(-c2cncc(N3CCOCC3)c2)cn1] |
| 18 | 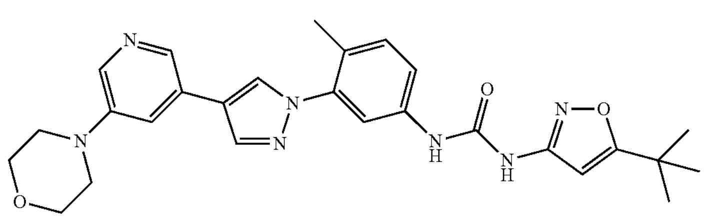 [SMILES: Cc1ccc(NC(=O)Nc2cc(C(C)(C)C)on2)cc1-n1cc(-c2cncc(N3CCOCC3)c2)cn1] |

-continued
| No. | Structure |
|---|---|
| 19 | 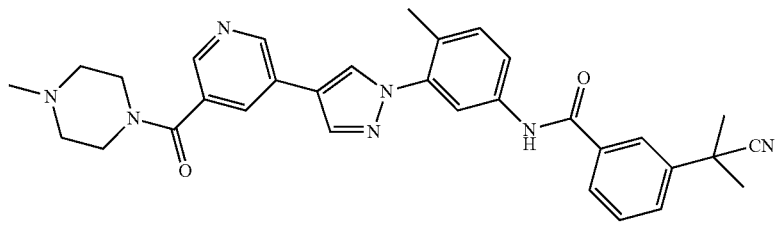 [SMILES: Cc1ccc(NC(=O)c2cccc(C(C)(C)C#N)c2)cc1-n1cc(-c2cncc(C(=O)N3CCN(C)CC3)c2)cn1] |
| 20 | 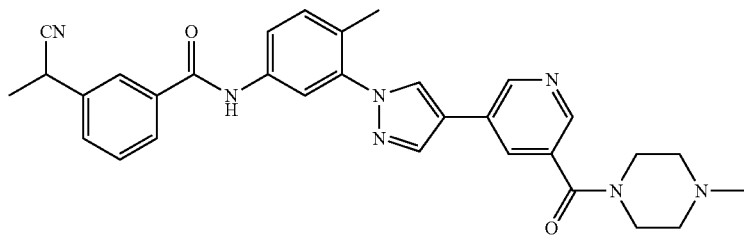 [SMILES: Cc1ccc(NC(=O)c2cccc(C(C)C#N)c2)cc1-n1cc(-c2cncc(C(=O)N3CCN(C)CC3)c2)cn1] |
| 21 | 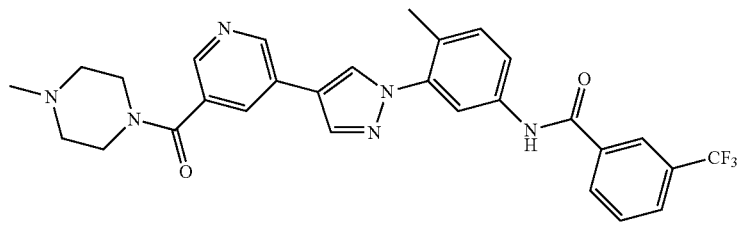 [SMILES: Cc1ccc(NC(=O)c2cccc(C(F)(F)F)c2)cc1-n1cc(-c2cncc(C(=O)N3CCN(C)CC3)c2)cn1] |
| 22 | 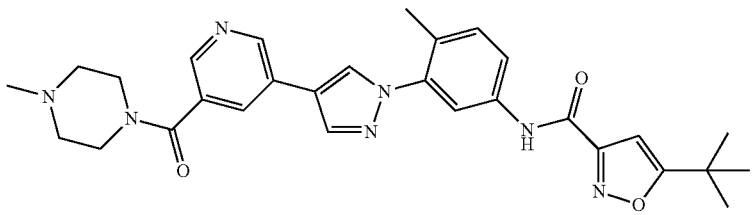 [SMILES: Cc1ccc(NC(=O)c2cc(C(C)(C)C)on2)cc1-n1cc(-c2cncc(C(=O)N3CCN(C)CC3)c2)cn1] |
| 23 | 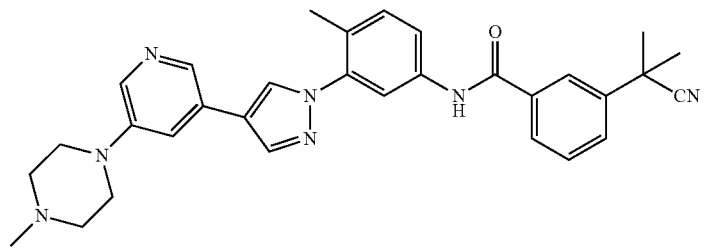 [SMILES: Cc1ccc(NC(=O)c2cccc(C(C)(C)C#N)c2)cc1-n1cc(-c2cncc(N3CCN(C)CC3)c2)cn1] |
| 24 | 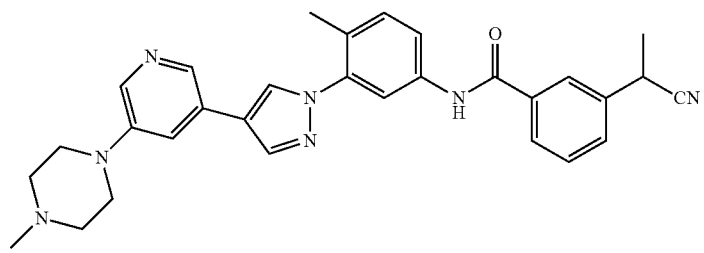 [SMILES: Cc1ccc(NC(=O)c2cccc(C(C)C#N)c2)cc1-n1cc(-c2cncc(N3CCN(C)CC3)c2)cn1] |

-continued
| No. | Structure |
|---|---|
| 25 | 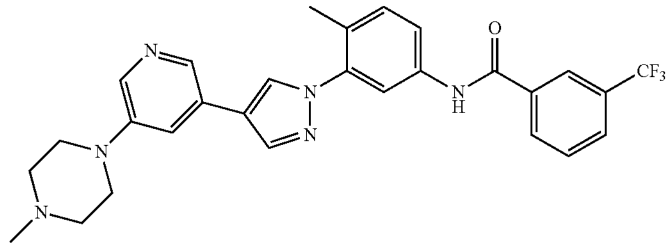 [SMILES: Cc1ccc(NC(=O)c2cccc(C(F)(F)F)c2)cc1-n1cc(-c2cncc(N3CCN(C)CC3)c2)cn1] |
| 26 | 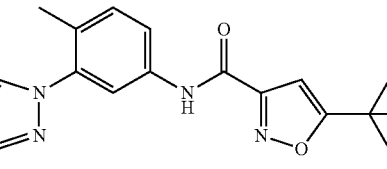 |
| 27 | 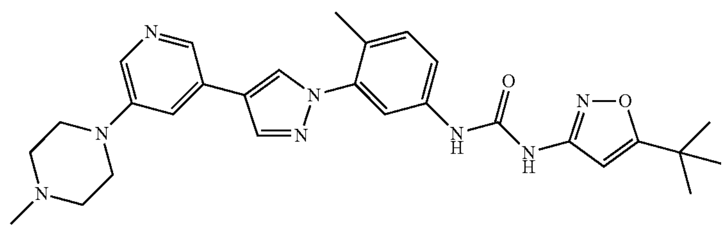 [SMILES: Cc1ccc(NC(=O)Nc2cc(C(C)(C)C)on2)cc1-n1cc(-c2cncc(N3CCN(C)CC3)c2)cn1] |
| 28 | 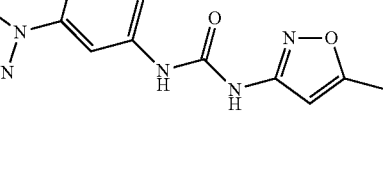 |
| 29 | 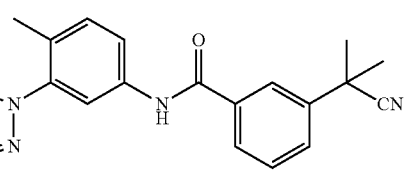 |
| 30 | 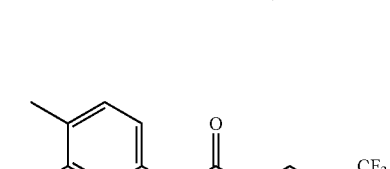 |

-continued

| No. | Structure |
|---|---|
| 31 | 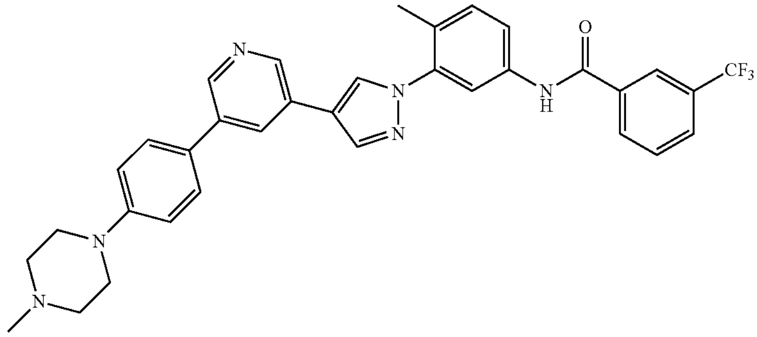 [SMILES: Cc1ccc(NC(=O)c2cccc(C(F)(F)F)c2)cc1-n1cc(-c2cncc(-c3ccc(N4CCN(C)CC4)cc3)c2)cn1] |
| 32 | 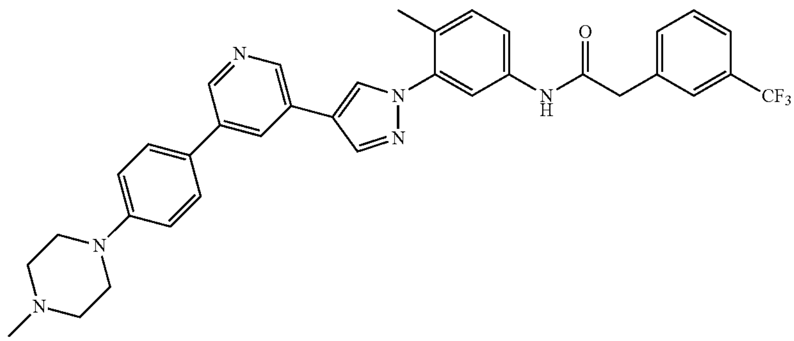 [SMILES: Cc1ccc(NC(=O)Cc2cccc(C(F)(F)F)c2)cc1-n1cc(-c2cncc(-c3ccc(N4CCN(C)CC4)cc3)c2)cn1] |
| 33 | 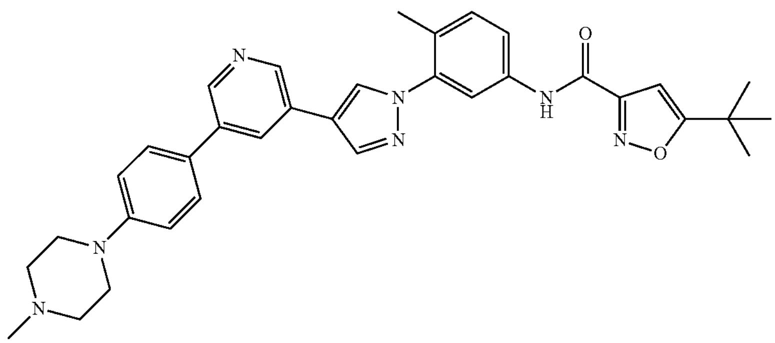 [SMILES: Cc1ccc(NC(=O)c2cc(C(C)(C)C)on2)cc1-n1cc(-c2cncc(-c3ccc(N4CCN(C)CC4)cc3)c2)cn1] |
| 34 | 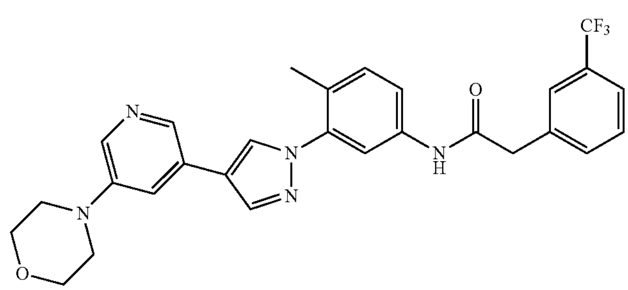 [SMILES: Cc1ccc(NC(=O)Cc2cccc(C(F)(F)F)c2)cc1-n1cc(-c2cncc(N3CCOCC3)c2)cn1] |
| 35 | 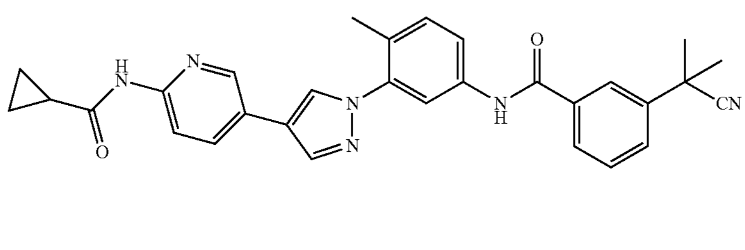 [SMILES: Cc1ccc(NC(=O)c2cccc(C(C)(C)C#N)c2)cc1-n1cc(-c2ccc(NC(=O)C3CC3)nc2)cn1] |

| No. | Structure |
|---|---|
| 36 | 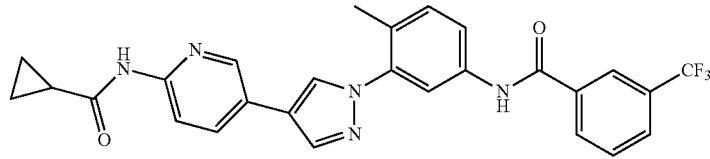 [SMILES: Cc1ccc(NC(=O)c2cccc(C(F)(F)F)c2)cc1-n1cc(-c2ccc(NC(=O)C3CC3)nc2)cn1] |
| 37 | 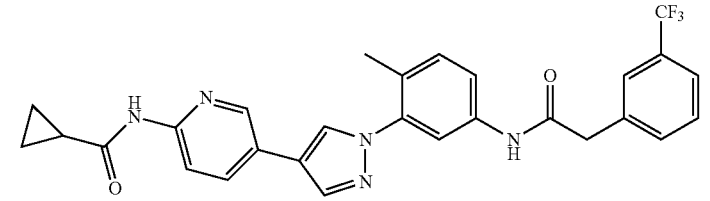 [SMILES: Cc1ccc(NC(=O)Cc2cccc(C(F)(F)F)c2)cc1-n1cc(-c2ccc(NC(=O)C3CC3)nc2)cn1] |
| 38 | 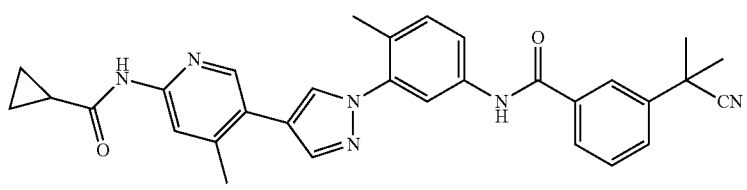 [SMILES: Cc1cc(NC(=O)C2CC2)ncc1-c1cnn(-c2cc(NC(=O)c3cccc(C(C)(C)C#N)c3)ccc2C)c1] |
| 39 | 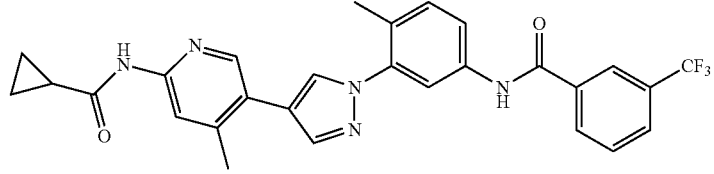 [SMILES: Cc1cc(NC(=O)C2CC2)ncc1-c1cnn(-c2cc(NC(=O)c3cccc(C(F)(F)F)c3)ccc2C)c1] |
| 40 | 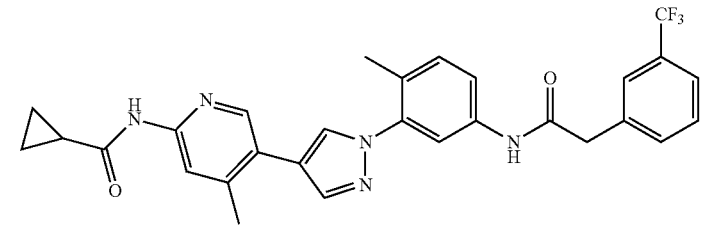 [SMILES: Cc1cc(NC(=O)C2CC2)ncc1-c1cnn(-c2cc(NC(=O)Cc3cccc(C(F)(F)F)c3)ccc2C)c1] |
| 41 | 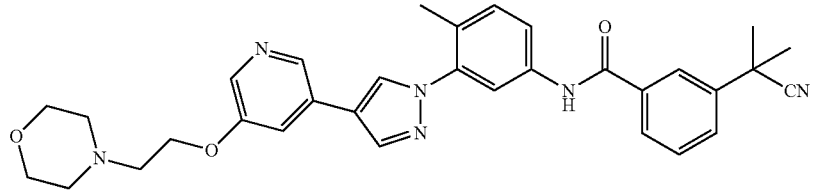 [SMILES: Cc1ccc(NC(=O)c2cccc(C(C)(C)C#N)c2)cc1-n1cc(-c2cncc(OCCN3CCOCC3)c2)cn1] |
| 42 | 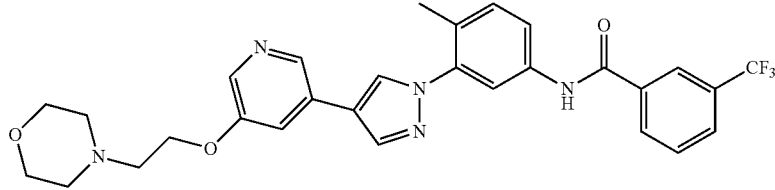 [SMILES: Cc1ccc(NC(=O)c2cccc(C(F)(F)F)c2)cc1-n1cc(-c2cncc(OCCN3CCOCC3)c2)cn1] |
| 43 | 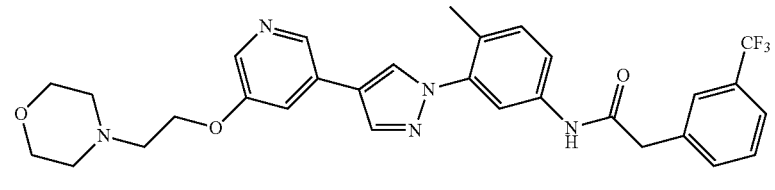 [SMILES: Cc1ccc(NC(=O)Cc2cccc(C(F)(F)F)c2)cc1-n1cc(-c2cncc(OCCN3CCOCC3)c2)cn1] |

| No. | Structure |
|---|---|
| 44 | 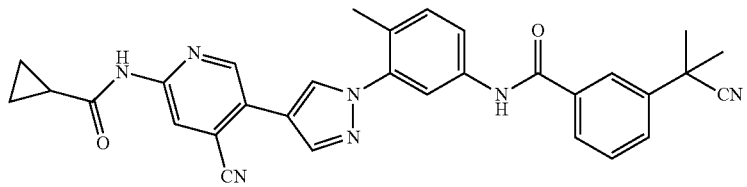 [SMILES: Cc1ccc(NC(=O)c2cccc(C(C)(C)C#N)c2)cc1-n1cc(-c2cnc(NC(=O)C3CC3)cc2C#N)cn1] |
| 45 | 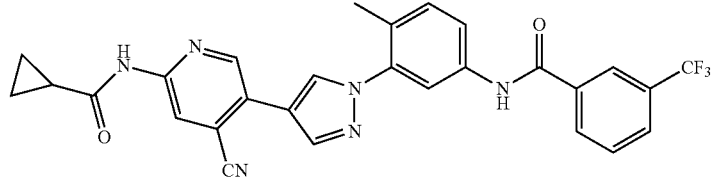 [SMILES: Cc1ccc(NC(=O)c2cccc(C(F)(F)F)c2)cc1-n1cc(-c2cnc(NC(=O)C3CC3)cc2C#N)cn1] |
| 46 | 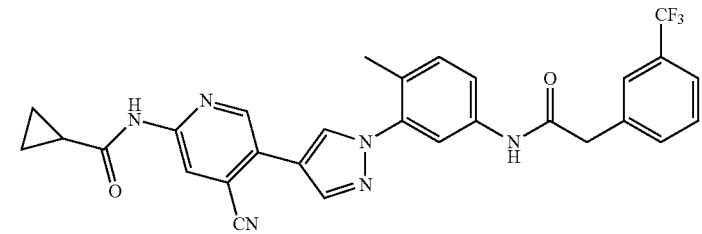 [SMILES: Cc1ccc(NC(=O)Cc2cccc(C(F)(F)F)c2)cc1-n1cc(-c2cnc(NC(=O)C3CC3)cc2C#N)cn1] |
| 47 | 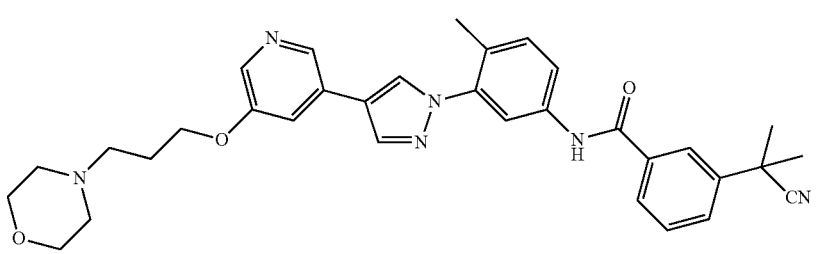 [SMILES: Cc1ccc(NC(=O)c2cccc(C(C)(C)C#N)c2)cc1-n1cc(-c2cncc(OCCCN3CCOCC3)c2)cn1] |
| 48 | 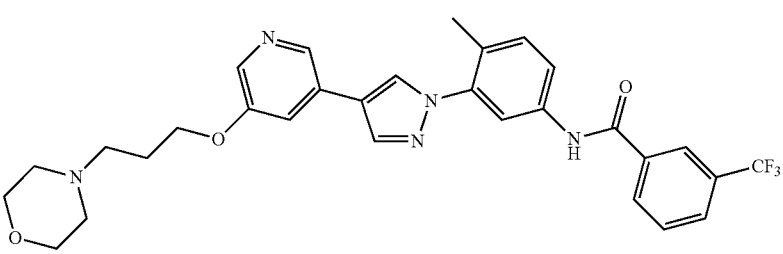 [SMILES: Cc1ccc(NC(=O)c2cccc(C(F)(F)F)c2)cc1-n1cc(-c2cncc(OCCCN3CCOCC3)c2)cn1] |
| 49 | 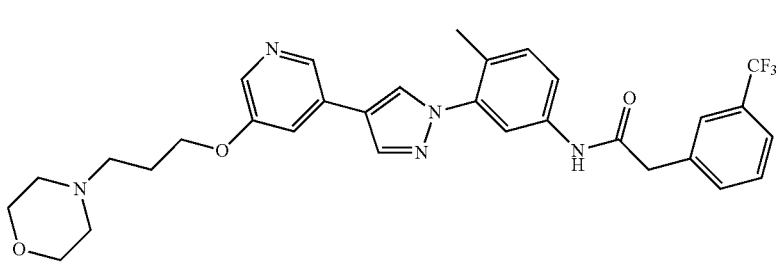 [SMILES: Cc1ccc(NC(=O)Cc2cccc(C(F)(F)F)c2)cc1-n1cc(-c2cncc(OCCCN3CCOCC3)c2)cn1] |
| 50 | 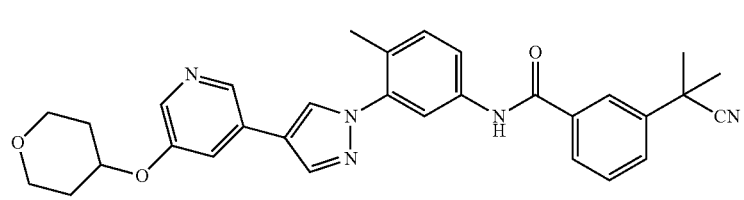 [SMILES: Cc1ccc(NC(=O)c2cccc(C(C)(C)C#N)c2)cc1-n1cc(-c2cncc(OC3CCOCC3)c2)cn1] |

-continued

| No. | Structure |
|---|---|
| 51 | 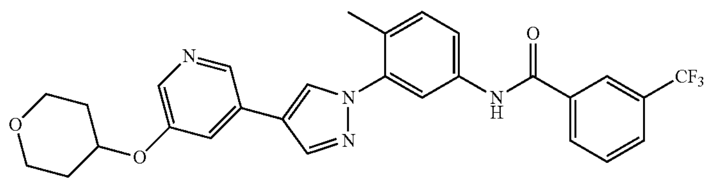 [SMILES: Cc1ccc(NC(=O)c2cccc(C(F)(F)F)c2)cc1-n1cc(-c2cncc(OC3CCOCC3)c2)cn1] |
| 52 | 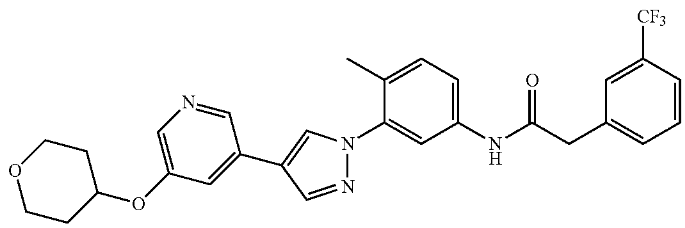 [SMILES: Cc1ccc(NC(=O)Cc2cccc(C(F)(F)F)c2)cc1-n1cc(-c2cncc(OC3CCOCC3)c2)cn1] |
| 53 | 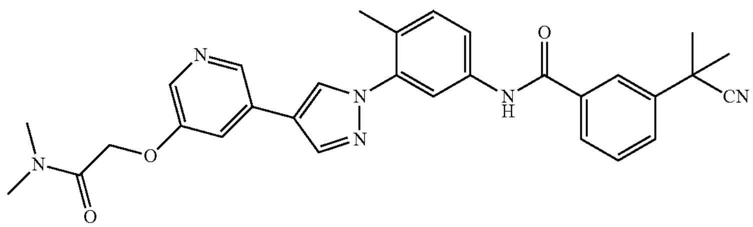 [SMILES: Cc1ccc(NC(=O)c2cccc(C(C)(C)C#N)c2)cc1-n1cc(-c2cncc(OCC(=O)N(C)C)c2)cn1] |
| 54 | 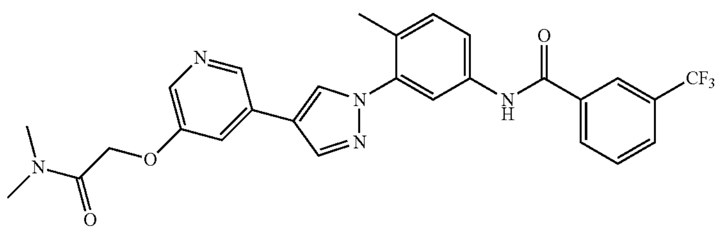 [SMILES: Cc1ccc(NC(=O)c2cccc(C(F)(F)F)c2)cc1-n1cc(-c2cncc(OCC(=O)N(C)C)c2)cn1] |
| 55 | 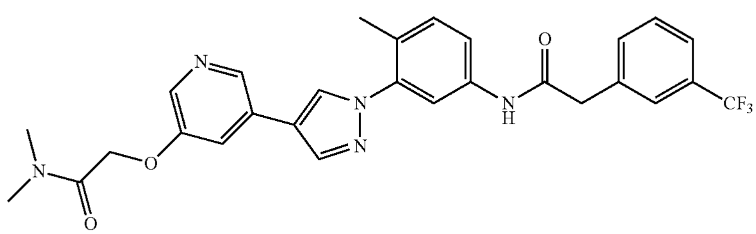 [SMILES: Cc1ccc(NC(=O)Cc2cccc(C(F)(F)F)c2)cc1-n1cc(-c2cncc(OCC(=O)N(C)C)c2)cn1] |
| 56 | 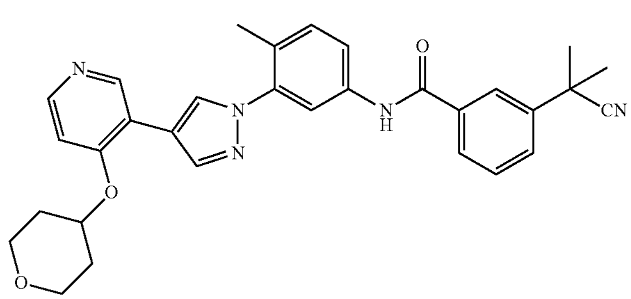 [SMILES: Cc1ccc(NC(=O)c2cccc(C(C)(C)C#N)c2)cc1-n1cc(-c2cnccc2OC2CCOCC2)cn1] |

-continued
| No. | Structure |
|---|---|
| 57 | 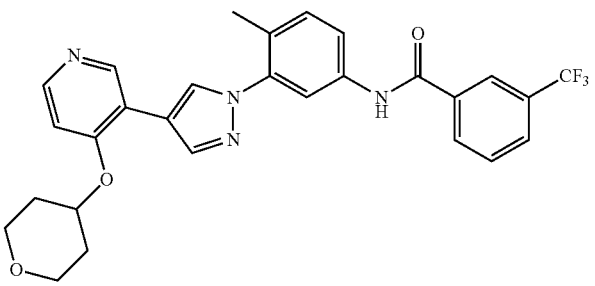 [SMILES: Cc1ccc(NC(=O)c2cccc(C(F)(F)F)c2)cc1-n1cc(-c2cnccc2OC2CCOCC2)cn1] |
| 58 | 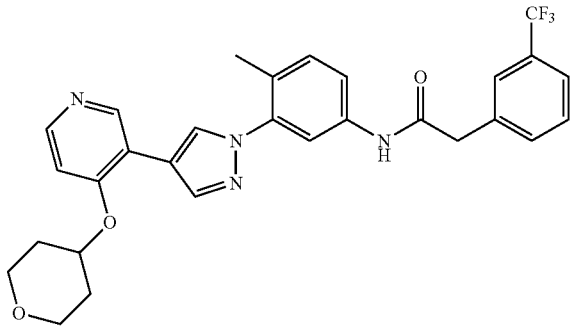 [SMILES: Cc1ccc(NC(=O)Cc2cccc(C(F)(F)F)c2)cc1-n1cc(-c2cnccc2OC2CCOCC2)cn1] |
| 59 | 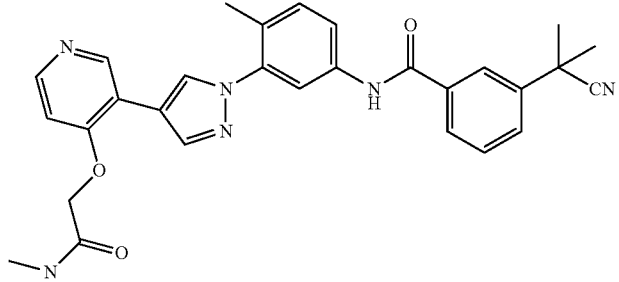 |
| 60 | 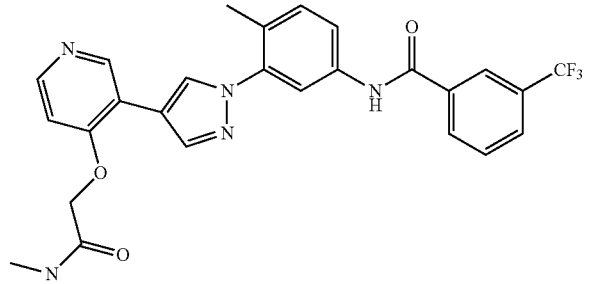 |

-continued

| No. | Structure |
|---|---|
| 61 | 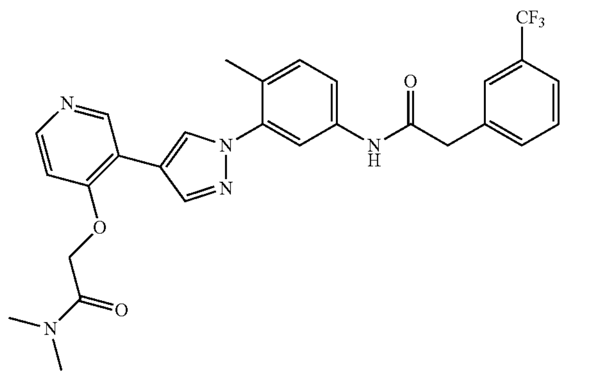 [SMILES: Cc1ccc(NC(=O)Cc2cccc(C(F)(F)F)c2)cc1-n1cc(-c2cnccc2OCC(=O)N(C)C)cn1] |
| 62 | 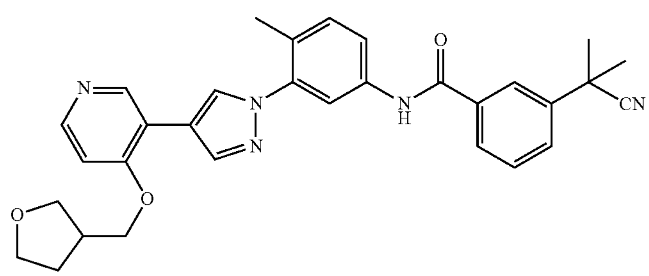 [SMILES: Cc1ccc(NC(=O)c2cccc(C(C)(C)C#N)c2)cc1-n1cc(-c2cnccc2OCC2CCOC2)cn1] |
| 63 | 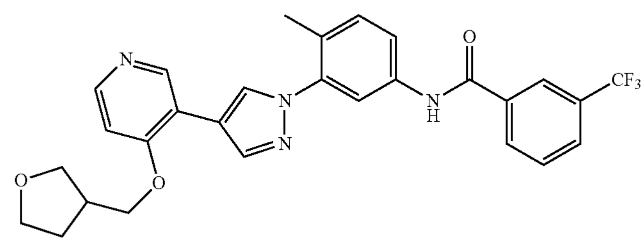 [SMILES: Cc1ccc(NC(=O)c2cccc(C(F)(F)F)c2)cc1-n1cc(-c2cnccc2OCC2CCOC2)cn1] |
| 64 | 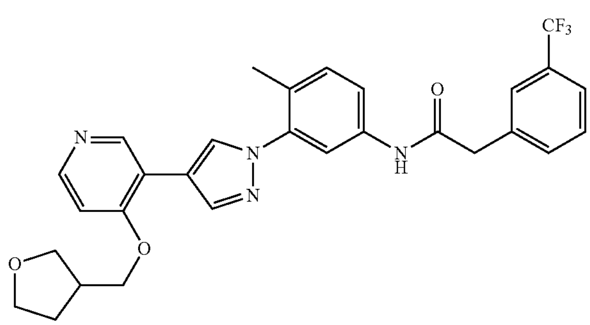 [SMILES: Cc1ccc(NC(=O)Cc2cccc(C(F)(F)F)c2)cc1-n1cc(-c2cnccc2OCC2CCOC2)cn1] |
| 65 | 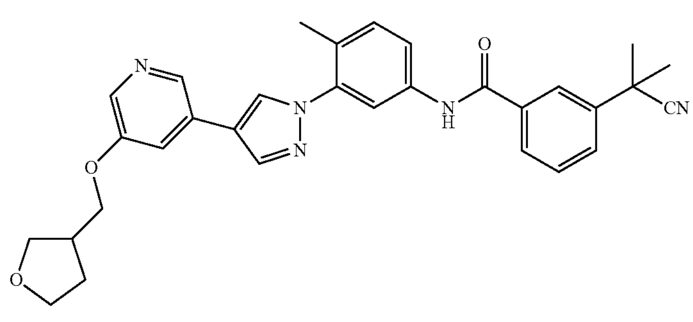 [SMILES: Cc1ccc(NC(=O)c2cccc(C(C)(C)C#N)c2)cc1-n1cc(-c2cncc(OCC3CCOC3)c2)cn1] |

| No. | Structure |
|---|---|
| 66 | 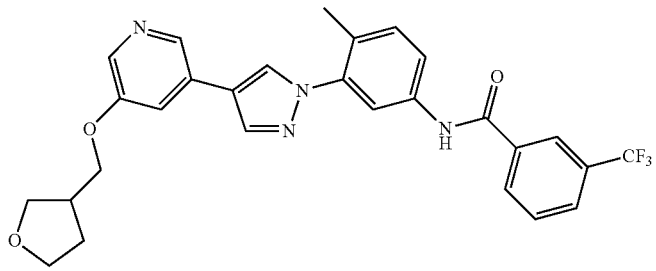 [SMILES: Cc1ccc(NC(=O)c2cccc(C(F)(F)F)c2)cc1-n1cc(-c2cncc(OCC3CCOC3)c2)cn1] |
| 67 | 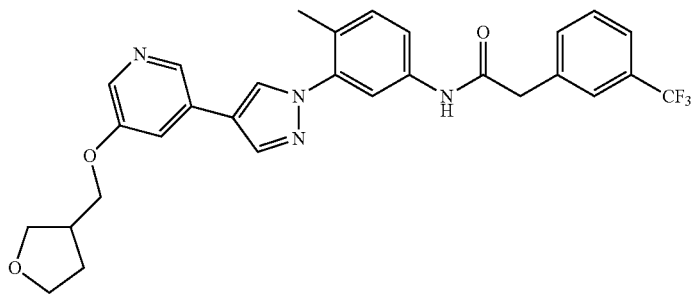 [SMILES: Cc1ccc(NC(=O)Cc2cccc(C(F)(F)F)c2)cc1-n1cc(-c2cncc(OCC3CCOC3)c2)cn1] |
| 68 | 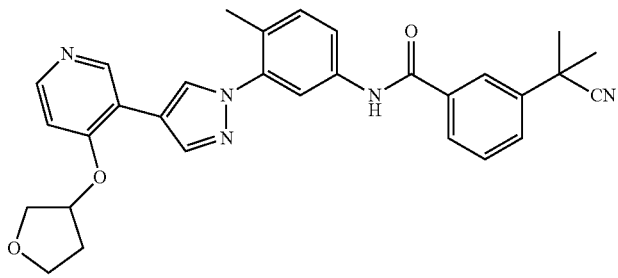 |
| 69 | 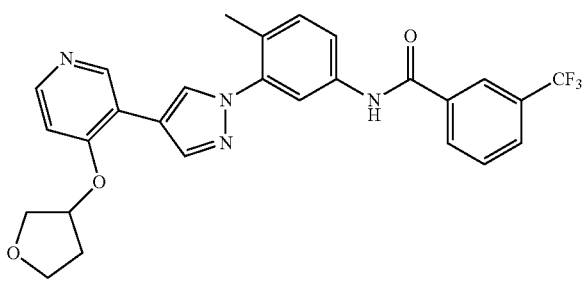 [SMILES: Cc1ccc(NC(=O)c2cccc(C(F)(F)F)c2)cc1-n1cc(-c2cnccc2OC2CCOC2)cn1] |
| 70 | 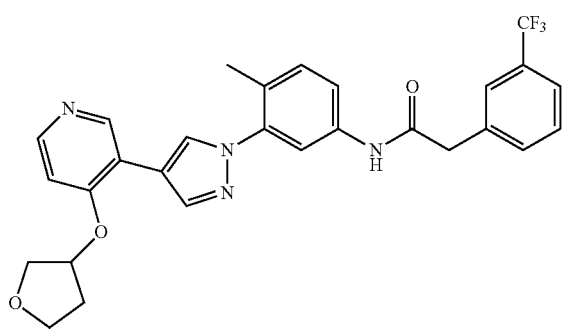 [SMILES: Cc1ccc(NC(=O)Cc2cccc(C(F)(F)F)c2)cc1-n1cc(-c2cnccc2OC2CCOC2)cn1] |

-continued
| No. | Structure |
|---|---|
| 71 | 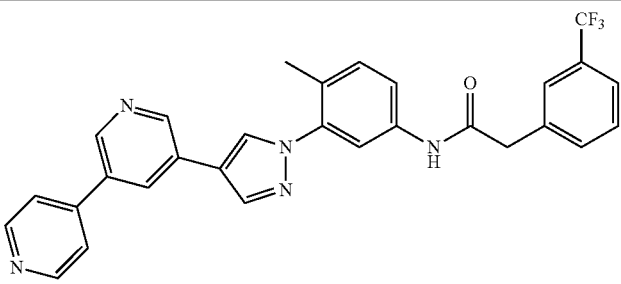 [SMILES: Cc1ccc(NC(=O)Cc2cccc(C(F)(F)F)c2)cc1-n1cc(-c2cncc(-c3ccncc3)c2)cn1] |
| 72 | 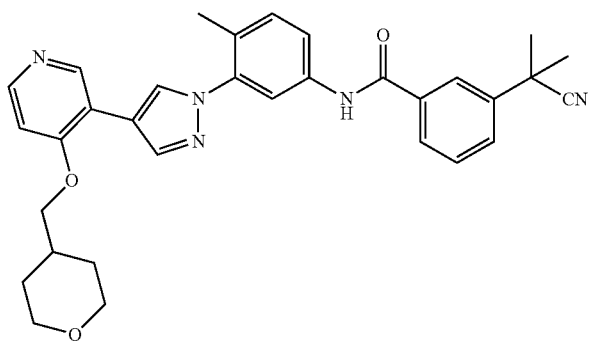 [SMILES: Cc1ccc(NC(=O)c2cccc(C(C)(C)C#N)c2)cc1-n1cc(-c2cnccc2OCC2CCOCC2)cn1] |
| 73 | 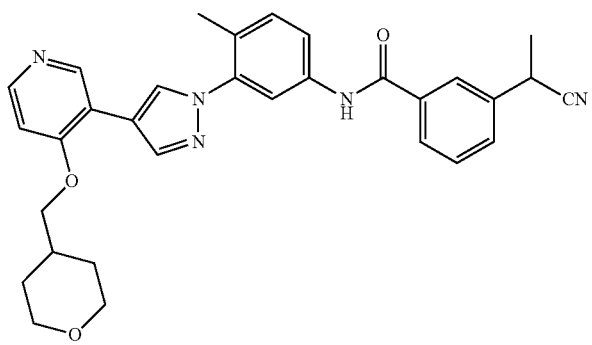 [SMILES: Cc1ccc(NC(=O)c2cccc(C(C)C#N)c2)cc1-n1cc(-c2cnccc2OCC2CCOCC2)cn1] |
| 74 | 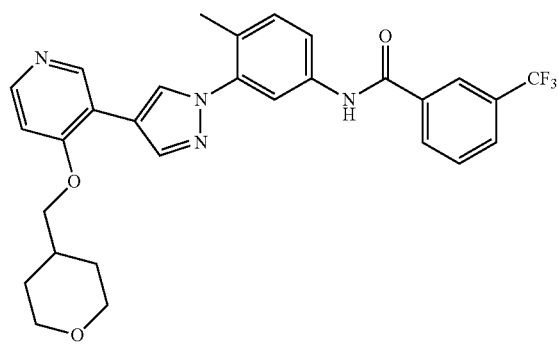 [SMILES: Cc1ccc(NC(=O)c2cccc(C(F)(F)F)c2)cc1-n1cc(-c2cnccc2OCC2CCOCC2)cn1] |

| No. | Structure |
|---|---|
| 75 | *(chemical structure)* |
| 76 | *(chemical structure)* |
| 77 | *(chemical structure)* |
| 78 | *(chemical structure)* |

-continued

| No. | Structure |
|---|---|
| 79 | 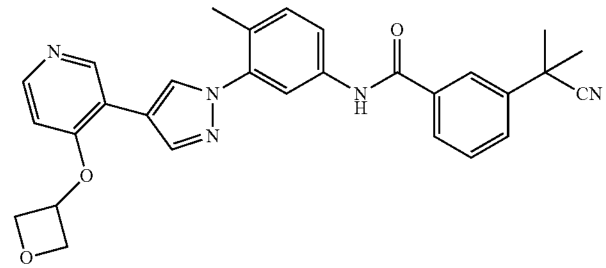 [SMILES: Cc1ccc(NC(=O)c2cccc(C(C)(C)C#N)c2)cc1-n1cc(-c2cnccc2OC2COC2)cn1] |
| 80 | 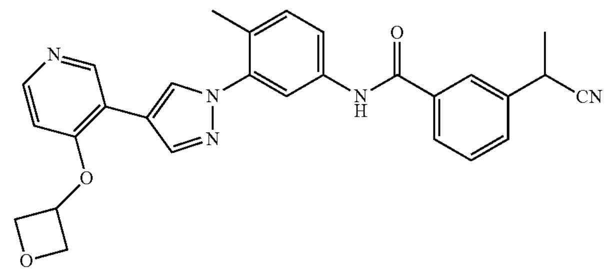 [SMILES: Cc1ccc(NC(=O)c2cccc(C(C)C#N)c2)cc1-n1cc(-c2cnccc2OC2COC2)cn1] |
| 81 | 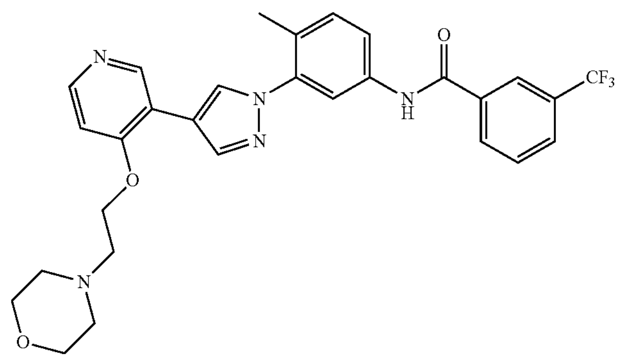 [SMILES: Cc1ccc(NC(=O)c2cccc(C(F)(F)F)c2)cc1-n1cc(-c2cnccc2OCCN2CCOCC2)cn1] |
| 82 | 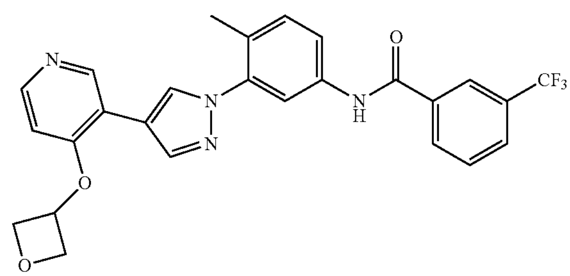 [SMILES: Cc1ccc(NC(=O)c2cccc(C(F)(F)F)c2)cc1-n1cc(-c2cnccc2OC2COC2)cn1] |
| 83 | 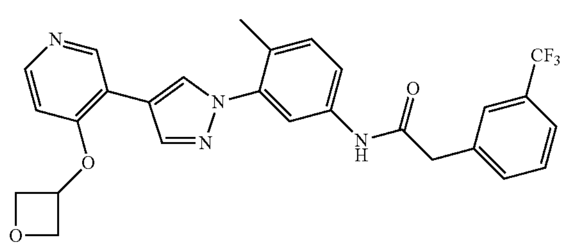 [SMILES: Cc1ccc(NC(=O)Cc2cccc(C(F)(F)F)c2)cc1-n1cc(-c2cnccc2OC2COC2)cn1] |
| 84 | 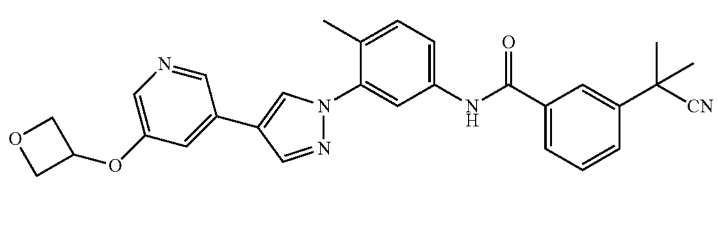 [SMILES: Cc1ccc(NC(=O)c2cccc(C(C)(C)C#N)c2)cc1-n1cc(-c2cncc(OC3COC3)c2)cn1] |

| No. | Structure |
|---|---|
| 85 | 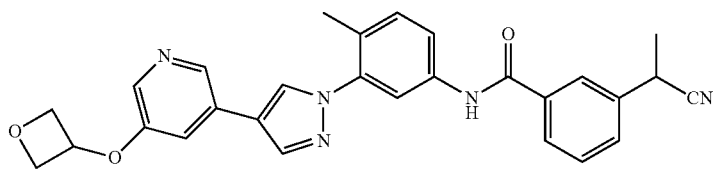 [SMILES: Cc1ccc(NC(=O)c2cccc(C(C)C#N)c2)cc1-n1cc(-c2cncc(OC3COC3)c2)cn1] |
| 86 | 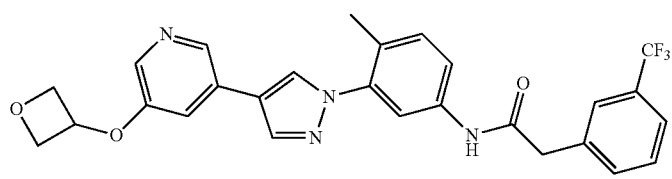 [SMILES: Cc1ccc(NC(=O)Cc2cccc(C(F)(F)F)c2)cc1-n1cc(-c2cncc(OC3COC3)c2)cn1] |
| 87 | 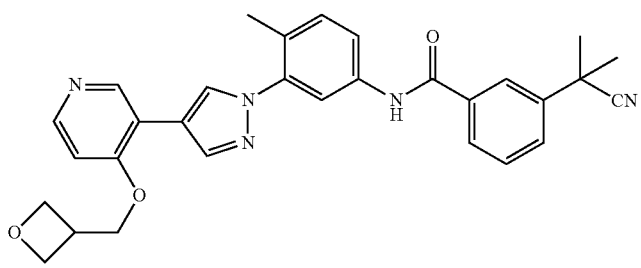 [SMILES: Cc1ccc(NC(=O)c2cccc(C(C)(C)C#N)c2)cc1-n1cc(-c2cnccc2OCC2COC2)cn1] |
| 88 | 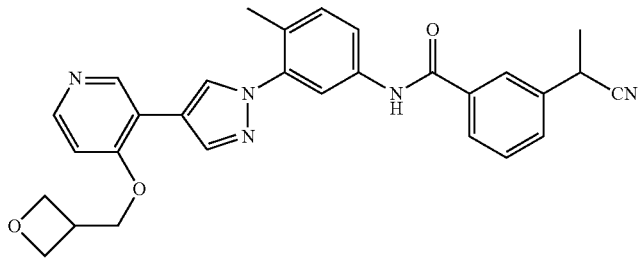 |
| 89 | 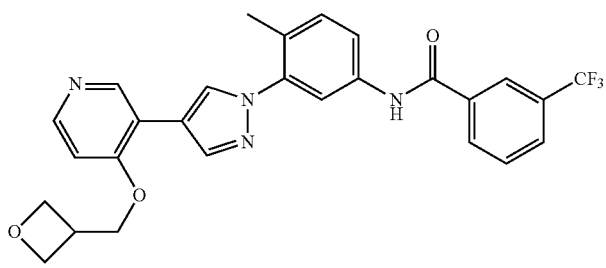 [SMILES: Cc1ccc(NC(=O)c2cccc(C(F)(F)F)c2)cc1-n1cc(-c2cnccc2OCC2COC2)cn1] |
| 90 | 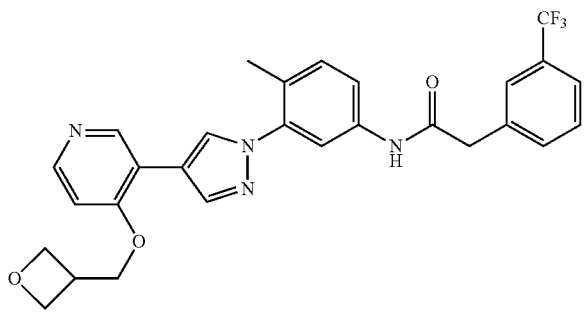 [SMILES: Cc1ccc(NC(=O)Cc2cccc(C(F)(F)F)c2)cc1-n1cc(-c2cnccc2OCC2COC2)cn1] |

-continued
| No. | Structure |
|---|---|
| 91 | 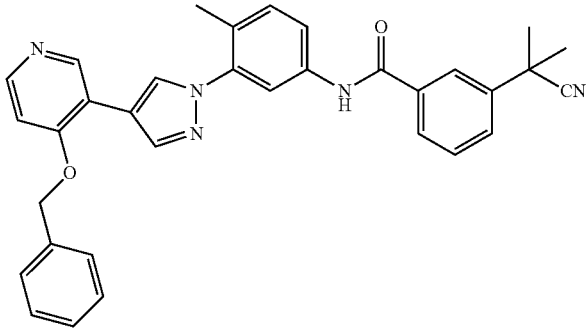 [SMILES: Cc1ccc(NC(=O)c2cccc(C(C)(C)C#N)c2)cc1-n1cc(-c2cnccc2OCc2ccccc2)cn1] |
| 92 | 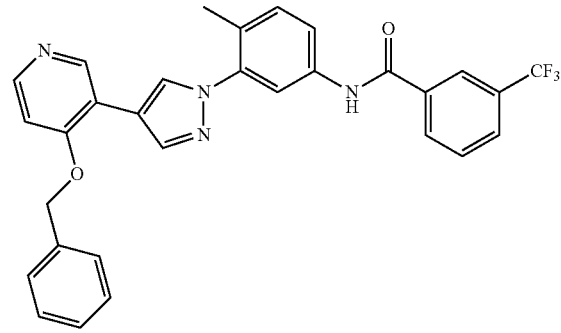 [SMILES: Cc1ccc(NC(=O)c2cccc(C(F)(F)F)c2)cc1-n1cc(-c2cnccc2OCc2ccccc2)cn1] |
| 93 | 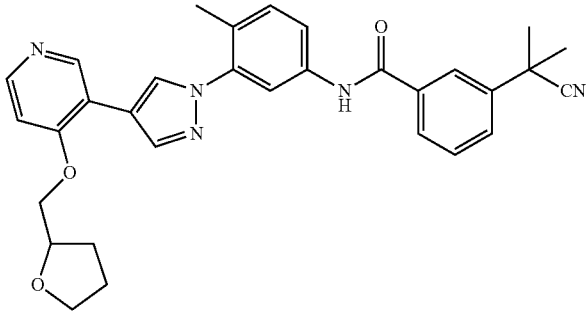 [SMILES: Cc1ccc(NC(=O)c2cccc(C(C)(C)C#N)c2)cc1-n1cc(-c2cnccc2OCC2CCCO2)cn1] |
| 94 | 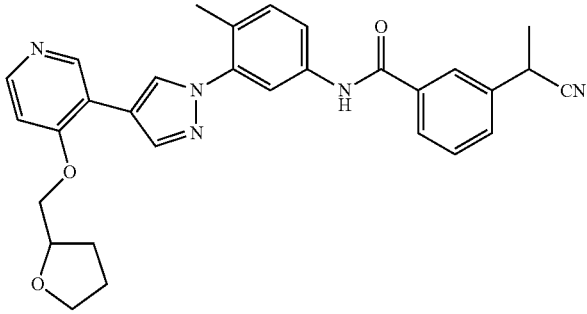 |

-continued

| No. | Structure |
|-----|-----------|
| 95 | 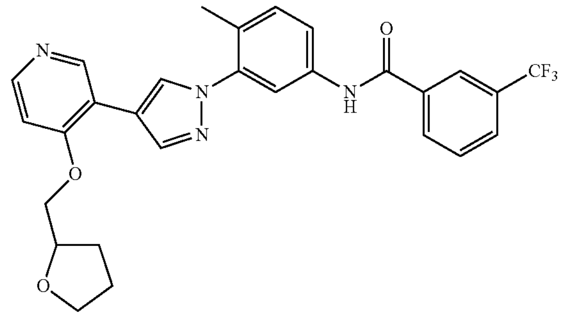 [SMILES: Cc1ccc(NC(=O)c2cccc(C(F)(F)F)c2)cc1-n1cc(-c2cnccc2OCC2CCCO2)cn1] |
| 96 | 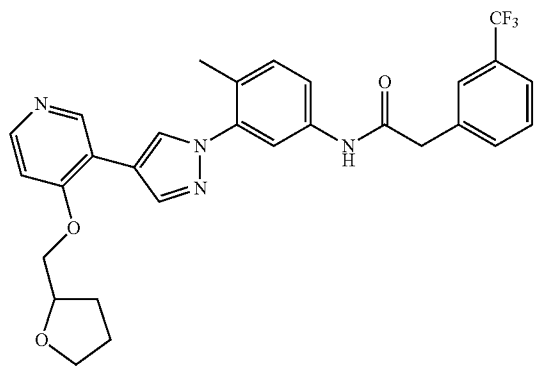 |
| 97 | 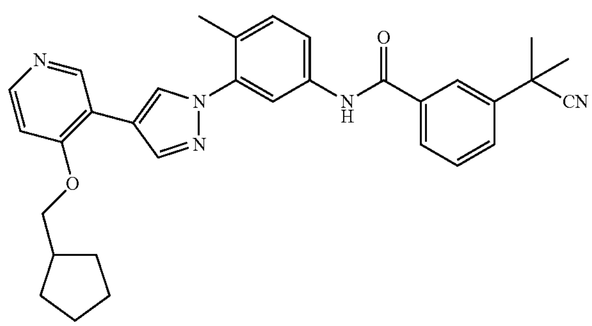 [SMILES: Cc1ccc(NC(=O)c2cccc(C(C)(C)C#N)c2)cc1-n1cc(-c2cnccc2OCC2CCCC2)cn1] |
| 98 | 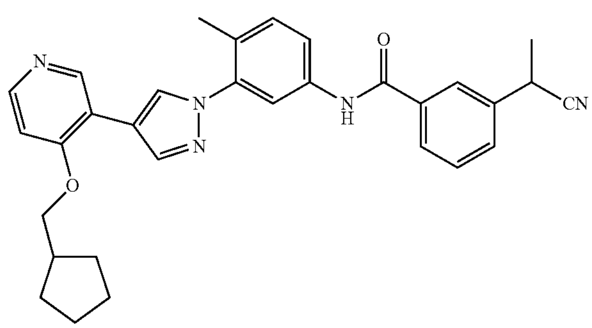 [SMILES: Cc1ccc(NC(=O)c2cccc(C(C)C#N)c2)cc1-n1cc(-c2cnccc2OCC2CCCC2)cn1] |

-continued
| No. | Structure |
|---|---|
| 99 | 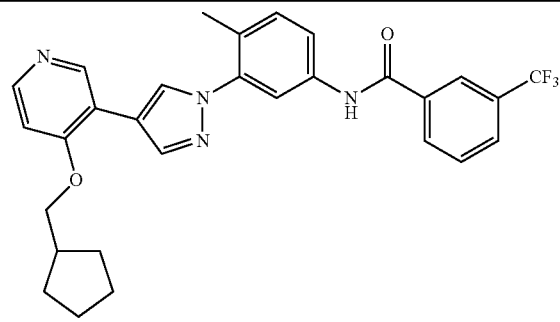 |
| 100 | 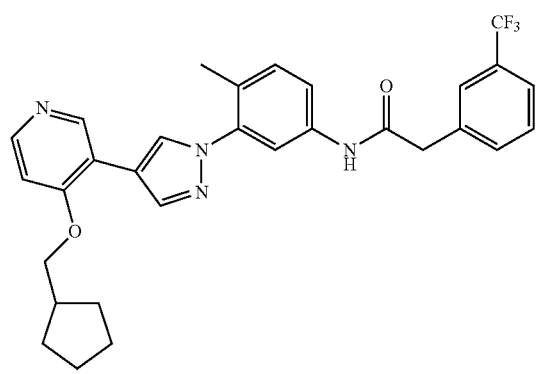 [SMILES: Cc1ccc(NC(=O)Cc2cccc(C(F)(F)F)c2)cc1-n1cc(-c2cnccc2OCC2CCCC2)cn1] |
| 101 | 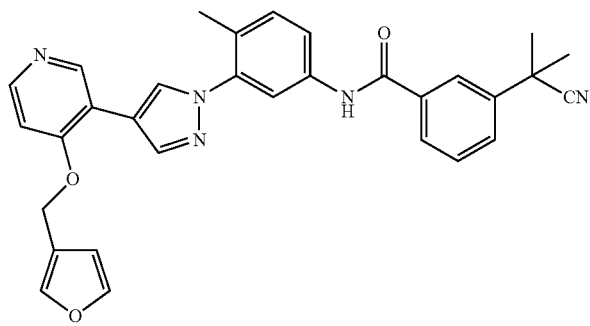 [SMILES: Cc1ccc(NC(=O)c2cccc(C(C)(C)C#N)c2)cc1-n1cc(-c2cnccc2OCc2ccoc2)cn1] |
| 102 | 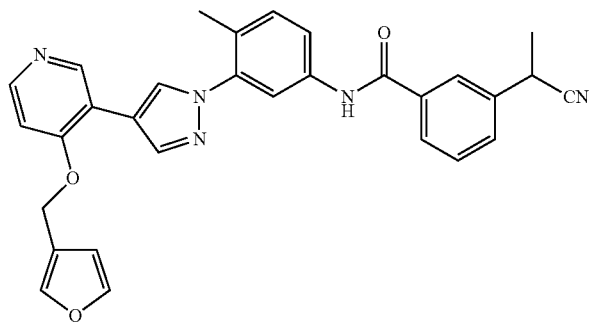 [SMILES: Cc1ccc(NC(=O)c2cccc(C(C)C#N)c2)cc1-n1cc(-c2cnccc2OCc2ccoc2)cn1] |

-continued

| No. | Structure |
|---|---|
| 103 | 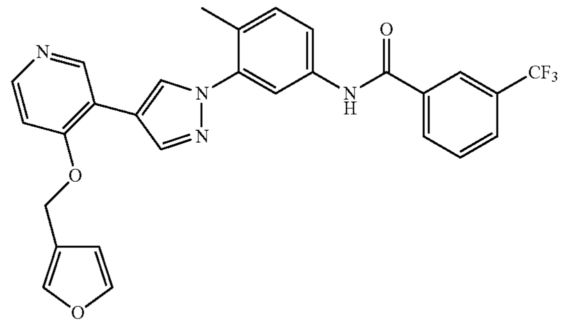 [SMILES: Cc1ccc(NC(=O)c2cccc(C(F)(F)F)c2)cc1-n1cc(-c2cnccc2OCc2ccoc2)cn1] |
| 104 | 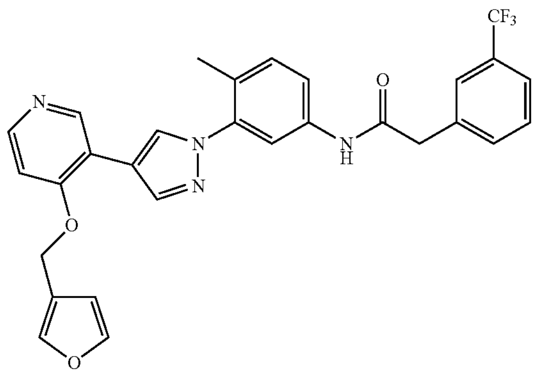 [SMILES: Cc1ccc(NC(=O)Cc2cccc(C(F)(F)F)c2)cc1-n1cc(-c2cnccc2OCc2ccoc2)cn1] |
| 105 | 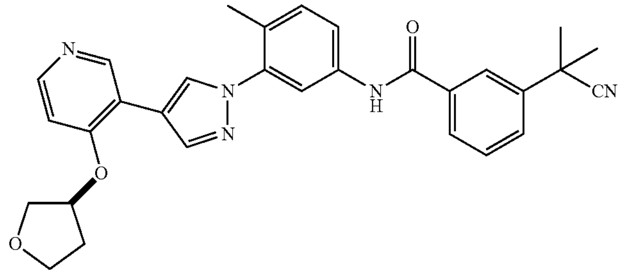 |
| 106 | 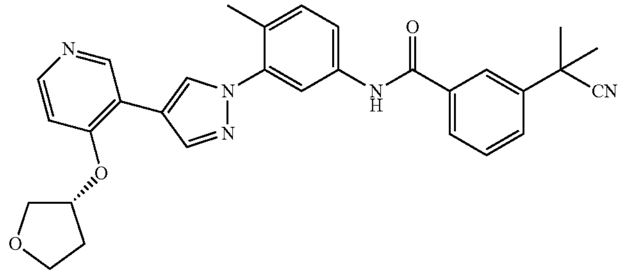 [SMILES: Cc1ccc(NC(=O)c2cccc(C(C)(C)C#N)c2)cc1-n1cc(-c2cnccc2O[C@@H]2CCOC2)cn1] |
| 107 | 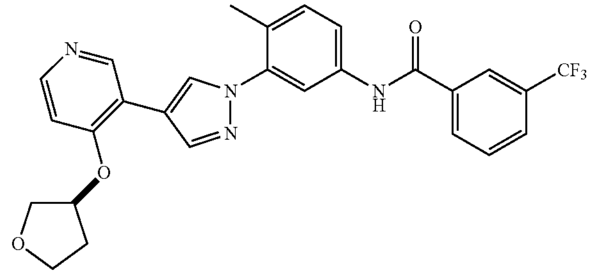 |

-continued
| No. | Structure |
|---|---|
| 108 | 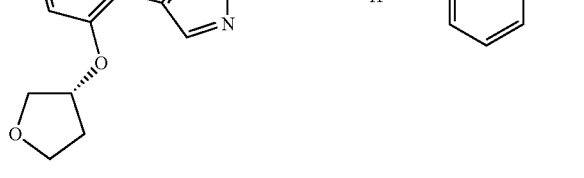 |
| 109 | 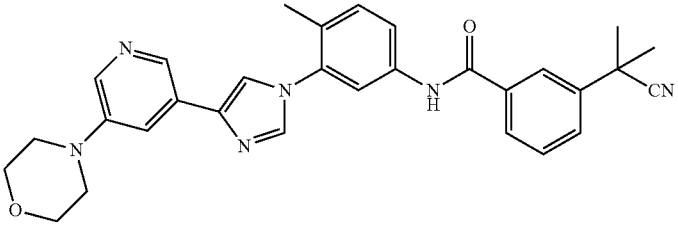 [SMILES: Cc1ccc(NC(=O)c2cccc(C(C)(C)C#N)c2)cc1-n1cnc(-c2cncc(N3CCOCC3)c2)c1] |
| 110 | 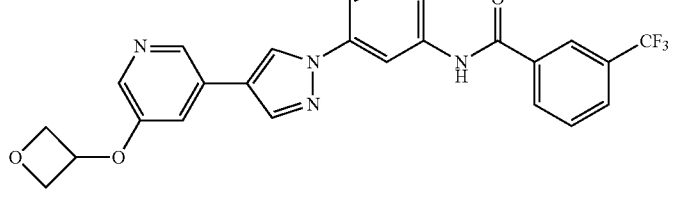 |
| 111 | 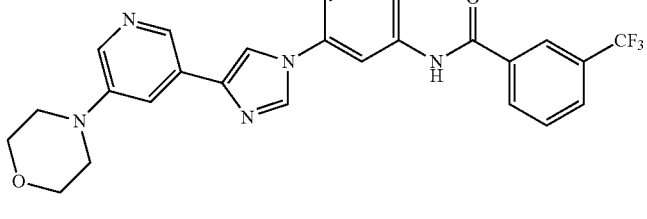 |
| 112 | 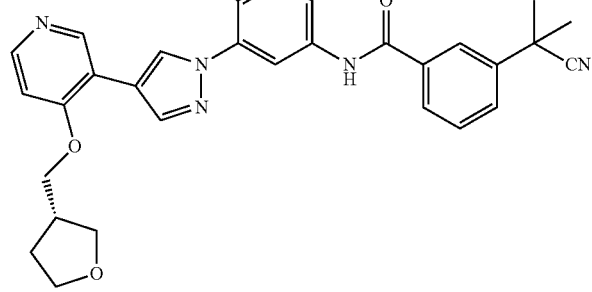 |

-continued
| No. | Structure |
|---|---|
| 113 | 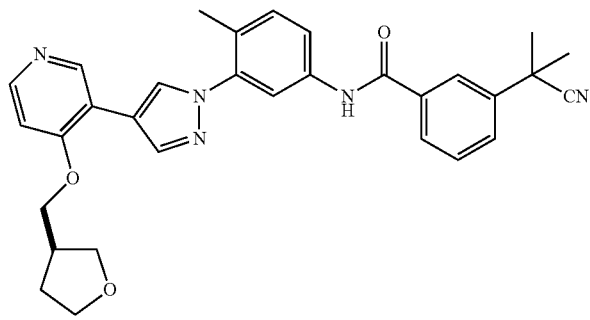 |
| 114 | 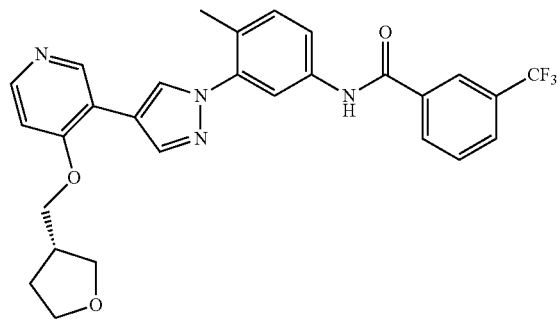 [SMILES: Cc1ccc(NC(=O)c2cccc(C(F)(F)F)c2)cc1-n1cc(-c2cnccc2OC[C@H]2CCOC2)cn1] |
| 115 | 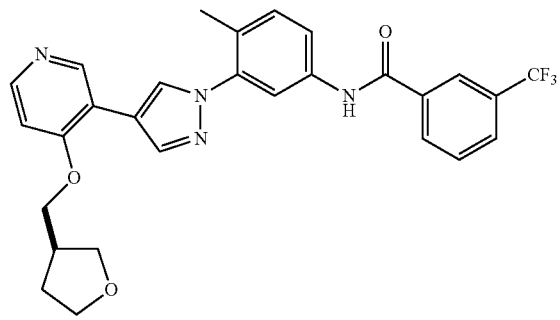 |
| 116 | 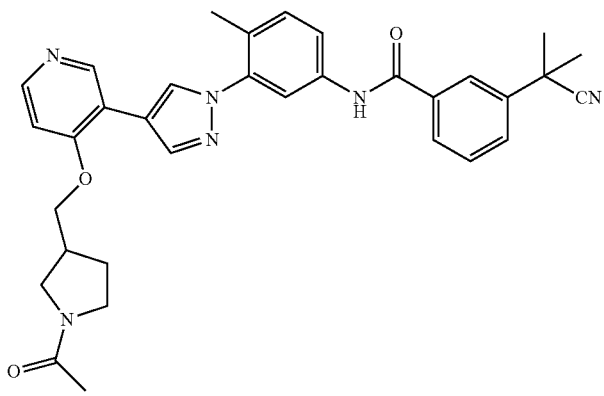 [SMILES: CC(=O)N1CCC(COc2ccncc2-c2cnn(-c3cc(NC(=O)c4cccc(C(C)(C)C#N)c4)ccc3C)c2)C1] |

-continued

| No. | Structure |
|---|---|
| 117 | 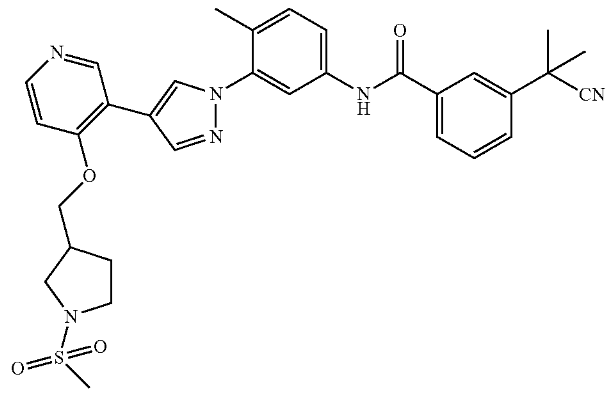 [SMILES: Cc1ccc(NC(=O)c2cccc(C(C)(C)C#N)c2)cc1-n1cc(-c2cnccc2OCC2CCN(S(C)(=O)=O)C2)cn1] |
| 118 | 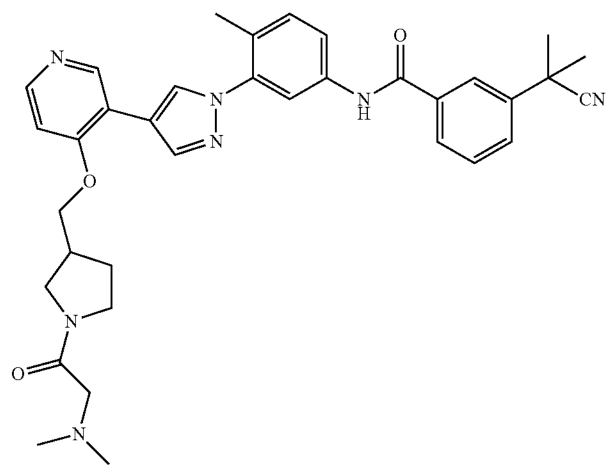 [SMILES: Cc1ccc(NC(=O)c2cccc(C(C)(C)C#N)c2)cc1-n1cc(-c2cnccc2OCC2CCN(C(=O)CN(C)C)C2)cn1] |
| 119 | 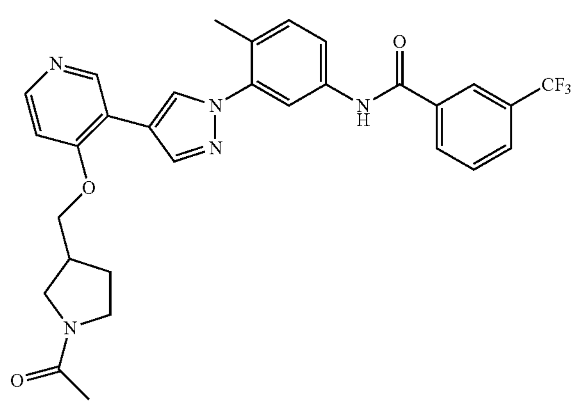 [SMILES: CC(=O)N1CCC(COc2ccncc2-c2cnn(-c3cc(NC(=O)c4cccc(C(F)(F)F)c4)ccc3C)c2)C1] |

-continued

| No. | Structure |
|---|---|
| 120 | 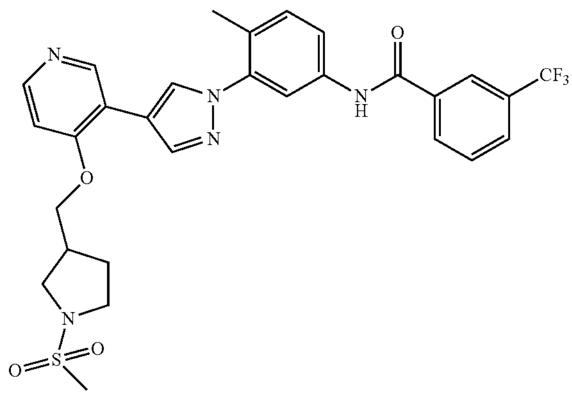 [SMILES: Cc1ccc(NC(=O)c2cccc(C(F)(F)F)c2)cc1-n1cc(-c2cnccc2OCC2CCN(S(C)(=O)=O)C2)cn1] |
| 121 | 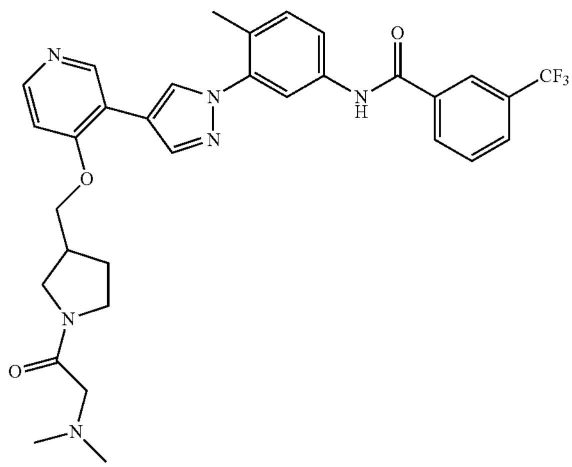 [SMILES: Cc1ccc(NC(=O)c2cccc(C(F)(F)F)c2)cc1-n1cc(-c2cnccc2OCC2CCN(C(=O)CN(C)C)C2)cn1] |
| 122 | 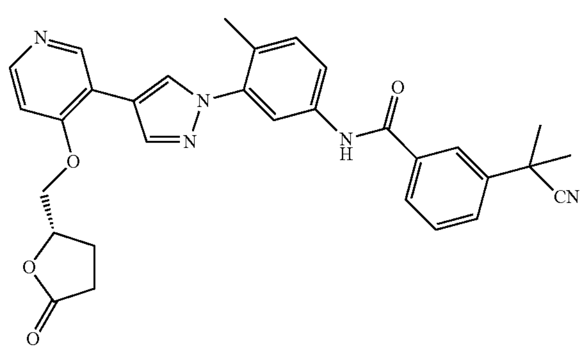 [SMILES: Cc1ccc(NC(=O)c2cccc(C(C)(C)C#N)c2)cc1-n1cc(-c2cnccc2OC[C@@H]2CCC(=O)O2)cn1] |
| 123 | 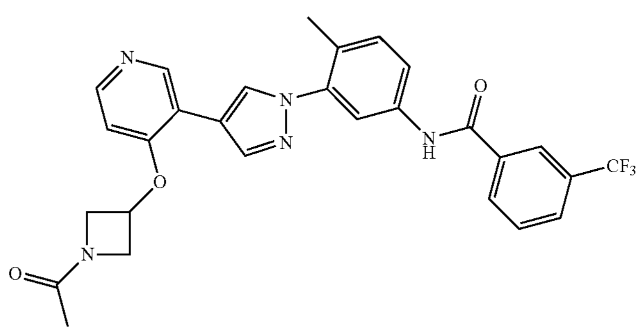 [SMILES: CC(=O)N1CC(Oc2ccncc2-c2cnn(-c3cc(NC(=O)c4cccc(C(F)(F)F)c4)ccc3C)c2)C1] |

| No. | Structure |
|---|---|
| 124 | 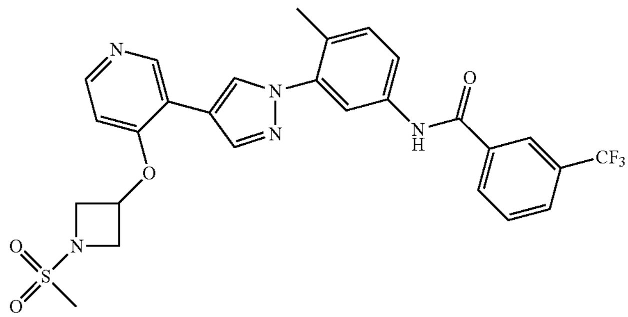 [SMILES: Cc1ccc(NC(=O)c2cccc(C(F)(F)F)c2)cc1-n1cc(-c2cnccc2OC2CN(S(C)(=O)=O)C2)cn1] |
| 125 | 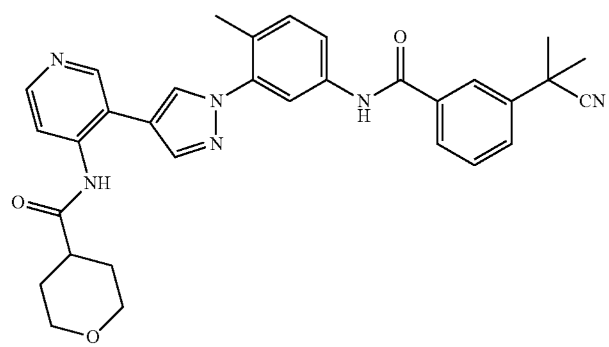 [SMILES: Cc1ccc(NC(=O)c2cccc(C(C)(C)C#N)c2)cc1-n1cc(-c2cnccc2NC(=O)C2CCOCC2)cn1] |
| 126 | 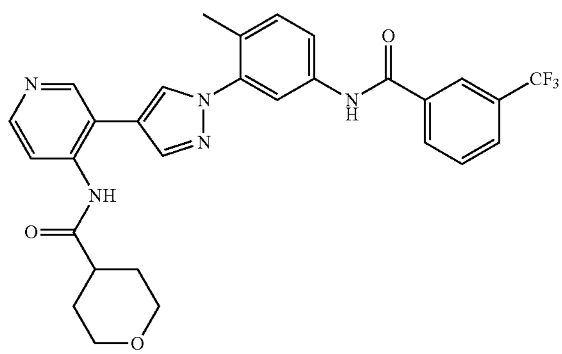 [SMILES: Cc1ccc(NC(=O)c2cccc(C(F)(F)F)c2)cc1-n1cc(-c2cnccc2NC(=O)C2CCOCC2)cn1] |
| 127 | 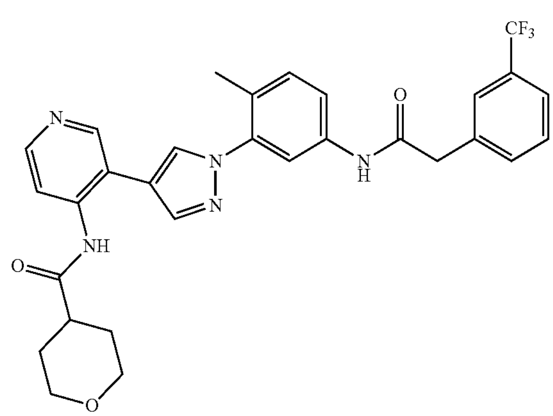 [SMILES: Cc1ccc(NC(=O)Cc2cccc(C(F)(F)F)c2)cc1-n1cc(-c2cnccc2NC(=O)C2CCOCC2)cn1] |

-continued
| No. | Structure |
|---|---|
| 128 | 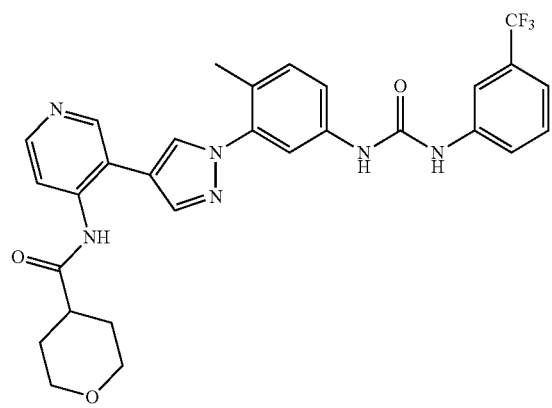 [SMILES: Cc1ccc(NC(=O)Nc2cccc(C(F)(F)F)c2)cc1-n1cc(-c2cnccc2NC(=O)C2CCOCC2)cn1] |
| 129 | 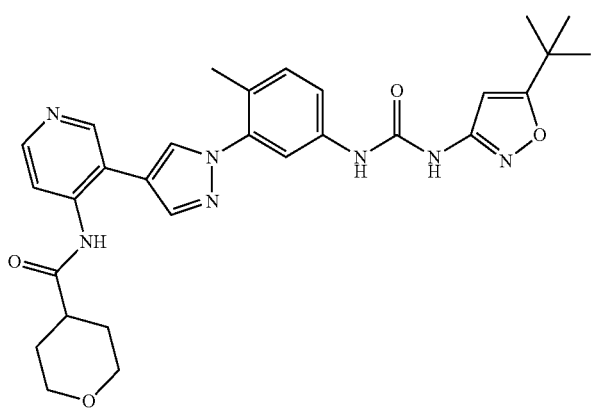 [SMILES: Cc1ccc(NC(=O)Nc2cc(C(C)(C)C)on2)cc1-n1cc(-c2cnccc2NC(=O)C2CCOCC2)cn1] |
| 130 | 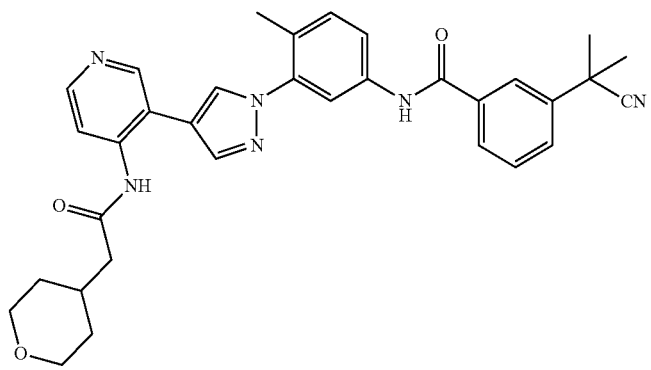 [SMILES: Cc1ccc(NC(=O)c2cccc(C(C)(C)C#N)c2)cc1-n1cc(-c2cnccc2NC(=O)CC2CCOCC2)cn1] |
| 131 | 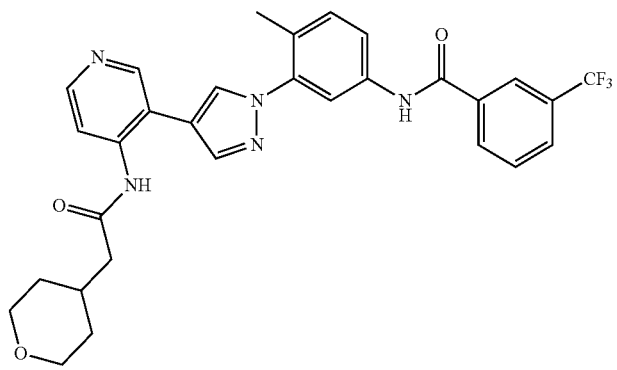 [SMILES: Cc1ccc(NC(=O)c2cccc(C(F)(F)F)c2)cc1-n1cc(-c2cnccc2NC(=O)CC2CCOCC2)cn1] |

-continued
| No. | Structure |
|---|---|
| 132 | 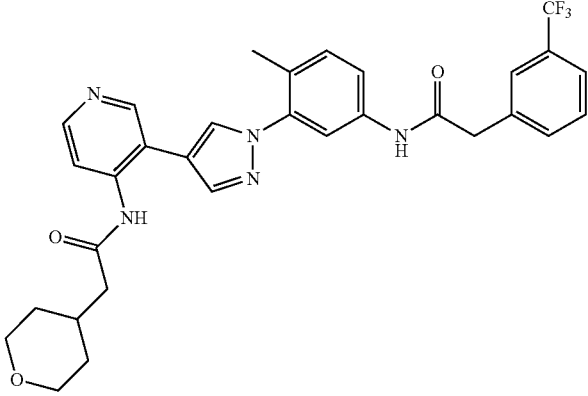 [SMILES: Cc1ccc(NC(=O)Cc2cccc(C(F)(F)F)c2)cc1-n1cc(-c2cnccc2NC(=O)CC2CCOCC2)cn1] |
| 133 | 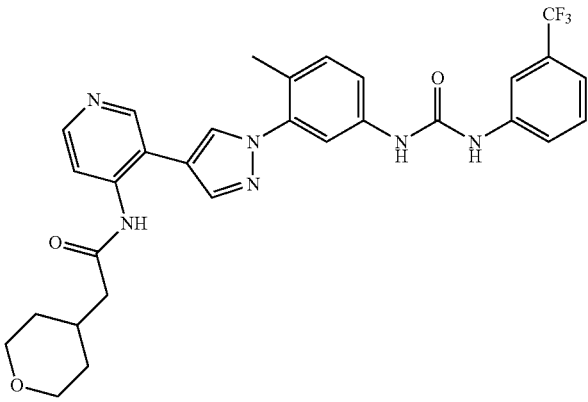 [SMILES: Cc1ccc(NC(=O)Nc2cccc(C(F)(F)F)c2)cc1-n1cc(-c2cnccc2NC(=O)CC2CCOCC2)cn1] |
| 134 | 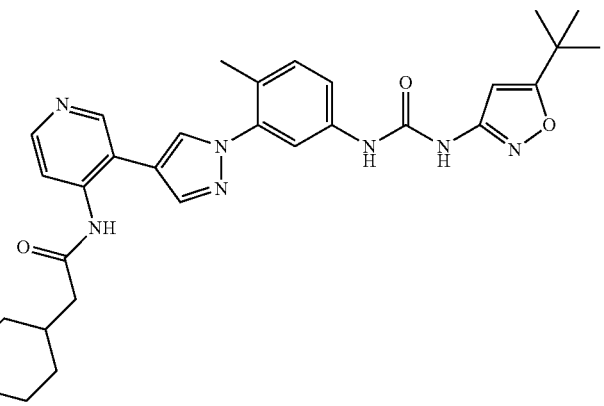 |
| 135 | 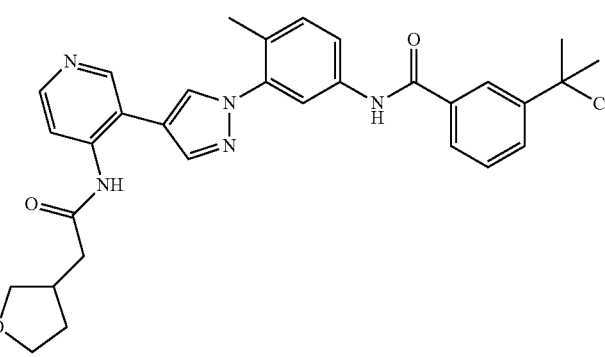 |

| No. | Structure |
|---|---|
| 136 | 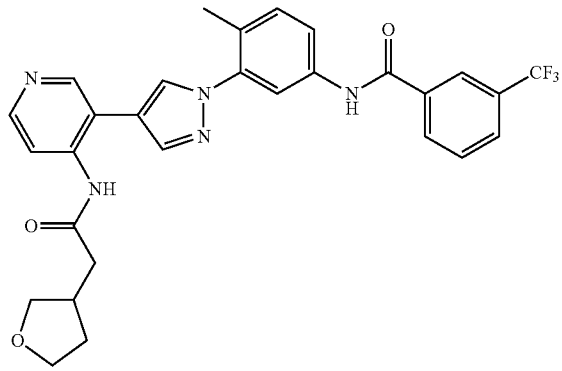 [SMILES: Cc1ccc(NC(=O)c2cccc(C(F)(F)F)c2)cc1-n1cc(-c2cnccc2NC(=O)CC2CCOC2)cn1] |
| 137 | 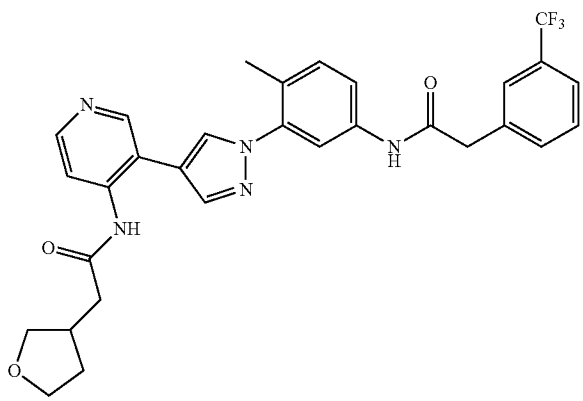 [SMILES: Cc1ccc(NC(=O)Cc2cccc(C(F)(F)F)c2)cc1-n1cc(-c2cnccc2NC(=O)CC2CCOC2)cn1] |
| 138 | 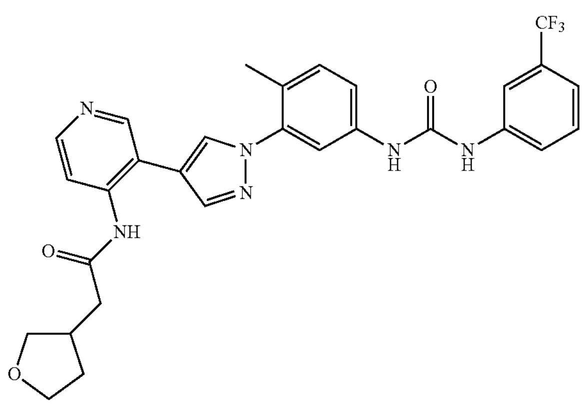 [SMILES: Cc1ccc(NC(=O)Nc2cccc(C(F)(F)F)c2)cc1-n1cc(-c2cnccc2NC(=O)CC2CCOC2)cn1] |
| 139 | 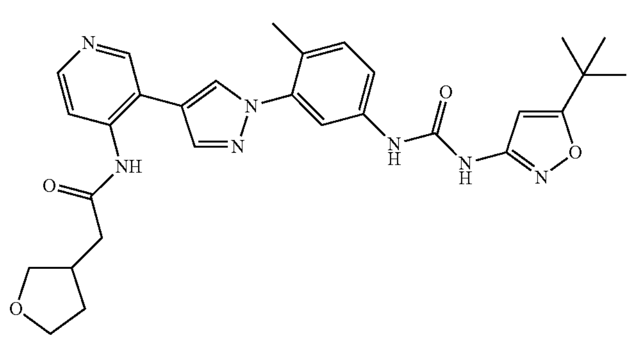 [SMILES: Cc1ccc(NC(=O)Nc2cc(C(C)(C)C)on2)cc1-n1cc(-c2cnccc2NC(=O)CC2CCOC2)cn1] |

-continued

| No. | Structure |
|---|---|
| 140 | 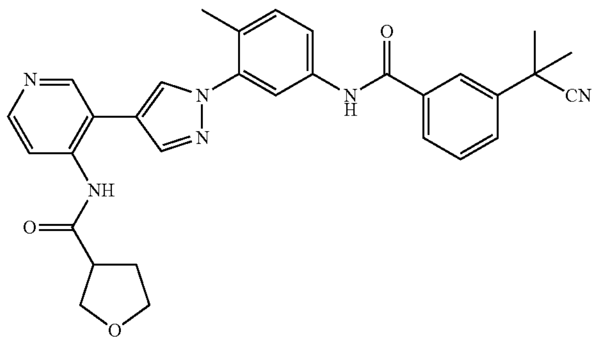 [SMILES: Cc1ccc(NC(=O)c2cccc(C(C)(C)C#N)c2)cc1-n1cc(-c2cnccc2NC(=O)C2CCOC2)cn1] |
| 141 | 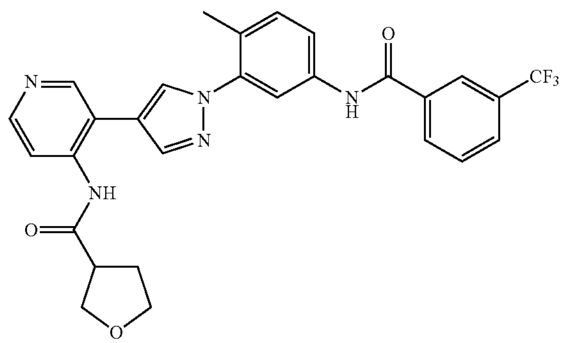 [SMILES: Cc1ccc(NC(=O)c2cccc(C(F)(F)F)c2)cc1-n1cc(-c2cnccc2NC(=O)C2CCOC2)cn1] |
| 142 | 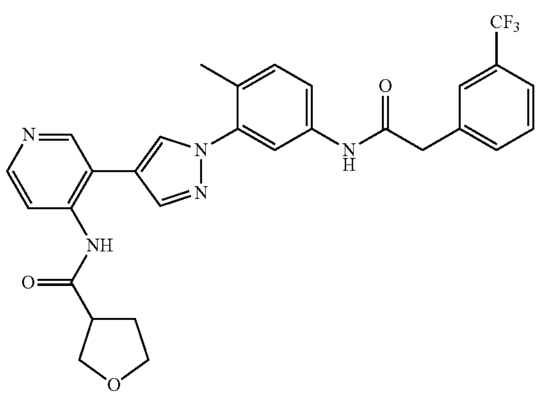 [SMILES: Cc1ccc(NC(=O)Cc2cccc(C(F)(F)F)c2)cc1-n1cc(-c2cnccc2NC(=O)C2CCOC2)cn1] |
| 143 | 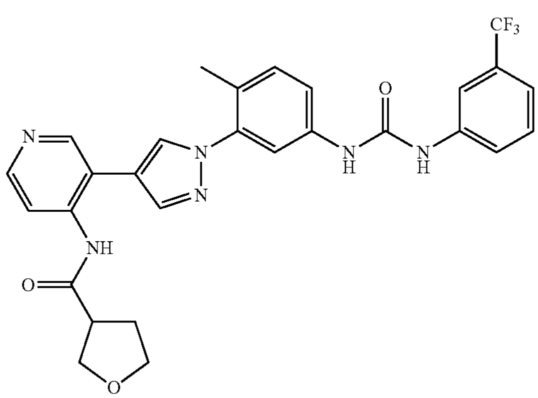 [SMILES: Cc1ccc(NC(=O)Nc2cccc(C(F)(F)F)c2)cc1-n1cc(-c2cnccc2NC(=O)C2CCOC2)cn1] |

-continued

| No. | Structure |
|---|---|
| 144 | 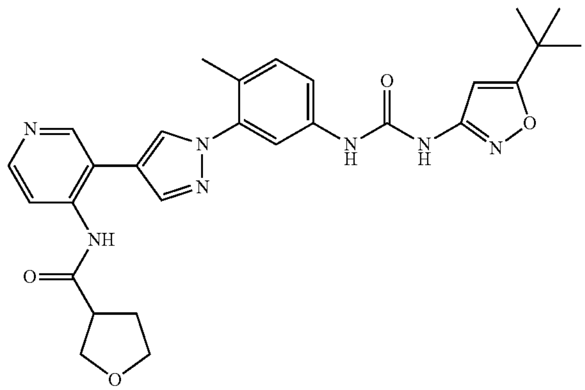 [SMILES: Cc1ccc(NC(=O)Nc2cc(C(C)(C)C)on2)cc1-n1cc(-c2cnccc2NC(=O)C2CCOC2)cn1] |
| 145 | 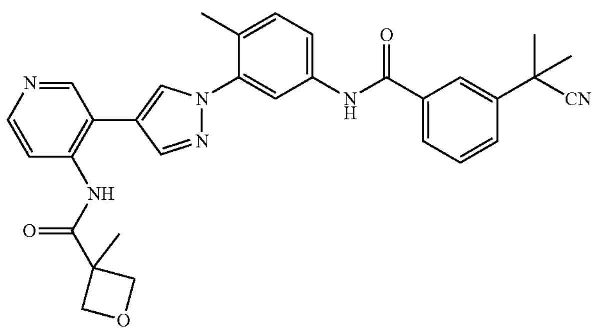 [SMILES: Cc1ccc(NC(=O)c2cccc(C(C)(C)C#N)c2)cc1-n1cc(-c2cnccc2NC(=O)C2(C)COC2)cn1] |
| 146 | 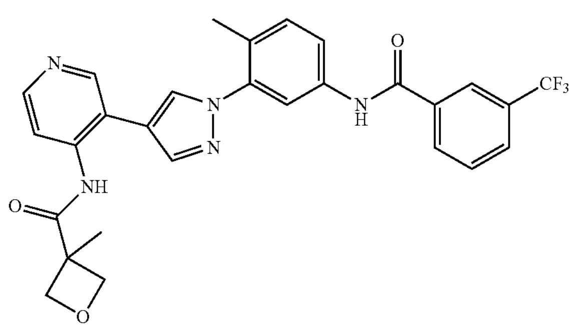 [SMILES: Cc1ccc(NC(=O)c2cccc(C(F)(F)F)c2)cc1-n1cc(-c2cnccc2NC(=O)C2(C)COC2)cn1] |
| 147 | 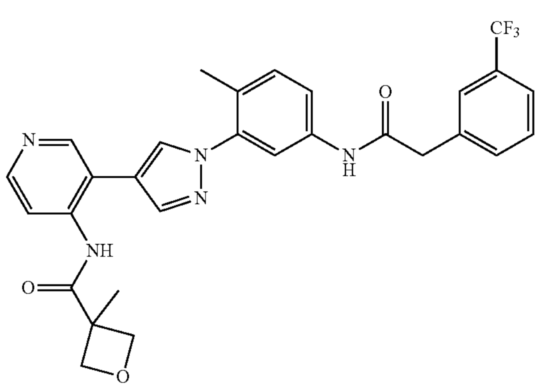 [SMILES: Cc1ccc(NC(=O)Cc2cccc(C(F)(F)F)c2)cc1-n1cc(-c2cnccc2NC(=O)C2(C)COC2)cn1] |

-continued
| No. | Structure |
|---|---|
| 148 | 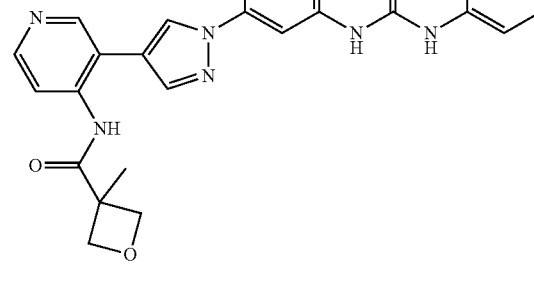 |
| 149 | 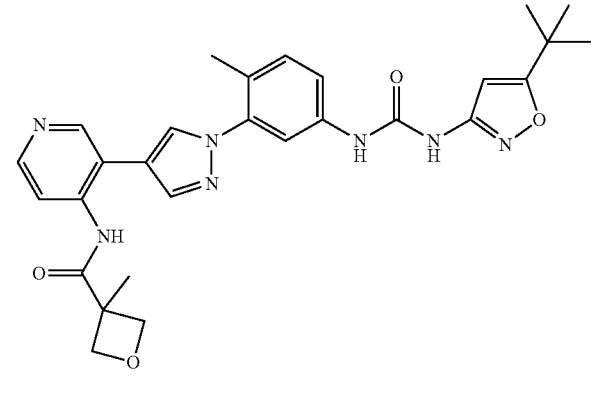 [SMILES: Cc1ccc(NC(=O)Nc2cc(C(C)(C)C)on2)cc1-n1cc(-c2cnccc2NC(=O)C2(C)COC2)cn1] |
| 150 | 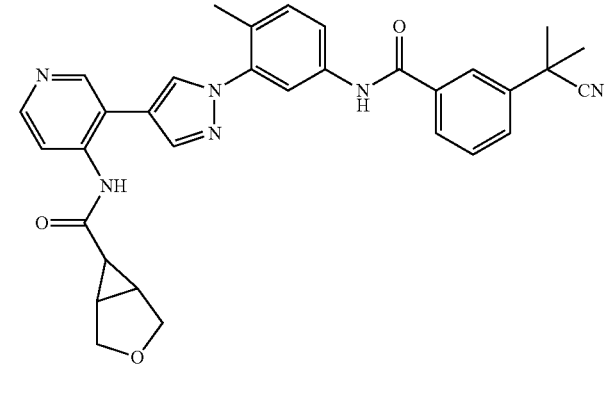 [SMILES: Cc1ccc(NC(=O)c2cccc(C(C)(C)C#N)c2)cc1-n1cc(-c2cnccc2NC(=O)C2C3COCC32)cn1] |
| 151 | 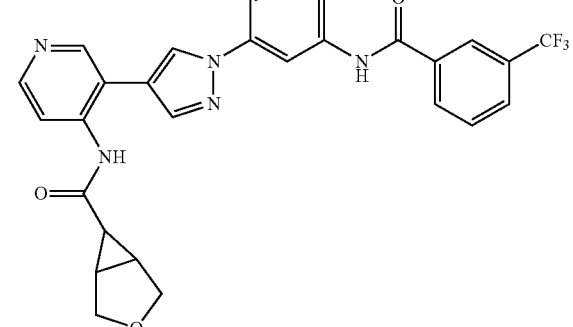 |

| No. | Structure |
|---|---|
| 152 | (structure) |
| 153 | (structure) |
| 154 | (structure) |
| 155 | (structure) |

-continued
| No. | Structure |
|---|---|
| 156 | 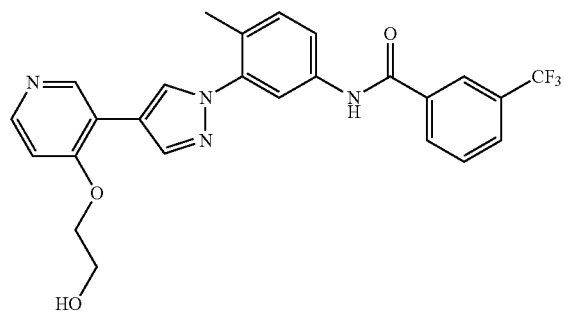 [SMILES: Cc1ccc(NC(=O)c2cccc(C(F)(F)F)c2)cc1-n1cc(-c2cnccc2OCCO)cn1] |
| 157 | 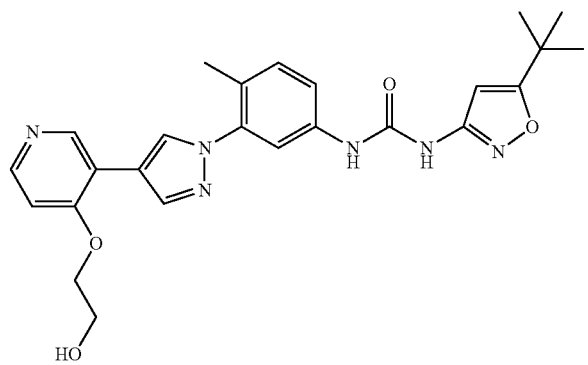 [SMILES: Cc1ccc(NC(=O)Nc2cc(C(C)(C)C)on2)cc1-n1cc(-c2cnccc2OCCO)cn1] |
| 158 | 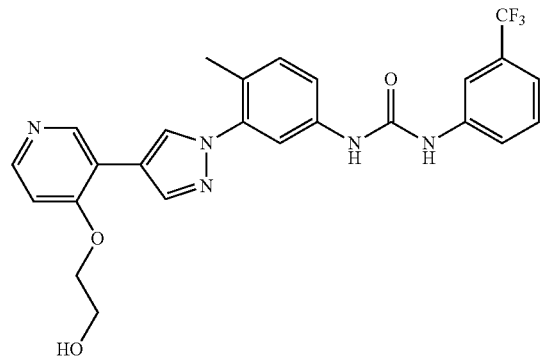 [SMILES: Cc1ccc(NC(=O)Nc2cccc(C(F)(F)F)c2)cc1-n1cc(-c2cnccc2OCCO)cn1] |
| 159 | 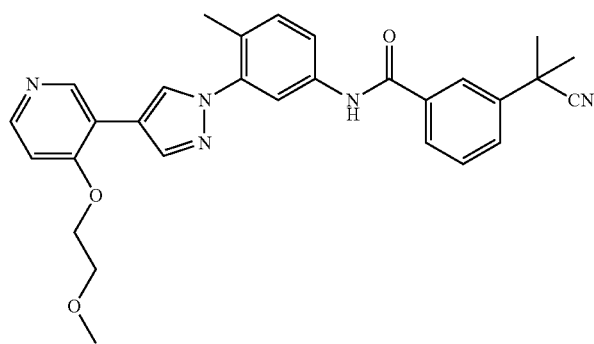 [SMILES: COCCOc1ccncc1-c1cnn(-c2cc(NC(=O)c3cccc(C(C)(C)C#N)c3)ccc2C)c1] |

-continued
| No. | Structure |
|---|---|
| 160 | 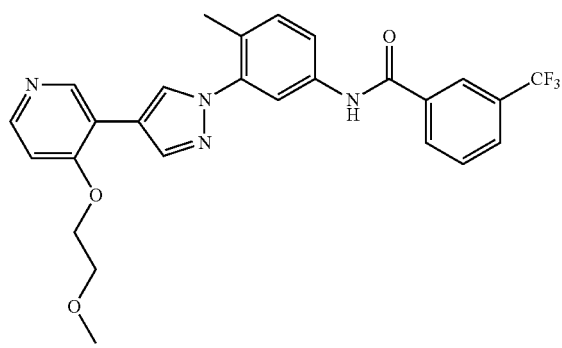 [SMILES: COCCOc1ccncc1-c1cnn(-c2cc(NC(=O)c3cccc(C(F)(F)F)c3)ccc2C)c1] |
| 161 | 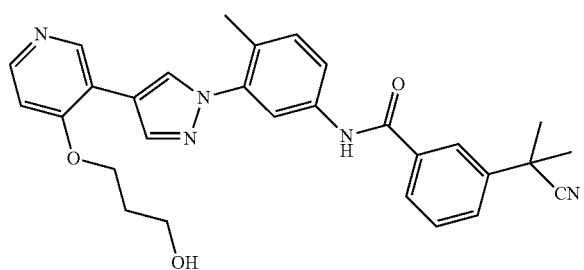 [SMILES: Cc1ccc(NC(=O)c2cccc(C(C)(C)C#N)c2)cc1-n1cc(-c2cnccc2OCCCO)cn1] |
| 162 | 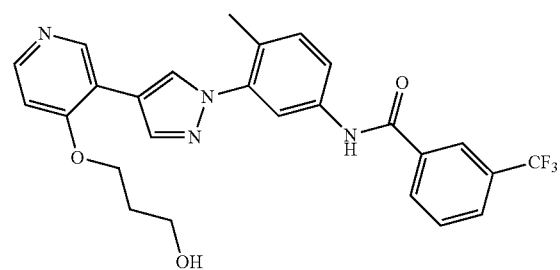 [SMILES: Cc1ccc(NC(=O)c2cccc(C(F)(F)F)c2)cc1-n1cc(-c2cnccc2OCCCO)cn1] |
| 163 | 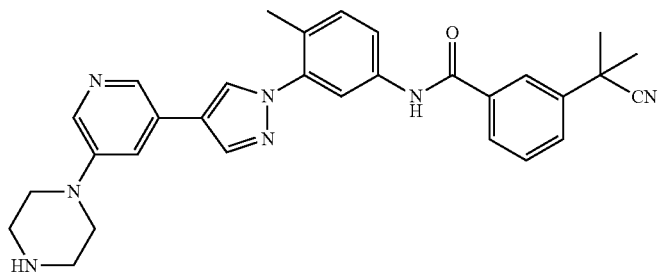 [SMILES: Cc1ccc(NC(=O)c2cccc(C(C)(C)C#N)c2)cc1-n1cc(-c2cncc(N3CCNCC3)c2)cn1] |
| 164 | 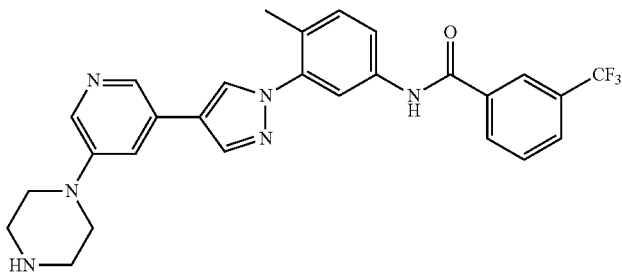 [SMILES: Cc1ccc(NC(=O)c2cccc(C(F)(F)F)c2)cc1-n1cc(-c2cncc(N3CCNCC3)c2)cn1] |

| No. | Structure |
|---|---|
| 165 | 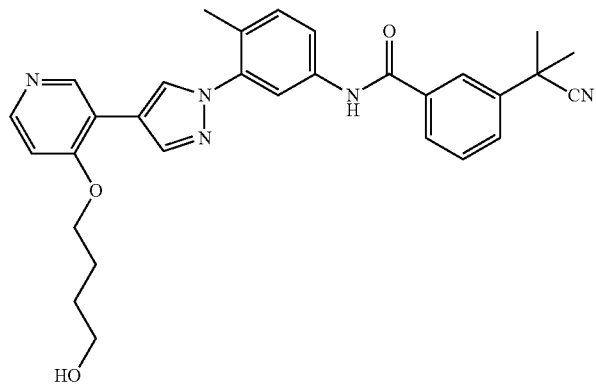 [SMILES: Cc1ccc(NC(=O)c2cccc(C(C)(C)C#N)c2)cc1-n1cc(-c2cnccc2OCCCCO)cn1] |
| 166 | 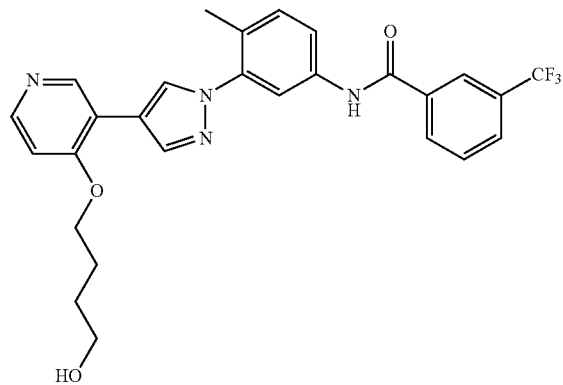 [SMILES: Cc1ccc(NC(=O)c2cccc(C(F)(F)F)c2)cc1-n1cc(-c2cnccc2OCCCCO)cn1] |
| 167 | 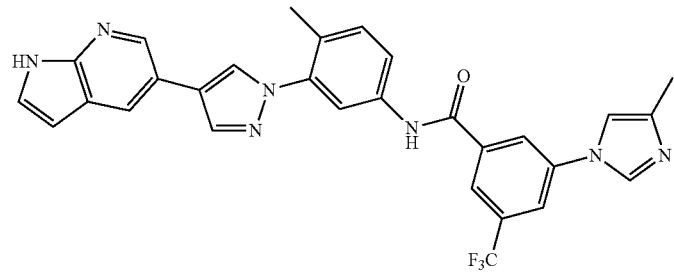 [SMILES: Cc1cn(-c2cc(C(=O)Nc3ccc(C)c(-n4cc(-c5cnc6[nH]ccc6c5)cn4)c3)cc(C(F)(F)F)c2)cn1] |
| 168 | 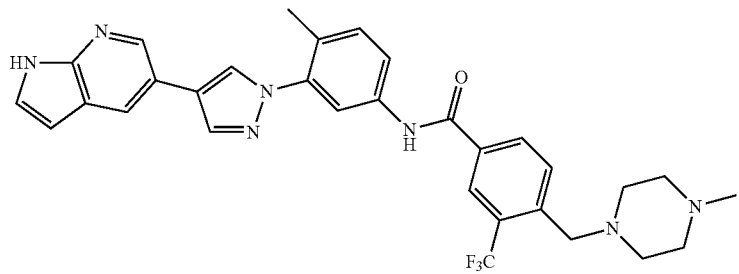 [SMILES: Cc1ccc(NC(=O)c2ccc(CN3CCN(C)CC3)c(C(F)(F)F)c2)cc1-n1cc(-c2cnc3[nH]ccc3c2)cn1] |

-continued
| No. | Structure |
|---|---|
| 169 | 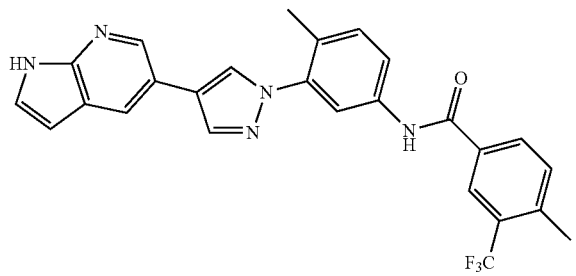 [SMILES: Cc1ccc(NC(=O)c2ccc(C)c(C(F)(F)F)c2)cc1-n1cc(-c2cnc3[nH]ccc3c2)cn1] |
| 170 | 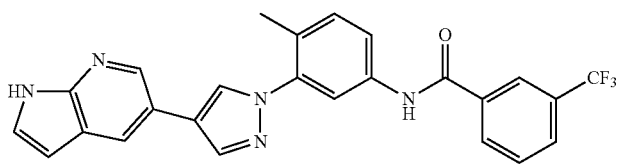 [SMILES: Cc1ccc(NC(=O)c2cccc(C(F)(F)F)c2)cc1-n1cc(-c2cnc3[nH]ccc3c2)cn1] |
| 171 | 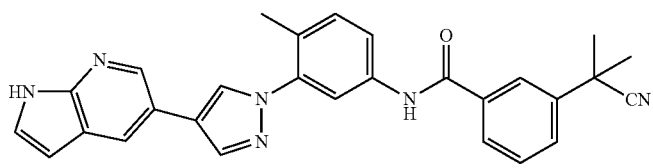 [SMILES: Cc1ccc(NC(=O)c2cccc(C(C)(C)C#N)c2)cc1-n1cc(-c2cnc3[nH]ccc3c2)cn1] |
| 172 | 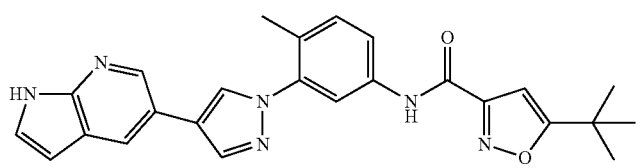 [SMILES: Cc1ccc(NC(=O)c2cc(C(C)(C)C)on2)cc1-n1cc(-c2cnc3[nH]ccc3c2)cn1] |
| 173 | 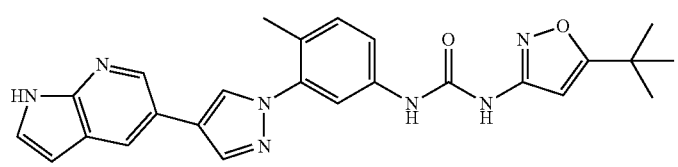 [SMILES: Cc1ccc(NC(=O)Nc2cc(C(C)(C)C)on2)cc1-n1cc(-c2cnc3[nH]ccc3c2)cn1] |
| 174 | 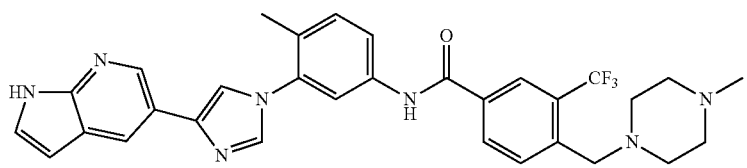 [SMILES: Cc1ccc(NC(=O)c2ccc(CN3CCN(C)CC3)c(C(F)(F)F)c2)cc1-n1cnc(-c2cnc3[nH]ccc3c2)c1] |
| 175 | 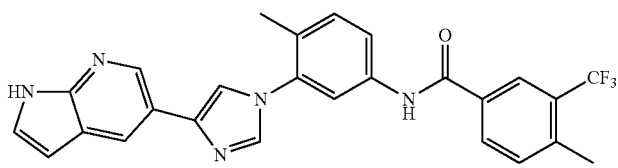 [SMILES: Cc1ccc(NC(=O)c2ccc(C)c(C(F)(F)F)c2)cc1-n1cnc(-c2cnc3[nH]ccc3c2)c1] |
| 176 | 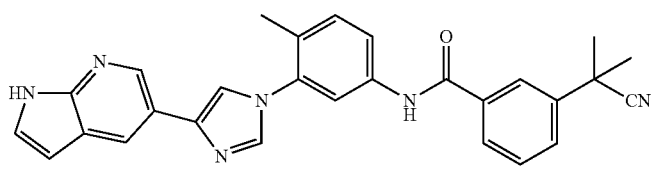 [SMILES: Cc1ccc(NC(=O)c2cccc(C(C)(C)C#N)c2)cc1-n1cnc(-c2cnc3[nH]ccc3c2)c1] |

| No. | Structure |
|---|---|
| 177 | 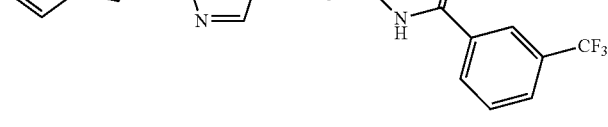 |
| 178 | 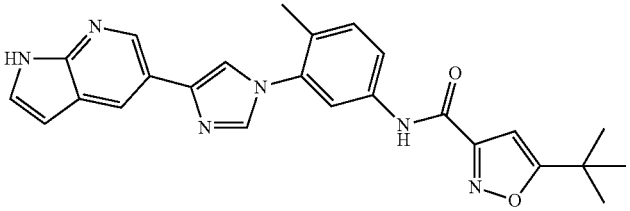 [SMILES: Cc1ccc(NC(=O)c2cc(C(C)(C)C)on2)cc1-n1cnc(-c2cnc3[nH]ccc3c2)c1] |
| 179 | 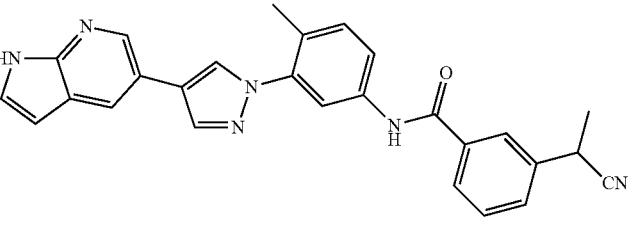 |
| 180 | 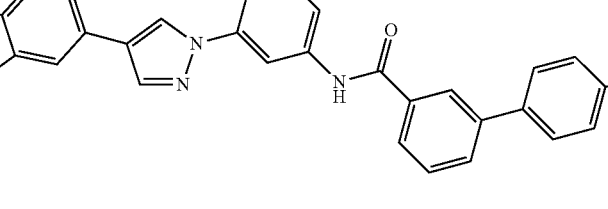 |
| 181 | 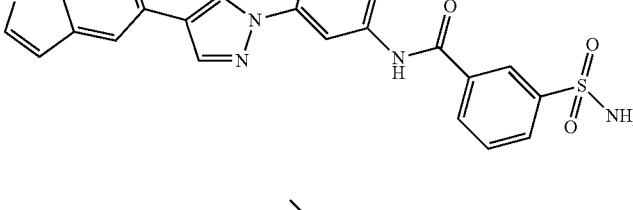 |
| 182 | 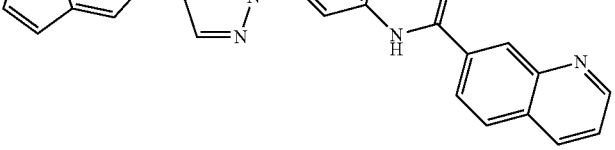 |

| No. | Structure |
|---|---|
| 183 | 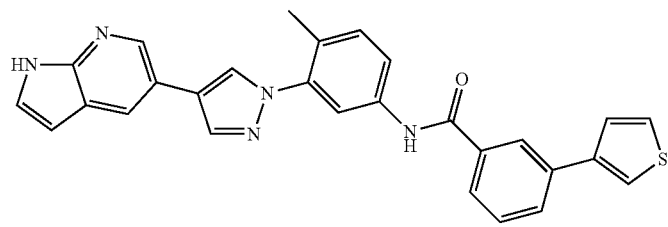 [SMILES: Cc1ccc(NC(=O)c2cccc(-c3ccsc3)c2)cc1-n1cc(-c2cnc3[nH]ccc3c2)cn1] |
| 184 | 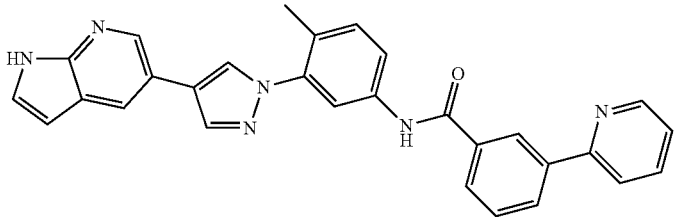 |
| 185 | 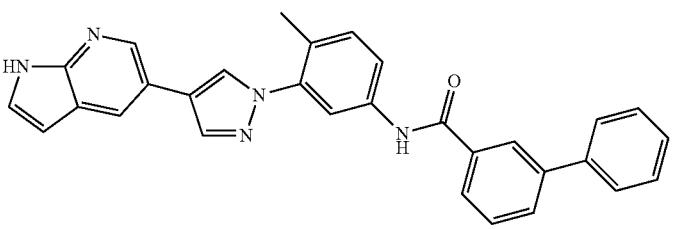 |

13. A pharmaceutical composition, comprising the kinase inhibitor of claim 1, a pharmaceutically acceptable carrier or excipient, and optionally another therapeutic agent.

14. A method for inhibiting the activity of tyrosine kinase RAF and/or RAS in a subject, comprising administering an effective amount of the kinase inhibitor of claim 1 to the subject.

15. A method for treating, preventing or ameliorating a disease, disorder or condition in a patient in need thereof, comprising administering an effective amount of the kinase inhibitor of claim 1 to the patient, wherein the disease, disorder or condition is modulated or affected by, or involved in the activity of tyrosine kinase RAF and/or RAS.

16. The method according to claim 15, wherein the disease, disorder, or condition is a proliferative disease selected from the group consisting of solid tumors, sarcoma, gastrointestinal stromal tumor, colorectal cancer, acute myeloblastic leukemia, chronic myelogenous leukemia, thyroid carcinoma, systemic mastocytosis, eosinophilia syndrome, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intra-epithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural mesothelioma, hemangioblastoma, hemangioma, kidney cancer, liver cancer, adrenal carcinoma, bladder cancer, stomach cancer, rectal cancer, vaginal cancer, cervical cancer, endometrial cancer, multiple myeloma, neck and head tumors, neoplasia, or a combination thereof.

17. The method according to claim 15, wherein the disease, disorder, or condition is a proliferative disease selected from the group consisting of head and neck cancer, thyroid carcinoma, melanoma, colorectal cancer, lung cancer, breast cancer, pancreatic cancer, esophagus cancer, liver cancer, leukaemia, neoplasia, or a combination thereof.

* * * * *